US006525185B1

(12) United States Patent
Fan et al.

(10) Patent No.: US 6,525,185 B1
(45) Date of Patent: Feb. 25, 2003

(54) POLYMORPHISMS ASSOCIATED WITH HYPERTENSION

(75) Inventors: Jian Bing Fan, Palo Alto, CA (US); Aravinda Chakravarti, Shaker Heights, OH (US); Marc Kenneth Halushka, Cleveland Heights, OH (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/304,232

(22) Filed: May 3, 1999

Related U.S. Application Data

(60) Provisional application No. 60/084,641, filed on May 7, 1998.

(51) Int. Cl.⁷ .................. C07H 21/02; C07H 21/04; C12Q 1/68; C12P 19/34; C12N 9/60

(52) U.S. Cl. .................. 536/23.1; 435/6; 435/91.1; 435/226; 536/24.3

(58) Field of Search .................. 435/6, 226, 91.1; 536/23.1, 24.3

(56) References Cited

U.S. PATENT DOCUMENTS

| | | |
|---|---|---|
| 4,286,330 A | 8/1981 | Isaacson |
| 4,917,999 A | 4/1990 | Byng et al. |
| 4,965,190 A | 10/1990 | Woo et al. |
| 5,206,137 A | 4/1993 | Ip et al. |
| 5,292,639 A | 3/1994 | Beitz et al. |
| 5,393,877 A | 2/1995 | McLean et al. |
| 5,400,249 A | 3/1995 | Soll et al. |
| 5,449,604 A | 9/1995 | Schellenberg et al. |
| 5,468,610 A | 11/1995 | Polymeropoulos et al. |
| 5,494,794 A | 2/1996 | Wallace |
| 5,521,301 A | 5/1996 | Wallace et al. |
| 5,558,988 A | 9/1996 | Prockop et al. |
| 5,639,607 A | 6/1997 | Desnick et al. |
| 5,670,330 A | 9/1997 | Sonenberg et al. |
| 5,747,259 A | 5/1998 | You |
| 5,763,566 A | 6/1998 | Jensen et al. |
| 5,780,611 A | 7/1998 | Guntaka et al. |
| 5,801,040 A * | 9/1998 | Soubrier et al. ............ 435/226 |
| 5,807,718 A | 9/1998 | Joyce et al. |
| 5,945,283 A | 8/1999 | Kwok et al. |
| 5,994,315 A | 11/1999 | Nyce et al. |

FOREIGN PATENT DOCUMENTS

| | | | |
|---|---|---|---|
| EP | 130 565 | 1/1985 | |
| EP | 431 880 | 6/1991 | |
| EP | 717 113 | 6/1996 | |
| EP | 955 382 | 11/1999 | |
| WO | WO 88/08457 | 11/1988 | |
| WO | WO 9003435 A2 * | 4/1990 | ........... C12N/15/57 |
| WO | WO 9100354 A1 * | 1/1991 | ........... C12N/9/64 |
| WO | WO 92/13083 | 8/1992 | |
| WO | WO 94/08048 | 4/1994 | |
| WO | WO 94/21790 | 9/1994 | |
| WO | WO 95/11995 | 5/1995 | |
| WO | WO 95/12607 | 5/1995 | |
| WO | WO 95/18223 | 7/1995 | |
| WO | WO 95/25538 | 9/1995 | |
| WO | WO 96/24686 | 8/1996 | |
| WO | WO 96/29401 | 9/1996 | |
| WO | WO 98/38846 | 9/1998 | |
| WO | WO 98/58529 | 12/1998 | |
| WO | WO 99/14228 | 3/1999 | |

OTHER PUBLICATIONS

Accession No. L29294 on GenBank database, Lin et al., Aug. 6, 1996.*
Accession No. L29297 on GenBank database, Lin et al., Aug. 6, 1996.*
Accession No. L29295 on GenBank database, Lin et al., Aug. 6, 1996.*
Accession No. L29291 on GenBank database, Lin et al., Aug. 6, 1996.*
Accession No. L07261 on GenBank database, Joshi et al., May 6, 1993.*
Accesion No. X58141 on GenBank database, Joshi et al., May 6, 1993.*
Accession No. M26657 on GenBank database, Ehlers et al., Jan. 13, 1995.*
Accession No. M29981 on GenBank database, Ehlers et al., Jan. 13, 1995.*
Accession No. X16295 on GenBank database, Lattion et al., Mar. 20, 1991.*
Bianchi et al., "Two point mutations within the adducin genes are involved in blood pressure variation," *PNAS*, 91:3999–4003 (1994).
Chen et al., "Cloning of 559 potential exons of genes of human chromosome by exon trapping," *Genome Research*, 6(8):747–760 (1996).
Cornall et al., "The generation of a library of PCR–analyzed microsatellite variants for genetic mapping of the mouse genome," *Genomics*, 10(4):874–881 (1991).
Cusi et al., "Polymorphisms of alpha–adducin and salt sensitivity in patients with essential hypertension," *The Lancet*, 349:1353–1357 (1997).
Halushka et al., "Patterns of single–nucleotide polymorphisms in candidate genes for blood–pressure homeostasis," *Nature Genetics*, 22:239–247 (1999).
Hudson et al., "Sequence of STS's," made public by the Whitehead Institute/MIT Center for Genome Research, (1995).
Jeunmaitre et al., "Haplotypes of angiotensinogen in essential hypertension," *Am. J. Hum. Genet.*, 60:1448–1460 (1997).

(List continued on next page.)

*Primary Examiner*—Kenneth R. Horlick
*Assistant Examiner*—Young Kim
(74) *Attorney, Agent, or Firm*—Townsend and Townsend and Crew LLP

(57) ABSTRACT

The invention discloses a collection of polymorphic sites in genes know or suspected to have a role in hypertension. The invention provides nucleic acids including such polymorphic sites. The nucleic acids can be used as probes or primers or for expressing variant proteins. The invention also provide methods of analyzing the polymorphic forms occupying the polymorphic sites.

13 Claims, 2 Drawing Sheets

OTHER PUBLICATIONS

Kwok, Pui–Yan et al., "Increasing the Information Content of STS–Based Genome Maps: Identifying Polymorphisms in Mapped STS's," *Genomics*, 31:123–126, article 19 (1996).

Landegren et al., "Oligonucleotide Ligation Assay," *PCR Protocols A Guide to Methods and Applications*, eds. Innis et al., Academic Press, San Diego, CA (1990).

Larsson et al., "A single mouse gene encodes the mitochondrial transcription factor A and testis–specific nuclear HMG– box protein," *Nature Genetics*, 13(3)296–302 (1996).

Lifton, R. P., "Genetic determinants of human hypertension," *PNAS*, 92:8545–8551 (1995).

Maskos et al., "A Novel Method for the Parallel Analysis of Multiple Mutations in Multiple Samples," *Nuc. Acids Res.*, 21(9):2269–2270 (1993).

Matthews et al., "Analytical Strategies for the Use of DNA Probes," *Analytical Biochemistry*, 169:1–25 (1988).

Melton et al., "Structure, expression, and mutation of the hypoxanthine phosphoribosyltransferase gene," *PNAS*, 81(7):2147–2151 (1984).

Okubo et al., "Large scale cDNA sequencing for analysis of quantitative and qualitative aspects of gene expression," *Nature Genetics*, 2:173–179 (1992).

Saiki et al., "Analysis of enzymatically amplified Beta–globin and HLA–DQalpha DNA with Allele–specific oligonucleotide probes," *Nature*, 324:163–166 (1988).

Sigma Chemical Catalog, Pub. 1990 by Sigma Chemical Co., P.O. Box 14508, St. Louis, MO 63178, p. 845. See Product No. P 0887 Polydeoxyadenylic Acid.

Sudhof, T.C., "The Structure of the Human Synapsin I Gene and Protein," *J. Biol. Chem.*, 265:7849–7852 (1990).

Tamaki et al., "Polymorphism of alpha–adducin in Japanese patients with essential hypertension," *Hypertension Research*, 21:29–32 (1998).

Ye et al., "Progression Of Coronary Atherosclerosis Is Associated With A Common Genetic Variant Of The Human Stromelysin–1 Promoter Which Results In Reduced Gene Expression", *J. Biol. Chem.*, 271(22):13055–13060 (1996).

Sommer et al., "Minimal Homology Requirements for PCR Primers," *Nuc. Acids Res.*, 17(16):6749 (1989).

\* cited by examiner

SEQUENCE LISTING

```
<160> NUMBER OF SEQ ID NOS: 909

<210> SEQ ID NO 1
<211> LENGTH: 29
<212> TYPE: DNA
<213> ORGANISM: Artificial Sequence
<220> FEATURE:
<223> OTHER INFORMATION: AADDEX1 305

<400> SEQUENCE: 1 acggggcgg agccrgagcc ggagccgac                                          29

<210> SEQ ID NO 2
<211> LENGTH: 29
<212> TYPE: DNA
<213> ORGANISM: Artificial Sequence
<220> FEATURE:
<223> OTHER INFORMATION: AADDEX10 246

<400> SEQUENCE: 2
aagcttccga ggaakggcag aatggaagc                                         29

<210> SEQ ID NO 3
<211> LENGTH: 29
<212> TYPE: DNA
<213> ORGANISM: Artificial Sequence
<220> FEATURE:
<223> OTHER INFORMATION: AADDEX12 43

<400> SEQUENCE: 3
gatccgagag cagawtttac aggacatta                                         29

<210> SEQ ID NO 4
```

```
<211> LENGTH: 29
<212> TYPE: DNA
<213> ORGANISM: Artificial Sequence
<220> FEATURE:
<223> OTHER INFORMATION: AADDEX13 173

<400> SEQUENCE: 4
gaagcagaag ggctstgaag gtgagtgct                                    29

<210> SEQ ID NO 5
<211> LENGTH: 29
<212> TYPE: DNA
<213> ORGANISM: Artificial Sequence
<220> FEATURE:
<223> OTHER INFORMATION: AADDEX15 74

<400> SEQUENCE: 5
cctagtaagt accgygctgc ctccgctct                                    29

<210> SEQ ID NO 6
<211> LENGTH: 29
<212> TYPE: DNA
<213> ORGANISM: Artificial Sequence
<220> FEATURE:
<223> OTHER INFORMATION: AADDEX16 1071

<400> SEQUENCE: 6
attcctgtca taggraaggt atatcagga                                    29

<210> SEQ ID NO 7
<211> LENGTH: 29
<212> TYPE: DNA
<213> ORGANISM: Artificial Sequence
<220> FEATURE:
<223> OTHER INFORMATION: AADDEX16 1321

<400> SEQUENCE: 7
gccctggggc ccctygacat caccgtcat                                    29

<210> SEQ ID NO 8
<211> LENGTH: 29
<212> TYPE: DNA
<213> ORGANISM: Artificial Sequence
<220> FEATURE:
<223> OTHER INFORMATION: AADDEX16 1328

<400> SEQUENCE: 8
ggcccctcga catcrccgtc attgatgga                                    29

<210> SEQ ID NO 9
<211> LENGTH: 29
<212> TYPE: DNA
<213> ORGANISM: Artificial Sequence
<220> FEATURE:
<223> OTHER INFORMATION: AADDEX16 1478

<400> SEQUENCE: 9
cagcctgact aggtrcaggc aagcttgtg                                    29

<210> SEQ ID NO 10
<211> LENGTH: 29
<212> TYPE: DNA
<213> ORGANISM: Artificial Sequence
<220> FEATURE:
<223> OTHER INFORMATION: AADDEX16 691

<400> SEQUENCE: 10
```
cagctttggc tgcasgtcac cctcctgag                                         29

<210> SEQ ID NO 11
<211> LENGTH: 29
<212> TYPE: DNA
<213> ORGANISM: Artificial Sequence
<220> FEATURE:
<223> OTHER INFORMATION: AADDEX16 995

<400> SEQUENCE: 11
tatgcatgtc tgacygacga tccctcgac                                         29

<210> SEQ ID NO 12
<211> LENGTH: 29
<212> TYPE: DNA
<213> ORGANISM: Artificial Sequence
<220> FEATURE:
<223> OTHER INFORMATION: AADDEX2 31

<400> SEQUENCE: 12
tttgattctg taggraccta gaaagattg                                         29

<210> SEQ ID NO 13
<211> LENGTH: 29
<212> TYPE: DNA
<213> ORGANISM: Artificial Sequence
<220> FEATURE:
<223> OTHER INFORMATION: AADDEX7 96

<400> SEQUENCE: 13
ttggagaagt ggctwatcat gactaccat                                         29

<210> SEQ ID NO 14
<211> LENGTH: 29
<212> TYPE: DNA
<213> ORGANISM: Artificial Sequence
<220> FEATURE:
<223> OTHER INFORMATION: AADDEX9 173

<400> SEQUENCE: 14
attggtgagc aggawtttga agccctcat                                         29

<210> SEQ ID NO 15
<211> LENGTH: 29
<212> TYPE: DNA
<213> ORGANISM: Artificial Sequence
<220> FEATURE:
<223> OTHER INFORMATION: ACEEX13 151

<400> SEQUENCE: 15
ccagccagga ggcaycccaa caggtgaca                                         29

<210> SEQ ID NO 16
<211> LENGTH: 29
<212> TYPE: DNA
<213> ORGANISM: Artificial Sequence
<220> FEATURE:
<223> OTHER INFORMATION: ACEEX13 202

<400> SEQUENCE: 16
aggcaacaac cagcrgccag acaaccacc                                         29

<210> SEQ ID NO 17
<211> LENGTH: 29
<212> TYPE: DNA

```
<213> ORGANISM: Artificial Sequence
<220> FEATURE:
<223> OTHER INFORMATION: ACEEX15 144

<400> SEQUENCE: 17
ctagaacggg cagcrctgcc tgcccagga                                29

<210> SEQ ID NO 18
<211> LENGTH: 29
<212> TYPE: DNA
<213> ORGANISM: Artificial Sequence
<220> FEATURE:
<223> OTHER INFORMATION: ACEEX17 19

<400> SEQUENCE: 18
ctcaagccat tcaamcccct accagatct                                29

<210> SEQ ID NO 19
<211> LENGTH: 29
<212> TYPE: DNA
<213> ORGANISM: Artificial Sequence
<220> FEATURE:
<223> OTHER INFORMATION: ACEEX18 130

<400> SEQUENCE: 19
cagccactct acctsaacct gcatgccta                                29

<210> SEQ ID NO 20
<211> LENGTH: 29
<212> TYPE: DNA
<213> ORGANISM: Artificial Sequence
<220> FEATURE:
<223> OTHER INFORMATION: ACEEX21 150

<400> SEQUENCE: 20
cttccatgag gccaytgggg acgtgctag                                29

<210> SEQ ID NO 21
<211> LENGTH: 29
<212> TYPE: DNA
<213> ORGANISM: Artificial Sequence
<220> FEATURE:
<223> OTHER INFORMATION: ACEEX22 19

<400> SEQUENCE: 21
agcatgacat caackttctg atgaagatg                                29

<210> SEQ ID NO 22
<211> LENGTH: 29
<212> TYPE: DNA
<213> ORGANISM: Artificial Sequence
<220> FEATURE:
<223> OTHER INFORMATION: ACEEX24 118

<400> SEQUENCE: 22
cagtccaagg aggcygggca gcgcctggg                                29

<210> SEQ ID NO 23
<211> LENGTH: 29
<212> TYPE: DNA
<213> ORGANISM: Artificial Sequence
<220> FEATURE:
<223> OTHER INFORMATION: ACEEX24 16

<400> SEQUENCE: 23
tgctccaggt acttygtcag cttcatcat                                29
```

<210> SEQ ID NO 24
<211> LENGTH: 29
<212> TYPE: DNA
<213> ORGANISM: Artificial Sequence
<220> FEATURE:
<223> OTHER INFORMATION: ACEEX26 154

<400> SEQUENCE: 24
gggcctcagc cagcrgctct tcagcatcc                                      29

<210> SEQ ID NO 25
<211> LENGTH: 29
<212> TYPE: DNA
<213> ORGANISM: Artificial Sequence
<220> FEATURE:
<223> OTHER INFORMATION: ACEEX26 174

<400> SEQUENCE: 25
tcagcatccg ccacmgcagc ctccaccgg                                      29

<210> SEQ ID NO 26
<211> LENGTH: 29
<212> TYPE: DNA
<213> ORGANISM: Artificial Sequence
<220> FEATURE:
<223> OTHER INFORMATION: ACEEX26 205

<400> SEQUENCE: 26
ctcccacggg ccccmgttcg gctccgagg                                      29

<210> SEQ ID NO 27
<211> LENGTH: 29
<212> TYPE: DNA
<213> ORGANISM: Artificial Sequence
<220> FEATURE:
<223> OTHER INFORMATION: ACEEX26 224

<400> SEQUENCE: 27
ggctccgagg tggarctgag acactcctg                                      29

<210> SEQ ID NO 28
<211> LENGTH: 29
<212> TYPE: DNA
<213> ORGANISM: Artificial Sequence
<220> FEATURE:
<223> OTHER INFORMATION: ADDBEX10 81

<400> SEQUENCE: 28
ctcctggagc aggakaagca ccggcccca                                      29

<210> SEQ ID NO 29
<211> LENGTH: 29
<212> TYPE: DNA
<213> ORGANISM: Artificial Sequence
<220> FEATURE:
<223> OTHER INFORMATION: ADDBEX15 68

<400> SEQUENCE: 29
gctctggtcc ggccrtgtgc gagttcttc                                      29

<210> SEQ ID NO 30
<211> LENGTH: 29
<212> TYPE: DNA
<213> ORGANISM: Artificial Sequence
<220> FEATURE:

<223> OTHER INFORMATION: ADDBEX15 85

<400> SEQUENCE: 30
tgcgagttct tcagygttgc cctccacat                              29

<210> SEQ ID NO 31
<211> LENGTH: 29
<212> TYPE: DNA
<213> ORGANISM: Artificial Sequence
<220> FEATURE:
<223> OTHER INFORMATION: ADDBEX17 147

<400> SEQUENCE: 31
gaggaaatcc tcagmaaagg cctgagcca                              29

<210> SEQ ID NO 32
<211> LENGTH: 29
<212> TYPE: DNA
<213> ORGANISM: Artificial Sequence
<220> FEATURE:
<223> OTHER INFORMATION: ADDBEX3 138

<400> SEQUENCE: 32
gcttctcaga ggacraccccc gagtacatg                             29

<210> SEQ ID NO 33
<211> LENGTH: 29
<212> TYPE: DNA
<213> ORGANISM: Artificial Sequence
<220> FEATURE:
<223> OTHER INFORMATION: ADDBEX4 134

<400> SEQUENCE: 33
catggccagc acctsccacg cagtcttcc                              29

<210> SEQ ID NO 34
<211> LENGTH: 29
<212> TYPE: DNA
<213> ORGANISM: Artificial Sequence
<220> FEATURE:
<223> OTHER INFORMATION: ADDBEX8 173

<400> SEQUENCE: 34
ccacctgcaa ggttrgctta gctcttctg                              29

<210> SEQ ID NO 35
<211> LENGTH: 29
<212> TYPE: DNA
<213> ORGANISM: Artificial Sequence
<220> FEATURE:
<223> OTHER INFORMATION: ADDBEX9 69

<400> SEQUENCE: 35
gtagaggagg cattytacaa gatcttcca                              29

<210> SEQ ID NO 36
<211> LENGTH: 29
<212> TYPE: DNA
<213> ORGANISM: Artificial Sequence
<220> FEATURE:
<223> OTHER INFORMATION: ADDG 2087

<400> SEQUENCE: 36
tgacattgca catcyaaata ccacattta                              29

```
<210> SEQ ID NO 37
<211> LENGTH: 29
<212> TYPE: DNA
<213> ORGANISM: Artificial Sequence
<220> FEATURE:
<223> OTHER INFORMATION: ADORA2AEX1 429

<400> SEQUENCE: 37
ggtgtcactg gcggyggccg acatcgcag                                     29

<210> SEQ ID NO 38
<211> LENGTH: 29
<212> TYPE: DNA
<213> ORGANISM: Artificial Sequence
<220> FEATURE:
<223> OTHER INFORMATION: ADORA2AEX2 1230

<400> SEQUENCE: 38
tgcagaagca tctgkaagca ccaccttgt                                     29

<210> SEQ ID NO 39
<211> LENGTH: 29
<212> TYPE: DNA
<213> ORGANISM: Artificial Sequence
<220> FEATURE:
<223> OTHER INFORMATION: ADORA2AEX2 596

<400> SEQUENCE: 39
ccgccagacc ttccrcaaga tcattcgca                                     29

<210> SEQ ID NO 40
<211> LENGTH: 29
<212> TYPE: DNA
<213> ORGANISM: Artificial Sequence
<220> FEATURE:
<223> OTHER INFORMATION: ADORA2AEX2 741

<400> SEQUENCE: 40
ggagtgtggg ccaayggcag tgctcccca                                     29

<210> SEQ ID NO 41
<211> LENGTH: 29
<212> TYPE: DNA
<213> ORGANISM: Artificial Sequence
<220> FEATURE:
<223> OTHER INFORMATION: ADRB3EX1 1020

<400> SEQUENCE: 41
ggccccggtg gggaygtgcg ctccgcccg                                     29

<210> SEQ ID NO 42
<211> LENGTH: 29
<212> TYPE: DNA
<213> ORGANISM: Artificial Sequence
<220> FEATURE:
<223> OTHER INFORMATION: ADRB3EX1 1354

<400> SEQUENCE: 42
tgcgccgccg cccgyccggc cctcttccc                                     29

<210> SEQ ID NO 43
<211> LENGTH: 29
<212> TYPE: DNA
<213> ORGANISM: Artificial Sequence
<220> FEATURE:
<223> OTHER INFORMATION: ADRB3EX1 1445
```

```
<400> SEQUENCE: 43
ggtaggtaac cgggkcagag ggaccggcg                                29

<210> SEQ ID NO 44
<211> LENGTH: 29
<212> TYPE: DNA
<213> ORGANISM: Artificial Sequence
<220> FEATURE:
<223> OTHER INFORMATION: ADRB3EX1 44

<400> SEQUENCE: 44
gctactcctc ccccragagc ggtggcacc                                29

<210> SEQ ID NO 45
<211> LENGTH: 29
<212> TYPE: DNA
<213> ORGANISM: Artificial Sequence
<220> FEATURE:
<223> OTHER INFORMATION: ADRB3EX2 301

<400> SEQUENCE: 45
gtggtagtgt ccagstgccg tggagcagc                                29

<210> SEQ ID NO 46
<211> LENGTH: 29
<212> TYPE: DNA
<213> ORGANISM: Artificial Sequence
<220> FEATURE:
<223> OTHER INFORMATION: ADRB3EX2 408

<400> SEQUENCE: 46
tggttccatt ccttytgcca cccaaaccc                                29

<210> SEQ ID NO 47
<211> LENGTH: 29
<212> TYPE: DNA
<213> ORGANISM: Artificial Sequence
<220> FEATURE:
<223> OTHER INFORMATION: ADROMEX1 1197

<400> SEQUENCE: 47
tgggacgtct gagaytttct ccttcaagt                                29

<210> SEQ ID NO 48
<211> LENGTH: 29
<212> TYPE: DNA
<213> ORGANISM: Artificial Sequence
<220> FEATURE:
<223> OTHER INFORMATION: ADROMEX1 154

<400> SEQUENCE: 48
atgttacctt ccttkcctga ctcaagggt                                29

<210> SEQ ID NO 49
<211> LENGTH: 29
<212> TYPE: DNA
<213> ORGANISM: Artificial Sequence
<220> FEATURE:
<223> OTHER INFORMATION: ADROMEX1 723

<400> SEQUENCE: 49
gggctcttgc tgttyttcgc caggaggct                                29

<210> SEQ ID NO 50
<211> LENGTH: 29
```

```
<212> TYPE: DNA
<213> ORGANISM: Artificial Sequence
<220> FEATURE:
<223> OTHER INFORMATION: ADROMEX1 981

<400> SEQUENCE: 50
gagcaggagc gcgcrtggct gaggaaaga                              29

<210> SEQ ID NO 51
<211> LENGTH: 29
<212> TYPE: DNA
<213> ORGANISM: Artificial Sequence
<220> FEATURE:
<223> OTHER INFORMATION: ADROMEX2 101

<400> SEQUENCE: 51
tcgctcgcct tcctmggcgc tgacaccgc                              29

<210> SEQ ID NO 52
<211> LENGTH: 29
<212> TYPE: DNA
<213> ORGANISM: Artificial Sequence
<220> FEATURE:
<223> OTHER INFORMATION: ADROMEX3 81

<400> SEQUENCE: 52
ctgcggatgt ccagsagcta ccccaccgg                              29

<210> SEQ ID NO 53
<211> LENGTH: 29
<212> TYPE: DNA
<213> ORGANISM: Artificial Sequence
<220> FEATURE:
<223> OTHER INFORMATION: ADROMEX4 1033

<400> SEQUENCE: 53
accgagtctc tgtayaatct atttacata                              29

<210> SEQ ID NO 54
<211> LENGTH: 29
<212> TYPE: DNA
<213> ORGANISM: Artificial Sequence
<220> FEATURE:
<223> OTHER INFORMATION: ADROMEX4 1292

<400> SEQUENCE: 54
tgtcctgggt gcgartcagg gcttcgcgg                              29

<210> SEQ ID NO 55
<211> LENGTH: 29
<212> TYPE: DNA
<213> ORGANISM: Artificial Sequence
<220> FEATURE:
<223> OTHER INFORMATION: ADROMEX4 1389

<400> SEQUENCE: 55
gcgagcctgg actcycgggt tgcgcaacg                              29

<210> SEQ ID NO 56
<211> LENGTH: 29
<212> TYPE: DNA
<213> ORGANISM: Artificial Sequence
<220> FEATURE:
<223> OTHER INFORMATION: ADROMEX4 388

<400> SEQUENCE: 56
```

```
caagcatccc gctgstgcct cccgggacg                                              29
```

<210> SEQ ID NO 57
<211> LENGTH: 29
<212> TYPE: DNA
<213> ORGANISM: Artificial Sequence
<220> FEATURE:
<223> OTHER INFORMATION: ADROMEX4 536

<400> SEQUENCE: 57

```
cgcttcctta gcctkgctca ggtgcaagt                                              29
```

<210> SEQ ID NO 58
<211> LENGTH: 29
<212> TYPE: DNA
<213> ORGANISM: Artificial Sequence
<220> FEATURE:
<223> OTHER INFORMATION: ADROMEX4 918

<400> SEQUENCE: 58

```
attttaagac gtgartgtct cagcgaggt                                              29
```

<210> SEQ ID NO 59
<211> LENGTH: 29
<212> TYPE: DNA
<213> ORGANISM: Artificial Sequence
<220> FEATURE:
<223> OTHER INFORMATION: AE1EX1 298

<400> SEQUENCE: 59

```
ggggcatgag tcagrggttt gcgagctgc                                              29
```

<210> SEQ ID NO 60
<211> LENGTH: 29
<212> TYPE: DNA
<213> ORGANISM: Artificial Sequence
<220> FEATURE:
<223> OTHER INFORMATION: AE1EX1 80

<400> SEQUENCE: 60

```
tcaaaccttc atccmcaaag gaagagtca                                              29
```

<210> SEQ ID NO 61
<211> LENGTH: 29
<212> TYPE: DNA
<213> ORGANISM: Artificial Sequence
<220> FEATURE:
<223> OTHER INFORMATION: AE1EX10 77

<400> SEQUENCE: 61

```
cgaggggagc tgctrcactc cctagaggg                                              29
```

<210> SEQ ID NO 62
<211> LENGTH: 29
<212> TYPE: DNA
<213> ORGANISM: Artificial Sequence
<220> FEATURE:
<223> OTHER INFORMATION: AE1EX11 181

<400> SEQUENCE: 62

```
gtcatcttca tctaytttgc tgcactgtc                                              29
```

<210> SEQ ID NO 63
<211> LENGTH: 29
<212> TYPE: DNA
<213> ORGANISM: Artificial Sequence

```
<220> FEATURE:
<223> OTHER INFORMATION: AE1EX11 191

<400> SEQUENCE: 63
tctactttgc tgcaytgtca cccgccatc                                              29

<210> SEQ ID NO 64
<211> LENGTH: 29
<212> TYPE: DNA
<213> ORGANISM: Artificial Sequence
<220> FEATURE:
<223> OTHER INFORMATION: AE1EX11 228

<400> SEQUENCE: 64
cggcctcctg ggtcwgtgcc aatacctgt                                              29

<210> SEQ ID NO 65
<211> LENGTH: 29
<212> TYPE: DNA
<213> ORGANISM: Artificial Sequence
<220> FEATURE:
<223> OTHER INFORMATION: AE1EX12 70

<400> SEQUENCE: 65
gtgtcggagc tgctratctc cactgcagt                                              29

<210> SEQ ID NO 66
<211> LENGTH: 29
<212> TYPE: DNA
<213> ORGANISM: Artificial Sequence
<220> FEATURE:
<223> OTHER INFORMATION: AE1EX12 71

<400> SEQUENCE: 66
tgtcggagct gctgwtctcc actgcagtg                                              29

<210> SEQ ID NO 67
<211> LENGTH: 29
<212> TYPE: DNA
<213> ORGANISM: Artificial Sequence
<220> FEATURE:
<223> OTHER INFORMATION: AE1EX14 159

<400> SEQUENCE: 67
ccttcttctt tgccwtgatg ctgcgcaag                                              29

<210> SEQ ID NO 68
<211> LENGTH: 29
<212> TYPE: DNA
<213> ORGANISM: Artificial Sequence
<220> FEATURE:
<223> OTHER INFORMATION: AE1EX15 107

<400> SEQUENCE: 68
ttcttcattc aggayaccta cacccaggt                                              29

<210> SEQ ID NO 69
<211> LENGTH: 29
<212> TYPE: DNA
<213> ORGANISM: Artificial Sequence
<220> FEATURE:
<223> OTHER INFORMATION: AE1EX16 92

<400> SEQUENCE: 69
ggctgggtca tccayccact gggcttgcg                                              29
```

<210> SEQ ID NO 70
<211> LENGTH: 29
<212> TYPE: DNA
<213> ORGANISM: Artificial Sequence
<220> FEATURE:
<223> OTHER INFORMATION: AE1EX17 34

<400> SEQUENCE: 70
cctacagtag gctgrttgtc agcaaacct                                    29

<210> SEQ ID NO 71
<211> LENGTH: 29
<212> TYPE: DNA
<213> ORGANISM: Artificial Sequence
<220> FEATURE:
<223> OTHER INFORMATION: AE1EX17 40

<400> SEQUENCE: 71
gtaggctgat tgtcrgcaaa cctgagcgc                                    29

<210> SEQ ID NO 72
<211> LENGTH: 29
<212> TYPE: DNA
<213> ORGANISM: Artificial Sequence
<220> FEATURE:
<223> OTHER INFORMATION: AE1EX17 72

<400> SEQUENCE: 72
atggtcaagg gctcyggctt ccacctgga                                    29

<210> SEQ ID NO 73
<211> LENGTH: 29
<212> TYPE: DNA
<213> ORGANISM: Artificial Sequence
<220> FEATURE:
<223> OTHER INFORMATION: AE1EX19 132

<400> SEQUENCE: 73
tggccctgcc cttcrtcctc atcctcact                                    29

<210> SEQ ID NO 74
<211> LENGTH: 29
<212> TYPE: DNA
<213> ORGANISM: Artificial Sequence
<220> FEATURE:
<223> OTHER INFORMATION: AE1EX19 43

<400> SEQUENCE: 74
ggtgaagacc tggcrcatgc acttattca                                    29

<210> SEQ ID NO 75
<211> LENGTH: 29
<212> TYPE: DNA
<213> ORGANISM: Artificial Sequence
<220> FEATURE:
<223> OTHER INFORMATION: AE1EX20 1007

<400> SEQUENCE: 75
aatcagtgga ctccragggg actgagaca                                    29

<210> SEQ ID NO 76
<211> LENGTH: 29
<212> TYPE: DNA
<213> ORGANISM: Artificial Sequence
<220> FEATURE:
<223> OTHER INFORMATION: AE1EX20 1213

```
<400> SEQUENCE: 76
atttgagagc cattwtcctc aactccatc                              29

<210> SEQ ID NO 77
<211> LENGTH: 29
<212> TYPE: DNA
<213> ORGANISM: Artificial Sequence
<220> FEATURE:
<223> OTHER INFORMATION: AE1EX20 1542

<400> SEQUENCE: 77
aaaaatacaa aaatyagctg ggtgtctcg                              29

<210> SEQ ID NO 78
<211> LENGTH: 29
<212> TYPE: DNA
<213> ORGANISM: Artificial Sequence
<220> FEATURE:
<223> OTHER INFORMATION: AE1EX20 1628

<400> SEQUENCE: 78
cccaggaggt ggagsttgca gtgagccaa                              29

<210> SEQ ID NO 79
<211> LENGTH: 29
<212> TYPE: DNA
<213> ORGANISM: Artificial Sequence
<220> FEATURE:
<223> OTHER INFORMATION: AE1EX20 1679

<400> SEQUENCE: 79
ctgggcaaca gagcragacc ctgtctcaa                              29

<210> SEQ ID NO 80
<211> LENGTH: 29
<212> TYPE: DNA
<213> ORGANISM: Artificial Sequence
<220> FEATURE:
<223> OTHER INFORMATION: AE1EX20 379

<400> SEQUENCE: 80
tcactgggga tcccrtgctg gaagactta                              29

<210> SEQ ID NO 81
<211> LENGTH: 29
<212> TYPE: DNA
<213> ORGANISM: Artificial Sequence
<220> FEATURE:
<223> OTHER INFORMATION: AE1EX20 418

<400> SEQUENCE: 81
ctccctcttc ccagmacagg cagggtag                               29

<210> SEQ ID NO 82
<211> LENGTH: 29
<212> TYPE: DNA
<213> ORGANISM: Artificial Sequence
<220> FEATURE:
<223> OTHER INFORMATION: AE1EX20 991

<400> SEQUENCE: 82
ttactgaggg ccccrgaatc agtggactc                              29

<210> SEQ ID NO 83
```

-continued

<210> SEQ ID NO 83
<211> LENGTH: 29
<212> TYPE: DNA
<213> ORGANISM: Artificial Sequence
<220> FEATURE:
<223> OTHER INFORMATION: AE1EX4 17

<400> SEQUENCE: 83
caatactaac cgacytctgg ttttcagct                                   29

<210> SEQ ID NO 84
<211> LENGTH: 29
<212> TYPE: DNA
<213> ORGANISM: Artificial Sequence
<220> FEATURE:
<223> OTHER INFORMATION: AE1EX4 36

<400> SEQUENCE: 84
gttttcagct cacgmcaccg aggcaacag                                   29

<210> SEQ ID NO 85
<211> LENGTH: 29
<212> TYPE: DNA
<213> ORGANISM: Artificial Sequence
<220> FEATURE:
<223> OTHER INFORMATION: AE1EX4 89

<400> SEQUENCE: 85
acccgggtac ccacraggtg aggacccca                                   29

<210> SEQ ID NO 86
<211> LENGTH: 29
<212> TYPE: DNA
<213> ORGANISM: Artificial Sequence
<220> FEATURE:
<223> OTHER INFORMATION: AE1EX5 197

<400> SEQUENCE: 86
ctagagctgc gtagwgtctt caccaaggg                                   29

<210> SEQ ID NO 87
<211> LENGTH: 29
<212> TYPE: DNA
<213> ORGANISM: Artificial Sequence
<220> FEATURE:
<223> OTHER INFORMATION: AE1EX8 35

<400> SEQUENCE: 87
ttcccacagg gagayggggg cacagaagg                                   29

<210> SEQ ID NO 88
<211> LENGTH: 29
<212> TYPE: DNA
<213> ORGANISM: Artificial Sequence
<220> FEATURE:
<223> OTHER INFORMATION: AGTEX2 181

<400> SEQUENCE: 88
agagtacctg tgagyagctg gcaaaggcc                                   29

<210> SEQ ID NO 89
<211> LENGTH: 29
<212> TYPE: DNA
<213> ORGANISM: Artificial Sequence
<220> FEATURE:
<223> OTHER INFORMATION: AGTEX2 354

<400> SEQUENCE: 89

```
gtcgggatgc tggcyaactt cttgggctt                                29

<210> SEQ ID NO 90
<211> LENGTH: 29
<212> TYPE: DNA
<213> ORGANISM: Artificial Sequence
<220> FEATURE:
<223> OTHER INFORMATION: AGTEX2 755

<400> SEQUENCE: 90
ggacttcaca gaackggatg ttgctgctg                                29

<210> SEQ ID NO 91
<211> LENGTH: 29
<212> TYPE: DNA
<213> ORGANISM: Artificial Sequence
<220> FEATURE:
<223> OTHER INFORMATION: AGTEX5 258

<400> SEQUENCE: 91
tggcaaggcc tctgyccctg gcctttgag                                29

<210> SEQ ID NO 92
<211> LENGTH: 29
<212> TYPE: DNA
<213> ORGANISM: Artificial Sequence
<220> FEATURE:
<223> OTHER INFORMATION: AGTEX5 376

<400> SEQUENCE: 92
agctggaaag cagcsgtttc tccttggtc                                29

<210> SEQ ID NO 93
<211> LENGTH: 29
<212> TYPE: DNA
<213> ORGANISM: Artificial Sequence
<220> FEATURE:
<223> OTHER INFORMATION: AGTEX5385

<400> SEQUENCE: 93
gcagccgttt ctccytggtc taagtgtgc                                29

<210> SEQ ID NO 94
<211> LENGTH: 29
<212> TYPE: DNA
<213> ORGANISM: Artificial Sequence
<220> FEATURE:
<223> OTHER INFORMATION: AGTEX5 641

<400> SEQUENCE: 94
gccttcggtt tgtakttagt gtcttgaat                                29

<210> SEQ ID NO 95
<211> LENGTH: 29
<212> TYPE: DNA
<213> ORGANISM: Artificial Sequence
<220> FEATURE:
<223> OTHER INFORMATION: AGTEXP1 101

<400> SEQUENCE: 95
ctggctgtgc tattsttggt gtttaacag                                29

<210> SEQ ID NO 96
<211> LENGTH: 29
<212> TYPE: DNA
```

```
<213> ORGANISM: Artificial Sequence
<220> FEATURE:
<223> OTHER INFORMATION: AGTEXP2 160

<400> SEQUENCE: 96
ggaaccttgg ccccractcc tgcaaactt                                29

<210> SEQ ID NO 97
<211> LENGTH: 29
<212> TYPE: DNA
<213> ORGANISM: Artificial Sequence
<220> FEATURE:
<223> OTHER INFORMATION: AGTEXP2 35

<400> SEQUENCE: 97
ccctctgcac ctccrgcctg catgtccct                                29

<210> SEQ ID NO 98
<211> LENGTH: 29
<212> TYPE: DNA
<213> ORGANISM: Artificial Sequence
<220> FEATURE:
<223> OTHER INFORMATION: AGTEXP3 158

<400> SEQUENCE: 98
ctcgtgaccc ggccrgggga agaagctgc                                29

<210> SEQ ID NO 99
<211> LENGTH: 29
<212> TYPE: DNA
<213> ORGANISM: Artificial Sequence
<220> FEATURE:
<223> OTHER INFORMATION: AGTEXP3 173

<400> SEQUENCE: 99
ggggaagaag ctgcygttgt tctgggtac                                29

<210> SEQ ID NO 100
<211> LENGTH: 29
<212> TYPE: DNA
<213> ORGANISM: Artificial Sequence
<220> FEATURE:
<223> OTHER INFORMATION: ALDREDEX1 162

<400> SEQUENCE: 100
gcgccaagat gcccwtcctg gggttgggt                                29

<210> SEQ ID NO 101
<211> LENGTH: 29
<212> TYPE: DNA
<213> ORGANISM: Artificial Sequence
<220> FEATURE:
<223> OTHER INFORMATION: ALDREDEX1 71

<400> SEQUENCE: 101
aaaggtacgc gccgsggcca aggccgcac                                29

<210> SEQ ID NO 102
<211> LENGTH: 29
<212> TYPE: DNA
<213> ORGANISM: Artificial Sequence
<220> FEATURE:
<223> OTHER INFORMATION: ALDREDEX10 150

<400> SEQUENCE: 102
ttgcaaatgt agtakggcct gtgtcactc                                29
```

<210> SEQ ID NO 103
<211> LENGTH: 29
<212> TYPE: DNA
<213> ORGANISM: Artificial Sequence
<220> FEATURE:
<223> OTHER INFORMATION: ALDREDEX2 180

<400> SEQUENCE: 103
tgaagcgtga ggagstcttc atcgtcagc                                29

<210> SEQ ID NO 104
<211> LENGTH: 29
<212> TYPE: DNA
<213> ORGANISM: Artificial Sequence
<220> FEATURE:
<223> OTHER INFORMATION: ALDREDEX2 204

<400> SEQUENCE: 104
tcagcaaggt atcgktccgc ggtggggct                                29

<210> SEQ ID NO 105
<211> LENGTH: 29
<212> TYPE: DNA
<213> ORGANISM: Artificial Sequence
<220> FEATURE:
<223> OTHER INFORMATION: ALDREDEX2 88

<400> SEQUENCE: 105
cgtcgggtac cgccwcatcg actgtgccc                                29

<210> SEQ ID NO 106
<211> LENGTH: 29
<212> TYPE: DNA
<213> ORGANISM: Artificial Sequence
<220> FEATURE:
<223> OTHER INFORMATION: ALDREDEX3 28

<400> SEQUENCE: 106
cctctcgctg gcttwgctgt ggtgcacgt                                29

<210> SEQ ID NO 107
<211> LENGTH: 29
<212> TYPE: DNA
<213> ORGANISM: Artificial Sequence
<220> FEATURE:
<223> OTHER INFORMATION: ALDREDEX4 101

<400> SEQUENCE: 107
aacattctgg acacrtgggc ggtaagaca                                29

<210> SEQ ID NO 108
<211> LENGTH: 29
<212> TYPE: DNA
<213> ORGANISM: Artificial Sequence
<220> FEATURE:
<223> OTHER INFORMATION: ALDREDEX6 87

<400> SEQUENCE: 108
actgccagtc caaargcatc gtggtgacc                                29

<210> SEQ ID NO 109
<211> LENGTH: 29
<212> TYPE: DNA
<213> ORGANISM: Artificial Sequence
<220> FEATURE:

```
<223> OTHER INFORMATION: ALDREDEX9 67

<400> SEQUENCE: 109
ccaggatatg accaycttac tcagctaca                              29

<210> SEQ ID NO 110
<211> LENGTH: 29
<212> TYPE: DNA
<213> ORGANISM: Artificial Sequence
<220> FEATURE:
<223> OTHER INFORMATION: ANPEX1 252

<400> SEQUENCE: 110
ccatgtacaa tgccrtgtcc aacgcagac                              29

<210> SEQ ID NO 111
<211> LENGTH: 29
<212> TYPE: DNA
<213> ORGANISM: Artificial Sequence
<220> FEATURE:
<223> OTHER INFORMATION: ANPEX1 297

<400> SEQUENCE: 111
tagggccagg aaagygggtg cagtctggg                              29

<210> SEQ ID NO 112
<211> LENGTH: 29
<212> TYPE: DNA
<213> ORGANISM: Artificial Sequence
<220> FEATURE:
<223> OTHER INFORMATION: ANPEX3 106

<400> SEQUENCE: 112
tcctgtcccc tgggktctct gctgcattt                              29

<210> SEQ ID NO 113
<211> LENGTH: 29
<212> TYPE: DNA
<213> ORGANISM: Artificial Sequence
<220> FEATURE:
<223> OTHER INFORMATION: ANPEX3 127

<400> SEQUENCE: 113
ctgcatttgt gtcaycttgt tgccatgga                              29

<210> SEQ ID NO 114
<211> LENGTH: 29
<212> TYPE: DNA
<213> ORGANISM: Artificial Sequence
<220> FEATURE:
<223> OTHER INFORMATION: APOA1 101

<400> SEQUENCE: 114
gccttgcccc aggcygggcc tctgggtac                              29

<210> SEQ ID NO 115
<211> LENGTH: 29
<212> TYPE: DNA
<213> ORGANISM: Artificial Sequence
<220> FEATURE:
<223> OTHER INFORMATION: APOA1 1016

<400> SEQUENCE: 115
cgtaactggg caccmgtccc agctctgtc                              29
```

-continued

```
<210> SEQ ID NO 116
<211> LENGTH: 29
<212> TYPE: DNA
<213> ORGANISM: Artificial Sequence
<220> FEATURE:
<223> OTHER INFORMATION: APOA1 1162

<400> SEQUENCE: 116
aggtgtcacc caggsctcac ccctgatag                              29

<210> SEQ ID NO 117
<211> LENGTH: 29
<212> TYPE: DNA
<213> ORGANISM: Artificial Sequence
<220> FEATURE:
<223> OTHER INFORMATION: APOA1 1163

<400> SEQUENCE: 117
ggtgtcaccc agggytcacc cctgatagg                              29

<210> SEQ ID NO 118
<211> LENGTH: 29
<212> TYPE: DNA
<213> ORGANISM: Artificial Sequence
<220> FEATURE:
<223> OTHER INFORMATION: APOA1 1401

<400> SEQUENCE: 118
tgcagcccta cctgsacgac ttccagaag                              29

<210> SEQ ID NO 119
<211> LENGTH: 29
<212> TYPE: DNA
<213> ORGANISM: Artificial Sequence
<220> FEATURE:
<223> OTHER INFORMATION: APOA1 1576

<400> SEQUENCE: 119
tgtggacgcg ctgcscacgc atctggccc                              29

<210> SEQ ID NO 120
<211> LENGTH: 29
<212> TYPE: DNA
<213> ORGANISM: Artificial Sequence
<220> FEATURE:
<223> OTHER INFORMATION: APOA1 1643

<400> SEQUENCE: 120
cttgaggctc tcaargagaa cggcggcgc                              29

<210> SEQ ID NO 121
<211> LENGTH: 29
<212> TYPE: DNA
<213> ORGANISM: Artificial Sequence
<220> FEATURE:
<223> OTHER INFORMATION: APOA1 1757

<400> SEQUENCE: 121
caaggcctgc tgccsgtgct ggagagctt                              29

<210> SEQ ID NO 122
<211> LENGTH: 29
<212> TYPE: DNA
<213> ORGANISM: Artificial Sequence
<220> FEATURE:
<223> OTHER INFORMATION: APOA1 2007
```

```
<400> SEQUENCE: 122
ctccgtgccc agacwggacg tcttagggc                                              29

<210> SEQ ID NO 123
<211> LENGTH: 29
<212> TYPE: DNA
<213> ORGANISM: Artificial Sequence
<220> FEATURE:
<223> OTHER INFORMATION: APOA1 334

<400> SEQUENCE: 123
aaccatcggg gggcyttctc cctaaatcc                                              29

<210> SEQ ID NO 124
<211> LENGTH: 29
<212> TYPE: DNA
<213> ORGANISM: Artificial Sequence
<220> FEATURE:
<223> OTHER INFORMATION: APOA1 620

<400> SEQUENCE: 124
tttgaaggct ccgcyttggg aaaacagct                                              29

<210> SEQ ID NO 125
<211> LENGTH: 29
<212> TYPE: DNA
<213> ORGANISM: Artificial Sequence
<220> FEATURE:
<223> OTHER INFORMATION: APOA1 771

<400> SEQUENCE: 125
ctggatggag aaacyggaat ggatctcca                                              29

<210> SEQ ID NO 126
<211> LENGTH: 29
<212> TYPE: DNA
<213> ORGANISM: Artificial Sequence
<220> FEATURE:
<223> OTHER INFORMATION: APOA1 840

<400> SEQUENCE: 126
gggctgcccg atgcrtgatc acagagcca                                              29

<210> SEQ ID NO 127
<211> LENGTH: 29
<212> TYPE: DNA
<213> ORGANISM: Artificial Sequence
<220> FEATURE:
<223> OTHER INFORMATION: APOA2 1334

<400> SEQUENCE: 127
agattaggct taaawtgcag agaaaaagt                                              29

<210> SEQ ID NO 128
<211> LENGTH: 29
<212> TYPE: DNA
<213> ORGANISM: Artificial Sequence
<220> FEATURE:
<223> OTHER INFORMATION: APOA2 1412

<400> SEQUENCE: 128
aagaactggg ccttsaattt cagtctcta                                              29

<210> SEQ ID NO 129
<211> LENGTH: 29
```

<210> SEQ ID NO 129
<211> LENGTH: 29
<212> TYPE: DNA
<213> ORGANISM: Artificial Sequence
<220> FEATURE:
<223> OTHER INFORMATION: APOA2 1414

<400> SEQUENCE: 129
gaactgggcc ttgawtttca gtctctaga                              29

<210> SEQ ID NO 130
<211> LENGTH: 29
<212> TYPE: DNA
<213> ORGANISM: Artificial Sequence
<220> FEATURE:
<223> OTHER INFORMATION: APOA2 1459

<400> SEQUENCE: 130
agcaaaggtc ttgaytctat tcctaccta                              29

<210> SEQ ID NO 131
<211> LENGTH: 29
<212> TYPE: DNA
<213> ORGANISM: Artificial Sequence
<220> FEATURE:
<223> OTHER INFORMATION: APOA2 1672

<400> SEQUENCE: 131
aggctggaac ggaaytggtt aacttcttg                              29

<210> SEQ ID NO 132
<211> LENGTH: 29
<212> TYPE: DNA
<213> ORGANISM: Artificial Sequence
<220> FEATURE:
<223> OTHER INFORMATION: APOA2 249

<400> SEQUENCE: 132
tgcttcctgt tgcaytcaag tccaaggac                              29

<210> SEQ ID NO 133
<211> LENGTH: 29
<212> TYPE: DNA
<213> ORGANISM: Artificial Sequence
<220> FEATURE:
<223> OTHER INFORMATION: APOA2 547

<400> SEQUENCE: 133
gacgctggct aggtmagata aggaggcaa                              29

<210> SEQ ID NO 134
<211> LENGTH: 29
<212> TYPE: DNA
<213> ORGANISM: Artificial Sequence
<220> FEATURE:
<223> OTHER INFORMATION: APOA4 1228

<400> SEQUENCE: 134
gaccaggtgg ccacrgtgat gtgggacta                              29

<210> SEQ ID NO 135
<211> LENGTH: 29
<212> TYPE: DNA
<213> ORGANISM: Artificial Sequence
<220> FEATURE:
<223> OTHER INFORMATION: APOA4 1338

<400> SEQUENCE: 135

-continued gggactacag tgtgyggtgg tgacgggga                              29

<210> SEQ ID NO 136
<211> LENGTH: 29
<212> TYPE: DNA
<213> ORGANISM: Artificial Sequence
<220> FEATURE:
<223> OTHER INFORMATION: APOA4 1479

<400> SEQUENCE: 136
ccacatatgt aaacyggaag tttggaccg                              29

<210> SEQ ID NO 137
<211> LENGTH: 29
<212> TYPE: DNA
<213> ORGANISM: Artificial Sequence
<220> FEATURE:
<223> OTHER INFORMATION: APOA4 1529

<400> SEQUENCE: 137
ttgctttgac gttcyagagt ttgacaaat                              29

<210> SEQ ID NO 138
<211> LENGTH: 29
<212> TYPE: DNA
<213> ORGANISM: Artificial Sequence
<220> FEATURE:
<223> OTHER INFORMATION: APOA4 1597

<400> SEQUENCE: 138
ggaggaaaat gtcaygtgag ctgatttct                              29

<210> SEQ ID NO 139
<211> LENGTH: 29
<212> TYPE: DNA
<213> ORGANISM: Artificial Sequence
<220> FEATURE:
<223> OTHER INFORMATION: APOA4 1617

<400> SEQUENCE: 139
ctgatttcta atacrtttca gaaagacag                              29

<210> SEQ ID NO 140
<211> LENGTH: 29
<212> TYPE: DNA
<213> ORGANISM: Artificial Sequence
<220> FEATURE:
<223> OTHER INFORMATION: APOA4 1879

<400> SEQUENCE: 140
gattctgaga caaastatgt gggagatcc                              29

<210> SEQ ID NO 141
<211> LENGTH: 29
<212> TYPE: DNA
<213> ORGANISM: Artificial Sequence
<220> FEATURE:
<223> OTHER INFORMATION: APOA4 1961

<400> SEQUENCE: 141
ctgcaccacc atagrgaggg tgaactcgg                              29

<210> SEQ ID NO 142
<211> LENGTH: 29
<212> TYPE: DNA
<213> ORGANISM: Artificial Sequence

```
<220> FEATURE:
<223> OTHER INFORMATION: APOA4 1998

<400> SEQUENCE: 142
agcactcacc tgtcytagca cgtgtgcat                                              29

<210> SEQ ID NO 143
<211> LENGTH: 29
<212> TYPE: DNA
<213> ORGANISM: Artificial Sequence
<220> FEATURE:
<223> OTHER INFORMATION: APOA4 2134

<400> SEQUENCE: 143
gaagtgaaca cttaygcagg tgacctgca                                              29

<210> SEQ ID NO 144
<211> LENGTH: 29
<212> TYPE: DNA
<213> ORGANISM: Artificial Sequence
<220> FEATURE:
<223> OTHER INFORMATION: APOA4 2138

<400> SEQUENCE: 144
tgaacactta cgcargtgac ctgcagaag                                              29

<210> SEQ ID NO 145
<211> LENGTH: 29
<212> TYPE: DNA
<213> ORGANISM: Artificial Sequence
<220> FEATURE:
<223> OTHER INFORMATION: APOA4 2140

<400> SEQUENCE: 145
aacacttacg caggygacct gcagaagaa                                              29

<210> SEQ ID NO 146
<211> LENGTH: 29
<212> TYPE: DNA
<213> ORGANISM: Artificial Sequence
<220> FEATURE:
<223> OTHER INFORMATION: APOA4 2358

<400> SEQUENCE: 146
gcgcacccag gtcarcacgc aggccgagc                                              29

<210> SEQ ID NO 147
<211> LENGTH: 29
<212> TYPE: DNA
<213> ORGANISM: Artificial Sequence
<220> FEATURE:
<223> OTHER INFORMATION: APOA4 2698

<400> SEQUENCE: 147
atctcggcca gtgcygagga gctgcggca                                              29

<210> SEQ ID NO 148
<211> LENGTH: 29
<212> TYPE: DNA
<213> ORGANISM: Artificial Sequence
<220> FEATURE:
<223> OTHER INFORMATION: APOA4 2764

<400> SEQUENCE: 148 ctgagggca acacygaggg gctgcagaa                                               29
```

<210> SEQ ID NO 149
<211> LENGTH: 29
<212> TYPE: DNA
<213> ORGANISM: Artificial Sequence
<220> FEATURE:
<223> OTHER INFORMATION: APOA4 2806

<400> SEQUENCE: 149
ctgggtgggc acctrgacca gcaggtgga                              29

<210> SEQ ID NO 150
<211> LENGTH: 29
<212> TYPE: DNA
<213> ORGANISM: Artificial Sequence
<220> FEATURE:
<223> OTHER INFORMATION: APOA4 2837

<400> SEQUENCE: 150
agttccgacg ccggstggag ccctacggg                              29

<210> SEQ ID NO 151
<211> LENGTH: 29
<212> TYPE: DNA
<213> ORGANISM: Artificial Sequence
<220> FEATURE:
<223> OTHER INFORMATION: APOA4 2926

<400> SEQUENCE: 151
catgcggggg acgtkgaagg ccacttgag                              29

<210> SEQ ID NO 152
<211> LENGTH: 29
<212> TYPE: DNA
<213> ORGANISM: Artificial Sequence
<220> FEATURE:
<223> OTHER INFORMATION: APOA4 3058

<400> SEQUENCE: 152
cagcaggaac agcakcagga gcagcagca                              29

<210> SEQ ID NO 153
<211> LENGTH: 29
<212> TYPE: DNA
<213> ORGANISM: Artificial Sequence
<220> FEATURE:
<223> OTHER INFORMATION: APOA4 350

<400> SEQUENCE: 153
gccagcaggg cctcraggca tcagtcccg                              29

<210> SEQ ID NO 154
<211> LENGTH: 29
<212> TYPE: DNA
<213> ORGANISM: Artificial Sequence
<220> FEATURE:
<223> OTHER INFORMATION: APOA4 637

<400> SEQUENCE: 154
tggcgatagg gagasagttt aaatgtctg                              29

<210> SEQ ID NO 155
<211> LENGTH: 29
<212> TYPE: DNA
<213> ORGANISM: Artificial Sequence
<220> FEATURE:
<223> OTHER INFORMATION: APOA4 687

<400> SEQUENCE: 155
gttcccactg cagcrcaggt gagctctcc                                29

<210> SEQ ID NO 156
<211> LENGTH: 29
<212> TYPE: DNA
<213> ORGANISM: Artificial Sequence
<220> FEATURE:
<223> OTHER INFORMATION: APOC1EX1 1020

<400> SEQUENCE: 156
ttgtattttc agtakagaca gggtttcac                                29

<210> SEQ ID NO 157
<211> LENGTH: 29
<212> TYPE: DNA
<213> ORGANISM: Artificial Sequence
<220> FEATURE:
<223> OTHER INFORMATION: APOC1EX1 1044

<400> SEQUENCE: 157
ttcaccgtgg tctcratctc ctgactttg                                29

<210> SEQ ID NO 158
<211> LENGTH: 29
<212> TYPE: DNA
<213> ORGANISM: Artificial Sequence
<220> FEATURE:
<223> OTHER INFORMATION: APOC1EX1 1057

<400> SEQUENCE: 158
cgatctcctg acttygtgat ccgcctgcc                                29

<210> SEQ ID NO 159
<211> LENGTH: 29
<212> TYPE: DNA
<213> ORGANISM: Artificial Sequence
<220> FEATURE:
<223> OTHER INFORMATION: APOC1EX1 1111

<400> SEQUENCE: 159
caggcgtgag ccacygcgtc cggccattc                                29

<210> SEQ ID NO 160
<211> LENGTH: 29
<212> TYPE: DNA
<213> ORGANISM: Artificial Sequence
<220> FEATURE:
<223> OTHER INFORMATION: APOC1EX1 1376

<400> SEQUENCE: 160
gcacgcgcct gtagkcccag ctactcggg                                29

<210> SEQ ID NO 161
<211> LENGTH: 29
<212> TYPE: DNA
<213> ORGANISM: Artificial Sequence
<220> FEATURE:
<223> OTHER INFORMATION: APOC1EX1 1411

<400> SEQUENCE: 161
aggcaggaga atcasttgaa cccgggagg                                29

<210> SEQ ID NO 162

```
<211> LENGTH: 29
<212> TYPE: DNA
<213> ORGANISM: Artificial Sequence
<220> FEATURE:
<223> OTHER INFORMATION: APOC1EX1 432

<400> SEQUENCE: 162
aggctcttcc tgtcrctccc ggtcctggt                                        29

<210> SEQ ID NO 163
<211> LENGTH: 29
<212> TYPE: DNA
<213> ORGANISM: Artificial Sequence
<220> FEATURE:
<223> OTHER INFORMATION: APOC1EX1 462

<400> SEQUENCE: 163
gtggttctgt cgatsgtctt ggaaggtaa                                        29

<210> SEQ ID NO 164
<211> LENGTH: 29
<212> TYPE: DNA
<213> ORGANISM: Artificial Sequence
<220> FEATURE:
<223> OTHER INFORMATION: APOC1EX1 496

<400> SEQUENCE: 164
ggatgggaga attgsggagt ttggagatt                                        29

<210> SEQ ID NO 165
<211> LENGTH: 29
<212> TYPE: DNA
<213> ORGANISM: Artificial Sequence
<220> FEATURE:
<223> OTHER INFORMATION: APOC1EX1 713

<400> SEQUENCE: 165
acctctggga ttggytgtcc tgcttcgac                                        29

<210> SEQ ID NO 166
<211> LENGTH: 29
<212> TYPE: DNA
<213> ORGANISM: Artificial Sequence
<220> FEATURE:
<223> OTHER INFORMATION: APOC2 1084

<400> SEQUENCE: 166
tctgaggact caagkgccaa gatggaggg                                        29

<210> SEQ ID NO 167
<211> LENGTH: 29
<212> TYPE: DNA
<213> ORGANISM: Artificial Sequence
<220> FEATURE:
<223> OTHER INFORMATION: APOC2 126

<400> SEQUENCE: 167
caggtctctg gacaytatgg gcacacgac                                        29

<210> SEQ ID NO 168
<211> LENGTH: 29
<212> TYPE: DNA
<213> ORGANISM: Artificial Sequence
<220> FEATURE:
<223> OTHER INFORMATION: APOC2 13

<400> SEQUENCE: 168
```

```
ctgggacacc gagcwcacac agagcagga                                29

<210> SEQ ID NO 169
<211> LENGTH: 29
<212> TYPE: DNA
<213> ORGANISM: Artificial Sequence
<220> FEATURE:
<223> OTHER INFORMATION: APOC2 472

<400> SEQUENCE: 169
cccagaacct gtacragaag acatacctg                                29

<210> SEQ ID NO 170
<211> LENGTH: 29
<212> TYPE: DNA
<213> ORGANISM: Artificial Sequence
<220> FEATURE:
<223> OTHER INFORMATION: APOC2 553

<400> SEQUENCE: 170
tggcccatac caccractgc atccaggac                                29

<210> SEQ ID NO 171
<211> LENGTH: 29
<212> TYPE: DNA
<213> ORGANISM: Artificial Sequence
<220> FEATURE:
<223> OTHER INFORMATION: APOC2 725

<400> SEQUENCE: 171
cccaggagtc caggycccca gaccctcct                                29

<210> SEQ ID NO 172
<211> LENGTH: 29
<212> TYPE: DNA
<213> ORGANISM: Artificial Sequence
<220> FEATURE:
<223> OTHER INFORMATION: APOC2 804

<400> SEQUENCE: 172
tgtgctttct ccccwgggac ttgtacagc                                29

<210> SEQ ID NO 173
<211> LENGTH: 29
<212> TYPE: DNA
<213> ORGANISM: Artificial Sequence
<220> FEATURE:
<223> OTHER INFORMATION: APOC2 819

<400> SEQUENCE: 173
gggacttgta cagcmaaagc acagcagcc                                29

<210> SEQ ID NO 174
<211> LENGTH: 29
<212> TYPE: DNA
<213> ORGANISM: Artificial Sequence
<220> FEATURE:
<223> OTHER INFORMATION: APOC3 1148

<400> SEQUENCE: 174
ctggggacta agaawgttta tgaacacct                                29

<210> SEQ ID NO 175
<211> LENGTH: 29
<212> TYPE: DNA
```

<213> ORGANISM: Artificial Sequence
<220> FEATURE:
<223> OTHER INFORMATION: APOC3 1322

<400> SEQUENCE: 175
cacgggcttg aattrggtca ggtggggcc                               29

<210> SEQ ID NO 176
<211> LENGTH: 29
<212> TYPE: DNA
<213> ORGANISM: Artificial Sequence
<220> FEATURE:
<223> OTHER INFORMATION: APOC3 1468

<400> SEQUENCE: 176
atacgcctga gctcmgcctc ctgtcagat                               29

<210> SEQ ID NO 177
<211> LENGTH: 29
<212> TYPE: DNA
<213> ORGANISM: Artificial Sequence
<220> FEATURE:
<223> OTHER INFORMATION: APOC3 1519

<400> SEQUENCE: 177
ggagtgtgaa ccctrttgtg aactgcaca                               29

<210> SEQ ID NO 178
<211> LENGTH: 29
<212> TYPE: DNA
<213> ORGANISM: Artificial Sequence
<220> FEATURE:
<223> OTHER INFORMATION: APOC3 1637

<400> SEQUENCE: 178
ggcccatgga aaaawtgtcc accacaaaa                               29

<210> SEQ ID NO 179
<211> LENGTH: 29
<212> TYPE: DNA
<213> ORGANISM: Artificial Sequence
<220> FEATURE:
<223> OTHER INFORMATION: APOC3 1722

<400> SEQUENCE: 179
aggaaaatgg ggccrggcgc agtggctcg                               29

<210> SEQ ID NO 180
<211> LENGTH: 29
<212> TYPE: DNA
<213> ORGANISM: Artificial Sequence
<220> FEATURE:
<223> OTHER INFORMATION: APOC3 1728

<400> SEQUENCE: 180
atggggccag gcgcrgtggc tcatgcctg                               29

<210> SEQ ID NO 181
<211> LENGTH: 29
<212> TYPE: DNA
<213> ORGANISM: Artificial Sequence
<220> FEATURE:
<223> OTHER INFORMATION: APOC3 1736

<400> SEQUENCE: 181
aggcgcagtg gctcrtgcct gtaatccca                               29

<210> SEQ ID NO 182
<211> LENGTH: 29
<212> TYPE: DNA
<213> ORGANISM: Artificial Sequence
<220> FEATURE:
<223> OTHER INFORMATION: APOC3 1774

<400> SEQUENCE: 182
gaggccgagg caggmggatc ccctgaggt                                           29

<210> SEQ ID NO 183
<211> LENGTH: 29
<212> TYPE: DNA
<213> ORGANISM: Artificial Sequence
<220> FEATURE:
<223> OTHER INFORMATION: APOC3 1817

<400> SEQUENCE: 183
caacctggcc aacayggtga aaccccatc                                           29

<210> SEQ ID NO 184
<211> LENGTH: 29
<212> TYPE: DNA
<213> ORGANISM: Artificial Sequence
<220> FEATURE:
<223> OTHER INFORMATION: APOC3 1931

<400> SEQUENCE: 184
ttgaacccgg gagayggagg ttgcagtga                                           29

<210> SEQ ID NO 185
<211> LENGTH: 29
<212> TYPE: DNA
<213> ORGANISM: Artificial Sequence
<220> FEATURE:
<223> OTHER INFORMATION: APOC3 1975

<400> SEQUENCE: 185
ctgcactcca gcctrggtga cagagggag                                           29

<210> SEQ ID NO 186
<211> LENGTH: 29
<212> TYPE: DNA
<213> ORGANISM: Artificial Sequence
<220> FEATURE:
<223> OTHER INFORMATION: APOC3 2221

<400> SEQUENCE: 186
agggctaaaa cggcrcggcc ctaggactg                                           29

<210> SEQ ID NO 187
<211> LENGTH: 29
<212> TYPE: DNA
<213> ORGANISM: Artificial Sequence
<220> FEATURE:
<223> OTHER INFORMATION: APOC3 2535

<400> SEQUENCE: 187
gcgtgcttca tgtarccctg catgaagct                                           29

<210> SEQ ID NO 188
<211> LENGTH: 29
<212> TYPE: DNA
<213> ORGANISM: Artificial Sequence
<220> FEATURE:

```
<223> OTHER INFORMATION: APOC3 2854

<400> SEQUENCE: 188
ccctggggag gtggygtggc ccctaaggt                              29

<210> SEQ ID NO 189
<211> LENGTH: 29
<212> TYPE: DNA
<213> ORGANISM: Artificial Sequence
<220> FEATURE:
<223> OTHER INFORMATION: APOC3 429

<400> SEQUENCE: 189
gcaacctaca ggggmagccc tggagattg                              29

<210> SEQ ID NO 190
<211> LENGTH: 29
<212> TYPE: DNA
<213> ORGANISM: Artificial Sequence
<220> FEATURE:
<223> OTHER INFORMATION: APOC3 460

<400> SEQUENCE: 190
ggacccaagg agctsgcagg atggatagg                              29

<210> SEQ ID NO 191
<211> LENGTH: 29
<212> TYPE: DNA
<213> ORGANISM: Artificial Sequence
<220> FEATURE:
<223> OTHER INFORMATION: APOC3 636

<400> SEQUENCE: 191
taaatcagtc agggraagca acagagcag                              29

<210> SEQ ID NO 192
<211> LENGTH: 29
<212> TYPE: DNA
<213> ORGANISM: Artificial Sequence
<220> FEATURE:
<223> OTHER INFORMATION: APOC3 954

<400> SEQUENCE: 192
gtgcaaacag caccrcctgg agttgcaca                              29

<210> SEQ ID NO 193
<211> LENGTH: 29
<212> TYPE: DNA
<213> ORGANISM: Artificial Sequence
<220> FEATURE:
<223> OTHER INFORMATION: APOC4 1150

<400> SEQUENCE: 193
aagtgctagg attayaggcg tgagccact                              29

<210> SEQ ID NO 194
<211> LENGTH: 29
<212> TYPE: DNA
<213> ORGANISM: Artificial Sequence
<220> FEATURE:
<223> OTHER INFORMATION: APOC4 1246

<400> SEQUENCE: 194
aggctggtct tgaamtcctg acctcaggt                              29
```

<210> SEQ ID NO 195
<211> LENGTH: 29
<212> TYPE: DNA
<213> ORGANISM: Artificial Sequence
<220> FEATURE:
<223> OTHER INFORMATION: APOC4 1281

<400> SEQUENCE: 195
cccgccttgg cctcycaaag tgctgggat                              29

<210> SEQ ID NO 196
<211> LENGTH: 29
<212> TYPE: DNA
<213> ORGANISM: Artificial Sequence
<220> FEATURE:
<223> OTHER INFORMATION: APOC4 1287

<400> SEQUENCE: 196
ttggcctccc aaagygctgg gattacagg                              29

<210> SEQ ID NO 197
<211> LENGTH: 29
<212> TYPE: DNA
<213> ORGANISM: Artificial Sequence
<220> FEATURE:
<223> OTHER INFORMATION: APOC4 1313

<400> SEQUENCE: 197
aggcatgagc caccrcgccc ggccatgta                              29

<210> SEQ ID NO 198
<211> LENGTH: 29
<212> TYPE: DNA
<213> ORGANISM: Artificial Sequence
<220> FEATURE:
<223> OTHER INFORMATION: APOC4 1406

<400> SEQUENCE: 198
acagggccag gcacrgtggc tcatgcctg                              29

<210> SEQ ID NO 199
<211> LENGTH: 29
<212> TYPE: DNA
<213> ORGANISM: Artificial Sequence
<220> FEATURE:
<223> OTHER INFORMATION: APOC4 1446

<400> SEQUENCE: 199
ctttcggagg ccgargcggg tggatcgca                              29

<210> SEQ ID NO 200
<211> LENGTH: 29
<212> TYPE: DNA
<213> ORGANISM: Artificial Sequence
<220> FEATURE:
<223> OTHER INFORMATION: APOC4 1587

<400> SEQUENCE: 200
cgggaggctg aggcmggaga atcacttga                              29

<210> SEQ ID NO 201
<211> LENGTH: 29
<212> TYPE: DNA
<213> ORGANISM: Artificial Sequence
<220> FEATURE:
<223> OTHER INFORMATION: APOC4 1782

```
<400> SEQUENCE: 201
ataaccctga ggtasatatt attacccccg                                          29

<210> SEQ ID NO 202
<211> LENGTH: 29
<212> TYPE: DNA
<213> ORGANISM: Artificial Sequence
<220> FEATURE:
<223> OTHER INFORMATION: APOC4 1794

<400> SEQUENCE: 202
tagatattat taccycgttc tacaaaagg                                           29

<210> SEQ ID NO 203
<211> LENGTH: 29
<212> TYPE: DNA
<213> ORGANISM: Artificial Sequence
<220> FEATURE:
<223> OTHER INFORMATION: APOC4 1842

<400> SEQUENCE: 203
caggataagt caccrgccaa ggcacacag                                           29

<210> SEQ ID NO 204
<211> LENGTH: 29
<212> TYPE: DNA
<213> ORGANISM: Artificial Sequence
<220> FEATURE:
<223> OTHER INFORMATION: APOC4 1858

<400> SEQUENCE: 204
ccaaggcaca cagcyagcta catgtggcc                                           29

<210> SEQ ID NO 205
<211> LENGTH: 29
<212> TYPE: DNA
<213> ORGANISM: Artificial Sequence
<220> FEATURE:
<223> OTHER INFORMATION: APOC4 1875

<400> SEQUENCE: 205
ctacatgtgg ccccygcgtg acggctggt                                           29

<210> SEQ ID NO 206
<211> LENGTH: 29
<212> TYPE: DNA
<213> ORGANISM: Artificial Sequence
<220> FEATURE:
<223> OTHER INFORMATION: APOC4 2206

<400> SEQUENCE: 206
tgaagagatg gcccrgccgg acggggtgg                                           29

<210> SEQ ID NO 207
<211> LENGTH: 29
<212> TYPE: DNA
<213> ORGANISM: Artificial Sequence
<220> FEATURE:
<223> OTHER INFORMATION: APOC4 2237

<400> SEQUENCE: 207
cacatctgta atccyagcat tttgggagc                                           29

<210> SEQ ID NO 208
<211> LENGTH: 29
```

```
<212> TYPE: DNA
<213> ORGANISM: Artificial Sequence
<220> FEATURE:
<223> OTHER INFORMATION: APOC4 2276

<400> SEQUENCE: 208
tggatcactt gaggycagga gttcgaggc                                29

<210> SEQ ID NO 209
<211> LENGTH: 29
<212> TYPE: DNA
<213> ORGANISM: Artificial Sequence
<220> FEATURE:
<223> OTHER INFORMATION: APOC4 2345

<400> SEQUENCE: 209
attagccggg catgrtggca gatgcctgt                                29

<210> SEQ ID NO 210
<211> LENGTH: 29
<212> TYPE: DNA
<213> ORGANISM: Artificial Sequence
<220> FEATURE:
<223> OTHER INFORMATION: APOC4 2366

<400> SEQUENCE: 210
atgcctgtaa tcccwgctac tcgggaggc                                29

<210> SEQ ID NO 211
<211> LENGTH: 29
<212> TYPE: DNA
<213> ORGANISM: Artificial Sequence
<220> FEATURE:
<223> OTHER INFORMATION: APOC4 2767

<400> SEQUENCE: 211
aagatgagtc gctgragcct ggtgagggg                                29

<210> SEQ ID NO 212
<211> LENGTH: 29
<212> TYPE: DNA
<213> ORGANISM: Artificial Sequence
<220> FEATURE:
<223> OTHER INFORMATION: APOC4 3027

<400> SEQUENCE: 212
tcacagagag gagcrgataa atggggcag                                29

<210> SEQ ID NO 213
<211> LENGTH: 29
<212> TYPE: DNA
<213> ORGANISM: Artificial Sequence
<220> FEATURE:
<223> OTHER INFORMATION: APOC4 3078

<400> SEQUENCE: 213
gcctccactg tgatstcctc tctcctgta                                29

<210> SEQ ID NO 214
<211> LENGTH: 29
<212> TYPE: DNA
<213> ORGANISM: Artificial Sequence
<220> FEATURE:
<223> OTHER INFORMATION: APOC4 3162

<400> SEQUENCE: 214
```

-continued

```
ggacctgggt ccgckcacca aggcctggt                                            29

<210> SEQ ID NO 215
<211> LENGTH: 29
<212> TYPE: DNA
<213> ORGANISM: Artificial Sequence
<220> FEATURE:
<223> OTHER INFORMATION: APOC4 3252

<400> SEQUENCE: 215
tggggacaag gaccwgggtt aaaatgttc                                            29

<210> SEQ ID NO 216
<211> LENGTH: 29
<212> TYPE: DNA
<213> ORGANISM: Artificial Sequence
<220> FEATURE:
<223> OTHER INFORMATION: APOC4 483

<400> SEQUENCE: 216
ctgagagtga agtgkgaatg tcacattgg                                            29

<210> SEQ ID NO 217
<211> LENGTH: 29
<212> TYPE: DNA
<213> ORGANISM: Artificial Sequence
<220> FEATURE:
<223> OTHER INFORMATION: APOC4 931

<400> SEQUENCE: 217
ccaggctgga gtgcrgtggc gtgatcttg                                            29

<210> SEQ ID NO 218
<211> LENGTH: 29
<212> TYPE: DNA
<213> ORGANISM: Artificial Sequence
<220> FEATURE:
<223> OTHER INFORMATION: APOC4 968

<400> SEQUENCE: 218
caagctccgc ctccygggtt cacgccatt                                            29

<210> SEQ ID NO 219
<211> LENGTH: 29
<212> TYPE: DNA
<213> ORGANISM: Artificial Sequence
<220> FEATURE:
<223> OTHER INFORMATION: APOER2EX1 454

<400> SEQUENCE: 219
cgcggcaagg actcsgaggg ctgagacgc                                            29

<210> SEQ ID NO 220
<211> LENGTH: 29
<212> TYPE: DNA
<213> ORGANISM: Artificial Sequence
<220> FEATURE:
<223> OTHER INFORMATION: APOER2EX12 68

<400> SEQUENCE: 220
accaactgtc cagcmttgac ttcagtgga                                            29

<210> SEQ ID NO 221
<211> LENGTH: 29
<212> TYPE: DNA
<213> ORGANISM: Artificial Sequence
```

```
<220> FEATURE:
<223> OTHER INFORMATION: APOER2EX13 55

<400> SEQUENCE: 221
cgaggccatt ttcastgcaa atcggctca                                      29

<210> SEQ ID NO 222
<211> LENGTH: 29
<212> TYPE: DNA
<213> ORGANISM: Artificial Sequence
<220> FEATURE:
<223> OTHER INFORMATION: APOER2EX14 162

<400> SEQUENCE: 222
gaagaggtgc taccraggta agcagacct                                      29

<210> SEQ ID NO 223
<211> LENGTH: 29
<212> TYPE: DNA
<213> ORGANISM: Artificial Sequence
<220> FEATURE:
<223> OTHER INFORMATION: APOER2EX17 55

<400> SEQUENCE: 223
tacctgatct ggagraactg gaagcggaa                                      29

<210> SEQ ID NO 224
<211> LENGTH: 29
<212> TYPE: DNA
<213> ORGANISM: Artificial Sequence
<220> FEATURE:
<223> OTHER INFORMATION: APOER2EX19 1005

<400> SEQUENCE: 224
agagtgctca gaaastcaag ataggatat                                      29

<210> SEQ ID NO 225
<211> LENGTH: 29
<212> TYPE: DNA
<213> ORGANISM: Artificial Sequence
<220> FEATURE:
<223> OTHER INFORMATION: APOER2EX19 1060

<400> SEQUENCE: 225
taaagttcag ctctytgagt aacttcttc                                      29

<210> SEQ ID NO 226
<211> LENGTH: 29
<212> TYPE: DNA
<213> ORGANISM: Artificial Sequence
<220> FEATURE:
<223> OTHER INFORMATION: APOER2EX19 1149

<400> SEQUENCE: 226
tgccatcctt acagwgctaa gtggagacg                                      29

<210> SEQ ID NO 227
<211> LENGTH: 29
<212> TYPE: DNA
<213> ORGANISM: Artificial Sequence
<220> FEATURE:
<223> OTHER INFORMATION: APOER2EX19 13

<400> SEQUENCE: 227
gttgtctccc cagcragtgg cattaagcc                                      29
```

<210> SEQ ID NO 228
<211> LENGTH: 29
<212> TYPE: DNA
<213> ORGANISM: Artificial Sequence
<220> FEATURE:
<223> OTHER INFORMATION: APOER2EX19 602

<400> SEQUENCE: 228
tttagagaag tgagrgtatt tatttttgg                                29

<210> SEQ ID NO 229
<211> LENGTH: 29
<212> TYPE: DNA
<213> ORGANISM: Artificial Sequence
<220> FEATURE:
<223> OTHER INFORMATION: APOER2EX19 931

<400> SEQUENCE: 229
ccatggctgc tgtgmctcct accagggct                                29

<210> SEQ ID NO 230
<211> LENGTH: 29
<212> TYPE: DNA
<213> ORGANISM: Artificial Sequence
<220> FEATURE:
<223> OTHER INFORMATION: APOER2EX9 116

<400> SEQUENCE: 230
tgctcaagaa tgtcrtggca ctagatgtg                                29

<210> SEQ ID NO 231
<211> LENGTH: 29
<212> TYPE: DNA
<213> ORGANISM: Artificial Sequence
<220> FEATURE:
<223> OTHER INFORMATION: APOER2EX9 157

<400> SEQUENCE: 231
aatcgcatct actgstgtga cctctccta                                29

<210> SEQ ID NO 232
<211> LENGTH: 29
<212> TYPE: DNA
<213> ORGANISM: Artificial Sequence
<220> FEATURE:
<223> OTHER INFORMATION: AT1EX5 1158

<400> SEQUENCE: 232
tgaggttgag tgacrtgttc gaaacctgt                                29

<210> SEQ ID NO 233
<211> LENGTH: 29
<212> TYPE: DNA
<213> ORGANISM: Artificial Sequence
<220> FEATURE:
<223> OTHER INFORMATION: AT1EX5 1226

<400> SEQUENCE: 233
tcctctgcag cactkcacta ccaaatgag                                29

<210> SEQ ID NO 234
<211> LENGTH: 29
<212> TYPE: DNA
<213> ORGANISM: Artificial Sequence
<220> FEATURE:
<223> OTHER INFORMATION: AT1EX5 1242

<400> SEQUENCE: 234
actaccaaat gagcmttagc tacttttca                                29

<210> SEQ ID NO 235
<211> LENGTH: 29
<212> TYPE: DNA
<213> ORGANISM: Artificial Sequence
<220> FEATURE:
<223> OTHER INFORMATION: AT1EX5 1249

<400> SEQUENCE: 235
aatgagcatt agctrctttt cagaattga                                29

<210> SEQ ID NO 236
<211> LENGTH: 29
<212> TYPE: DNA
<213> ORGANISM: Artificial Sequence
<220> FEATURE:
<223> OTHER INFORMATION: AT1EX5 1473

<400> SEQUENCE: 236
cctgcttttg tcctrttatt ttttatttc                                29

<210> SEQ ID NO 237
<211> LENGTH: 29
<212> TYPE: DNA
<213> ORGANISM: Artificial Sequence
<220> FEATURE:
<223> OTHER INFORMATION: AT2EX3 1355

<400> SEQUENCE: 237
gtttgtacaa gattktcatt ggtgagaca                                29

<210> SEQ ID NO 238
<211> LENGTH: 29
<212> TYPE: DNA
<213> ORGANISM: Artificial Sequence
<220> FEATURE:
<223> OTHER INFORMATION: AT2EX3 1361

<400> SEQUENCE: 238
acaagatttt cattrgtgag acatattta                                29

<210> SEQ ID NO 239
<211> LENGTH: 29
<212> TYPE: DNA
<213> ORGANISM: Artificial Sequence
<220> FEATURE:
<223> OTHER INFORMATION: AT2EX3 562

<400> SEQUENCE: 239
tatatagttc ccctygtttg gtgtatggc                                29

<210> SEQ ID NO 240
<211> LENGTH: 29
<212> TYPE: DNA
<213> ORGANISM: Artificial Sequence
<220> FEATURE:
<223> OTHER INFORMATION: AT2EX3 807

<400> SEQUENCE: 240
ctatgggaag aacargataa cccgtgacc                                29

<210> SEQ ID NO 241

-continued

```
<211> LENGTH: 29
<212> TYPE: DNA
<213> ORGANISM: Artificial Sequence
<220> FEATURE:
<223> OTHER INFORMATION: AT2EX3 844

<400> SEQUENCE: 241
aagatggcag ctgcygttgt tctggcctt                                29

<210> SEQ ID NO 242
<211> LENGTH: 29
<212> TYPE: DNA
<213> ORGANISM: Artificial Sequence
<220> FEATURE:
<223> OTHER INFORMATION: AVPEX2 154

<400> SEQUENCE: 242
ggagaactac ctgcygtcgc cctgccagt                                29

<210> SEQ ID NO 243
<211> LENGTH: 29
<212> TYPE: DNA
<213> ORGANISM: Artificial Sequence
<220> FEATURE:
<223> OTHER INFORMATION: AVPR2EX1 114

<400> SEQUENCE: 243
tcatggcgtc caccwcttcc ggtaaggct                                29

<210> SEQ ID NO 244
<211> LENGTH: 29
<212> TYPE: DNA
<213> ORGANISM: Artificial Sequence
<220> FEATURE:
<223> OTHER INFORMATION: AVPR2EX2 109

<400> SEQUENCE: 244
acccgggacc cgctrctagc ccgggcgga                                29

<210> SEQ ID NO 245
<211> LENGTH: 29
<212> TYPE: DNA
<213> ORGANISM: Artificial Sequence
<220> FEATURE:
<223> OTHER INFORMATION: AVPR2EX2 129

<400> SEQUENCE: 245
ccgggcggag ctggygctgc tctccatag                                29

<210> SEQ ID NO 246
<211> LENGTH: 29
<212> TYPE: DNA
<213> ORGANISM: Artificial Sequence
<220> FEATURE:
<223> OTHER INFORMATION: AVPR2EX2 184

<400> SEQUENCE: 246
ggcctggtgc tggckgccct agctcggcg                                29

<210> SEQ ID NO 247
<211> LENGTH: 29
<212> TYPE: DNA
<213> ORGANISM: Artificial Sequence
<220> FEATURE:
<223> OTHER INFORMATION: AVPR2EX2 444

<400> SEQUENCE: 247
```
ccgtcccatg ctggygtacc gccatggaa                                29

<210> SEQ ID NO 248
<211> LENGTH: 29
<212> TYPE: DNA
<213> ORGANISM: Artificial Sequence
<220> FEATURE:
<223> OTHER INFORMATION: AVPR2EX3 112

<400> SEQUENCE: 248
tctttcagca gcagygtgtc ctcagagct                                29

<210> SEQ ID NO 249
<211> LENGTH: 29
<212> TYPE: DNA
<213> ORGANISM: Artificial Sequence
<220> FEATURE:
<223> OTHER INFORMATION: AVPR2EX3 232

<400> SEQUENCE: 249
aaggacactt catcrtgagg agctgttgg                                29

<210> SEQ ID NO 250
<211> LENGTH: 29
<212> TYPE: DNA
<213> ORGANISM: Artificial Sequence
<220> FEATURE:
<223> OTHER INFORMATION: AVPR2EX3 252

<400> SEQUENCE: 250
agctgttggg tgtcytgcct ctagaggct                                29

<210> SEQ ID NO 251
<211> LENGTH: 29
<212> TYPE: DNA
<213> ORGANISM: Artificial Sequence
<220> FEATURE:
<223> OTHER INFORMATION: AVPR2EX3 46

<400> SEQUENCE: 251
gcgccctttg tgctrctcat gttgctggc                                29

<210> SEQ ID NO 252
<211> LENGTH: 29
<212> TYPE: DNA
<213> ORGANISM: Artificial Sequence
<220> FEATURE:
<223> OTHER INFORMATION: BIR 1069

<400> SEQUENCE: 252
caggactggc tggaygcaca gctctaggg                                29

<210> SEQ ID NO 253
<211> LENGTH: 29
<212> TYPE: DNA
<213> ORGANISM: Artificial Sequence
<220> FEATURE:
<223> OTHER INFORMATION: BIR 1142

<400> SEQUENCE: 253
ggtgagccag tcctraattg ggttgggag                                29

<210> SEQ ID NO 254
<211> LENGTH: 29
<212> TYPE: DNA

```
<213> ORGANISM: Artificial Sequence
<220> FEATURE:
<223> OTHER INFORMATION: BIR 1185

<400> SEQUENCE: 254
ataacccagt acagkttcct gctgaggcc                                      29

<210> SEQ ID NO 255
<211> LENGTH: 29
<212> TYPE: DNA
<213> ORGANISM: Artificial Sequence
<220> FEATURE:
<223> OTHER INFORMATION: BIR 1265

<400> SEQUENCE: 255
ggaggctgag ctgargctgg cccagcctc                                      29

<210> SEQ ID NO 256
<211> LENGTH: 29
<212> TYPE: DNA
<213> ORGANISM: Artificial Sequence
<220> FEATURE:
<223> OTHER INFORMATION: BIR 1295

<400> SEQUENCE: 256
caccaggccc tggcygggct acataccac                                      29

<210> SEQ ID NO 257
<211> LENGTH: 29
<212> TYPE: DNA
<213> ORGANISM: Artificial Sequence
<220> FEATURE:
<223> OTHER INFORMATION: BIR 1441

<400> SEQUENCE: 257
aggggcccgc gggcygaggc gagggtcag                                      29

<210> SEQ ID NO 258
<211> LENGTH: 29
<212> TYPE: DNA
<213> ORGANISM: Artificial Sequence
<220> FEATURE:
<223> OTHER INFORMATION: BIR 1521

<400> SEQUENCE: 258
tgtgggcact ttgayggtgt tgccaaact                                      29

<210> SEQ ID NO 259
<211> LENGTH: 29
<212> TYPE: DNA
<213> ORGANISM: Artificial Sequence
<220> FEATURE:
<223> OTHER INFORMATION: BIR 1729

<400> SEQUENCE: 259
ggtgccaggt cgtasagtgg gctgttggc                                      29

<210> SEQ ID NO 260
<211> LENGTH: 29
<212> TYPE: DNA
<213> ORGANISM: Artificial Sequence
<220> FEATURE:
<223> OTHER INFORMATION: BIR 1946

<400> SEQUENCE: 260
gcatgaagca gaggyggccg tggcgcagg                                      29
```

```
<210> SEQ ID NO 261
<211> LENGTH: 29
<212> TYPE: DNA
<213> ORGANISM: Artificial Sequence
<220> FEATURE:
<223> OTHER INFORMATION: BIR 1960

<400> SEQUENCE: 261
cggccgtggc gcagrgcgat caccgcatg                              29

<210> SEQ ID NO 262
<211> LENGTH: 29
<212> TYPE: DNA
<213> ORGANISM: Artificial Sequence
<220> FEATURE:
<223> OTHER INFORMATION: BIR 2463

<400> SEQUENCE: 262
acggtacctg ggctyggcag ggtcctctg                              29

<210> SEQ ID NO 263
<211> LENGTH: 29
<212> TYPE: DNA
<213> ORGANISM: Artificial Sequence
<220> FEATURE:
<223> OTHER INFORMATION: BIR 2664

<400> SEQUENCE: 263
tgtgctggcc tcacytctga gataactcc                              29

<210> SEQ ID NO 264
<211> LENGTH: 29
<212> TYPE: DNA
<213> ORGANISM: Artificial Sequence
<220> FEATURE:
<223> OTHER INFORMATION: BIR 2894

<400> SEQUENCE: 264
tggtggtgcg cacckgtaat cccacctac                              29

<210> SEQ ID NO 265
<211> LENGTH: 29
<212> TYPE: DNA
<213> ORGANISM: Artificial Sequence
<220> FEATURE:
<223> OTHER INFORMATION: BIR 2954

<400> SEQUENCE: 265
cccgagaggc ggagsttgca gtgagccaa                              29

<210> SEQ ID NO 266
<211> LENGTH: 29
<212> TYPE: DNA
<213> ORGANISM: Artificial Sequence
<220> FEATURE:
<223> OTHER INFORMATION: BIR 3174

<400> SEQUENCE: 266
tcccgctaag agccyttctc cccgcccag                              29

<210> SEQ ID NO 267
<211> LENGTH: 29
<212> TYPE: DNA
<213> ORGANISM: Artificial Sequence
<220> FEATURE:
```

```
<223> OTHER INFORMATION: BIR 369

<400> SEQUENCE: 267
caacactgct ccaarggtcc aggcacggg                                    29

<210> SEQ ID NO 268
<211> LENGTH: 29
<212> TYPE: DNA
<213> ORGANISM: Artificial Sequence
<220> FEATURE:
<223> OTHER INFORMATION: BIR 510

<400> SEQUENCE: 268
ccttctggac aaagygagtg gcagccact                                    29

<210> SEQ ID NO 269
<211> LENGTH: 29
<212> TYPE: DNA
<213> ORGANISM: Artificial Sequence
<220> FEATURE:
<223> OTHER INFORMATION: BIR 657

<400> SEQUENCE: 269
cacagagccc tcacwgcacg aggccgatg                                    29

<210> SEQ ID NO 270
<211> LENGTH: 29
<212> TYPE: DNA
<213> ORGANISM: Artificial Sequence
<220> FEATURE:
<223> OTHER INFORMATION: BIR 981

<400> SEQUENCE: 270
ttggagccac agacrcaaag cagcagccc                                    29

<210> SEQ ID NO 271
<211> LENGTH: 29
<212> TYPE: DNA
<213> ORGANISM: Artificial Sequence
<220> FEATURE:
<223> OTHER INFORMATION: BKRB2EX1 55

<400> SEQUENCE: 271
ggtggggacg gtggkgacgg tggggacat                                    29

<210> SEQ ID NO 272
<211> LENGTH: 29
<212> TYPE: DNA
<213> ORGANISM: Artificial Sequence
<220> FEATURE:
<223> OTHER INFORMATION: BKRB2EX3 1513

<400> SEQUENCE: 272
atctccagga gaacygccat ccagctttg                                    29

<210> SEQ ID NO 273
<211> LENGTH: 29
<212> TYPE: DNA
<213> ORGANISM: Artificial Sequence
<220> FEATURE:
<223> OTHER INFORMATION: BKRB2EX3 1833

<400> SEQUENCE: 273
actcaagtgg gaacractgg gcactgcca                                    29
```

```
<210> SEQ ID NO 274
<211> LENGTH: 29
<212> TYPE: DNA
<213> ORGANISM: Artificial Sequence
<220> FEATURE:
<223> OTHER INFORMATION: BKRB2EX3 747

<400> SEQUENCE: 274
aaggagatcc agacrgagag gagggccac                                         29

<210> SEQ ID NO 275
<211> LENGTH: 29
<212> TYPE: DNA
<213> ORGANISM: Artificial Sequence
<220> FEATURE:
<223> OTHER INFORMATION: BNPEX1 343

<400> SEQUENCE: 275
tttcctggga ggtckttccc acccgctgg                                         29

<210> SEQ ID NO 276
<211> LENGTH: 29
<212> TYPE: DNA
<213> ORGANISM: Artificial Sequence
<220> FEATURE:
<223> OTHER INFORMATION: BNPEX2 15

<400> SEQUENCE: 276
tgaggcttgg acgcscccat tcattgcag                                         29

<210> SEQ ID NO 277
<211> LENGTH: 29
<212> TYPE: DNA
<213> ORGANISM: Artificial Sequence
<220> FEATURE:
<223> OTHER INFORMATION: BNPEX2 174

<400> SEQUENCE: 277
gtgggcaccg caaawtggtc ctctacacc                                         29

<210> SEQ ID NO 278
<211> LENGTH: 29
<212> TYPE: DNA
<213> ORGANISM: Artificial Sequence
<220> FEATURE:
<223> OTHER INFORMATION: BNPEX2 37

<400> SEQUENCE: 278
attgcaggag cagcrcaacc atttgcagg                                         29

<210> SEQ ID NO 279
<211> LENGTH: 29
<212> TYPE: DNA
<213> ORGANISM: Artificial Sequence
<220> FEATURE:
<223> OTHER INFORMATION: BRS3EX1 424

<400> SEQUENCE: 279
agaactgaag caaargagta tctggatgt                                         29

<210> SEQ ID NO 280
<211> LENGTH: 29
<212> TYPE: DNA
<213> ORGANISM: Artificial Sequence
<220> FEATURE:
<223> OTHER INFORMATION: BRS3EX1 730
```

<400> SEQUENCE: 280
gtgccatcta tattmcttat gctgtgatc                               29

<210> SEQ ID NO 281
<211> LENGTH: 29
<212> TYPE: DNA
<213> ORGANISM: Artificial Sequence
<220> FEATURE:
<223> OTHER INFORMATION: BRS3EX1 879

<400> SEQUENCE: 281
ctaacttgtg tgccwgtgga tgcaactca                               29

<210> SEQ ID NO 282
<211> LENGTH: 29
<212> TYPE: DNA
<213> ORGANISM: Artificial Sequence
<220> FEATURE:
<223> OTHER INFORMATION: BRS3EX2 144

<400> SEQUENCE: 282
gctctacctg aggcwatatt ttcaaatgt                               29

<210> SEQ ID NO 283
<211> LENGTH: 29
<212> TYPE: DNA
<213> ORGANISM: Artificial Sequence
<220> FEATURE:
<223> OTHER INFORMATION: BRS3EX2 80

<400> SEQUENCE: 283
ctccaatgcc atccwgaaga cttgtgtaa                               29

<210> SEQ ID NO 284
<211> LENGTH: 29
<212> TYPE: DNA
<213> ORGANISM: Artificial Sequence
<220> FEATURE:
<223> OTHER INFORMATION: BRS3EX3 173

<400> SEQUENCE: 284
gccatgcatt tcatyttcac cattttctc                               29

<210> SEQ ID NO 285
<211> LENGTH: 29
<212> TYPE: DNA
<213> ORGANISM: Artificial Sequence
<220> FEATURE:
<223> OTHER INFORMATION: CAL/CGREPEX1+2 1063

<400> SEQUENCE: 285
ccccagtcac aggckctggg agcaaagag                               29

<210> SEQ ID NO 286
<211> LENGTH: 29
<212> TYPE: DNA
<213> ORGANISM: Artificial Sequence
<220> FEATURE:
<223> OTHER INFORMATION: CAL/CGREPEX1+2 940

<400> SEQUENCE: 286
gtgcgatcag ggacrgcgtc tggagccca                               29

<210> SEQ ID NO 287
<211> LENGTH: 29

```
<212> TYPE: DNA
<213> ORGANISM: Artificial Sequence
<220> FEATURE:
<223> OTHER INFORMATION: CAL/CGREPEX3 112

<400> SEQUENCE: 287
ctgcactggt gcagractat gtgcagatg                              29

<210> SEQ ID NO 288
<211> LENGTH: 29
<212> TYPE: DNA
<213> ORGANISM: Artificial Sequence
<220> FEATURE:
<223> OTHER INFORMATION: CAL/CGREPEX3 120

<400> SEQUENCE: 288
gtgcaggact atgtkcagat gaaggccag                              29

<210> SEQ ID NO 289
<211> LENGTH: 29
<212> TYPE: DNA
<213> ORGANISM: Artificial Sequence
<220> FEATURE:
<223> OTHER INFORMATION: CAL/CGREPEX4 30

<400> SEQUENCE: 289
tgttttccct gcagmctgga cagccccag                              29

<210> SEQ ID NO 290
<211> LENGTH: 29
<212> TYPE: DNA
<213> ORGANISM: Artificial Sequence
<220> FEATURE:
<223> OTHER INFORMATION: CAL/CGREPEX5 309

<400> SEQUENCE: 290
atgtggtttt aaaawatcca taagggaag                              29

<210> SEQ ID NO 291
<211> LENGTH: 29
<212> TYPE: DNA
<213> ORGANISM: Artificial Sequence
<220> FEATURE:
<223> OTHER INFORMATION: CAL/CGREPEX5 433

<400> SEQUENCE: 291
cagaccaaga aatayagatc ctgtttatt                              29

<210> SEQ ID NO 292
<211> LENGTH: 29
<212> TYPE: DNA
<213> ORGANISM: Artificial Sequence
<220> FEATURE:
<223> OTHER INFORMATION: CAL/CGREPEX5 719

<400> SEQUENCE: 292
aaagagcaag tgagrtaata gatgttaag                              29

<210> SEQ ID NO 293
<211> LENGTH: 29
<212> TYPE: DNA
<213> ORGANISM: Artificial Sequence
<220> FEATURE:
<223> OTHER INFORMATION: CHYEX1 158

<400> SEQUENCE: 293
```
ttgccttctg ggagwtataa aacccaaga                                              29

<210> SEQ ID NO 294
<211> LENGTH: 29
<212> TYPE: DNA
<213> ORGANISM: Artificial Sequence
<220> FEATURE:
<223> OTHER INFORMATION: CHYEX1 65

<400> SEQUENCE: 294
tctaggggaa cttcygatca gaaacagcc                                              29

<210> SEQ ID NO 295
<211> LENGTH: 29
<212> TYPE: DNA
<213> ORGANISM: Artificial Sequence
<220> FEATURE:
<223> OTHER INFORMATION: CHYEX2 107

<400> SEQUENCE: 295
ttgtaacttc caacsgtccc tcaaaattt                                              29

<210> SEQ ID NO 296
<211> LENGTH: 29
<212> TYPE: DNA
<213> ORGANISM: Artificial Sequence
<220> FEATURE:
<223> OTHER INFORMATION: CHYEX2 168

<400> SEQUENCE: 296
gctgacggct gctcrttgtg caggaaggt                                              29

<210> SEQ ID NO 297
<211> LENGTH: 29
<212> TYPE: DNA
<213> ORGANISM: Artificial Sequence
<220> FEATURE:
<223> OTHER INFORMATION: CHYEX3 26

<400> SEQUENCE: 297
ccttcttcct cacarcaggt ctataacag                                              29

<210> SEQ ID NO 298
<211> LENGTH: 29
<212> TYPE: DNA
<213> ORGANISM: Artificial Sequence
<220> FEATURE:
<223> OTHER INFORMATION: CHYEX4 83

<400> SEQUENCE: 298
ctccccttcc catcmcaatt caactttgt                                              29

<210> SEQ ID NO 299
<211> LENGTH: 29
<212> TYPE: DNA
<213> ORGANISM: Artificial Sequence
<220> FEATURE:
<223> OTHER INFORMATION: CHYEX5 274

<400> SEQUENCE: 299
tccctcagcc acaaycctaa gcctccaga                                              29

<210> SEQ ID NO 300
<211> LENGTH: 29
<212> TYPE: DNA
<213> ORGANISM: Artificial Sequence

```
<220> FEATURE:
<223> OTHER INFORMATION: CLCNKBEX10 33

<400> SEQUENCE: 300
ctctggccac cttgsttctc gcctccatc                                              29

<210> SEQ ID NO 301
<211> LENGTH: 29
<212> TYPE: DNA
<213> ORGANISM: Artificial Sequence
<220> FEATURE:
<223> OTHER INFORMATION: CLCNKBEX13 12

<400> SEQUENCE: 301
ggaggagctg ctatygggcg cctctttgg                                              29

<210> SEQ ID NO 302
<211> LENGTH: 29
<212> TYPE: DNA
<213> ORGANISM: Artificial Sequence
<220> FEATURE:
<223> OTHER INFORMATION: CLCNKBEX15 64

<400> SEQUENCE: 302
actggccaag gacaygccac tggaggagg                                              29

<210> SEQ ID NO 303
<211> LENGTH: 29
<212> TYPE: DNA
<213> ORGANISM: Artificial Sequence
<220> FEATURE:
<223> OTHER INFORMATION: CLCNKBEX15 68

<400> SEQUENCE: 303
gccaaggaca cgccrctgga ggaggtggt                                              29

<210> SEQ ID NO 304
<211> LENGTH: 29
<212> TYPE: DNA
<213> ORGANISM: Artificial Sequence
<220> FEATURE:
<223> OTHER INFORMATION: CLCNKBEX18 51

<400> SEQUENCE: 304
cctctttgtg acgtygcggg gcagagctg                                              29

<210> SEQ ID NO 305
<211> LENGTH: 29
<212> TYPE: DNA
<213> ORGANISM: Artificial Sequence
<220> FEATURE:
<223> OTHER INFORMATION: CLCNKBEX3 34

<400> SEQUENCE: 305
gggagattgg ggacmgccac ctgctccgg                                              29

<210> SEQ ID NO 306
<211> LENGTH: 29
<212> TYPE: DNA
<213> ORGANISM: Artificial Sequence
<220> FEATURE:
<223> OTHER INFORMATION: CLCNKBEX3 96

<400> SEQUENCE: 306
gtctctttct cttcrggctt ctctcagag                                              29
```

<210> SEQ ID NO 307
<211> LENGTH: 29
<212> TYPE: DNA
<213> ORGANISM: Artificial Sequence
<220> FEATURE:
<223> OTHER INFORMATION: CLCNKBEX4 19

<400> SEQUENCE: 307
ctggaatccc ggagstgaag accatgttg                               29

<210> SEQ ID NO 308
<211> LENGTH: 29
<212> TYPE: DNA
<213> ORGANISM: Artificial Sequence
<220> FEATURE:
<223> OTHER INFORMATION: CLCNKBEX4 70

<400> SEQUENCE: 308
acctggatat caagmactttg ggggccaaa                              29

<210> SEQ ID NO 309
<211> LENGTH: 29
<212> TYPE: DNA
<213> ORGANISM: Artificial Sequence
<220> FEATURE:
<223> OTHER INFORMATION: CLCNKBEX7 108

<400> SEQUENCE: 309
ttccggctcc tggcrgtctt caacagcga                               29

<210> SEQ ID NO 310
<211> LENGTH: 29
<212> TYPE: DNA
<213> ORGANISM: Artificial Sequence
<220> FEATURE:
<223> OTHER INFORMATION: CNPEX1 1018

<400> SEQUENCE: 310
gcagcgccaa ctttmtgcct gtatgactt                               29

<210> SEQ ID NO 311
<211> LENGTH: 29
<212> TYPE: DNA
<213> ORGANISM: Artificial Sequence
<220> FEATURE:
<223> OTHER INFORMATION: CNPEX1 144

<400> SEQUENCE: 311
gccttcacgc ctggkgacag ccactgcac                               29

<210> SEQ ID NO 312
<211> LENGTH: 29
<212> TYPE: DNA
<213> ORGANISM: Artificial Sequence
<220> FEATURE:
<223> OTHER INFORMATION: CNPEX1 1457

<400> SEQUENCE: 312
gcagcactgg gaccstgctc gccctgcag                               29

<210> SEQ ID NO 313
<211> LENGTH: 29
<212> TYPE: DNA
<213> ORGANISM: Artificial Sequence
<220> FEATURE:
<223> OTHER INFORMATION: CNPEX1 578

<400> SEQUENCE: 313
attgttccca cagarggagt tcaccagcg                                29

<210> SEQ ID NO 314
<211> LENGTH: 29
<212> TYPE: DNA
<213> ORGANISM: Artificial Sequence
<220> FEATURE:
<223> OTHER INFORMATION: CNPEX1 592

<400> SEQUENCE: 314
gggagttcac cagcrgagtc agacccgg                                 29

<210> SEQ ID NO 315
<211> LENGTH: 29
<212> TYPE: DNA
<213> ORGANISM: Artificial Sequence
<220> FEATURE:
<223> OTHER INFORMATION: CNPEX2 1171

<400> SEQUENCE: 315
aacatcccag cctcwgacat tgacagtca                                29

<210> SEQ ID NO 316
<211> LENGTH: 29
<212> TYPE: DNA
<213> ORGANISM: Artificial Sequence
<220> FEATURE:
<223> OTHER INFORMATION: CNPEX2 139

<400> SEQUENCE: 316
ggacaccaag tcgcrggcag cgtgggctc                                29

<210> SEQ ID NO 317
<211> LENGTH: 29
<212> TYPE: DNA
<213> ORGANISM: Artificial Sequence
<220> FEATURE:
<223> OTHER INFORMATION: CNPEX2 357

<400> SEQUENCE: 317
cccgccgccc agccrgcctt cggaggcgc                                29

<210> SEQ ID NO 318
<211> LENGTH: 29
<212> TYPE: DNA
<213> ORGANISM: Artificial Sequence
<220> FEATURE:
<223> OTHER INFORMATION: CNPEX2 41

<400> SEQUENCE: 318
gctgcgggcg gcggycagaa gaagggcga                                29

<210> SEQ ID NO 319
<211> LENGTH: 29
<212> TYPE: DNA
<213> ORGANISM: Artificial Sequence
<220> FEATURE:
<223> OTHER INFORMATION: COX1 1063

<400> SEQUENCE: 319
tttcctgcag ctgaratttg acccagagc                                29

<210> SEQ ID NO 320

<211> LENGTH: 29
<212> TYPE: DNA
<213> ORGANISM: Artificial Sequence
<220> FEATURE:
<223> OTHER INFORMATION: COX1 1314

<400> SEQUENCE: 320
acatggacca ccacrtcctg catgtggct                             29

<210> SEQ ID NO 321
<211> LENGTH: 29
<212> TYPE: DNA
<213> ORGANISM: Artificial Sequence
<220> FEATURE:
<223> OTHER INFORMATION: COX1 1386

<400> SEQUENCE: 321
tcaatgagta ccgcragagg tttggcatg                             29

<210> SEQ ID NO 322
<211> LENGTH: 29
<212> TYPE: DNA
<213> ORGANISM: Artificial Sequence
<220> FEATURE:
<223> OTHER INFORMATION: COX1 1428

<400> SEQUENCE: 322
ccttccagga gctcrtagga gagaaggag                             29

<210> SEQ ID NO 323
<211> LENGTH: 29
<212> TYPE: DNA
<213> ORGANISM: Artificial Sequence
<220> FEATURE:
<223> OTHER INFORMATION: COX1 1906

<400> SEQUENCE: 323
ggtgagtgtt ggggytgaca tttagaact                             29

<210> SEQ ID NO 324
<211> LENGTH: 29
<212> TYPE: DNA
<213> ORGANISM: Artificial Sequence
<220> FEATURE:
<223> OTHER INFORMATION: COX1 1948

<400> SEQUENCE: 324
attatctgga atatygtgat tctgtttat                             29

<210> SEQ ID NO 325
<211> LENGTH: 29
<212> TYPE: DNA
<213> ORGANISM: Artificial Sequence
<220> FEATURE:
<223> OTHER INFORMATION: COX1 2037

<400> SEQUENCE: 325
gtctgccaga atackgggtt cttagttga                             29

<210> SEQ ID NO 326
<211> LENGTH: 29
<212> TYPE: DNA
<213> ORGANISM: Artificial Sequence
<220> FEATURE:
<223> OTHER INFORMATION: COX1 310

<400> SEQUENCE: 326
tgccaccttc atccragaga tgctcatgc                                    29

<210> SEQ ID NO 327
<211> LENGTH: 29
<212> TYPE: DNA
<213> ORGANISM: Artificial Sequence
<220> FEATURE:
<223> OTHER INFORMATION: COX1 626

<400> SEQUENCE: 327
ttcaaaactt ctggmaagat gggtcctgg                                    29

<210> SEQ ID NO 328
<211> LENGTH: 29
<212> TYPE: DNA
<213> ORGANISM: Artificial Sequence
<220> FEATURE:
<223> OTHER INFORMATION: COX1 696

<400> SEQUENCE: 328
tttatggaga caatmtggag cgtcagtat                                    29

<210> SEQ ID NO 329
<211> LENGTH: 29
<212> TYPE: DNA
<213> ORGANISM: Artificial Sequence
<220> FEATURE:
<223> OTHER INFORMATION: COX1 938

<400> SEQUENCE: 329
gacctgctga aggcygagca ccccacctg                                    29

<210> SEQ ID NO 330
<211> LENGTH: 29
<212> TYPE: DNA
<213> ORGANISM: Artificial Sequence
<220> FEATURE:
<223> OTHER INFORMATION: COX2EX1 186

<400> SEQUENCE: 330
cgattttctc atttscgtgg gtaaaaaac                                    29

<210> SEQ ID NO 331
<211> LENGTH: 29
<212> TYPE: DNA
<213> ORGANISM: Artificial Sequence
<220> FEATURE:
<223> OTHER INFORMATION: COX2EX1 358

<400> SEQUENCE: 331
gcgaccaatt gtcakacgac ttgcagtga                                    29

<210> SEQ ID NO 332
<211> LENGTH: 29
<212> TYPE: DNA
<213> ORGANISM: Artificial Sequence
<220> FEATURE:
<223> OTHER INFORMATION: COX2EX10 156

<400> SEQUENCE: 332
aaccatggta gaagytggag caccattct                                    29

<210> SEQ ID NO 333
<211> LENGTH: 29
<212> TYPE: DNA

```
<213> ORGANISM: Artificial Sequence
<220> FEATURE:
<223> OTHER INFORMATION: COX2EX1 379

<400> SEQUENCE: 333
gcaagttctt cccgmtccgg actagatga                                29

<210> SEQ ID NO 334
<211> LENGTH: 29
<212> TYPE: DNA
<213> ORGANISM: Artificial Sequence
<220> FEATURE:
<223> OTHER INFORMATION: COX2EX10 866

<400> SEQUENCE: 334 aaagtactttt tggtyattttt tctgtcatc                              29

<210> SEQ ID NO 335
<211> LENGTH: 29
<212> TYPE: DNA
<213> ORGANISM: Artificial Sequence
<220> FEATURE:
<223> OTHER INFORMATION: COX2EX10 87

<400> SEQUENCE: 335
catcgatgct gtggrgctgt atcctgccc                                29

<210> SEQ ID NO 336
<211> LENGTH: 29
<212> TYPE: DNA
<213> ORGANISM: Artificial Sequence
<220> FEATURE:
<223> OTHER INFORMATION: COX2EX10 937

<400> SEQUENCE: 336
attagacatt accartaatt tcatgtcta                                29

<210> SEQ ID NO 337
<211> LENGTH: 29
<212> TYPE: DNA
<213> ORGANISM: Artificial Sequence
<220> FEATURE:
<223> OTHER INFORMATION: COX2EX3 166

<400> SEQUENCE: 337
attatgagtt atgtsttgac atgtaagta                                29

<210> SEQ ID NO 338
<211> LENGTH: 29
<212> TYPE: DNA
<213> ORGANISM: Artificial Sequence
<220> FEATURE:
<223> OTHER INFORMATION: COX2EX7 206

<400> SEQUENCE: 338
aacagagtat gcgaygtgct taaacagga                                29

<210> SEQ ID NO 339
<211> LENGTH: 29
<212> TYPE: DNA
<213> ORGANISM: Artificial Sequence
<220> FEATURE:
<223> OTHER INFORMATION: COX2EX8 268

<400> SEQUENCE: 339
atattgctgg aacayggaat tacccagtt                                29
```

<210> SEQ ID NO 340
<211> LENGTH: 29
<212> TYPE: DNA
<213> ORGANISM: Artificial Sequence
<220> FEATURE:
<223> OTHER INFORMATION: CYP11B1EX1 351

<400> SEQUENCE: 340
tgacgtgatc cctcycgaag gcaaggcac                               29

<210> SEQ ID NO 341
<211> LENGTH: 29
<212> TYPE: DNA
<213> ORGANISM: Artificial Sequence
<220> FEATURE:
<223> OTHER INFORMATION: CYP11B1EX1 525

<400> SEQUENCE: 341
aggacagtgc tgccstttga agccatgcc                               29

<210> SEQ ID NO 342
<211> LENGTH: 29
<212> TYPE: DNA
<213> ORGANISM: Artificial Sequence
<220> FEATURE:
<223> OTHER INFORMATION: CYP11B1EX1 542

<400> SEQUENCE: 342
tgaagccatg ccccrgcgtc caggcaaca                               29

<210> SEQ ID NO 343
<211> LENGTH: 29
<212> TYPE: DNA
<213> ORGANISM: Artificial Sequence
<220> FEATURE:
<223> OTHER INFORMATION: CYP11B1EX1 601

<400> SEQUENCE: 343
agcagggtta tgagsacctg cacctggaa                               29

<210> SEQ ID NO 344
<211> LENGTH: 29
<212> TYPE: DNA
<213> ORGANISM: Artificial Sequence
<220> FEATURE:
<223> OTHER INFORMATION: CYP11B1EX2 184

<400> SEQUENCE: 344
gtggcgtgtt cttgytgtaa gcggcgagc                               29

<210> SEQ ID NO 345
<211> LENGTH: 29
<212> TYPE: DNA
<213> ORGANISM: Artificial Sequence
<220> FEATURE:
<223> OTHER INFORMATION: CYP11B1EX2 188

<400> SEQUENCE: 345
cgtgttcttg ctgtragcgg cgagctgag                               29

<210> SEQ ID NO 346
<211> LENGTH: 29
<212> TYPE: DNA
<213> ORGANISM: Artificial Sequence
<220> FEATURE:

-continued

<223> OTHER INFORMATION: CYP11B1EX2 36

<400> SEQUENCE: 346
ccccacaggt acgayttggg aggagcagg                                    29

<210> SEQ ID NO 347
<211> LENGTH: 29
<212> TYPE: DNA
<213> ORGANISM: Artificial Sequence
<220> FEATURE:
<223> OTHER INFORMATION: CYP11B1EX2 78

<400> SEQUENCE: 347
atgctgccgg aggaygtgga gaagctgca                                    29

<210> SEQ ID NO 348
<211> LENGTH: 29
<212> TYPE: DNA
<213> ORGANISM: Artificial Sequence
<220> FEATURE:
<223> OTHER INFORMATION: CYP11B1EX3 114

<400> SEQUENCE: 348
aggttcctcc cgatsgtgga tgcagtggc                                    29

<210> SEQ ID NO 349
<211> LENGTH: 29
<212> TYPE: DNA
<213> ORGANISM: Artificial Sequence
<220> FEATURE:
<223> OTHER INFORMATION: CYP11B1EX4 177

<400> SEQUENCE: 349
cctgtctcgc tggaycagcc ccaaggtgt                                    29

<210> SEQ ID NO 350
<211> LENGTH: 29
<212> TYPE: DNA
<213> ORGANISM: Artificial Sequence
<220> FEATURE:
<223> OTHER INFORMATION: CYP11B1EX4 205

<400> SEQUENCE: 350
tggaaggagc acttkgaggc ctgggactg                                    29

<210> SEQ ID NO 351
<211> LENGTH: 29
<212> TYPE: DNA
<213> ORGANISM: Artificial Sequence
<220> FEATURE:
<223> OTHER INFORMATION: CYP11B1EX4 247

<400> SEQUENCE: 351
ggtgaggcca gggasccggg cagtgctat                                    29

<210> SEQ ID NO 352
<211> LENGTH: 29
<212> TYPE: DNA
<213> ORGANISM: Artificial Sequence
<220> FEATURE:
<223> OTHER INFORMATION: CYP11B1EX5 103

<400> SEQUENCE: 352
accagcatcg tggcrgagct cctgttgaa                                    29

```
<210> SEQ ID NO 353
<211> LENGTH: 29
<212> TYPE: DNA
<213> ORGANISM: Artificial Sequence
<220> FEATURE:
<223> OTHER INFORMATION: CYP11B1EX5 107

<400> SEQUENCE: 353
gcatcgtggc ggagstcctg ttgaatgcg                                    29

<210> SEQ ID NO 354
<211> LENGTH: 29
<212> TYPE: DNA
<213> ORGANISM: Artificial Sequence
<220> FEATURE:
<223> OTHER INFORMATION: CYP11B1EX5 16

<400> SEQUENCE: 354
tgagggctgc ctccygctcc ccggatagg                                    29

<210> SEQ ID NO 355
<211> LENGTH: 29
<212> TYPE: DNA
<213> ORGANISM: Artificial Sequence
<220> FEATURE:
<223> OTHER INFORMATION: CYP11B1EX5 55

<400> SEQUENCE: 355
atccagaaaa tctaycagga actggccttt                                   29

<210> SEQ ID NO 356
<211> LENGTH: 29
<212> TYPE: DNA
<213> ORGANISM: Artificial Sequence
<220> FEATURE:
<223> OTHER INFORMATION: CYP11B1EX5 72

<400> SEQUENCE: 356
ggaactggcc ttcarccgcc ctcaacagt                                    29

<210> SEQ ID NO 357
<211> LENGTH: 29
<212> TYPE: DNA
<213> ORGANISM: Artificial Sequence
<220> FEATURE:
<223> OTHER INFORMATION: CYP11B1EX7 52

<400> SEQUENCE: 357
ctgtgggtct gtttytggag cgagtggcg                                    29

<210> SEQ ID NO 358
<211> LENGTH: 29
<212> TYPE: DNA
<213> ORGANISM: Artificial Sequence
<220> FEATURE:
<223> OTHER INFORMATION: CYP11B1EX8 144

<400> SEQUENCE: 358
ccggcaggaa cttcyaccac gtgcccttt                                    29

<210> SEQ ID NO 359
<211> LENGTH: 29
<212> TYPE: DNA
<213> ORGANISM: Artificial Sequence
<220> FEATURE:
<223> OTHER INFORMATION: CYP11B1EX9 16
```

-continued

<210> SEQ ID NO 359

<400> SEQUENCE: 359
ccagatggaa acccsgcttc tgtcctagg                                29

<210> SEQ ID NO 360
<211> LENGTH: 29
<212> TYPE: DNA
<213> ORGANISM: Artificial Sequence
<220> FEATURE:
<223> OTHER INFORMATION: CYP11B1EX9 274

<400> SEQUENCE: 360
agccccagca caaayggaac tcccgaggg                                29

<210> SEQ ID NO 361
<211> LENGTH: 29
<212> TYPE: DNA
<213> ORGANISM: Artificial Sequence
<220> FEATURE:
<223> OTHER INFORMATION: CYP11B1EX9 350

<400> SEQUENCE: 361
gctggggaag atctkgctga ccttgtccc                                29

<210> SEQ ID NO 362
<211> LENGTH: 29
<212> TYPE: DNA
<213> ORGANISM: Artificial Sequence
<220> FEATURE:
<223> OTHER INFORMATION: CYP11B1EX9 459

<400> SEQUENCE: 362
cctcgtgtgg ccatrcaagg gtgctgtgg                                29

<210> SEQ ID NO 363
<211> LENGTH: 29
<212> TYPE: DNA
<213> ORGANISM: Artificial Sequence
<220> FEATURE:
<223> OTHER INFORMATION: CYP11B1EX9 592

<400> SEQUENCE: 363
tctagagtcc agtcmagttc cctcctgca                                29

<210> SEQ ID NO 364
<211> LENGTH: 29
<212> TYPE: DNA
<213> ORGANISM: Artificial Sequence
<220> FEATURE:
<223> OTHER INFORMATION: CYP11B1EX9 62

<400> SEQUENCE: 364
gtggagacac taacycaaga ggacataaa                                29

<210> SEQ ID NO 365
<211> LENGTH: 29
<212> TYPE: DNA
<213> ORGANISM: Artificial Sequence
<220> FEATURE:
<223> OTHER INFORMATION: CYP11B1EX9 657

<400> SEQUENCE: 365
ctctgaaagt tgtcrccctg gaatagggt                                29

<210> SEQ ID NO 366
<211> LENGTH: 29

```
<212> TYPE: DNA
<213> ORGANISM: Artificial Sequence
<220> FEATURE:
<223> OTHER INFORMATION: CYP11B1EX9 786

<400> SEQUENCE: 366
atcgtgtcag cctcrtgccc ctggcctca                                    29

<210> SEQ ID NO 367
<211> LENGTH: 29
<212> TYPE: DNA
<213> ORGANISM: Artificial Sequence
<220> FEATURE:
<223> OTHER INFORMATION: CYP11B1EX9 835

<400> SEQUENCE: 367
gttccaggag tgggygttgg gtcctctgc                                    29

<210> SEQ ID NO 368
<211> LENGTH: 29
<212> TYPE: DNA
<213> ORGANISM: Artificial Sequence
<220> FEATURE:
<223> OTHER INFORMATION: CYP11B1EX9 879

<400> SEQUENCE: 368
ctggggaagg tcccraggat gctgtcagg                                    29

<210> SEQ ID NO 369
<211> LENGTH: 29
<212> TYPE: DNA
<213> ORGANISM: Artificial Sequence
<220> FEATURE:
<223> OTHER INFORMATION: CYP11B2EX1 163

<400> SEQUENCE: 369
tcctgggtga gataraagga tttgggctg                                    29

<210> SEQ ID NO 370
<211> LENGTH: 29
<212> TYPE: DNA
<213> ORGANISM: Artificial Sequence
<220> FEATURE:
<223> OTHER INFORMATION: CYP11B2EX3 138

<400> SEQUENCE: 370
gtggccaggg acttytccca ggccctgaa                                    29

<210> SEQ ID NO 371
<211> LENGTH: 29
<212> TYPE: DNA
<213> ORGANISM: Artificial Sequence
<220> FEATURE:
<223> OTHER INFORMATION: CYP11B2EX3 152

<400> SEQUENCE: 371
ctcccaggcc ctgargaaga aggtgctgc                                    29

<210> SEQ ID NO 372
<211> LENGTH: 29
<212> TYPE: DNA
<213> ORGANISM: Artificial Sequence
<220> FEATURE:
<223> OTHER INFORMATION: CYP11B2EX3 20

<400> SEQUENCE: 372
```
caagctctgc cctgscctct gtaggaatg                                29

<210> SEQ ID NO 373
<211> LENGTH: 29
<212> TYPE: DNA
<213> ORGANISM: Artificial Sequence
<220> FEATURE:
<223> OTHER INFORMATION: CYP11B2EX3 243

<400> SEQUENCE: 373
ggtgtgggcc atgcrggaag gtccagccc                                29

<210> SEQ ID NO 374
<211> LENGTH: 29
<212> TYPE: DNA
<213> ORGANISM: Artificial Sequence
<220> FEATURE:
<223> OTHER INFORMATION: CYP11B2EX4 177

<400> SEQUENCE: 374
cctgtctcgc tggaycagcc ccaaggtgt                                29

<210> SEQ ID NO 375
<211> LENGTH: 29
<212> TYPE: DNA
<213> ORGANISM: Artificial Sequence
<220> FEATURE:
<223> OTHER INFORMATION: CYP11B2EX4 250

<400> SEQUENCE: 375
gaggccaggg acccrggcag tgctatggg                                29

<210> SEQ ID NO 376
<211> LENGTH: 29
<212> TYPE: DNA
<213> ORGANISM: Artificial Sequence
<220> FEATURE:
<223> OTHER INFORMATION: CYP11B2EX4 99

<400> SEQUENCE: 376
ttctgccagc ctgamcttcc tccatgccc                                29

<210> SEQ ID NO 377
<211> LENGTH: 29
<212> TYPE: DNA
<213> ORGANISM: Artificial Sequence
<220> FEATURE:
<223> OTHER INFORMATION: CYP11B2EX5 103

<400> SEQUENCE: 377
acaggcatcg tggcrgagct cctgttgaa                                29

<210> SEQ ID NO 378
<211> LENGTH: 29
<212> TYPE: DNA
<213> ORGANISM: Artificial Sequence
<220> FEATURE:
<223> OTHER INFORMATION: CYP11B2EX5 121

<400> SEQUENCE: 378
ctcctgttga aggcrgaact gtcactaga                                29

<210> SEQ ID NO 379
<211> LENGTH: 29
<212> TYPE: DNA
<213> ORGANISM: Artificial Sequence

```
<220> FEATURE:
<223> OTHER INFORMATION: CYP11B2EX5 55

<400> SEQUENCE: 379
atccagaaaa tctaycagga actggcctt                                29

<210> SEQ ID NO 380
<211> LENGTH: 29
<212> TYPE: DNA
<213> ORGANISM: Artificial Sequence
<220> FEATURE:
<223> OTHER INFORMATION: CYP11B2EX5 72

<400> SEQUENCE: 380
ggaactggcc ttcarccgcc ctcaacact                                29

<210> SEQ ID NO 381
<211> LENGTH: 29
<212> TYPE: DNA
<213> ORGANISM: Artificial Sequence
<220> FEATURE:
<223> OTHER INFORMATION: CYP11B2EX6 195

<400> SEQUENCE: 381
tcaaggagac cttgmggtgg gtgctggct                                29

<210> SEQ ID NO 382
<211> LENGTH: 29
<212> TYPE: DNA
<213> ORGANISM: Artificial Sequence
<220> FEATURE:
<223> OTHER INFORMATION: CYP11B2EX6 91

<400> SEQUENCE: 382
cgacgtgcag cagayccctgc gccaggaga                               29

<210> SEQ ID NO 383
<211> LENGTH: 29
<212> TYPE: DNA
<213> ORGANISM: Artificial Sequence
<220> FEATURE:
<223> OTHER INFORMATION: CYP11B2EX7 52

<400> SEQUENCE: 383
ctgtgggtct gtttytggag cgagtggtg                                29

<210> SEQ ID NO 384
<211> LENGTH: 29
<212> TYPE: DNA
<213> ORGANISM: Artificial Sequence
<220> FEATURE:
<223> OTHER INFORMATION: CYP11B2EX7 56

<400> SEQUENCE: 384
gggtctgttt ttggwgcgag tggtgagct                                29

<210> SEQ ID NO 385
<211> LENGTH: 29
<212> TYPE: DNA
<213> ORGANISM: Artificial Sequence
<220> FEATURE:
<223> OTHER INFORMATION: CYP11B2EX7 65

<400> SEQUENCE: 385
tttggagcga gtggygagct cagacttgg                                29
```

<210> SEQ ID NO 386
<211> LENGTH: 29
<212> TYPE: DNA
<213> ORGANISM: Artificial Sequence
<220> FEATURE:
<223> OTHER INFORMATION: CYP11B2EX7 78

<400> SEQUENCE: 386
gtgagctcag acttrgtgct tcagaacta                              29

<210> SEQ ID NO 387
<211> LENGTH: 29
<212> TYPE: DNA
<213> ORGANISM: Artificial Sequence
<220> FEATURE:
<223> OTHER INFORMATION: CYP11B2EX8 132

<400> SEQUENCE: 387
acatcagggg ctccrgcagg aacttccac                              29

<210> SEQ ID NO 388
<211> LENGTH: 29
<212> TYPE: DNA
<213> ORGANISM: Artificial Sequence
<220> FEATURE:
<223> OTHER INFORMATION: CYP11B2EX8 18

<400> SEQUENCE: 388
tgatccctgc tctgyaccgt ccgcagaca                              29

<210> SEQ ID NO 389
<211> LENGTH: 29
<212> TYPE: DNA
<213> ORGANISM: Artificial Sequence
<220> FEATURE:
<223> OTHER INFORMATION: CYP11B2EX8 182

<400> SEQUENCE: 389
atgcgccagt gcctygggcg gcgcctggc                              29

<210> SEQ ID NO 390
<211> LENGTH: 29
<212> TYPE: DNA
<213> ORGANISM: Artificial Sequence
<220> FEATURE:
<223> OTHER INFORMATION: CYP11B2EX8 37

<400> SEQUENCE: 390
tccgcagaca ttggwacagg ttttcctct                              29

<210> SEQ ID NO 391
<211> LENGTH: 29
<212> TYPE: DNA
<213> ORGANISM: Artificial Sequence
<220> FEATURE:
<223> OTHER INFORMATION: CYP11B2EX9 224

<400> SEQUENCE: 391
gtcttctctc ccacrtgcac agcttcctg                              29

<210> SEQ ID NO 392
<211> LENGTH: 29
<212> TYPE: DNA
<213> ORGANISM: Artificial Sequence
<220> FEATURE:
<223> OTHER INFORMATION: CYP11B2EX9 90

<400> SEQUENCE: 392
agatggtcta cagcktcata ttgaggcct                              29

<210> SEQ ID NO 393
<211> LENGTH: 29
<212> TYPE: DNA
<213> ORGANISM: Artificial Sequence
<220> FEATURE:
<223> OTHER INFORMATION: DBHEX1 152

<400> SEQUENCE: 393
gggccagcct gcccrgcccc agcatgcgg                              29

<210> SEQ ID NO 394
<211> LENGTH: 29
<212> TYPE: DNA
<213> ORGANISM: Artificial Sequence
<220> FEATURE:
<223> OTHER INFORMATION: DBHEX3 153

<400> SEQUENCE: 394
agttgccctc agacrcgtgc accatggag                              29

<210> SEQ ID NO 395
<211> LENGTH: 29
<212> TYPE: DNA
<213> ORGANISM: Artificial Sequence
<220> FEATURE:
<223> OTHER INFORMATION: DBHEX3 239

<400> SEQUENCE: 395
aaggagcttc caaasggctt ctctcggca                              29

<210> SEQ ID NO 396
<211> LENGTH: 29
<212> TYPE: DNA
<213> ORGANISM: Artificial Sequence
<220> FEATURE:
<223> OTHER INFORMATION: DBHEX3 257

<400> SEQUENCE: 396
ttctctcggc accayattat caaggtacg                              29

<210> SEQ ID NO 397
<211> LENGTH: 29
<212> TYPE: DNA
<213> ORGANISM: Artificial Sequence
<220> FEATURE:
<223> OTHER INFORMATION: DBHEX3 63

<400> SEQUENCE: 397
cgttccggtc actgsaggcc atcaacggc                              29

<210> SEQ ID NO 398
<211> LENGTH: 29
<212> TYPE: DNA
<213> ORGANISM: Artificial Sequence
<220> FEATURE:
<223> OTHER INFORMATION: DBHEX4 12

<400> SEQUENCE: 398
cctcctcaca gtacsagccc atcgtcacc                              29

<210> SEQ ID NO 399

```
<211> LENGTH: 29
<212> TYPE: DNA
<213> ORGANISM: Artificial Sequence
<220> FEATURE:
<223> OTHER INFORMATION: DBHEX4 132

<400> SEQUENCE: 399
ccaagatgaa acccraccgc ctcaactac                                29

<210> SEQ ID NO 400
<211> LENGTH: 29
<212> TYPE: DNA
<213> ORGANISM: Artificial Sequence
<220> FEATURE:
<223> OTHER INFORMATION: DBHEX5 37

<400> SEQUENCE: 400
agaggaagcc ggccytgcct tcggggggtc                               29

<210> SEQ ID NO 401
<211> LENGTH: 29
<212> TYPE: DNA
<213> ORGANISM: Artificial Sequence
<220> FEATURE:
<223> OTHER INFORMATION: DBHEX5 39

<400> SEQUENCE: 401
aggaagccgg ccttkccttc ggggtcca                                 29

<210> SEQ ID NO 402
<211> LENGTH: 29
<212> TYPE: DNA
<213> ORGANISM: Artificial Sequence
<220> FEATURE:
<223> OTHER INFORMATION: DD1R 122

<400> SEQUENCE: 402
cctattccct gcttrggaac ttgaggggt                                29

<210> SEQ ID NO 403
<211> LENGTH: 29
<212> TYPE: DNA
<213> ORGANISM: Artificial Sequence
<220> FEATURE:
<223> OTHER INFORMATION: DD1R 1521

<400> SEQUENCE: 403
ctgaactcgc agatraatcc tgccacaca                                29

<210> SEQ ID NO 404
<211> LENGTH: 29
<212> TYPE: DNA
<213> ORGANISM: Artificial Sequence
<220> FEATURE:
<223> OTHER INFORMATION: DD1R 278

<400> SEQUENCE: 404
tgctcatcct gtccmcgctc ctggggaac                                29

<210> SEQ ID NO 405
<211> LENGTH: 29
<212> TYPE: DNA
<213> ORGANISM: Artificial Sequence
<220> FEATURE:
<223> OTHER INFORMATION: DD1R 279

<400> SEQUENCE: 405
```
gctcatcctg tccasgctcc tggggaaca                                29

<210> SEQ ID NO 406
<211> LENGTH: 29
<212> TYPE: DNA
<213> ORGANISM: Artificial Sequence
<220> FEATURE:
<223> OTHER INFORMATION: DD1R 310

<400> SEQUENCE: 406
ctggtctgtg ctgcsgttat caggttccg                                29

<210> SEQ ID NO 407
<211> LENGTH: 29
<212> TYPE: DNA
<213> ORGANISM: Artificial Sequence
<220> FEATURE:
<223> OTHER INFORMATION: DD1R 319

<400> SEQUENCE: 407
gctgccgtta tcagkttccg acacctgcg                                29

<210> SEQ ID NO 408
<211> LENGTH: 29
<212> TYPE: DNA
<213> ORGANISM: Artificial Sequence
<220> FEATURE:
<223> OTHER INFORMATION: DD1R 76

<400> SEQUENCE: 408
gcaaagtgct gcctrgtggg gaggactcc                                29

<210> SEQ ID NO 409
<211> LENGTH: 29
<212> TYPE: DNA
<213> ORGANISM: Artificial Sequence
<220> FEATURE:
<223> OTHER INFORMATION: DD1R 764

<400> SEQUENCE: 409
atgccatctc atcckctgta ataagcttt                                29

<210> SEQ ID NO 410
<211> LENGTH: 29
<212> TYPE: DNA
<213> ORGANISM: Artificial Sequence
<220> FEATURE:
<223> OTHER INFORMATION: EDNRAEX6 124

<400> SEQUENCE: 410
actgtgtata acgaratgga caagaaccg                                29

<210> SEQ ID NO 411
<211> LENGTH: 29
<212> TYPE: DNA
<213> ORGANISM: Artificial Sequence
<220> FEATURE:
<223> OTHER INFORMATION: EDNRAEX6 88

<400> SEQUENCE: 411
tggttccctc ttcayttaag ccgtatatt                                29

<210> SEQ ID NO 412
<211> LENGTH: 29
<212> TYPE: DNA

```
<213> ORGANISM: Artificial Sequence
<220> FEATURE:
<223> OTHER INFORMATION: EDNRAEX8 1157

<400> SEQUENCE: 412
ttttcagatg attcrgaaat tttcattca                                29

<210> SEQ ID NO 413
<211> LENGTH: 29
<212> TYPE: DNA
<213> ORGANISM: Artificial Sequence
<220> FEATURE:
<223> OTHER INFORMATION: EDNRAEX8 1380

<400> SEQUENCE: 413
acgattcttc acttyttggg gttttcagt                                29

<210> SEQ ID NO 414
<211> LENGTH: 29
<212> TYPE: DNA
<213> ORGANISM: Artificial Sequence
<220> FEATURE:
<223> OTHER INFORMATION: EDNRAEX8 1687

<400> SEQUENCE: 414
ttgtgccaaa gtgcrtagtc tgagctaaa                                29

<210> SEQ ID NO 415
<211> LENGTH: 29
<212> TYPE: DNA
<213> ORGANISM: Artificial Sequence
<220> FEATURE:
<223> OTHER INFORMATION: EDNRAEX8 228

<400> SEQUENCE: 415
caaggcaact gtgastccgg gaatctctt                                29

<210> SEQ ID NO 416
<211> LENGTH: 29
<212> TYPE: DNA
<213> ORGANISM: Artificial Sequence
<220> FEATURE:
<223> OTHER INFORMATION: EDNRAEX8 295

<400> SEQUENCE: 416
aagaaatgct ttccraaacc gcaaggtag                                29

<210> SEQ ID NO 417
<211> LENGTH: 29
<212> TYPE: DNA
<213> ORGANISM: Artificial Sequence
<220> FEATURE:
<223> OTHER INFORMATION: EDNRAEX8 622

<400> SEQUENCE: 417
acaatatggg ctcargtcac ttttatttg                                29

<210> SEQ ID NO 418
<211> LENGTH: 29
<212> TYPE: DNA
<213> ORGANISM: Artificial Sequence
<220> FEATURE:
<223> OTHER INFORMATION: EDNRAEX8 655

<400> SEQUENCE: 418
gtcatttggt gccartattt tttaactgc                                29
```

```
<210> SEQ ID NO 419
<211> LENGTH: 29
<212> TYPE: DNA
<213> ORGANISM: Artificial Sequence
<220> FEATURE:
<223> OTHER INFORMATION: EDNRAEX8 788

<400> SEQUENCE: 419
ctatttattt ttttraaaca caaattcta                              29

<210> SEQ ID NO 420
<211> LENGTH: 29
<212> TYPE: DNA
<213> ORGANISM: Artificial Sequence
<220> FEATURE:
<223> OTHER INFORMATION: EDNRAEX8 950

<400> SEQUENCE: 420
gaacatgttt tgtaygttaa attcaaaag                              29

<210> SEQ ID NO 421
<211> LENGTH: 29
<212> TYPE: DNA
<213> ORGANISM: Artificial Sequence
<220> FEATURE:
<223> OTHER INFORMATION: EDNRAEX8 985

<400> SEQUENCE: 421
ttcaatcaga tagtyctttt tcacaagtt                              29

<210> SEQ ID NO 422
<211> LENGTH: 29
<212> TYPE: DNA
<213> ORGANISM: Artificial Sequence
<220> FEATURE:
<223> OTHER INFORMATION: EDNRBEX1 33

<400> SEQUENCE: 422
gccgcctcca agtcwgtgcg gacgcgccc                              29

<210> SEQ ID NO 423
<211> LENGTH: 29
<212> TYPE: DNA
<213> ORGANISM: Artificial Sequence
<220> FEATURE:
<223> OTHER INFORMATION: EDNRBEX1 347

<400> SEQUENCE: 423
tgtcctgcct tgtgktcgtg ctggggatc                              29

<210> SEQ ID NO 424
<211> LENGTH: 29
<212> TYPE: DNA
<213> ORGANISM: Artificial Sequence
<220> FEATURE:
<223> OTHER INFORMATION: EDNRBEX1 62

<400> SEQUENCE: 424
tggttgcgct ggttyttgcc tgcggcctg                              29

<210> SEQ ID NO 425
<211> LENGTH: 29
<212> TYPE: DNA
<213> ORGANISM: Artificial Sequence
<220> FEATURE:
```

-continued

<223> OTHER INFORMATION: EDNRBEX2 78

<400> SEQUENCE: 425
atacagaaag cctcygtggg aatcactgt                                29

<210> SEQ ID NO 426
<211> LENGTH: 29
<212> TYPE: DNA
<213> ORGANISM: Artificial Sequence
<220> FEATURE:
<223> OTHER INFORMATION: EDNRBEX2 87

<400> SEQUENCE: 426
gcctccgtgg gaatyactgt gctgagtct                                29

<210> SEQ ID NO 427
<211> LENGTH: 29
<212> TYPE: DNA
<213> ORGANISM: Artificial Sequence
<220> FEATURE:
<223> OTHER INFORMATION: EDNRBEX3 144

<400> SEQUENCE: 427
ttttgatata attaygatgg actacaaag                                29

<210> SEQ ID NO 428
<211> LENGTH: 29
<212> TYPE: DNA
<213> ORGANISM: Artificial Sequence
<220> FEATURE:
<223> OTHER INFORMATION: EDNRBEX4 122

<400> SEQUENCE: 428
gttgagaaag aaaartggca tgcagattg                                29

<210> SEQ ID NO 429
<211> LENGTH: 29
<212> TYPE: DNA
<213> ORGANISM: Artificial Sequence
<220> FEATURE:
<223> OTHER INFORMATION: EDNRBEX4 39

<400> SEQUENCE: 429
aaagattggt ggctrttcag tttctattt                                29

<210> SEQ ID NO 430
<211> LENGTH: 29
<212> TYPE: DNA
<213> ORGANISM: Artificial Sequence
<220> FEATURE:
<223> OTHER INFORMATION: ELAM1EX1 143

<400> SEQUENCE: 430
tctttgacct aaatratgaa agtcttaaa                                29

<210> SEQ ID NO 431
<211> LENGTH: 29
<212> TYPE: DNA
<213> ORGANISM: Artificial Sequence
<220> FEATURE:
<223> OTHER INFORMATION: ELAM1EX1 209

<400> SEQUENCE: 431
ttattgcact agtgkccttt gcccaaaat                                29

-continued

```
<210> SEQ ID NO 432
<211> LENGTH: 29
<212> TYPE: DNA
<213> ORGANISM: Artificial Sequence
<220> FEATURE:
<223> OTHER INFORMATION: ELAM1EX10 107

<400> SEQUENCE: 432
cattagcacc atttytcctc tggcttcgg                                    29

<210> SEQ ID NO 433
<211> LENGTH: 29
<212> TYPE: DNA
<213> ORGANISM: Artificial Sequence
<220> FEATURE:
<223> OTHER INFORMATION: ELAM1EX12 54

<400> SEQUENCE: 433
agccttgaat cagayggaag ctaccaaaa                                    29

<210> SEQ ID NO 434
<211> LENGTH: 29
<212> TYPE: DNA
<213> ORGANISM: Artificial Sequence
<220> FEATURE:
<223> OTHER INFORMATION: ELAM1EX13 1004

<400> SEQUENCE: 434
cagaaatatg tggtktccac gatgaaaaa                                    29

<210> SEQ ID NO 435
<211> LENGTH: 29
<212> TYPE: DNA
<213> ORGANISM: Artificial Sequence
<220> FEATURE:
<223> OTHER INFORMATION: ELAM1EX13 1158

<400> SEQUENCE: 435
gatgtttgtc agatrtgata tgtaaacat                                    29

<210> SEQ ID NO 436
<211> LENGTH: 29
<212> TYPE: DNA
<213> ORGANISM: Artificial Sequence
<220> FEATURE:
<223> OTHER INFORMATION: ELAM1EX13 1549

<400> SEQUENCE: 436
tgaacactgg caacracaaa gccaacagt                                    29

<210> SEQ ID NO 437
<211> LENGTH: 29
<212> TYPE: DNA
<213> ORGANISM: Artificial Sequence
<220> FEATURE:
<223> OTHER INFORMATION: ELAM1EX13 967

<400> SEQUENCE: 437
actgaatgga aggtytgtat attgtcaga                                    29

<210> SEQ ID NO 438
<211> LENGTH: 29
<212> TYPE: DNA
<213> ORGANISM: Artificial Sequence
<220> FEATURE:
<223> OTHER INFORMATION: ELAM1EX2 382
```

```
<400> SEQUENCE: 438
aatgatgaga ggtgsagcaa gaagaagct                                         29

<210> SEQ ID NO 439
<211> LENGTH: 29
<212> TYPE: DNA
<213> ORGANISM: Artificial Sequence
<220> FEATURE:
<223> OTHER INFORMATION: ELAM1EX3 152

<400> SEQUENCE: 439
gtaagtctgg ttctygcctc tttcttcac                                         29

<210> SEQ ID NO 440
<211> LENGTH: 29
<212> TYPE: DNA
<213> ORGANISM: Artificial Sequence
<220> FEATURE:
<223> OTHER INFORMATION: ELAM1EX3 53

<400> SEQUENCE: 440
ccaatacatc ctgcmgtggc cacggtgaa                                         29

<210> SEQ ID NO 441
<211> LENGTH: 29
<212> TYPE: DNA
<213> ORGANISM: Artificial Sequence
<220> FEATURE:
<223> OTHER INFORMATION: ELAM1EX5 197

<400> SEQUENCE: 441
ggaattggga caacragaag ccaacgtgt                                         29

<210> SEQ ID NO 442
<211> LENGTH: 29
<212> TYPE: DNA
<213> ORGANISM: Artificial Sequence
<220> FEATURE:
<223> OTHER INFORMATION: ELAM1EX5 55

<400> SEQUENCE: 442
gatgctgtga caaayccagc caatgggtt                                         29

<210> SEQ ID NO 443
<211> LENGTH: 29
<212> TYPE: DNA
<213> ORGANISM: Artificial Sequence
<220> FEATURE:
<223> OTHER INFORMATION: ELAM1EX7 199

<400> SEQUENCE: 443
ggggagtggg acaaygagaa gcccacatg                                         29

<210> SEQ ID NO 444
<211> LENGTH: 29
<212> TYPE: DNA
<213> ORGANISM: Artificial Sequence
<220> FEATURE:
<223> OTHER INFORMATION: ELAM1EX7 200

<400> SEQUENCE: 444
gggagtggga caacsagaag cccacatgt                                         29

<210> SEQ ID NO 445
<211> LENGTH: 29
```

```
<212> TYPE: DNA
<213> ORGANISM: Artificial Sequence
<220> FEATURE:
<223> OTHER INFORMATION: ELAM1EX8 152

<400> SEQUENCE: 445
agggatttga attayatgga tcaactcaa                                    29

<210> SEQ ID NO 446
<211> LENGTH: 29
<212> TYPE: DNA
<213> ORGANISM: Artificial Sequence
<220> FEATURE:
<223> OTHER INFORMATION: ELAM1EX8 22

<400> SEQUENCE: 446
agtgctctct cgtgygttcc agctgtgag                                    29

<210> SEQ ID NO 447
<211> LENGTH: 29
<212> TYPE: DNA
<213> ORGANISM: Artificial Sequence
<220> FEATURE:
<223> OTHER INFORMATION: ENDOTHELIN2 440

<400> SEQUENCE: 447
cccctgcaga cgtgytccag actggcaag                                    29

<210> SEQ ID NO 448
<211> LENGTH: 29
<212> TYPE: DNA
<213> ORGANISM: Artificial Sequence
<220> FEATURE:
<223> OTHER INFORMATION: ENDOTHELIN2 556

<400> SEQUENCE: 448
atgcgggagc ctcgrtccac acattccag                                    29

<210> SEQ ID NO 449
<211> LENGTH: 29
<212> TYPE: DNA
<213> ORGANISM: Artificial Sequence
<220> FEATURE:
<223> OTHER INFORMATION: ENDOTHELIN2 976

<400> SEQUENCE: 449
agccagccct ggagrctgga tggctcccc                                    29

<210> SEQ ID NO 450
<211> LENGTH: 29
<212> TYPE: DNA
<213> ORGANISM: Artificial Sequence
<220> FEATURE:
<223> OTHER INFORMATION: ET1EX3 114

<400> SEQUENCE: 450
gcaacagacc gtgaraatag atgccaatg                                    29

<210> SEQ ID NO 451
<211> LENGTH: 29
<212> TYPE: DNA
<213> ORGANISM: Artificial Sequence
<220> FEATURE:
<223> OTHER INFORMATION: ET1EX5 90

<400> SEQUENCE: 451
```
aagctgaaag gcaakccctc cagagagcg                              29

<210> SEQ ID NO 452
<211> LENGTH: 29
<212> TYPE: DNA
<213> ORGANISM: Artificial Sequence
<220> FEATURE:
<223> OTHER INFORMATION: GALNREX1 1052

<400> SEQUENCE: 452
ctgcccacct gggtkctggg cgccttcat                              29

<210> SEQ ID NO 453
<211> LENGTH: 29
<212> TYPE: DNA
<213> ORGANISM: Artificial Sequence
<220> FEATURE:
<223> OTHER INFORMATION: GALNREX1 325

<400> SEQUENCE: 453
ggtgcagcac gcagscgctc cgggagcca                              29

<210> SEQ ID NO 454
<211> LENGTH: 29
<212> TYPE: DNA
<213> ORGANISM: Artificial Sequence
<220> FEATURE:
<223> OTHER INFORMATION: GALNREX1 327

<400> SEQUENCE: 454
tgcagcacgc agccsctccg ggagccagg                              29

<210> SEQ ID NO 455
<211> LENGTH: 29
<212> TYPE: DNA
<213> ORGANISM: Artificial Sequence
<220> FEATURE:
<223> OTHER INFORMATION: GALNREX1 553

<400> SEQUENCE: 455
tctctcagaa ggtcscggcg caaagacgg                              29

<210> SEQ ID NO 456
<211> LENGTH: 29
<212> TYPE: DNA
<213> ORGANISM: Artificial Sequence
<220> FEATURE:
<223> OTHER INFORMATION: GALNREX1 887

<400> SEQUENCE: 456
atcttcgcgc tgggygtgct gggcaacag                              29

<210> SEQ ID NO 457
<211> LENGTH: 29
<212> TYPE: DNA
<213> ORGANISM: Artificial Sequence
<220> FEATURE:
<223> OTHER INFORMATION: GALNREX3 298

<400> SEQUENCE: 457
tgatactaaa gaaartaaaa gtcgaatag                              29

<210> SEQ ID NO 458
<211> LENGTH: 29
<212> TYPE: DNA
<213> ORGANISM: Artificial Sequence

```
<220> FEATURE:
<223> OTHER INFORMATION: GALNREX3 322

<400> SEQUENCE: 458
aatagacacc ccacyatcaa ccaattgta                                29

<210> SEQ ID NO 459
<211> LENGTH: 29
<212> TYPE: DNA
<213> ORGANISM: Artificial Sequence
<220> FEATURE:
<223> OTHER INFORMATION: GALNREX3 388

<400> SEQUENCE: 459
agtttccata taagyggacc agacacaga                                29

<210> SEQ ID NO 460
<211> LENGTH: 29
<212> TYPE: DNA
<213> ORGANISM: Artificial Sequence
<220> FEATURE:
<223> OTHER INFORMATION: GALNREX3 418

<400> SEQUENCE: 460
acaaacagaa tgagstagta agcgatgct                                29

<210> SEQ ID NO 461
<211> LENGTH: 29
<212> TYPE: DNA
<213> ORGANISM: Artificial Sequence
<220> FEATURE:
<223> OTHER INFORMATION: GALNREX3 523

<400> SEQUENCE: 461
taggaaattc ctagktctag tgagaatta                                29

<210> SEQ ID NO 462
<211> LENGTH: 29
<212> TYPE: DNA
<213> ORGANISM: Artificial Sequence
<220> FEATURE:
<223> OTHER INFORMATION: GALNREX3 650

<400> SEQUENCE: 462
tccatatata tgttyaactc ttcatagat                                29

<210> SEQ ID NO 463
<211> LENGTH: 29
<212> TYPE: DNA
<213> ORGANISM: Artificial Sequence
<220> FEATURE:
<223> OTHER INFORMATION: GALNREX3 799

<400> SEQUENCE: 463
atgtatttta aaatrtgatc atggacaca                                29

<210> SEQ ID NO 464
<211> LENGTH: 29
<212> TYPE: DNA
<213> ORGANISM: Artificial Sequence
<220> FEATURE:
<223> OTHER INFORMATION: GGREX1 125

<400> SEQUENCE: 464
ctgctgttgc tgctrctgct ggcctgcca                                29
```

<210> SEQ ID NO 465
<211> LENGTH: 29
<212> TYPE: DNA
<213> ORGANISM: Artificial Sequence
<220> FEATURE:
<223> OTHER INFORMATION: GGREX11 57

<400> SEQUENCE: 465
cacgaagtgg tcttygcctt cgtgacgga                               29

<210> SEQ ID NO 466
<211> LENGTH: 29
<212> TYPE: DNA
<213> ORGANISM: Artificial Sequence
<220> FEATURE:
<223> OTHER INFORMATION: GGREX4 68

<400> SEQUENCE: 466
gaccccgggg gcagscttgg cgtgatgcc                               29

<210> SEQ ID NO 467
<211> LENGTH: 29
<212> TYPE: DNA
<213> ORGANISM: Artificial Sequence
<220> FEATURE:
<223> OTHER INFORMATION: GGREX5 71

<400> SEQUENCE: 467
ctgtccctgg gggcsctgct cctcgcctt                               29

<210> SEQ ID NO 468
<211> LENGTH: 29
<212> TYPE: DNA
<213> ORGANISM: Artificial Sequence
<220> FEATURE:
<223> OTHER INFORMATION: GGREX9 29

<400> SEQUENCE: 468
tgacaacatg ggctkctggt ggatcctgc                               29

<210> SEQ ID NO 469
<211> LENGTH: 29
<212> TYPE: DNA
<213> ORGANISM: Artificial Sequence
<220> FEATURE:
<223> OTHER INFORMATION: GH1EX4 144

<400> SEQUENCE: 469
cctctgacag caacrtctat gacctccta                               29

<210> SEQ ID NO 470
<211> LENGTH: 29
<212> TYPE: DNA
<213> ORGANISM: Artificial Sequence
<220> FEATURE:
<223> OTHER INFORMATION: GH2EX3 126

<400> SEQUENCE: 470
caacaccttc caacwgggtg aaaacgcag                               29

<210> SEQ ID NO 471
<211> LENGTH: 29
<212> TYPE: DNA
<213> ORGANISM: Artificial Sequence
<220> FEATURE:
<223> OTHER INFORMATION: GIPREX2 72

-continued

<400> SEQUENCE: 471
cttcgccgcc ctcasgatga ctacctctc                               29

<210> SEQ ID NO 472
<211> LENGTH: 29
<212> TYPE: DNA
<213> ORGANISM: Artificial Sequence
<220> FEATURE:
<223> OTHER INFORMATION: GIPREX7 51

<400> SEQUENCE: 472
cattgcacta gaaaytatat ccacatcaa                               29

<210> SEQ ID NO 473
<211> LENGTH: 29
<212> TYPE: DNA
<213> ORGANISM: Artificial Sequence
<220> FEATURE:
<223> OTHER INFORMATION: GIPREX8 180

<400> SEQUENCE: 473
gctactacct gctcstcggc tggggtgag                               29

<210> SEQ ID NO 474
<211> LENGTH: 29
<212> TYPE: DNA
<213> ORGANISM: Artificial Sequence
<220> FEATURE:
<223> OTHER INFORMATION: GLUT2EX1 137

<400> SEQUENCE: 474
ccacagcact aattmtctgt ggagcagag                               29

<210> SEQ ID NO 475
<211> LENGTH: 29
<212> TYPE: DNA
<213> ORGANISM: Artificial Sequence
<220> FEATURE:
<223> OTHER INFORMATION: GLUT2EX1 164

<400> SEQUENCE: 475
agtgcagtgt gcctyccatg ctccacagc                               29

<210> SEQ ID NO 476
<211> LENGTH: 29
<212> TYPE: DNA
<213> ORGANISM: Artificial Sequence
<220> FEATURE:
<223> OTHER INFORMATION: GLUT2EX1 237

<400> SEQUENCE: 476
aaagatttct ctttycaccg gctcccaat                               29

<210> SEQ ID NO 477
<211> LENGTH: 29
<212> TYPE: DNA
<213> ORGANISM: Artificial Sequence
<220> FEATURE:
<223> OTHER INFORMATION: GLUT2EX1 242

<400> SEQUENCE: 477
tttctctttt caccrgctcc caattactg                               29

<210> SEQ ID NO 478

```
<211> LENGTH: 29
<212> TYPE: DNA
<213> ORGANISM: Artificial Sequence
<220> FEATURE:
<223> OTHER INFORMATION: GLUT2EX10 161

<400> SEQUENCE: 478
gaattccaaa agaaragtgg ctcagccca                                              29

<210> SEQ ID NO 479
<211> LENGTH: 29
<212> TYPE: DNA
<213> ORGANISM: Artificial Sequence
<220> FEATURE:
<223> OTHER INFORMATION: GLUT2EX10 87

<400> SEQUENCE: 479
tcctggcctt taccstgttt acatttttt                                              29

<210> SEQ ID NO 480
<211> LENGTH: 29
<212> TYPE: DNA
<213> ORGANISM: Artificial Sequence
<220> FEATURE:
<223> OTHER INFORMATION: GLUT2EX10 92

<400> SEQUENCE: 480
gcctttaccc tgttyacatt ttttaaagt                                              29

<210> SEQ ID NO 481
<211> LENGTH: 29
<212> TYPE: DNA
<213> ORGANISM: Artificial Sequence
<220> FEATURE:
<223> OTHER INFORMATION: GLUT2EX3 250

<400> SEQUENCE: 481
agttggtgga atgaytgcat cattctttg                                              29

<210> SEQ ID NO 482
<211> LENGTH: 29
<212> TYPE: DNA
<213> ORGANISM: Artificial Sequence
<220> FEATURE:
<223> OTHER INFORMATION: GLUT2EX4A 153

<400> SEQUENCE: 482
tcaggactat attgyggtaa gtctcacac                                              29

<210> SEQ ID NO 483
<211> LENGTH: 29
<212> TYPE: DNA
<213> ORGANISM: Artificial Sequence
<220> FEATURE:
<223> OTHER INFORMATION: GLUT2EX4A 162

<400> SEQUENCE: 483
tattgtggta agtcwcacac acacacaca                                              29

<210> SEQ ID NO 484
<211> LENGTH: 29
<212> TYPE: DNA
<213> ORGANISM: Artificial Sequence
<220> FEATURE:
<223> OTHER INFORMATION: GLUT2EX4A 164

<400> SEQUENCE: 484
```

```
ttgtggtaag tctcwcacac acacacaca                                       29

<210> SEQ ID NO 485
<211> LENGTH: 29
<212> TYPE: DNA
<213> ORGANISM: Artificial Sequence
<220> FEATURE:
<223> OTHER INFORMATION: GLUT2EX4B 127

<400> SEQUENCE: 485
ctggccatcg tcacrggcat tcttattag                                       29

<210> SEQ ID NO 486
<211> LENGTH: 29
<212> TYPE: DNA
<213> ORGANISM: Artificial Sequence
<220> FEATURE:
<223> OTHER INFORMATION: GLUT2EX5 78

<400> SEQUENCE: 486
atctgtggca catcytgctt ggcctgtct                                       29

<210> SEQ ID NO 487
<211> LENGTH: 29
<212> TYPE: DNA
<213> ORGANISM: Artificial Sequence
<220> FEATURE:
<223> OTHER INFORMATION: GLUT2EX6 15

<400> SEQUENCE: 487
tgtttcaacc tgatyatttt cttggacag                                       29

<210> SEQ ID NO 488
<211> LENGTH: 29
<212> TYPE: DNA
<213> ORGANISM: Artificial Sequence
<220> FEATURE:
<223> OTHER INFORMATION: GLUT2EX8 21

<400> SEQUENCE: 488
taatttcttt aaaaytgtcc taggtattc                                       29

<210> SEQ ID NO 489
<211> LENGTH: 29
<212> TYPE: DNA
<213> ORGANISM: Artificial Sequence
<220> FEATURE:
<223> OTHER INFORMATION: GLUT2EX8 38

<400> SEQUENCE: 489
tcctaggtat tcctygtgga gaaggcagg                                       29

<210> SEQ ID NO 490
<211> LENGTH: 29
<212> TYPE: DNA
<213> ORGANISM: Artificial Sequence
<220> FEATURE:
<223> OTHER INFORMATION: GLUT4EX1 1002

<400> SEQUENCE: 490
cgttgtggga acggmatttc ctggccccc                                       29

<210> SEQ ID NO 491
<211> LENGTH: 29
<212> TYPE: DNA
```

```
<213> ORGANISM: Artificial Sequence
<220> FEATURE:
<223> OTHER INFORMATION: GLUT4EX1 1051

<400> SEQUENCE: 491
agcatgtcgc ggacycttta aggcgtcat                                    29

<210> SEQ ID NO 492
<211> LENGTH: 29
<212> TYPE: DNA
<213> ORGANISM: Artificial Sequence
<220> FEATURE:
<223> OTHER INFORMATION: GLUT4EX1 1228

<400> SEQUENCE: 492
tctcaggccg ctggwgtttc cccggggca                                    29

<210> SEQ ID NO 493
<211> LENGTH: 29
<212> TYPE: DNA
<213> ORGANISM: Artificial Sequence
<220> FEATURE:
<223> OTHER INFORMATION: GLUT4EX1 1632

<400> SEQUENCE: 493
cagccccgct ccacmagatc cgcgggagc                                    29

<210> SEQ ID NO 494
<211> LENGTH: 29
<212> TYPE: DNA
<213> ORGANISM: Artificial Sequence
<220> FEATURE:
<223> OTHER INFORMATION: GLUT4EX1 1662

<400> SEQUENCE: 494
ccactgctct ccggrtcctt ggcttgtgg                                    29

<210> SEQ ID NO 495
<211> LENGTH: 29
<212> TYPE: DNA
<213> ORGANISM: Artificial Sequence
<220> FEATURE:
<223> OTHER INFORMATION: GLUT4EX1 1683

<400> SEQUENCE: 495
gcttgtggct gtggstccca tcgggcccg                                    29

<210> SEQ ID NO 496
<211> LENGTH: 29
<212> TYPE: DNA
<213> ORGANISM: Artificial Sequence
<220> FEATURE:
<223> OTHER INFORMATION: GLUT4EX1 1691

<400> SEQUENCE: 496
ctgtgggtcc catcrggccc gccctcgca                                    29

<210> SEQ ID NO 497
<211> LENGTH: 29
<212> TYPE: DNA
<213> ORGANISM: Artificial Sequence
<220> FEATURE:
<223> OTHER INFORMATION: GLUT4EX1 368

<400> SEQUENCE: 497
acaggaggaa tcgarcctga cttctacca                                    29
```

<210> SEQ ID NO 498
<211> LENGTH: 29
<212> TYPE: DNA
<213> ORGANISM: Artificial Sequence
<220> FEATURE:
<223> OTHER INFORMATION: GLUT4EX1 560

<400> SEQUENCE: 498
gcggaaaggc gagaratagt gggttgaga                                       29

<210> SEQ ID NO 499
<211> LENGTH: 29
<212> TYPE: DNA
<213> ORGANISM: Artificial Sequence
<220> FEATURE:
<223> OTHER INFORMATION: GLUT4EX1 615

<400> SEQUENCE: 499
tcgctcgccc tccargtggc agcacaacc                                       29

<210> SEQ ID NO 500
<211> LENGTH: 29
<212> TYPE: DNA
<213> ORGANISM: Artificial Sequence
<220> FEATURE:
<223> OTHER INFORMATION: GLUT4EX1 91

<400> SEQUENCE: 500
caggaggttt tgttyactct gaaaaggga                                       29

<210> SEQ ID NO 501
<211> LENGTH: 29
<212> TYPE: DNA
<213> ORGANISM: Artificial Sequence
<220> FEATURE:
<223> OTHER INFORMATION: GLUT4EX1 966

<400> SEQUENCE: 501
ctgaaagaca ggacmaagca gcccggcca                                       29

<210> SEQ ID NO 502
<211> LENGTH: 29
<212> TYPE: DNA
<213> ORGANISM: Artificial Sequence
<220> FEATURE:
<223> OTHER INFORMATION: GLUT4EX10 19

<400> SEQUENCE: 502
tccaccctcc ctgtstggcc cctaggagc                                       29

<210> SEQ ID NO 503
<211> LENGTH: 29
<212> TYPE: DNA
<213> ORGANISM: Artificial Sequence
<220> FEATURE:
<223> OTHER INFORMATION: GLUT4EX11 1005

<400> SEQUENCE: 503
gtgctgggat tacargcgtg agccaccgc                                       29

<210> SEQ ID NO 504
<211> LENGTH: 29
<212> TYPE: DNA
<213> ORGANISM: Artificial Sequence
<220> FEATURE:

<223> OTHER INFORMATION: GLUT4EX11 1099

<400> SEQUENCE: 504
gaaagtatgt gcccmtgtgt ggcaagatg                                              29

<210> SEQ ID NO 505
<211> LENGTH: 29
<212> TYPE: DNA
<213> ORGANISM: Artificial Sequence
<220> FEATURE:
<223> OTHER INFORMATION: GLUT4EX11 791

<400> SEQUENCE: 505
cgagtgcagt ggcgygatct tgcttcact                                              29

<210> SEQ ID NO 506
<211> LENGTH: 29
<212> TYPE: DNA
<213> ORGANISM: Artificial Sequence
<220> FEATURE:
<223> OTHER INFORMATION: GLUT4EX11 827

<400> SEQUENCE: 506
gtctcccagg ttcaygccat tctcctgcc                                              29

<210> SEQ ID NO 507
<211> LENGTH: 29
<212> TYPE: DNA
<213> ORGANISM: Artificial Sequence
<220> FEATURE:
<223> OTHER INFORMATION: GLUT4EX11 872

<400> SEQUENCE: 507
ctgggactac aggcrcatgc caccacacc                                              29

<210> SEQ ID NO 508
<211> LENGTH: 29
<212> TYPE: DNA
<213> ORGANISM: Artificial Sequence
<220> FEATURE:
<223> OTHER INFORMATION: GLUT4EX11 874

<400> SEQUENCE: 508
gggactacag gcgcmtgcca ccacacctg                                              29

<210> SEQ ID NO 509
<211> LENGTH: 29
<212> TYPE: DNA
<213> ORGANISM: Artificial Sequence
<220> FEATURE:
<223> OTHER INFORMATION: GLUT4EX11 884

<400> SEQUENCE: 509
gcgcatgcca ccacrcctgg ctaatttat                                              29

<210> SEQ ID NO 510
<211> LENGTH: 29
<212> TYPE: DNA
<213> ORGANISM: Artificial Sequence
<220> FEATURE:
<223> OTHER INFORMATION: GLUT4EX11 897

<400> SEQUENCE: 510
cacctggcta atttwttttg tattttag                                               29

```
<210> SEQ ID NO 511
<211> LENGTH: 29
<212> TYPE: DNA
<213> ORGANISM: Artificial Sequence
<220> FEATURE:
<223> OTHER INFORMATION: GLUT4EX11 930

<400> SEQUENCE: 511
tacgcggttt caccrtgtta gccagaatg                                    29

<210> SEQ ID NO 512
<211> LENGTH: 29
<212> TYPE: DNA
<213> ORGANISM: Artificial Sequence
<220> FEATURE:
<223> OTHER INFORMATION: GLUT4EX11 935

<400> SEQUENCE: 512
ggtttcacca tgttrgccag aatggtctc                                    29

<210> SEQ ID NO 513
<211> LENGTH: 29
<212> TYPE: DNA
<213> ORGANISM: Artificial Sequence
<220> FEATURE:
<223> OTHER INFORMATION: GLUT4EX11 941

<400> SEQUENCE: 513
accatgttag ccagratggt ctcgatctc                                    29

<210> SEQ ID NO 514
<211> LENGTH: 29
<212> TYPE: DNA
<213> ORGANISM: Artificial Sequence
<220> FEATURE:
<223> OTHER INFORMATION: GLUT4EX11 963

<400> SEQUENCE: 514
cgatctcctg acctygtgat ctgcctgcc                                    29

<210> SEQ ID NO 515
<211> LENGTH: 29
<212> TYPE: DNA
<213> ORGANISM: Artificial Sequence
<220> FEATURE:
<223> OTHER INFORMATION: GLUT4EX3 112

<400> SEQUENCE: 515
tccaggcacc ctcascaccc tctgggccc                                    29

<210> SEQ ID NO 516
<211> LENGTH: 29
<212> TYPE: DNA
<213> ORGANISM: Artificial Sequence
<220> FEATURE:
<223> OTHER INFORMATION: GLUT4EX4 96

<400> SEQUENCE: 516
atgggcctgg ccaaygctgc tgcctccta                                    29

<210> SEQ ID NO 517
<211> LENGTH: 29
<212> TYPE: DNA
<213> ORGANISM: Artificial Sequence
<220> FEATURE:
<223> OTHER INFORMATION: GLUT4EX7 19
```

```
<400> SEQUENCE: 517
tcaggcctga ccttyccttc tccaggtct                              29

<210> SEQ ID NO 518
<211> LENGTH: 29
<212> TYPE: DNA
<213> ORGANISM: Artificial Sequence
<220> FEATURE:
<223> OTHER INFORMATION: GLUT4EX7 227

<400> SEQUENCE: 518
atgctgtatg tgtgsagcag cctccaggc                              29

<210> SEQ ID NO 519
<211> LENGTH: 29
<212> TYPE: DNA
<213> ORGANISM: Artificial Sequence
<220> FEATURE:
<223> OTHER INFORMATION: GLUT5EX1 184

<400> SEQUENCE: 519
aaaaggaggt gagcrgcact ctgcccttc                              29

<210> SEQ ID NO 520
<211> LENGTH: 29
<212> TYPE: DNA
<213> ORGANISM: Artificial Sequence
<220> FEATURE:
<223> OTHER INFORMATION: GNB3EX1 184

<400> SEQUENCE: 520
gacagatggg gaacmctgtg cctccctga                              29

<210> SEQ ID NO 521
<211> LENGTH: 29
<212> TYPE: DNA
<213> ORGANISM: Artificial Sequence
<220> FEATURE:
<223> OTHER INFORMATION: GNB3EX1 201

<400> SEQUENCE: 521
gtgcctccct gaacrgaaat ggcagggga                              29

<210> SEQ ID NO 522
<211> LENGTH: 29
<212> TYPE: DNA
<213> ORGANISM: Artificial Sequence
<220> FEATURE:
<223> OTHER INFORMATION: GNB3EX1 328

<400> SEQUENCE: 522 gccagggggcc agtcragtgt atcacagat                             29

<210> SEQ ID NO 523
<211> LENGTH: 29
<212> TYPE: DNA
<213> ORGANISM: Artificial Sequence
<220> FEATURE:
<223> OTHER INFORMATION: GNB3EX10 144

<400> SEQUENCE: 523
agagcatcat ctgcrgcatc acgtccgtg                              29

<210> SEQ ID NO 524
<211> LENGTH: 29
```

```
<212> TYPE: DNA
<213> ORGANISM: Artificial Sequence
<220> FEATURE:
<223> OTHER INFORMATION: GNB3EX10 155

<400> SEQUENCE: 524
tgcggcatca cgtcygtggc cttctccct                               29

<210> SEQ ID NO 525
<211> LENGTH: 29
<212> TYPE: DNA
<213> ORGANISM: Artificial Sequence
<220> FEATURE:
<223> OTHER INFORMATION: GNB3EX11 129

<400> SEQUENCE: 525
cttcctcaaa atctkgaact gaggaggct                               29

<210> SEQ ID NO 526
<211> LENGTH: 29
<212> TYPE: DNA
<213> ORGANISM: Artificial Sequence
<220> FEATURE:
<223> OTHER INFORMATION: GNB3EX11 254

<400> SEQUENCE: 526
ccactaagct ttctyctttg agggcagtg                               29

<210> SEQ ID NO 527
<211> LENGTH: 29
<212> TYPE: DNA
<213> ORGANISM: Artificial Sequence
<220> FEATURE:
<223> OTHER INFORMATION: GNB3EX11 536

<400> SEQUENCE: 527
tatggctctg gcacyactag ggtcctggc                               29

<210> SEQ ID NO 528
<211> LENGTH: 29
<212> TYPE: DNA
<213> ORGANISM: Artificial Sequence
<220> FEATURE:
<223> OTHER INFORMATION: GSY1EX10 46

<400> SEQUENCE: 528
ggagccttcc cgacrtgaac aagatgctg                               29

<210> SEQ ID NO 529
<211> LENGTH: 29
<212> TYPE: DNA
<213> ORGANISM: Artificial Sequence
<220> FEATURE:
<223> OTHER INFORMATION: GSY1EX12 152

<400> SEQUENCE: 529
ccttggggct acacrccggg tgagtgtag                               29

<210> SEQ ID NO 530
<211> LENGTH: 29
<212> TYPE: DNA
<213> ORGANISM: Artificial Sequence
<220> FEATURE:
<223> OTHER INFORMATION: GSY1EX12 163

<400> SEQUENCE: 530
```

-continued cacaccgggt gagtrtagtg ggcagggga                                              29

<210> SEQ ID NO 531
<211> LENGTH: 29
<212> TYPE: DNA
<213> ORGANISM: Artificial Sequence
<220> FEATURE:
<223> OTHER INFORMATION: GSY1EX15 75

<400> SEQUENCE: 531
ccaaggcctt tccasagcac ttcacctac                                              29

<210> SEQ ID NO 532
<211> LENGTH: 29
<212> TYPE: DNA
<213> ORGANISM: Artificial Sequence
<220> FEATURE:
<223> OTHER INFORMATION: GSY1EX16 152

<400> SEQUENCE: 532
ccgctggagg aagayggcga gcgctacga                                              29

<210> SEQ ID NO 533
<211> LENGTH: 29
<212> TYPE: DNA
<213> ORGANISM: Artificial Sequence
<220> FEATURE:
<223> OTHER INFORMATION: GSY1EX16 210

<400> SEQUENCE: 533
gcaacatccg tgcascagag tggccgcgc                                              29

<210> SEQ ID NO 534
<211> LENGTH: 29
<212> TYPE: DNA
<213> ORGANISM: Artificial Sequence
<220> FEATURE:
<223> OTHER INFORMATION: GSY1EX16 65

<400> SEQUENCE: 534
cggccagcct cggtrccacc gtcgccctc                                              29

<210> SEQ ID NO 535
<211> LENGTH: 29
<212> TYPE: DNA
<213> ORGANISM: Artificial Sequence
<220> FEATURE:
<223> OTHER INFORMATION: GSY1EX2 219

<400> SEQUENCE: 535
ctgcaaggtg ggacrtggcc cagcccagg                                              29

<210> SEQ ID NO 536
<211> LENGTH: 29
<212> TYPE: DNA
<213> ORGANISM: Artificial Sequence
<220> FEATURE:
<223> OTHER INFORMATION: GSY1EX3 117

<400> SEQUENCE: 536
ccctggagcg ctggraggga gagctctgg                                              29

<210> SEQ ID NO 537
<211> LENGTH: 29
<212> TYPE: DNA
<213> ORGANISM: Artificial Sequence

<220> FEATURE:
<223> OTHER INFORMATION: GSY1EX3 134

<400> SEQUENCE: 537
ggagagctct gggayacctg caacatcgg                                29

<210> SEQ ID NO 538
<211> LENGTH: 29
<212> TYPE: DNA
<213> ORGANISM: Artificial Sequence
<220> FEATURE:
<223> OTHER INFORMATION: GSY1EX3 149

<400> SEQUENCE: 538
acctgcaaca tcggrgtgcc gtggtacga                                29

<210> SEQ ID NO 539
<211> LENGTH: 29
<212> TYPE: DNA
<213> ORGANISM: Artificial Sequence
<220> FEATURE:
<223> OTHER INFORMATION: GSY1EX3 53

<400> SEQUENCE: 539
gggcgctggc tgatsgaggg aggccctct                                29

<210> SEQ ID NO 540
<211> LENGTH: 29
<212> TYPE: DNA
<213> ORGANISM: Artificial Sequence
<220> FEATURE:
<223> OTHER INFORMATION: GSY1EX3 53

<400> SEQUENCE: 540
acagtggccc tgtcyctgtt gcccacagt                                29

<210> SEQ ID NO 541
<211> LENGTH: 29
<212> TYPE: DNA
<213> ORGANISM: Artificial Sequence
<220> FEATURE:
<223> OTHER INFORMATION: GSY1EX5 44

<400> SEQUENCE: 541
ttcaacgtgg acaargaagc aggggagag                                29

<210> SEQ ID NO 542
<211> LENGTH: 29
<212> TYPE: DNA
<213> ORGANISM: Artificial Sequence
<220> FEATURE:
<223> OTHER INFORMATION: GSY1EX6 54

<400> SEQUENCE: 542
ccccaatggg ctgartgtga agaagtttt                                29

<210> SEQ ID NO 543
<211> LENGTH: 29
<212> TYPE: DNA
<213> ORGANISM: Artificial Sequence
<220> FEATURE:
<223> OTHER INFORMATION: GSY1EX7 114

<400> SEQUENCE: 543
ggtgctgacg tcttyctgga ggcattggc                                29

```
<210> SEQ ID NO 544
<211> LENGTH: 29
<212> TYPE: DNA
<213> ORGANISM: Artificial Sequence
<220> FEATURE:
<223> OTHER INFORMATION: GSY1EX7 16

<400> SEQUENCE: 544
gctttaccgt gcctkgtggg ttctttagg                                    29

<210> SEQ ID NO 545
<211> LENGTH: 29
<212> TYPE: DNA
<213> ORGANISM: Artificial Sequence
<220> FEATURE:
<223> OTHER INFORMATION: GSY1EX7 17

<400> SEQUENCE: 545
ctttaccgtg ccttstgggt tctttaggc                                    29

<210> SEQ ID NO 546
<211> LENGTH: 29
<212> TYPE: DNA
<213> ORGANISM: Artificial Sequence
<220> FEATURE:
<223> OTHER INFORMATION: GSY1EX8 43

<400> SEQUENCE: 546
ggtgaacggc agcgrgcaga cagtggttg                                    29

<210> SEQ ID NO 547
<211> LENGTH: 29
<212> TYPE: DNA
<213> ORGANISM: Artificial Sequence
<220> FEATURE:
<223> OTHER INFORMATION: HAPTEX1 135

<400> SEQUENCE: 547
gataaagaga cagaytgatg gttcctgcc                                    29

<210> SEQ ID NO 548
<211> LENGTH: 29
<212> TYPE: DNA
<213> ORGANISM: Artificial Sequence
<220> FEATURE:
<223> OTHER INFORMATION: HAPTEX1 188

<400> SEQUENCE: 548
gatttcagga aataytttgg caggtttgt                                    29

<210> SEQ ID NO 549
<211> LENGTH: 29
<212> TYPE: DNA
<213> ORGANISM: Artificial Sequence
<220> FEATURE:
<223> OTHER INFORMATION: HAPTEX1 239

<400> SEQUENCE: 549
cttgggattt gtaakagaac atcacaaga                                    29

<210> SEQ ID NO 550
<211> LENGTH: 29
<212> TYPE: DNA
<213> ORGANISM: Artificial Sequence
<220> FEATURE:
<223> OTHER INFORMATION: HAPTEX1 326
```

<400> SEQUENCE: 550
actggaaaag atagwgacct taccagggc                              29

<210> SEQ ID NO 551
<211> LENGTH: 29
<212> TYPE: DNA
<213> ORGANISM: Artificial Sequence
<220> FEATURE:
<223> OTHER INFORMATION: HAPTEX1 329

<400> SEQUENCE: 551
ggaaaagata gtgascttac cagggccaa                              29

<210> SEQ ID NO 552
<211> LENGTH: 29
<212> TYPE: DNA
<213> ORGANISM: Artificial Sequence
<220> FEATURE:
<223> OTHER INFORMATION: HAPTEX1 369

<400> SEQUENCE: 552
acaggaatta cgaamtggag aaggggag                               29

<210> SEQ ID NO 553
<211> LENGTH: 29
<212> TYPE: DNA
<213> ORGANISM: Artificial Sequence
<220> FEATURE:
<223> OTHER INFORMATION: HAPTEX1 375

<400> SEQUENCE: 553
attacgaaat ggagragggg gagaagtga                              29

<210> SEQ ID NO 554
<211> LENGTH: 29
<212> TYPE: DNA
<213> ORGANISM: Artificial Sequence
<220> FEATURE:
<223> OTHER INFORMATION: HAPTEX4 34

<400> SEQUENCE: 554
tttgtttcag gagtrtacac cttaaatga                              29

<210> SEQ ID NO 555
<211> LENGTH: 29
<212> TYPE: DNA
<213> ORGANISM: Artificial Sequence
<220> FEATURE:
<223> OTHER INFORMATION: HAPTEX6 34

<400> SEQUENCE: 555
tttgtttcag gagtrtacac cttaaacaa                              29

<210> SEQ ID NO 556
<211> LENGTH: 29
<212> TYPE: DNA
<213> ORGANISM: Artificial Sequence
<220> FEATURE:
<223> OTHER INFORMATION: HAPTEX7 1331

<400> SEQUENCE: 556
catgctgttg cctcytcaaa gtgaattag                              29

<210> SEQ ID NO 557

```
<211> LENGTH: 29
<212> TYPE: DNA
<213> ORGANISM: Artificial Sequence
<220> FEATURE:
<223> OTHER INFORMATION: HAPTEX7 367

<400> SEQUENCE: 557
gtgtctgtta atgaragagt gatgcccat                                    29

<210> SEQ ID NO 558
<211> LENGTH: 29
<212> TYPE: DNA
<213> ORGANISM: Artificial Sequence
<220> FEATURE:
<223> OTHER INFORMATION: HAPTEX7 610

<400> SEQUENCE: 558
cacaccttct gtgcyggcat gtctaagta                                    29

<210> SEQ ID NO 559
<211> LENGTH: 29
<212> TYPE: DNA
<213> ORGANISM: Artificial Sequence
<220> FEATURE:
<223> OTHER INFORMATION: HAPTEX7 673

<400> SEQUENCE: 559
gcctttgccg ttcaygacct ggaggagga                                    29

<210> SEQ ID NO 560
<211> LENGTH: 29
<212> TYPE: DNA
<213> ORGANISM: Artificial Sequence
<220> FEATURE:
<223> OTHER INFORMATION: HSD11KEX2 232

<400> SEQUENCE: 560
accaaggccc acacmaccag caccggtca                                    29

<210> SEQ ID NO 561
<211> LENGTH: 29
<212> TYPE: DNA
<213> ORGANISM: Artificial Sequence
<220> FEATURE:
<223> OTHER INFORMATION: HSD11KEX3 139

<400> SEQUENCE: 561
aatttctttg gcgcrctcga gctgaccaa                                    29

<210> SEQ ID NO 562
<211> LENGTH: 29
<212> TYPE: DNA
<213> ORGANISM: Artificial Sequence
<220> FEATURE:
<223> OTHER INFORMATION: HSD11KEX5 951

<400> SEQUENCE: 562
actgtacttc ccaawtgcca cattttaaa                                    29

<210> SEQ ID NO 563
<211> LENGTH: 29
<212> TYPE: DNA
<213> ORGANISM: Artificial Sequence
<220> FEATURE:
<223> OTHER INFORMATION: HSTSCGENE 1392

<400> SEQUENCE: 563
```

```
atcttcgggg ccacyctctc ctctgccct                                              29

<210> SEQ ID NO 564
<211> LENGTH: 29
<212> TYPE: DNA
<213> ORGANISM: Artificial Sequence
<220> FEATURE:
<223> OTHER INFORMATION: HSTSCGENE 1881

<400> SEQUENCE: 564
gccctcagct actcrgtggg cctcaatga                                              29

<210> SEQ ID NO 565
<211> LENGTH: 29
<212> TYPE: DNA
<213> ORGANISM: Artificial Sequence
<220> FEATURE:
<223> OTHER INFORMATION: HSTSCGENE 2139

<400> SEQUENCE: 565
tcggatgtca ttgcygagga cctccgcag                                              29

<210> SEQ ID NO 566
<211> LENGTH: 29
<212> TYPE: DNA
<213> ORGANISM: Artificial Sequence
<220> FEATURE:
<223> OTHER INFORMATION: HSTSCGENE 2595

<400> SEQUENCE: 566
cgtgtgttcg taggyggcca gattaacag                                              29

<210> SEQ ID NO 567
<211> LENGTH: 29
<212> TYPE: DNA
<213> ORGANISM: Artificial Sequence
<220> FEATURE:
<223> OTHER INFORMATION: HSTSCGENE 3269

<400> SEQUENCE: 567
ggtcttgtgt ttatrggcta gagaaatag                                              29

<210> SEQ ID NO 568
<211> LENGTH: 29
<212> TYPE: DNA
<213> ORGANISM: Artificial Sequence
<220> FEATURE:
<223> OTHER INFORMATION: HSTSCGENE 3660

<400> SEQUENCE: 568
ctgcaacctc ctccygggtt caagcattt                                              29

<210> SEQ ID NO 569
<211> LENGTH: 29
<212> TYPE: DNA
<213> ORGANISM: Artificial Sequence
<220> FEATURE:
<223> OTHER INFORMATION: HSTSCGENE 3710

<400> SEQUENCE: 569
tagctgggat tacasgcacc tgccatcac                                              29

<210> SEQ ID NO 570
<211> LENGTH: 29
<212> TYPE: DNA
```

```
<213> ORGANISM: Artificial Sequence
<220> FEATURE:
<223> OTHER INFORMATION: HSTSCGENE 3727

<400> SEQUENCE: 570
acctgccatc acacsagcta attttgta                                          29

<210> SEQ ID NO 571
<211> LENGTH: 29
<212> TYPE: DNA
<213> ORGANISM: Artificial Sequence
<220> FEATURE:
<223> OTHER INFORMATION: HSTSCGENE 3838

<400> SEQUENCE: 571
cccaaagtgc tgggrttaca ggcctgagc                                         29

<210> SEQ ID NO 572
<211> LENGTH: 29
<212> TYPE: DNA
<213> ORGANISM: Artificial Sequence
<220> FEATURE:
<223> OTHER INFORMATION: HUMAPNH1A 3057

<400> SEQUENCE: 572
agggcatctc tgagygtctc tgcctggag                                         29

<210> SEQ ID NO 573
<211> LENGTH: 29
<212> TYPE: DNA
<213> ORGANISM: Artificial Sequence
<220> FEATURE:
<223> OTHER INFORMATION: HUMGFAT 2930

<400> SEQUENCE: 573
atctcctaaa agtgktttttt atttccttg                                        29

<210> SEQ ID NO 574
<211> LENGTH: 29
<212> TYPE: DNA
<213> ORGANISM: Artificial Sequence
<220> FEATURE:
<223> OTHER INFORMATION: HUMGLUTRN 2110

<400> SEQUENCE: 574
ggctatggcc acccsttctg ctggcctgg                                         29

<210> SEQ ID NO 575
<211> LENGTH: 29
<212> TYPE: DNA
<213> ORGANISM: Artificial Sequence
<220> FEATURE:
<223> OTHER INFORMATION: HUMGLUTRN 933

<400> SEQUENCE: 575
gatgatgcgg gagamgaagg tcaccatcc                                         29

<210> SEQ ID NO 576
<211> LENGTH: 29
<212> TYPE: DNA
<213> ORGANISM: Artificial Sequence
<220> FEATURE:
<223> OTHER INFORMATION: HUMGUANCYC 2388

<400> SEQUENCE: 576
attgtcactg aataytgtcc tcgtgggag                                         29
```

<210> SEQ ID NO 577
<211> LENGTH: 29
<212> TYPE: DNA
<213> ORGANISM: Artificial Sequence
<220> FEATURE:
<223> OTHER INFORMATION: HUMGUANCYC 2571

<400> SEQUENCE: 577
cgttttgtgc tcaaratcac agactatgg                              29

<210> SEQ ID NO 578
<211> LENGTH: 29
<212> TYPE: DNA
<213> ORGANISM: Artificial Sequence
<220> FEATURE:
<223> OTHER INFORMATION: HUMGUANCYC 2643

<400> SEQUENCE: 578
gccctctatg ccaaraagct gtggactgc                              29

<210> SEQ ID NO 579
<211> LENGTH: 29
<212> TYPE: DNA
<213> ORGANISM: Artificial Sequence
<220> FEATURE:
<223> OTHER INFORMATION: HUMGUANCYC 2787

<400> SEQUENCE: 579
gagggcctgg acctsagccc caaagagat                              29

<210> SEQ ID NO 580
<211> LENGTH: 29
<212> TYPE: DNA
<213> ORGANISM: Artificial Sequence
<220> FEATURE:
<223> OTHER INFORMATION: HUMGUANCYC 2905

<400> SEQUENCE: 580
agcgatgttg ggctsaggac ccagctgag                              29

<210> SEQ ID NO 581
<211> LENGTH: 29
<212> TYPE: DNA
<213> ORGANISM: Artificial Sequence
<220> FEATURE:
<223> OTHER INFORMATION: HUMGUANCYC 3300

<400> SEQUENCE: 581
gacaactttg atgtstacaa ggtggagac                              29

<210> SEQ ID NO 582
<211> LENGTH: 29
<212> TYPE: DNA
<213> ORGANISM: Artificial Sequence
<220> FEATURE:
<223> OTHER INFORMATION: HUMGUANCYC 3663

<400> SEQUENCE: 582 cttcggggg atgtrgaaat gaagggaaa                               29

<210> SEQ ID NO 583
<211> LENGTH: 29
<212> TYPE: DNA
<213> ORGANISM: Artificial Sequence
<220> FEATURE:

```
<223> OTHER INFORMATION: IAPPEX1-2 199

<400> SEQUENCE: 583
tttatttaga gaaaygcaca cttggtgtt                                29

<210> SEQ ID NO 584
<211> LENGTH: 29
<212> TYPE: DNA
<213> ORGANISM: Artificial Sequence
<220> FEATURE:
<223> OTHER INFORMATION: IAPPEX1-2 358

<400> SEQUENCE: 584
gactgtatca ataamaattt tgatccttg                                29

<210> SEQ ID NO 585
<211> LENGTH: 29
<212> TYPE: DNA
<213> ORGANISM: Artificial Sequence
<220> FEATURE:
<223> OTHER INFORMATION: IAPPEX3 1050

<400> SEQUENCE: 585
taaagtctat tgttygttgt gcttgctgg                                29

<210> SEQ ID NO 586
<211> LENGTH: 29
<212> TYPE: DNA
<213> ORGANISM: Artificial Sequence
<220> FEATURE:
<223> OTHER INFORMATION: IAPPEX3 1076

<400> SEQUENCE: 586
tggtactaag aggcwattta aaagtataa                                29

<210> SEQ ID NO 587
<211> LENGTH: 29
<212> TYPE: DNA
<213> ORGANISM: Artificial Sequence
<220> FEATURE:
<223> OTHER INFORMATION: IAPPEX3 1184

<400> SEQUENCE: 587
tttaagtggc tttcmgcaaa cctcagtca                                29

<210> SEQ ID NO 588
<211> LENGTH: 29
<212> TYPE: DNA
<213> ORGANISM: Artificial Sequence
<220> FEATURE:
<223> OTHER INFORMATION: IAPPEX3 296

<400> SEQUENCE: 588 tgccctttc atctycagtg tgaatatat                                 29

<210> SEQ ID NO 589
<211> LENGTH: 29
<212> TYPE: DNA
<213> ORGANISM: Artificial Sequence
<220> FEATURE:
<223> OTHER INFORMATION: IAPPEX3 848

<400> SEQUENCE: 589
ctccagcctg ggtgrcagag tgagactcg                                29
```

```
<210> SEQ ID NO 590
<211> LENGTH: 29
<212> TYPE: DNA
<213> ORGANISM: Artificial Sequence
<220> FEATURE:
<223> OTHER INFORMATION: IAPPEX3 959

<400> SEQUENCE: 590 ttccttttg cagtrtattt ctgaaatga                                    29

<210> SEQ ID NO 591
<211> LENGTH: 29
<212> TYPE: DNA
<213> ORGANISM: Artificial Sequence
<220> FEATURE:
<223> OTHER INFORMATION: ICAM1EX1 683

<400> SEQUENCE: 591
agagttgcaa cctcmgcctc gctatggct                                   29

<210> SEQ ID NO 592
<211> LENGTH: 29
<212> TYPE: DNA
<213> ORGANISM: Artificial Sequence
<220> FEATURE:
<223> OTHER INFORMATION: ICAM1EX2 115

<400> SEQUENCE: 592
ctgtgaccag cccawgttgt tgggcatag                                   29

<210> SEQ ID NO 593
<211> LENGTH: 29
<212> TYPE: DNA
<213> ORGANISM: Artificial Sequence
<220> FEATURE:
<223> OTHER INFORMATION: ICAM1EX3 151

<400> SEQUENCE: 593
ctccgtgggg agaasgagct gaaacggga                                   29

<210> SEQ ID NO 594
<211> LENGTH: 29
<212> TYPE: DNA
<213> ORGANISM: Artificial Sequence
<220> FEATURE:
<223> OTHER INFORMATION: ICAM1EX4 115

<400> SEQUENCE: 594
tgttccctgg acggkctgtt cccagtctc                                   29

<210> SEQ ID NO 595
<211> LENGTH: 29
<212> TYPE: DNA
<213> ORGANISM: Artificial Sequence
<220> FEATURE:
<223> OTHER INFORMATION: ICAM1EX4 238

<400> SEQUENCE: 595
gtgaccgcag aggaygaggg cacccagcg                                   29

<210> SEQ ID NO 596
<211> LENGTH: 29
<212> TYPE: DNA
<213> ORGANISM: Artificial Sequence
<220> FEATURE:
<223> OTHER INFORMATION: ICAM1EX5 47
```

```
<400> SEQUENCE: 596
ttccggcgcc caacrtgatt ctgacgaag                                    29

<210> SEQ ID NO 597
<211> LENGTH: 29
<212> TYPE: DNA
<213> ORGANISM: Artificial Sequence
<220> FEATURE:
<223> OTHER INFORMATION: ICAM1EX6 18

<400> SEQUENCE: 597
catgtcatct catcrtgttt ttccagatg                                    29

<210> SEQ ID NO 598
<211> LENGTH: 29
<212> TYPE: DNA
<213> ORGANISM: Artificial Sequence
<220> FEATURE:
<223> OTHER INFORMATION: ICAM1EX6 254

<400> SEQUENCE: 598
gggaggtcac ccgcraggtg accgtgaat                                    29

<210> SEQ ID NO 599
<211> LENGTH: 29
<212> TYPE: DNA
<213> ORGANISM: Artificial Sequence
<220> FEATURE:
<223> OTHER INFORMATION: ICAM1EX6 39

<400> SEQUENCE: 599
tccagatggc ccccractgg acgagaggg                                    29

<210> SEQ ID NO 600
<211> LENGTH: 29
<212> TYPE: DNA
<213> ORGANISM: Artificial Sequence
<220> FEATURE:
<223> OTHER INFORMATION: ICAM1EX7 304

<400> SEQUENCE: 600
gcagctacac ctacyggccc tgggacgcc                                    29

<210> SEQ ID NO 601
<211> LENGTH: 29
<212> TYPE: DNA
<213> ORGANISM: Artificial Sequence
<220> FEATURE:
<223> OTHER INFORMATION: ICAM1EX7 869

<400> SEQUENCE: 601
tggcaaaaag atcaratggg gctgggact                                    29

<210> SEQ ID NO 602
<211> LENGTH: 29
<212> TYPE: DNA
<213> ORGANISM: Artificial Sequence
<220> FEATURE:
<223> OTHER INFORMATION: ICAM1EX7 929

<400> SEQUENCE: 602
gagtgatttt tctaycggca caaaagcac                                    29

<210> SEQ ID NO 603
<211> LENGTH: 29
```

-continued

```
<212> TYPE: DNA
<213> ORGANISM: Artificial Sequence
<220> FEATURE:
<223> OTHER INFORMATION: ICAM2EX1 300

<400> SEQUENCE: 603
gagatgtcct ctttyggtta caggaccct                              29

<210> SEQ ID NO 604
<211> LENGTH: 29
<212> TYPE: DNA
<213> ORGANISM: Artificial Sequence
<220> FEATURE:
<223> OTHER INFORMATION: ICAM2EX2 63

<400> SEQUENCE: 604
ggccaaagaa gctgrcggtt gagcccaaa                              29

<210> SEQ ID NO 605
<211> LENGTH: 29
<212> TYPE: DNA
<213> ORGANISM: Artificial Sequence
<220> FEATURE:
<223> OTHER INFORMATION: ICAM2EX3 281

<400> SEQUENCE: 605
ggacttgatg tctcrcggtg gcaacatct                              29

<210> SEQ ID NO 606
<211> LENGTH: 29
<212> TYPE: DNA
<213> ORGANISM: Artificial Sequence
<220> FEATURE:
<223> OTHER INFORMATION: INSEX1 233

<400> SEQUENCE: 606
cagccctgcc tgtcwcccag atcactgtc                              29

<210> SEQ ID NO 607
<211> LENGTH: 29
<212> TYPE: DNA
<213> ORGANISM: Artificial Sequence
<220> FEATURE:
<223> OTHER INFORMATION: INSEX1 247

<400> SEQUENCE: 607
tcccagatca ctgtycttct gccatggcc                              29

<210> SEQ ID NO 608
<211> LENGTH: 29
<212> TYPE: DNA
<213> ORGANISM: Artificial Sequence
<220> FEATURE:
<223> OTHER INFORMATION: INSEX1 453

<400> SEQUENCE: 608
cagggtgagc caacygccca ttgctgccc                              29

<210> SEQ ID NO 609
<211> LENGTH: 29
<212> TYPE: DNA
<213> ORGANISM: Artificial Sequence
<220> FEATURE:
<223> OTHER INFORMATION: INSEX2 14

<400> SEQUENCE: 609
```

```
gaacctgctc tgcgyggcac gtcctggca                                29
```

<210> SEQ ID NO 610
<211> LENGTH: 29
<212> TYPE: DNA
<213> ORGANISM: Artificial Sequence
<220> FEATURE:
<223> OTHER INFORMATION: KALSTEX1 133

<400> SEQUENCE: 610

```
ctgctcctcc tgctkgttgg actactggc                                29
```

<210> SEQ ID NO 611
<211> LENGTH: 29
<212> TYPE: DNA
<213> ORGANISM: Artificial Sequence
<220> FEATURE:
<223> OTHER INFORMATION: KALSTEX1 511

<400> SEQUENCE: 611

```
catgggctgg aaacrcgcgt gggcagtgc                                29
```

<210> SEQ ID NO 612
<211> LENGTH: 29
<212> TYPE: DNA
<213> ORGANISM: Artificial Sequence
<220> FEATURE:
<223> OTHER INFORMATION: KALSTEX2 318

<400> SEQUENCE: 612

```
gtaatcagtg tgctwtgggg gctgaatct                                29
```

<210> SEQ ID NO 613
<211> LENGTH: 29
<212> TYPE: DNA
<213> ORGANISM: Artificial Sequence
<220> FEATURE:
<223> OTHER INFORMATION: KALSTEX2 79

<400> SEQUENCE: 613

```
actcccaaag acttytatgt tgatgagaa                                29
```

<210> SEQ ID NO 614
<211> LENGTH: 29
<212> TYPE: DNA
<213> ORGANISM: Artificial Sequence
<220> FEATURE:
<223> OTHER INFORMATION: KALSTEX3 17

<400> SEQUENCE: 614

```
aatgttctaa ctcartgccc ctttcagga                                29
```

<210> SEQ ID NO 615
<211> LENGTH: 29
<212> TYPE: DNA
<213> ORGANISM: Artificial Sequence
<220> FEATURE:
<223> OTHER INFORMATION: KALSTEX3 91

<400> SEQUENCE: 615

```
ctggctccta tgtaytagat cagattttg                                29
```

<210> SEQ ID NO 616
<211> LENGTH: 29
<212> TYPE: DNA
<213> ORGANISM: Artificial Sequence

<220> FEATURE:
<223> OTHER INFORMATION: KLKEX1 105

<400> SEQUENCE: 616
agggcattct gaagkccaag gcttatatt                                29

<210> SEQ ID NO 617
<211> LENGTH: 29
<212> TYPE: DNA
<213> ORGANISM: Artificial Sequence
<220> FEATURE:
<223> OTHER INFORMATION: KLKEX3 253

<400> SEQUENCE: 617
tggagttgcc caccsaggaa cccgaagtg                                29

<210> SEQ ID NO 618
<211> LENGTH: 29
<212> TYPE: DNA
<213> ORGANISM: Artificial Sequence
<220> FEATURE:
<223> OTHER INFORMATION: KLKEX3 50

<400> SEQUENCE: 618
gctctggctg ggtcrccaca acttgtttg                                29

<210> SEQ ID NO 619
<211> LENGTH: 29
<212> TYPE: DNA
<213> ORGANISM: Artificial Sequence
<220> FEATURE:
<223> OTHER INFORMATION: KLKEX4 110

<400> SEQUENCE: 619
ccacgtccag aaggwgacag acttcatgc                                29

<210> SEQ ID NO 620
<211> LENGTH: 29
<212> TYPE: DNA
<213> ORGANISM: Artificial Sequence
<220> FEATURE:
<223> OTHER INFORMATION: KLKEX4 88

<400> SEQUENCE: 620
ctaatgatga gtgcraaaaa gcccacgtc                                29

<210> SEQ ID NO 621
<211> LENGTH: 29
<212> TYPE: DNA
<213> ORGANISM: Artificial Sequence
<220> FEATURE:
<223> OTHER INFORMATION: KLKEX5 318

<400> SEQUENCE: 621
ccccagctgt gtcartctca tggcctgga                                29

<210> SEQ ID NO 622
<211> LENGTH: 29
<212> TYPE: DNA
<213> ORGANISM: Artificial Sequence
<220> FEATURE:
<223> OTHER INFORMATION: MRLEX1B 156

<400> SEQUENCE: 622
ccgatcagcc aataytggac ttgctggtg                                29

-continued

<210> SEQ ID NO 623
<211> LENGTH: 29
<212> TYPE: DNA
<213> ORGANISM: Artificial Sequence
<220> FEATURE:
<223> OTHER INFORMATION: MRLEX1B 16

<400> SEQUENCE: 623
gggcgggtgc ccgcstcccc ctctgcgcg                29

<210> SEQ ID NO 624
<211> LENGTH: 29
<212> TYPE: DNA
<213> ORGANISM: Artificial Sequence
<220> FEATURE:
<223> OTHER INFORMATION: MRLEX2 1338

<400> SEQUENCE: 624
ctcttttaaa gggamtccaa cagtaaacc                29

<210> SEQ ID NO 625
<211> LENGTH: 29
<212> TYPE: DNA
<213> ORGANISM: Artificial Sequence
<220> FEATURE:
<223> OTHER INFORMATION: MRLEX2 1405

<400> SEQUENCE: 625
gatgataaag actaytattc cctatcagg                29

<210> SEQ ID NO 626
<211> LENGTH: 29
<212> TYPE: DNA
<213> ORGANISM: Artificial Sequence
<220> FEATURE:
<223> OTHER INFORMATION: MRLEX2 1617

<400> SEQUENCE: 626
aatatcttta tcacratcgg ctagagacc                29

<210> SEQ ID NO 627
<211> LENGTH: 29
<212> TYPE: DNA
<213> ORGANISM: Artificial Sequence
<220> FEATURE:
<223> OTHER INFORMATION: MRLEX2 1668

<400> SEQUENCE: 627
ctttcctcct gtcartactt tagtggagt                29

<210> SEQ ID NO 628
<211> LENGTH: 29
<212> TYPE: DNA
<213> ORGANISM: Artificial Sequence
<220> FEATURE:
<223> OTHER INFORMATION: MRLEX2 1696

<400> SEQUENCE: 628
tcatggaaat cacayggcga cctgtcgtc                29

<210> SEQ ID NO 629
<211> LENGTH: 29
<212> TYPE: DNA
<213> ORGANISM: Artificial Sequence
<220> FEATURE:
<223> OTHER INFORMATION: MRLEX2 1720

<400> SEQUENCE: 629
tcgtctagaa gaagygatgg gtatccggt 29

<210> SEQ ID NO 630
<211> LENGTH: 29
<212> TYPE: DNA
<213> ORGANISM: Artificial Sequence
<220> FEATURE:
<223> OTHER INFORMATION: MRLEX9 1326

<400> SEQUENCE: 630
ggaatgacac actgyggtgt ctgcagctc 29

<210> SEQ ID NO 631
<211> LENGTH: 29
<212> TYPE: DNA
<213> ORGANISM: Artificial Sequence
<220> FEATURE:
<223> OTHER INFORMATION: MRLEX9 1572

<400> SEQUENCE: 631
gttaaagatc agctrttccc ttctgatct 29

<210> SEQ ID NO 632
<211> LENGTH: 29
<212> TYPE: DNA
<213> ORGANISM: Artificial Sequence
<220> FEATURE:
<223> OTHER INFORMATION: MRLEX9 1670

<400> SEQUENCE: 632
ggcccatctt ggcarggttc agtctgaat 29

<210> SEQ ID NO 633
<211> LENGTH: 29
<212> TYPE: DNA
<213> ORGANISM: Artificial Sequence
<220> FEATURE:
<223> OTHER INFORMATION: MRLEX9 1964

<400> SEQUENCE: 633
aatcttttaa aaatratgat aatcatcag 29

<210> SEQ ID NO 634
<211> LENGTH: 29
<212> TYPE: DNA
<213> ORGANISM: Artificial Sequence
<220> FEATURE:
<223> OTHER INFORMATION: MRLEX9 247

<400> SEQUENCE: 634
acctgttttt aacaygtgat ggttgattc 29

<210> SEQ ID NO 635
<211> LENGTH: 29
<212> TYPE: DNA
<213> ORGANISM: Artificial Sequence
<220> FEATURE:
<223> OTHER INFORMATION: MRLEX9 2551

<400> SEQUENCE: 635
ccaaattgtc tgtcygctct tattttgt 29

<210> SEQ ID NO 636

```
<211> LENGTH: 29
<212> TYPE: DNA
<213> ORGANISM: Artificial Sequence
<220> FEATURE:
<223> OTHER INFORMATION: MRLEX9 2635

<400> SEQUENCE: 636
tcatataatt taaaraaaca ctaaattag                               29

<210> SEQ ID NO 637
<211> LENGTH: 29
<212> TYPE: DNA
<213> ORGANISM: Artificial Sequence
<220> FEATURE:
<223> OTHER INFORMATION: MRLEX9 869

<400> SEQUENCE: 637
tttgctgtgc tgtasattac tgtatgtat                               29

<210> SEQ ID NO 638
<211> LENGTH: 29
<212> TYPE: DNA
<213> ORGANISM: Artificial Sequence
<220> FEATURE:
<223> OTHER INFORMATION: MRLEX9 916

<400> SEQUENCE: 638
aataaggtat aaggmtcttt tgtaaatga                               29

<210> SEQ ID NO 639
<211> LENGTH: 29
<212> TYPE: DNA
<213> ORGANISM: Artificial Sequence
<220> FEATURE:
<223> OTHER INFORMATION: NCX1EX12 1135

<400> SEQUENCE: 639
agattcccag gaacrtgcaa aatcctttc                               29

<210> SEQ ID NO 640
<211> LENGTH: 29
<212> TYPE: DNA
<213> ORGANISM: Artificial Sequence
<220> FEATURE:
<223> OTHER INFORMATION: NCX1EX12 1190

<400> SEQUENCE: 640
tgattggcaa ggtcyttctt ccagcattc                               29

<210> SEQ ID NO 641
<211> LENGTH: 29
<212> TYPE: DNA
<213> ORGANISM: Artificial Sequence
<220> FEATURE:
<223> OTHER INFORMATION: NCX1EX12 1298

<400> SEQUENCE: 641
ataaccccat tcaaraagca catcatcgt                               29

<210> SEQ ID NO 642
<211> LENGTH: 29
<212> TYPE: DNA
<213> ORGANISM: Artificial Sequence
<220> FEATURE:
<223> OTHER INFORMATION: NCX1EX12 1366

<400> SEQUENCE: 642
```

```
cgttgcttgg gattstctgt cagttttat                              29

<210> SEQ ID NO 643
<211> LENGTH: 29
<212> TYPE: DNA
<213> ORGANISM: Artificial Sequence
<220> FEATURE:
<223> OTHER INFORMATION: NCX1EX12 1407

<400> SEQUENCE: 643
ccatggcttg cacartcctg ttccagtca                              29

<210> SEQ ID NO 644
<211> LENGTH: 29
<212> TYPE: DNA
<213> ORGANISM: Artificial Sequence
<220> FEATURE:
<223> OTHER INFORMATION: NCX1EX12 1841

<400> SEQUENCE: 644
acccattaat tcagsaaggc caaggagaa                              29

<210> SEQ ID NO 645
<211> LENGTH: 29
<212> TYPE: DNA
<213> ORGANISM: Artificial Sequence
<220> FEATURE:
<223> OTHER INFORMATION: NCX1EX12 2099

<400> SEQUENCE: 645
gaaagaagcc agggygacca acgggcctt                              29

<210> SEQ ID NO 646
<211> LENGTH: 29
<212> TYPE: DNA
<213> ORGANISM: Artificial Sequence
<220> FEATURE:
<223> OTHER INFORMATION: NCX1EX12 2123

<400> SEQUENCE: 646
gcctttaaaa gtgttgtctc ctctactta                              29

<210> SEQ ID NO 647
<211> LENGTH: 29
<212> TYPE: DNA
<213> ORGANISM: Artificial Sequence
<220> FEATURE:
<223> OTHER INFORMATION: NCX1EX12 2614

<400> SEQUENCE: 647
tgtgattact atttycatga gtaaaagtg                              29

<210> SEQ ID NO 648
<211> LENGTH: 29
<212> TYPE: DNA
<213> ORGANISM: Artificial Sequence
<220> FEATURE:
<223> OTHER INFORMATION: NCX1EX12 2810

<400> SEQUENCE: 648
tttatctttg accgrcttgc agataaata                              29

<210> SEQ ID NO 649
<211> LENGTH: 29
<212> TYPE: DNA
```

```
<213> ORGANISM: Artificial Sequence
<220> FEATURE:
<223> OTHER INFORMATION: NCX1EX12 2832

<400> SEQUENCE: 649
ataaatatat ctctscattt taaaccaag                                            29

<210> SEQ ID NO 650
<211> LENGTH: 29
<212> TYPE: DNA
<213> ORGANISM: Artificial Sequence
<220> FEATURE:
<223> OTHER INFORMATION: NCX1EX12 3079

<400> SEQUENCE: 650
taaacattag aaaamttttt gcactcatt                                            29

<210> SEQ ID NO 651
<211> LENGTH: 29
<212> TYPE: DNA
<213> ORGANISM: Artificial Sequence
<220> FEATURE:
<223> OTHER INFORMATION: NCX1EX12 3193

<400> SEQUENCE: 651
ttgaaagctt tttgstttgt ttgcttttt                                            29

<210> SEQ ID NO 652
<211> LENGTH: 29
<212> TYPE: DNA
<213> ORGANISM: Artificial Sequence
<220> FEATURE:
<223> OTHER INFORMATION: NCX1EX12 664

<400> SEQUENCE: 652
tctctccagg ttgayaaatc cttaaggct                                            29

<210> SEQ ID NO 653
<211> LENGTH: 29
<212> TYPE: DNA
<213> ORGANISM: Artificial Sequence
<220> FEATURE:
<223> OTHER INFORMATION: NCX1EX12 709

<400> SEQUENCE: 653
ttggttttgt tttcrgtgga gctggggag                                            29

<210> SEQ ID NO 654
<211> LENGTH: 29
<212> TYPE: DNA
<213> ORGANISM: Artificial Sequence
<220> FEATURE:
<223> OTHER INFORMATION: NCX1EX12 948

<400> SEQUENCE: 654
agcatgtctt catcrtatta ccaaagttc                                            29

<210> SEQ ID NO 655
<211> LENGTH: 29
<212> TYPE: DNA
<213> ORGANISM: Artificial Sequence
<220> FEATURE:
<223> OTHER INFORMATION: NCX1EX4 59

<400> SEQUENCE: 655
tagaatattt gaccrtgagg aatatgaga                                            29
```

<210> SEQ ID NO 656
<211> LENGTH: 29
<212> TYPE: DNA
<213> ORGANISM: Artificial Sequence
<220> FEATURE:
<223> OTHER INFORMATION: NCX1EX9 66

<400> SEQUENCE: 656
actgaccagc aaagwggaag aggagaggc                                    29

<210> SEQ ID NO 657
<211> LENGTH: 29
<212> TYPE: DNA
<213> ORGANISM: Artificial Sequence
<220> FEATURE:
<223> OTHER INFORMATION: NETEX11 123

<400> SEQUENCE: 657
cgtcagtcct gcctkcctcc tggtgtgta                                    29

<210> SEQ ID NO 658
<211> LENGTH: 29
<212> TYPE: DNA
<213> ORGANISM: Artificial Sequence
<220> FEATURE:
<223> OTHER INFORMATION: NETEX12 81

<400> SEQUENCE: 658
tcacctacga cgacyacatc ttcccgccc                                    29

<210> SEQ ID NO 659
<211> LENGTH: 29
<212> TYPE: DNA
<213> ORGANISM: Artificial Sequence
<220> FEATURE:
<223> OTHER INFORMATION: NETEX13 50

<400> SEQUENCE: 659
gcctatggca tcacrccaga gaacgagca                                    29

<210> SEQ ID NO 660
<211> LENGTH: 29
<212> TYPE: DNA
<213> ORGANISM: Artificial Sequence
<220> FEATURE:
<223> OTHER INFORMATION: NETEX14 29

<400> SEQUENCE: 660
tgtctttctc tgcasttgca acactggct                                    29

<210> SEQ ID NO 661
<211> LENGTH: 29
<212> TYPE: DNA
<213> ORGANISM: Artificial Sequence
<220> FEATURE:
<223> OTHER INFORMATION: NETEX5 121

<400> SEQUENCE: 661
ctccaatggc atcamtgcct acctgcaca                                    29

<210> SEQ ID NO 662
<211> LENGTH: 29
<212> TYPE: DNA
<213> ORGANISM: Artificial Sequence
<220> FEATURE:

<223> OTHER INFORMATION: NETEX5 175

<400> SEQUENCE: 662
cacggtcagt gctcrgtgac caccaagcc                              29

<210> SEQ ID NO 663
<211> LENGTH: 29
<212> TYPE: DNA
<213> ORGANISM: Artificial Sequence
<220> FEATURE:
<223> OTHER INFORMATION: NETEX5 83

<400> SEQUENCE: 663
ttcgtgctcc tggtscatgg cgtcacgct                              29

<210> SEQ ID NO 664
<211> LENGTH: 29
<212> TYPE: DNA
<213> ORGANISM: Artificial Sequence
<220> FEATURE:
<223> OTHER INFORMATION: NETEX7 112

<400> SEQUENCE: 664
tccttggtta catgscccat gaacacaag                              29

<210> SEQ ID NO 665
<211> LENGTH: 29
<212> TYPE: DNA
<213> ORGANISM: Artificial Sequence
<220> FEATURE:
<223> OTHER INFORMATION: NETEX7 131

<400> SEQUENCE: 665
tgaacacaag gtcarcattg aggatgtgg                              29

<210> SEQ ID NO 666
<211> LENGTH: 29
<212> TYPE: DNA
<213> ORGANISM: Artificial Sequence
<220> FEATURE:
<223> OTHER INFORMATION: NETEX7 73

<400> SEQUENCE: 666
gtatcaccag cttcstctct gggttcgcc                              29

<210> SEQ ID NO 667
<211> LENGTH: 29
<212> TYPE: DNA
<213> ORGANISM: Artificial Sequence
<220> FEATURE:
<223> OTHER INFORMATION: NETEX8 17

<400> SEQUENCE: 667
tgatgaggtc cttgmtgttt cttacagga                              29

<210> SEQ ID NO 668
<211> LENGTH: 29
<212> TYPE: DNA
<213> ORGANISM: Artificial Sequence
<220> FEATURE:
<223> OTHER INFORMATION: NETEX9 157

<400> SEQUENCE: 668
gttctgcata accarggtga gtagggct                               29

```
<210> SEQ ID NO 669
<211> LENGTH: 29
<212> TYPE: DNA
<213> ORGANISM: Artificial Sequence
<220> FEATURE:
<223> OTHER INFORMATION: NETEX9 56

<400> SEQUENCE: 669
gaggctgtca tcacrggcct ggcagatga                              29

<210> SEQ ID NO 670
<211> LENGTH: 29
<212> TYPE: DNA
<213> ORGANISM: Artificial Sequence
<220> FEATURE:
<223> OTHER INFORMATION: NPYEX1 112

<400> SEQUENCE: 670
gcgctggccg aggcrtaccc ctccaagcc                              29

<210> SEQ ID NO 671
<211> LENGTH: 29
<212> TYPE: DNA
<213> ORGANISM: Artificial Sequence
<220> FEATURE:
<223> OTHER INFORMATION: NPYEX1 178

<400> SEQUENCE: 671
gccagatact actcrgcgct gggacacta                              29

<210> SEQ ID NO 672
<211> LENGTH: 29
<212> TYPE: DNA
<213> ORGANISM: Artificial Sequence
<220> FEATURE:
<223> OTHER INFORMATION: NPYEX1 92

<400> SEQUENCE: 672
ccctgctcgt gtgcmtgggt gcgctggcc                              29

<210> SEQ ID NO 673
<211> LENGTH: 29
<212> TYPE: DNA
<213> ORGANISM: Artificial Sequence
<220> FEATURE:
<223> OTHER INFORMATION: NPYEX2 45

<400> SEQUENCE: 673
tatggaaaac gatcyagccc agagacact                              29

<210> SEQ ID NO 674
<211> LENGTH: 29
<212> TYPE: DNA
<213> ORGANISM: Artificial Sequence
<220> FEATURE:
<223> OTHER INFORMATION: NPYE3 100

<400> SEQUENCE: 674
cctattttca gcccrtattt catcgtgta                              29

<210> SEQ ID NO 675
<211> LENGTH: 29
<212> TYPE: DNA
<213> ORGANISM: Artificial Sequence
<220> FEATURE:
<223> OTHER INFORMATION: NPYEX3 78
```

-continued

<400> SEQUENCE: 675
gagacttgct ctctkgcctt ttcctattt                                    29

<210> SEQ ID NO 676
<211> LENGTH: 29
<212> TYPE: DNA
<213> ORGANISM: Artificial Sequence
<220> FEATURE:
<223> OTHER INFORMATION: NPYR1EX2 144

<400> SEQUENCE: 676
aacatactgt ccatktgtct aaaataatc                                    29

<210> SEQ ID NO 677
<211> LENGTH: 29
<212> TYPE: DNA
<213> ORGANISM: Artificial Sequence
<220> FEATURE:
<223> OTHER INFORMATION: NPYR1EX3 451

<400> SEQUENCE: 677
agtcgcattt aaaamaatca acaacaatg                                    29

<210> SEQ ID NO 678
<211> LENGTH: 29
<212> TYPE: DNA
<213> ORGANISM: Artificial Sequence
<220> FEATURE:
<223> OTHER INFORMATION: PGISEX1 196

<400> SEQUENCE: 678
gcatataatc tcttmcttcc tgtaaatcc                                    29

<210> SEQ ID NO 679
<211> LENGTH: 29
<212> TYPE: DNA
<213> ORGANISM: Artificial Sequence
<220> FEATURE:
<223> OTHER INFORMATION: PGISEX1 396

<400> SEQUENCE: 679
tgcggggagc agggkttctc ccagagcgc                                    29

<210> SEQ ID NO 680
<211> LENGTH: 29
<212> TYPE: DNA
<213> ORGANISM: Artificial Sequence
<220> FEATURE:
<223> OTHER INFORMATION: PGISEX1 419

<400> SEQUENCE: 680
gagcgccccg gtccracccc tgcggacct                                    29

<210> SEQ ID NO 681
<211> LENGTH: 29
<212> TYPE: DNA
<213> ORGANISM: Artificial Sequence
<220> FEATURE:
<223> OTHER INFORMATION: PGISEX1 568

<400> SEQUENCE: 681
ccccgccagc cccgycagcc ccgccagcc                                    29

<210> SEQ ID NO 682
<211> LENGTH: 29

```
<212> TYPE: DNA
<213> ORGANISM: Artificial Sequence
<220> FEATURE:
<223> OTHER INFORMATION: PGISEX1 636

<400> SEQUENCE: 682
cactgttgct gctgytgcta ctgagccgc                                    29

<210> SEQ ID NO 683
<211> LENGTH: 29
<212> TYPE: DNA
<213> ORGANISM: Artificial Sequence
<220> FEATURE:
<223> OTHER INFORMATION: PGISEX10 1255

<400> SEQUENCE: 683
ttctgcattc acagygsctc ctggrcctg                                    29

<210> SEQ ID NO 684
<211> LENGTH: 29
<212> TYPE: DNA
<213> ORGANISM: Artificial Sequence
<220> FEATURE:
<223> OTHER INFORMATION: PGISEX10 149

<400> SEQUENCE: 684
gctaccgcat ccgcycatga cacagggag                                    29

<210> SEQ ID NO 685
<211> LENGTH: 29
<212> TYPE: DNA
<213> ORGANISM: Artificial Sequence
<220> FEATURE:
<223> OTHER INFORMATION: PGISEX10 1500

<400> SEQUENCE: 685
cctggccaac atggygaaac cccgtctct                                    29

<210> SEQ ID NO 686
<211> LENGTH: 29
<212> TYPE: DNA
<213> ORGANISM: Artificial Sequence
<220> FEATURE:
<223> OTHER INFORMATION: PGISEX10 1505

<400> SEQUENCE: 686
ccaacatggc gaaaycccgt ctctactaa                                    29

<210> SEQ ID NO 687
<211> LENGTH: 29
<212> TYPE: DNA
<213> ORGANISM: Artificial Sequence
<220> FEATURE:
<223> OTHER INFORMATION: PGISEX10 1521

<400> SEQUENCE: 687
ccgtctctac taaamataaa aaaattagt                                    29

<210> SEQ ID NO 688
<211> LENGTH: 29
<212> TYPE: DNA
<213> ORGANISM: Artificial Sequence
<220> FEATURE:
<223> OTHER INFORMATION: PGISEX10 1525

<400> SEQUENCE: 688
```

```
ctctactaaa catamaaaaa ttagtcagg                                29
```

<210> SEQ ID NO 689
<211> LENGTH: 29
<212> TYPE: DNA
<213> ORGANISM: Artificial Sequence
<220> FEATURE:
<223> OTHER INFORMATION: PGISEX10 1544

<400> SEQUENCE: 689

```
attagtcagg tgtgscggtg ccgtgcctg                                29
```

<210> SEQ ID NO 690
<211> LENGTH: 29
<212> TYPE: DNA
<213> ORGANISM: Artificial Sequence
<220> FEATURE:
<223> OTHER INFORMATION: PGISEX10 1760

<400> SEQUENCE: 690

```
ttatgatgct attktatta atataaagt                                29
```

<210> SEQ ID NO 691
<211> LENGTH: 29
<212> TYPE: DNA
<213> ORGANISM: Artificial Sequence
<220> FEATURE:
<223> OTHER INFORMATION: PGISEX10 1776

<400> SEQUENCE: 691

```
attaatataa agtcytgttt attgagacc                                29
```

<210> SEQ ID NO 692
<211> LENGTH: 29
<212> TYPE: DNA
<213> ORGANISM: Artificial Sequence
<220> FEATURE:
<223> OTHER INFORMATION: PGISEX10 1852

<400> SEQUENCE: 692

```
cagcatctct atgargagaa ggagggttg                                29
```

<210> SEQ ID NO 693
<211> LENGTH: 29
<212> TYPE: DNA
<213> ORGANISM: Artificial Sequence
<220> FEATURE:
<223> OTHER INFORMATION: PGISEX10 2474

<400> SEQUENCE: 693

```
cgcaggctgc aaccytggtg tgctgggcg                                29
```

<210> SEQ ID NO 694
<211> LENGTH: 29
<212> TYPE: DNA
<213> ORGANISM: Artificial Sequence
<220> FEATURE:
<223> OTHER INFORMATION: PGISEX10 2636

<400> SEQUENCE: 694

```
actcaaggaa aagaygtgct cccaccagg                                29
```

<210> SEQ ID NO 695
<211> LENGTH: 29
<212> TYPE: DNA
<213> ORGANISM: Artificial Sequence

```
<220> FEATURE:
<223> OTHER INFORMATION: PGISEX10 270

<400> SEQUENCE: 695
gctagcatta ccacytccct gcttttctc                                              29

<210> SEQ ID NO 696
<211> LENGTH: 29
<212> TYPE: DNA
<213> ORGANISM: Artificial Sequence
<220> FEATURE:
<223> OTHER INFORMATION: PGISEX10 2967

<400> SEQUENCE: 696
ttgagatgga gtctygctct gctgcccag                                              29

<210> SEQ ID NO 697
<211> LENGTH: 29
<212> TYPE: DNA
<213> ORGANISM: Artificial Sequence
<220> FEATURE:
<223> OTHER INFORMATION: PGISEX10 2974

<400> SEQUENCE: 697
ggagtctcgc tctgytgccc aggctagag                                              29

<210> SEQ ID NO 698
<211> LENGTH: 29
<212> TYPE: DNA
<213> ORGANISM: Artificial Sequence
<220> FEATURE:
<223> OTHER INFORMATION: PGISEX10 3009

<400> SEQUENCE: 698
ggcgtgatct cggcycactg caagctctg                                              29

<210> SEQ ID NO 699
<211> LENGTH: 29
<212> TYPE: DNA
<213> ORGANISM: Artificial Sequence
<220> FEATURE:
<223> OTHER INFORMATION: PGISEX10 3022

<400> SEQUENCE: 699
ctcactgcaa gctcygcctc ccgtgttca                                              29

<210> SEQ ID NO 700
<211> LENGTH: 29
<212> TYPE: DNA
<213> ORGANISM: Artificial Sequence
<220> FEATURE:
<223> OTHER INFORMATION: PGISEX10 3061

<400> SEQUENCE: 700
ctgcctcagc ctccygagta gctgggact                                              29

<210> SEQ ID NO 701
<211> LENGTH: 29
<212> TYPE: DNA
<213> ORGANISM: Artificial Sequence
<220> FEATURE:
<223> OTHER INFORMATION: PGISEX10 308

<400> SEQUENCE: 701
tgggtccagg ggagkgaaaa gctaagagg                                              29
```

<210> SEQ ID NO 702
<211> LENGTH: 29
<212> TYPE: DNA
<213> ORGANISM: Artificial Sequence
<220> FEATURE:
<223> OTHER INFORMATION: PGISEX10 3082

<400> SEQUENCE: 702
ctgggactac aggcrcccgc caccacacc                              29

<210> SEQ ID NO 703
<211> LENGTH: 29
<212> TYPE: DNA
<213> ORGANISM: Artificial Sequence
<220> FEATURE:
<223> OTHER INFORMATION: PGISEX10 3139

<400> SEQUENCE: 703
tgggatttca ccgtrttagc caggatggt                              29

<210> SEQ ID NO 704
<211> LENGTH: 29
<212> TYPE: DNA
<213> ORGANISM: Artificial Sequence
<220> FEATURE:
<223> OTHER INFORMATION: PGISEX10 3140

<400> SEQUENCE: 704
gggatttcac cgtaytagcc aggatggtc                              29

<210> SEQ ID NO 705
<211> LENGTH: 29
<212> TYPE: DNA
<213> ORGANISM: Artificial Sequence
<220> FEATURE:
<223> OTHER INFORMATION: PGISEX10 3186

<400> SEQUENCE: 705
tgatctgccc gcctyggcct cccaaagtg                              29

<210> SEQ ID NO 706
<211> LENGTH: 29
<212> TYPE: DNA
<213> ORGANISM: Artificial Sequence
<220> FEATURE:
<223> OTHER INFORMATION: PGISEX10 3214

<400> SEQUENCE: 706
gctgggatta caggygtgag ccaccgcgc                              29

<210> SEQ ID NO 707
<211> LENGTH: 29
<212> TYPE: DNA
<213> ORGANISM: Artificial Sequence
<220> FEATURE:
<223> OTHER INFORMATION: PGISEX10 3217

<400> SEQUENCE: 707
gggattacag gtgtragcca ccgcgccca                              29

<210> SEQ ID NO 708
<211> LENGTH: 29
<212> TYPE: DNA
<213> ORGANISM: Artificial Sequence
<220> FEATURE:
<223> OTHER INFORMATION: PGISEX10 3244

```
<400> SEQUENCE: 708
cagccaagaa taaamtactc ttaagttga                                29

<210> SEQ ID NO 709
<211> LENGTH: 29
<212> TYPE: DNA
<213> ORGANISM: Artificial Sequence
<220> FEATURE:
<223> OTHER INFORMATION: PGISEX10 3339

<400> SEQUENCE: 709
gtttaccaaa tattytcctt taaacagac                                29

<210> SEQ ID NO 710
<211> LENGTH: 29
<212> TYPE: DNA
<213> ORGANISM: Artificial Sequence
<220> FEATURE:
<223> OTHER INFORMATION: PGISEX10 3419

<400> SEQUENCE: 710
gcccaggctg gagtrcaatg gcacgatct                                29

<210> SEQ ID NO 711
<211> LENGTH: 29
<212> TYPE: DNA
<213> ORGANISM: Artificial Sequence
<220> FEATURE:
<223> OTHER INFORMATION: PGISEX10 3540

<400> SEQUENCE: 711
caactggttt ttgtwttttt agtagagac                                29

<210> SEQ ID NO 712
<211> LENGTH: 29
<212> TYPE: DNA
<213> ORGANISM: Artificial Sequence
<220> FEATURE:
<223> OTHER INFORMATION: PGISEX10 3651

<400> SEQUENCE: 712
gattacaggc atgarccacc atgcccggc                                29

<210> SEQ ID NO 713
<211> LENGTH: 29
<212> TYPE: DNA
<213> ORGANISM: Artificial Sequence
<220> FEATURE:
<223> OTHER INFORMATION: PGISEX10 3663

<400> SEQUENCE: 713
gagccaccat gcccrgccta aactttgtt                                29

<210> SEQ ID NO 714
<211> LENGTH: 29
<212> TYPE: DNA
<213> ORGANISM: Artificial Sequence
<220> FEATURE:
<223> OTHER INFORMATION: PGISEX10 3774

<400> SEQUENCE: 714
atgaaaaata aattygctgg ggaaggggg                                29

<210> SEQ ID NO 715
```

<211> LENGTH: 29
<212> TYPE: DNA
<213> ORGANISM: Artificial Sequence
<220> FEATURE:
<223> OTHER INFORMATION: PGISEX10 3840

<400> SEQUENCE: 715
tctctgttac aaaaygagat aagcaagtr                                29

<210> SEQ ID NO 716
<211> LENGTH: 29
<212> TYPE: DNA
<213> ORGANISM: Artificial Sequence
<220> FEATURE:
<223> OTHER INFORMATION: PGISEX10 400

<400> SEQUENCE: 716
tcaggctttg tctgytccca attcacctc                                29

<210> SEQ ID NO 717
<211> LENGTH: 29
<212> TYPE: DNA
<213> ORGANISM: Artificial Sequence
<220> FEATURE:
<223> OTHER INFORMATION: PGISEX10 4074

<400> SEQUENCE: 717
gattttaatg attaraaaga ataaacaca                                29

<210> SEQ ID NO 718
<211> LENGTH: 29
<212> TYPE: DNA
<213> ORGANISM: Artificial Sequence
<220> FEATURE:
<223> OTHER INFORMATION: PGISEX10 454

<400> SEQUENCE: 718
aaatgctatt cagayaaggc agaactagg                                29

<210> SEQ ID NO 719
<211> LENGTH: 29
<212> TYPE: DNA
<213> ORGANISM: Artificial Sequence
<220> FEATURE:
<223> OTHER INFORMATION: PGISEX10 573

<400> SEQUENCE: 719
ggatgctggc cacakaaagg ccactcagg                                29

<210> SEQ ID NO 720
<211> LENGTH: 29
<212> TYPE: DNA
<213> ORGANISM: Artificial Sequence
<220> FEATURE:
<223> OTHER INFORMATION: PGISEX10 578

<400> SEQUENCE: 720
ctggccacag aaagrccact caggatgtc                                29

<210> SEQ ID NO 721
<211> LENGTH: 29
<212> TYPE: DNA
<213> ORGANISM: Artificial Sequence
<220> FEATURE:
<223> OTHER INFORMATION: PGISEX10 948

<400> SEQUENCE: 721
ctccttagac tgatmaagcc aaaaaagaa 29

<210> SEQ ID NO 722
<211> LENGTH: 29
<212> TYPE: DNA
<213> ORGANISM: Artificial Sequence
<220> FEATURE:
<223> OTHER INFORMATION: PGISEX3 165

<400> SEQUENCE: 722
cattacagcc ccagwgatga aaaggccag 29

<210> SEQ ID NO 723
<211> LENGTH: 29
<212> TYPE: DNA
<213> ORGANISM: Artificial Sequence
<220> FEATURE:
<223> OTHER INFORMATION: PGISEX3 69

<400> SEQUENCE: 723
tcctacgacg cggtkgtgtg ggagcctcg 29

<210> SEQ ID NO 724
<211> LENGTH: 29
<212> TYPE: DNA
<213> ORGANISM: Artificial Sequence
<220> FEATURE:
<223> OTHER INFORMATION: PGISEX4 143

<400> SEQUENCE: 724
acttctccta cagcytcctg ctcaggtga 29

<210> SEQ ID NO 725
<211> LENGTH: 29
<212> TYPE: DNA
<213> ORGANISM: Artificial Sequence
<220> FEATURE:
<223> OTHER INFORMATION: PGISEX4 93

<400> SEQUENCE: 725
gggcgatgct acagmagcag gcagtggct 29

<210> SEQ ID NO 726
<211> LENGTH: 29
<212> TYPE: DNA
<213> ORGANISM: Artificial Sequence
<220> FEATURE:
<223> OTHER INFORMATION: PGISEX5 79

<400> SEQUENCE: 726
caggcccagg accgygtcca ctcagctga 29

<210> SEQ ID NO 727
<211> LENGTH: 29
<212> TYPE: DNA
<213> ORGANISM: Artificial Sequence
<220> FEATURE:
<223> OTHER INFORMATION: PGISEX6 35

<400> SEQUENCE: 727
gcagtgtcaa aagtygcctg tggaagctg 29

<210> SEQ ID NO 728
<211> LENGTH: 29
<212> TYPE: DNA

```
<213> ORGANISM: Artificial Sequence
<220> FEATURE:
<223> OTHER INFORMATION: PGISEX6 52

<400> SEQUENCE: 728
ctgtggaagc tgctrtcccc agccaggct                                              29

<210> SEQ ID NO 729
<211> LENGTH: 29
<212> TYPE: DNA
<213> ORGANISM: Artificial Sequence
<220> FEATURE:
<223> OTHER INFORMATION: PGISEX6 97

<400> SEQUENCE: 729
cggagcaaat ggctrgagag ttacctgct                                              29

<210> SEQ ID NO 730
<211> LENGTH: 29
<212> TYPE: DNA
<213> ORGANISM: Artificial Sequence
<220> FEATURE:
<223> OTHER INFORMATION: PGISEX8 102

<400> SEQUENCE: 730
ccatggcaga cgggmgagaa ttcaacctg                                              29

<210> SEQ ID NO 731
<211> LENGTH: 29
<212> TYPE: DNA
<213> ORGANISM: Artificial Sequence
<220> FEATURE:
<223> OTHER INFORMATION: PGISEX9 42

<400> SEQUENCE: 731
ttcctgaacc ctgayggatc agagaagaa                                              29

<210> SEQ ID NO 732
<211> LENGTH: 29
<212> TYPE: DNA
<213> ORGANISM: Artificial Sequence
<220> FEATURE:
<223> OTHER INFORMATION: PLA2AEX1 302

<400> SEQUENCE: 732
ccccgcagtc tcaawtcgag gttcccagt                                              29

<210> SEQ ID NO 733
<211> LENGTH: 29
<212> TYPE: DNA
<213> ORGANISM: Artificial Sequence
<220> FEATURE:
<223> OTHER INFORMATION: PLA2AEX2 118

<400> SEQUENCE: 733
gggagtgacc ccttyttgga atacaacaa                                              29

<210> SEQ ID NO 734
<211> LENGTH: 29
<212> TYPE: DNA
<213> ORGANISM: Artificial Sequence
<220> FEATURE:
<223> OTHER INFORMATION: PLA2AEX2 42

<400> SEQUENCE: 734
agtggccgcc gccgmcagcg gcatcagcc                                              29
```

<210> SEQ ID NO 735
<211> LENGTH: 29
<212> TYPE: DNA
<213> ORGANISM: Artificial Sequence
<220> FEATURE:
<223> OTHER INFORMATION: PLA2AEX3 103

<400> SEQUENCE: 735
atttctgctg gacamcccgt acacccaca                                29

<210> SEQ ID NO 736
<211> LENGTH: 29
<212> TYPE: DNA
<213> ORGANISM: Artificial Sequence
<220> FEATURE:
<223> OTHER INFORMATION: PLA2AEX3 104

<400> SEQUENCE: 736
tttctgctgg acaamccgta cacccacac                                29

<210> SEQ ID NO 737
<211> LENGTH: 29
<212> TYPE: DNA
<213> ORGANISM: Artificial Sequence
<220> FEATURE:
<223> OTHER INFORMATION: PLA2AEX3 131

<400> SEQUENCE: 737
acctattcat actcrtgctc tggctcggc                                29

<210> SEQ ID NO 738
<211> LENGTH: 29
<212> TYPE: DNA
<213> ORGANISM: Artificial Sequence
<220> FEATURE:
<223> OTHER INFORMATION: PLA2AEX3 59

<400> SEQUENCE: 738
catgacaact gctaygacca ggccaagaa                                29

<210> SEQ ID NO 739
<211> LENGTH: 29
<212> TYPE: DNA
<213> ORGANISM: Artificial Sequence
<220> FEATURE:
<223> OTHER INFORMATION: PNMTEX3 181

<400> SEQUENCE: 739
gcttggaggc tgtgwgccca gatcttgcc                                29

<210> SEQ ID NO 740
<211> LENGTH: 29
<212> TYPE: DNA
<213> ORGANISM: Artificial Sequence
<220> FEATURE:
<223> OTHER INFORMATION: PNMTEX3 251

<400> SEQUENCE: 740
gcctgggggg caccwcctcc tcatcgggg                                29

<210> SEQ ID NO 741
<211> LENGTH: 29
<212> TYPE: DNA
<213> ORGANISM: Artificial Sequence
<220> FEATURE:

```
<223> OTHER INFORMATION: PNMTEX3 269

<400> SEQUENCE: 741
cctcatcggg gcccwggagg agtcgtggt                                29

<210> SEQ ID NO 742
<211> LENGTH: 29
<212> TYPE: DNA
<213> ORGANISM: Artificial Sequence
<220> FEATURE:
<223> OTHER INFORMATION: PNMTEX3 380

<400> SEQUENCE: 742
ggtccgggac ctccrcacct atatcatgc                                29

<210> SEQ ID NO 743
<211> LENGTH: 29
<212> TYPE: DNA
<213> ORGANISM: Artificial Sequence
<220> FEATURE:
<223> OTHER INFORMATION: PNMTEX3 445

<400> SEQUENCE: 743
gcgtcttctt cgccwgggct cagaaggtt                                29

<210> SEQ ID NO 744
<211> LENGTH: 29
<212> TYPE: DNA
<213> ORGANISM: Artificial Sequence
<220> FEATURE:
<223> OTHER INFORMATION: PNMTEX3 554

<400> SEQUENCE: 744
aaataatacc ctgcygctgc ggtcagtgc                                29

<210> SEQ ID NO 745
<211> LENGTH: 29
<212> TYPE: DNA
<213> ORGANISM: Artificial Sequence
<220> FEATURE:
<223> OTHER INFORMATION: PNMTEX3 75

<400> SEQUENCE: 745
cgagccaggg tgaarcgggt cctgcccat                                29

<210> SEQ ID NO 746
<211> LENGTH: 29
<212> TYPE: DNA
<213> ORGANISM: Artificial Sequence
<220> FEATURE:
<223> OTHER INFORMATION: PPGLUCEX1 133

<400> SEQUENCE: 746
caggtattaa atccrtagtc tcgaactaa                                29

<210> SEQ ID NO 747
<211> LENGTH: 29
<212> TYPE: DNA
<213> ORGANISM: Artificial Sequence
<220> FEATURE:
<223> OTHER INFORMATION: PPGLUCEX1 44

<400> SEQUENCE: 747
atgaaaagca tttaytttgt ggctggatt                                29
```

```
<210> SEQ ID NO 748
<211> LENGTH: 29
<212> TYPE: DNA
<213> ORGANISM: Artificial Sequence
<220> FEATURE:
<223> OTHER INFORMATION: PPGLUCEX1 560

<400> SEQUENCE: 748
aagtactcaa aattyctctg tccaaagaa                                29

<210> SEQ ID NO 749
<211> LENGTH: 29
<212> TYPE: DNA
<213> ORGANISM: Artificial Sequence
<220> FEATURE:
<223> OTHER INFORMATION: PPGLUCEX1 635

<400> SEQUENCE: 749
acgtaaactg tacawaaata tctcttggc                                29

<210> SEQ ID NO 750
<211> LENGTH: 29
<212> TYPE: DNA
<213> ORGANISM: Artificial Sequence
<220> FEATURE:
<223> OTHER INFORMATION: PPGLUCEX2 196

<400> SEQUENCE: 750
agaggaacag gtaaragtct aagcctggc                                29

<210> SEQ ID NO 751
<211> LENGTH: 29
<212> TYPE: DNA
<213> ORGANISM: Artificial Sequence
<220> FEATURE:
<223> OTHER INFORMATION: PPGLUCEX3 119

<400> SEQUENCE: 751
tttggaaggc caagytgcca aggaattca                                29

<210> SEQ ID NO 752
<211> LENGTH: 29
<212> TYPE: DNA
<213> ORGANISM: Artificial Sequence
<220> FEATURE:
<223> OTHER INFORMATION: PPGLUCEX4 447

<400> SEQUENCE: 752
aaatgaaaca tgggwaatgt tacatcatt                                29

<210> SEQ ID NO 753
<211> LENGTH: 29
<212> TYPE: DNA
<213> ORGANISM: Artificial Sequence
<220> FEATURE:
<223> OTHER INFORMATION: PPGLUCEX4 571

<400> SEQUENCE: 753
tagtgagaac tggayaccga aaaatactt                                29

<210> SEQ ID NO 754
<211> LENGTH: 29
<212> TYPE: DNA
<213> ORGANISM: Artificial Sequence
<220> FEATURE:
<223> OTHER INFORMATION: PPGLUCEX4 615
```

-continued

```
<400> SEQUENCE: 754
gattttttaa taatyattca taattgttt                                    29

<210> SEQ ID NO 755
<211> LENGTH: 29
<212> TYPE: DNA
<213> ORGANISM: Artificial Sequence
<220> FEATURE:
<223> OTHER INFORMATION: PPGLUCEX4 672

<400> SEQUENCE: 755
aaataatctt taaaygaaaa tattttaag                                    29

<210> SEQ ID NO 756
<211> LENGTH: 29
<212> TYPE: DNA
<213> ORGANISM: Artificial Sequence
<220> FEATURE:
<223> OTHER INFORMATION: PPTHREX1 106

<400> SEQUENCE: 756
ccccggatcc cggasccatc ctgtggagc                                    29

<210> SEQ ID NO 757
<211> LENGTH: 29
<212> TYPE: DNA
<213> ORGANISM: Artificial Sequence
<220> FEATURE:
<223> OTHER INFORMATION: PPTHREX1 36

<400> SEQUENCE: 757
agagggctcg gcagscgccc ggggtcctc                                    29

<210> SEQ ID NO 758
<211> LENGTH: 29
<212> TYPE: DNA
<213> ORGANISM: Artificial Sequence
<220> FEATURE:
<223> OTHER INFORMATION: PPTHREX2 19

<400> SEQUENCE: 758
aacccagacg ccgcratgcc cggcccttg                                    29

<210> SEQ ID NO 759
<211> LENGTH: 29
<212> TYPE: DNA
<213> ORGANISM: Artificial Sequence
<220> FEATURE:
<223> OTHER INFORMATION: PPTHREX2 41

<400> SEQUENCE: 759
gcccttggtt gctgstcgct ctggctttg                                    29

<210> SEQ ID NO 760
<211> LENGTH: 29
<212> TYPE: DNA
<213> ORGANISM: Artificial Sequence
<220> FEATURE:
<223> OTHER INFORMATION: PPTHREX2 79

<400> SEQUENCE: 760
ctgaccggtg tcccsggcgg ccgtgctca                                    29

<210> SEQ ID NO 761
<211> LENGTH: 29
```

-continued

```
<212> TYPE: DNA
<213> ORGANISM: Artificial Sequence
<220> FEATURE:
<223> OTHER INFORMATION: PPTHREX3 1234

<400> SEQUENCE: 761
taatgataat aaaasctgca tccagataa                                29

<210> SEQ ID NO 762
<211> LENGTH: 29
<212> TYPE: DNA
<213> ORGANISM: Artificial Sequence
<220> FEATURE:
<223> OTHER INFORMATION: PPTHREX3 185

<400> SEQUENCE: 762
tcatggtcag tcgaygtaac ccagcacaa                                29

<210> SEQ ID NO 763
<211> LENGTH: 29
<212> TYPE: DNA
<213> ORGANISM: Artificial Sequence
<220> FEATURE:
<223> OTHER INFORMATION: PPTHREX3 401

<400> SEQUENCE: 763
ccctgtgggc cccarggagc ctatggtca                                29

<210> SEQ ID NO 764
<211> LENGTH: 29
<212> TYPE: DNA
<213> ORGANISM: Artificial Sequence
<220> FEATURE:
<223> OTHER INFORMATION: PPTHREX3 425

<400> SEQUENCE: 764
ggtcaagcgg gcctyctgct ggggctcct                                29

<210> SEQ ID NO 765
<211> LENGTH: 29
<212> TYPE: DNA
<213> ORGANISM: Artificial Sequence
<220> FEATURE:
<223> OTHER INFORMATION: PPTHREX3 512

<400> SEQUENCE: 765
gcagcctggg tcagrgagcc cctggagga                                29

<210> SEQ ID NO 766
<211> LENGTH: 29
<212> TYPE: DNA
<213> ORGANISM: Artificial Sequence
<220> FEATURE:
<223> OTHER INFORMATION: PPTHREX3 576

<400> SEQUENCE: 766
ctaaggatgt cttgrgccct gtgtgcccc                                29

<210> SEQ ID NO 767
<211> LENGTH: 29
<212> TYPE: DNA
<213> ORGANISM: Artificial Sequence
<220> FEATURE:
<223> OTHER INFORMATION: PPTHREX3 895

<400> SEQUENCE: 767
```

-continued agcccctggg agggmagcca gtgagggtg					29

<210> SEQ ID NO 768
<211> LENGTH: 29
<212> TYPE: DNA
<213> ORGANISM: Artificial Sequence
<220> FEATURE:
<223> OTHER INFORMATION: PPTHREX3 963

<400> SEQUENCE: 768
ccctccccca acctsgcagg attctccat					29

<210> SEQ ID NO 769
<211> LENGTH: 29
<212> TYPE: DNA
<213> ORGANISM: Artificial Sequence
<220> FEATURE:
<223> OTHER INFORMATION: PTGER3EX1 232

<400> SEQUENCE: 769
tgcggctctc tggaygccat ccctcctc					29

<210> SEQ ID NO 770
<211> LENGTH: 29
<212> TYPE: DNA
<213> ORGANISM: Artificial Sequence
<220> FEATURE:
<223> OTHER INFORMATION: PTGER3EX1 371

<400> SEQUENCE: 770
gcgcggggca acctsacgcg ccctccagg					29

<210> SEQ ID NO 771
<211> LENGTH: 29
<212> TYPE: DNA
<213> ORGANISM: Artificial Sequence
<220> FEATURE:
<223> OTHER INFORMATION: PTGER3EX1 765

<400> SEQUENCE: 771
ggtatgcgag ccacwtgaag acgcgtgcc					29

<210> SEQ ID NO 772
<211> LENGTH: 29
<212> TYPE: DNA
<213> ORGANISM: Artificial Sequence
<220> FEATURE:
<223> OTHER INFORMATION: PTGER3EX1 878

<400> SEQUENCE: 772
cagtggcccg ggacktggtg cttcatcag					29

<210> SEQ ID NO 773
<211> LENGTH: 29
<212> TYPE: DNA
<213> ORGANISM: Artificial Sequence
<220> FEATURE:
<223> OTHER INFORMATION: PTGER3EX10 206

<400> SEQUENCE: 773
acatgttttt gtacytttac tatatctac					29

<210> SEQ ID NO 774
<211> LENGTH: 29
<212> TYPE: DNA
<213> ORGANISM: Artificial Sequence

```
<220> FEATURE:
<223> OTHER INFORMATION: PTGER3EX10 281

<400> SEQUENCE: 774
gcgtatacat tatcrtatgt aaaatttgc                                29

<210> SEQ ID NO 775
<211> LENGTH: 29
<212> TYPE: DNA
<213> ORGANISM: Artificial Sequence
<220> FEATURE:
<223> OTHER INFORMATION: PTGER3EX2 1293

<400> SEQUENCE: 775
actaaaatgt ttttyctaca gtctacatg                                29

<210> SEQ ID NO 776
<211> LENGTH: 29
<212> TYPE: DNA
<213> ORGANISM: Artificial Sequence
<220> FEATURE:
<223> OTHER INFORMATION: PTGER3EX2 1295

<400> SEQUENCE: 776
taaaatgttt tttcyacagt ctacatgaa                                29

<210> SEQ ID NO 777
<211> LENGTH: 29
<212> TYPE: DNA
<213> ORGANISM: Artificial Sequence
<220> FEATURE:
<223> OTHER INFORMATION: PTGER3EX2 1393

<400> SEQUENCE: 777
gcacttctta aaaygtctc cccaccaaa                                 29

<210> SEQ ID NO 778
<211> LENGTH: 29
<212> TYPE: DNA
<213> ORGANISM: Artificial Sequence
<220> FEATURE:
<223> OTHER INFORMATION: PTGER3EX2 1403

<400> SEQUENCE: 778
aaaatgtctc cccamcaaac atagtaatc                                29

<210> SEQ ID NO 779
<211> LENGTH: 29
<212> TYPE: DNA
<213> ORGANISM: Artificial Sequence
<220> FEATURE:
<223> OTHER INFORMATION: PTGER3EX2 1614

<400> SEQUENCE: 779
taaagaatta atttygatag gtacaatat                                29

<210> SEQ ID NO 780
<211> LENGTH: 29
<212> TYPE: DNA
<213> ORGANISM: Artificial Sequence
<220> FEATURE:
<223> OTHER INFORMATION: PTGER3EX2 1719

<400> SEQUENCE: 780
tggagacaaa atctsttgag agtgcttat                                29
```

<210> SEQ ID NO 781
<211> LENGTH: 29
<212> TYPE: DNA
<213> ORGANISM: Artificial Sequence
<220> FEATURE:
<223> OTHER INFORMATION: PTGER3EX2 2153

<400> SEQUENCE: 781
agtccatcag gctgrtaaag tgaattatt                               29

<210> SEQ ID NO 782
<211> LENGTH: 29
<212> TYPE: DNA
<213> ORGANISM: Artificial Sequence
<220> FEATURE:
<223> OTHER INFORMATION: PTGER3EX2 2517

<400> SEQUENCE: 782
taggcattcg ttagyatggg gaaacctga                               29

<210> SEQ ID NO 783
<211> LENGTH: 29
<212> TYPE: DNA
<213> ORGANISM: Artificial Sequence
<220> FEATURE:
<223> OTHER INFORMATION: PTGER3EX2 3069

<400> SEQUENCE: 783
tagtgctgta tataycccaa gatatttta                               29

<210> SEQ ID NO 784
<211> LENGTH: 29
<212> TYPE: DNA
<213> ORGANISM: Artificial Sequence
<220> FEATURE:
<223> OTHER INFORMATION: PTGER3EX2 3101

<400> SEQUENCE: 784
aaatgtaagt gtttratcat gccagattt                               29

<210> SEQ ID NO 785
<211> LENGTH: 29
<212> TYPE: DNA
<213> ORGANISM: Artificial Sequence
<220> FEATURE:
<223> OTHER INFORMATION: PTGER3EX2 326

<400> SEQUENCE: 785
atatcgctaa acctwactgt gaatttagg                               29

<210> SEQ ID NO 786
<211> LENGTH: 29
<212> TYPE: DNA
<213> ORGANISM: Artificial Sequence
<220> FEATURE:
<223> OTHER INFORMATION: PTGER3EX2 3282

<400> SEQUENCE: 786
actaaaaact ggcaracagt attttaata                               29

<210> SEQ ID NO 787
<211> LENGTH: 29
<212> TYPE: DNA
<213> ORGANISM: Artificial Sequence
<220> FEATURE:
<223> OTHER INFORMATION: PTGER3EX2 3382

<400> SEQUENCE: 787 ttttataat tttgytctttt ttgactcca         29

<210> SEQ ID NO 788
<211> LENGTH: 29
<212> TYPE: DNA
<213> ORGANISM: Artificial Sequence
<220> FEATURE:
<223> OTHER INFORMATION: PTGER3EX2 557

<400> SEQUENCE: 788
tataaatgat cttgktctat tggggagcg         29

<210> SEQ ID NO 789
<211> LENGTH: 29
<212> TYPE: DNA
<213> ORGANISM: Artificial Sequence
<220> FEATURE:
<223> OTHER INFORMATION: PTGER3EX2 628

<400> SEQUENCE: 789
aaccacatac atcaytgaag acaagggat         29

<210> SEQ ID NO 790
<211> LENGTH: 29
<212> TYPE: DNA
<213> ORGANISM: Artificial Sequence
<220> FEATURE:
<223> OTHER INFORMATION: PTGER3EX2 769

<400> SEQUENCE: 790
gtataatgta tttawaatat tcatcgata         29

<210> SEQ ID NO 791
<211> LENGTH: 29
<212> TYPE: DNA
<213> ORGANISM: Artificial Sequence
<220> FEATURE:
<223> OTHER INFORMATION: PTGER3EX2 787

<400> SEQUENCE: 791
attcatcgat accaktattc aaatattgc         29

<210> SEQ ID NO 792
<211> LENGTH: 29
<212> TYPE: DNA
<213> ORGANISM: Artificial Sequence
<220> FEATURE:
<223> OTHER INFORMATION: PTGER3EX2 805

<400> SEQUENCE: 792
tcaaatattg ctcamtacag caaattagc         29

<210> SEQ ID NO 793
<211> LENGTH: 29
<212> TYPE: DNA
<213> ORGANISM: Artificial Sequence
<220> FEATURE:
<223> OTHER INFORMATION: PTGER3EX2 850

<400> SEQUENCE: 793
tttaagttta cttgrattga taattaggt         29

<210> SEQ ID NO 794

<211> LENGTH: 29
<212> TYPE: DNA
<213> ORGANISM: Artificial Sequence
<220> FEATURE:
<223> OTHER INFORMATION: PTGER3EX2 852

<400> SEQUENCE: 794
taagtttact tggawtgata attaggttt                                29

<210> SEQ ID NO 795
<211> LENGTH: 29
<212> TYPE: DNA
<213> ORGANISM: Artificial Sequence
<220> FEATURE:
<223> OTHER INFORMATION: PTGER3EX2 855

<400> SEQUENCE: 795
gtttacttgg attgwtaatt aggtttact                                29

<210> SEQ ID NO 796
<211> LENGTH: 29
<212> TYPE: DNA
<213> ORGANISM: Artificial Sequence
<220> FEATURE:
<223> OTHER INFORMATION: PTGER3EX3 76

<400> SEQUENCE: 796
ctccacctcc ttacyctgcc agtgttcct                                29

<210> SEQ ID NO 797
<211> LENGTH: 29
<212> TYPE: DNA
<213> ORGANISM: Artificial Sequence
<220> FEATURE:
<223> OTHER INFORMATION: PTGER3EX3 80

<400> SEQUENCE: 797
acctccttac cctgycagtg ttcctcaac                                29

<210> SEQ ID NO 798
<211> LENGTH: 29
<212> TYPE: DNA
<213> ORGANISM: Artificial Sequence
<220> FEATURE:
<223> OTHER INFORMATION: PTGER3EX4 719

<400> SEQUENCE: 798
tctaagcttt tgatkacaaa ggagtgatg                                29

<210> SEQ ID NO 799
<211> LENGTH: 29
<212> TYPE: DNA
<213> ORGANISM: Artificial Sequence
<220> FEATURE:
<223> OTHER INFORMATION: PTGER3EX4 94

<400> SEQUENCE: 799
tttgcatatt tcttyccacc tgagaagga                                29

<210> SEQ ID NO 800
<211> LENGTH: 29
<212> TYPE: DNA
<213> ORGANISM: Artificial Sequence
<220> FEATURE:
<223> OTHER INFORMATION: PTGER3EX6 197

<400> SEQUENCE: 800

-continued

```
gagtgctgtg ttttraaaaa gcaagctcc                              29

<210> SEQ ID NO 801
<211> LENGTH: 29
<212> TYPE: DNA
<213> ORGANISM: Artificial Sequence
<220> FEATURE:
<223> OTHER INFORMATION: PTGER3EX6 300

<400> SEQUENCE: 801
gagattacca gcaarccagg tcatttccg                              29

<210> SEQ ID NO 802
<211> LENGTH: 29
<212> TYPE: DNA
<213> ORGANISM: Artificial Sequence
<220> FEATURE:
<223> OTHER INFORMATION: PTGER3EX6 387

<400> SEQUENCE: 802
ccaatttaga cttawagtaa gaatagcac                              29

<210> SEQ ID NO 803
<211> LENGTH: 29
<212> TYPE: DNA
<213> ORGANISM: Artificial Sequence
<220> FEATURE:
<223> OTHER INFORMATION: PTGER3EX7 85

<400> SEQUENCE: 803
ttggtgcagt tctcrtgata gtgagtgag                              29

<210> SEQ ID NO 804
<211> LENGTH: 29
<212> TYPE: DNA
<213> ORGANISM: Artificial Sequence
<220> FEATURE:
<223> OTHER INFORMATION: PTGER3EX8 116

<400> SEQUENCE: 804
gatttgtcct ttccygccat gtcttcatc                              29

<210> SEQ ID NO 805
<211> LENGTH: 29
<212> TYPE: DNA
<213> ORGANISM: Artificial Sequence
<220> FEATURE:
<223> OTHER INFORMATION: PTGER3EX9 16

<400> SEQUENCE: 805
tgcctatcac ataayaggag aaccctgca                              29

<210> SEQ ID NO 806
<211> LENGTH: 29
<212> TYPE: DNA
<213> ORGANISM: Artificial Sequence
<220> FEATURE:
<223> OTHER INFORMATION: RENEX1 80

<400> SEQUENCE: 806
ggaagcatgg atggwtggag aaggatgcc                              29

<210> SEQ ID NO 807
<211> LENGTH: 29
<212> TYPE: DNA
```

<213> ORGANISM: Artificial Sequence
<220> FEATURE:
<223> OTHER INFORMATION: RENEX2 135

<400> SEQUENCE: 807
atgaagaggc tgacmcttgg caacaccac                                29

<210> SEQ ID NO 808
<211> LENGTH: 29
<212> TYPE: DNA
<213> ORGANISM: Artificial Sequence
<220> FEATURE:
<223> OTHER INFORMATION: RENEX4 151

<400> SEQUENCE: 808
gacatcatca ccgtragttg ggccgccct                                29

<210> SEQ ID NO 809
<211> LENGTH: 29
<212> TYPE: DNA
<213> ORGANISM: Artificial Sequence
<220> FEATURE:
<223> OTHER INFORMATION: RENEX4 165

<400> SEQUENCE: 809
aagttgggcc gccckaggtc atctgcccc                                29

<210> SEQ ID NO 810
<211> LENGTH: 29
<212> TYPE: DNA
<213> ORGANISM: Artificial Sequence
<220> FEATURE:
<223> OTHER INFORMATION: RENEX9 138

<400> SEQUENCE: 810
ttcaggtgag gttcragtcg gccccctcg                                29

<210> SEQ ID NO 811
<211> LENGTH: 29
<212> TYPE: DNA
<213> ORGANISM: Artificial Sequence
<220> FEATURE:
<223> OTHER INFORMATION: SAEX1 167

<400> SEQUENCE: 811
gttttgggcc agtcytgctc ctccggatt                                29

<210> SEQ ID NO 812
<211> LENGTH: 29
<212> TYPE: DNA
<213> ORGANISM: Artificial Sequence
<220> FEATURE:
<223> OTHER INFORMATION: SAEX1 76

<400> SEQUENCE: 812
attacctgta agagkaaccg ctgggagtc                                29

<210> SEQ ID NO 813
<211> LENGTH: 29
<212> TYPE: DNA
<213> ORGANISM: Artificial Sequence
<220> FEATURE:
<223> OTHER INFORMATION: SAEX11 143

<400> SEQUENCE: 813
agagcagatg atgtyatatt atcctctgg                                29

<210> SEQ ID NO 814
<211> LENGTH: 29
<212> TYPE: DNA
<213> ORGANISM: Artificial Sequence
<220> FEATURE:
<223> OTHER INFORMATION: SAEX2 54

<400> SEQUENCE: 814
ctctgtgcaa atccygagtg ctaaagctt                              29

<210> SEQ ID NO 815
<211> LENGTH: 29
<212> TYPE: DNA
<213> ORGANISM: Artificial Sequence
<220> FEATURE:
<223> OTHER INFORMATION: SAEX3 109

<400> SEQUENCE: 815
gagttttgag gaacygggat ctctgtcca                              29

<210> SEQ ID NO 816
<211> LENGTH: 29
<212> TYPE: DNA
<213> ORGANISM: Artificial Sequence
<220> FEATURE:
<223> OTHER INFORMATION: SAEX4 187

<400> SEQUENCE: 816
cactccaagc tgatygtatc agagaactc                              29

<210> SEQ ID NO 817
<211> LENGTH: 29
<212> TYPE: DNA
<213> ORGANISM: Artificial Sequence
<220> FEATURE:
<223> OTHER INFORMATION: SAEX5 182

<400> SEQUENCE: 817
tggaaggtat acttycacaa aagtgcagc                              29

<210> SEQ ID NO 818
<211> LENGTH: 29
<212> TYPE: DNA
<213> ORGANISM: Artificial Sequence
<220> FEATURE:
<223> OTHER INFORMATION: SAEX8 111

<400> SEQUENCE: 818
aaatggagaa acaasacggg cctggatat                              29

<210> SEQ ID NO 819
<211> LENGTH: 29
<212> TYPE: DNA
<213> ORGANISM: Artificial Sequence
<220> FEATURE:
<223> OTHER INFORMATION: SAEX9 101

<400> SEQUENCE: 819
ccttctcctg ctttygatgt taaggtttg                              29

<210> SEQ ID NO 820
<211> LENGTH: 29
<212> TYPE: DNA
<213> ORGANISM: Artificial Sequence
<220> FEATURE:

<223> OTHER INFORMATION: SCNN1GEX1 167

<400> SEQUENCE: 820
ggtggcccag gaagrcgcag cgcggccgg                                                29

<210> SEQ ID NO 821
<211> LENGTH: 29
<212> TYPE: DNA
<213> ORGANISM: Artificial Sequence
<220> FEATURE:
<223> OTHER INFORMATION: SCNN1GEX1 236

<400> SEQUENCE: 821
tgaagtcgtg gccckctccg ggcggtctc                                                29

<210> SEQ ID NO 822
<211> LENGTH: 29
<212> TYPE: DNA
<213> ORGANISM: Artificial Sequence
<220> FEATURE:
<223> OTHER INFORMATION: SCNN1GEX1 498

<400> SEQUENCE: 822
tggagcggat gccgrgcgcc agggcgtcg                                                29

<210> SEQ ID NO 823
<211> LENGTH: 29
<212> TYPE: DNA
<213> ORGANISM: Artificial Sequence
<220> FEATURE:
<223> OTHER INFORMATION: SCNN1GEX1 552

<400> SEQUENCE: 823
gagccagcat cagcsggtgg cggcttccc                                                29

<210> SEQ ID NO 824
<211> LENGTH: 29
<212> TYPE: DNA
<213> ORGANISM: Artificial Sequence
<220> FEATURE:
<223> OTHER INFORMATION: SCNN1GEX1 553

<400> SEQUENCE: 824
agccagcatc agccrgtggc ggcttcccg                                                29

<210> SEQ ID NO 825
<211> LENGTH: 29
<212> TYPE: DNA
<213> ORGANISM: Artificial Sequence
<220> FEATURE:
<223> OTHER INFORMATION: SCNN1GEX12 1016

<400> SEQUENCE: 825
agatcagagt gccgwggtgg aggtctggg                                                29

<210> SEQ ID NO 826
<211> LENGTH: 29
<212> TYPE: DNA
<213> ORGANISM: Artificial Sequence
<220> FEATURE:
<223> OTHER INFORMATION: SCNN1GEX12 1085

<400> SEQUENCE: 826
caggagatgg atttrgttat tcaattttg                                                29

<210> SEQ ID NO 827
<211> LENGTH: 29
<212> TYPE: DNA
<213> ORGANISM: Artificial Sequence
<220> FEATURE:
<223> OTHER INFORMATION: SCNN1GEX12 407

<400> SEQUENCE: 827
atgctggatg agctstgagg cagggttga                              29

<210> SEQ ID NO 828
<211> LENGTH: 29
<212> TYPE: DNA
<213> ORGANISM: Artificial Sequence
<220> FEATURE:
<223> OTHER INFORMATION: SCNN1GEX12 454

<400> SEQUENCE: 828
gaccaccagc catgktctaa ggacatgga                              29

<210> SEQ ID NO 829
<211> LENGTH: 29
<212> TYPE: DNA
<213> ORGANISM: Artificial Sequence
<220> FEATURE:
<223> OTHER INFORMATION: SCNN1GEX12 485

<400> SEQUENCE: 829
gggtgccccc agacrtgtgc acaggggac                              29

<210> SEQ ID NO 830
<211> LENGTH: 29
<212> TYPE: DNA
<213> ORGANISM: Artificial Sequence
<220> FEATURE:
<223> OTHER INFORMATION: SCNN1GEX12 569

<400> SEQUENCE: 830
cgcaagatgg ggcckgggca tgcgcagga                              29

<210> SEQ ID NO 831
<211> LENGTH: 29
<212> TYPE: DNA
<213> ORGANISM: Artificial Sequence
<220> FEATURE:
<223> OTHER INFORMATION: SCNN1GEX12 646

<400> SEQUENCE: 831
ataaatcccg ggacytgaac tattagcac                              29

<210> SEQ ID NO 832
<211> LENGTH: 29
<212> TYPE: DNA
<213> ORGANISM: Artificial Sequence
<220> FEATURE:
<223> OTHER INFORMATION: SCNN1GEX12 678

<400> SEQUENCE: 832
actagagact gggarccgag gcagtggtg                              29

<210> SEQ ID NO 833
<211> LENGTH: 29
<212> TYPE: DNA
<213> ORGANISM: Artificial Sequence
<220> FEATURE:
<223> OTHER INFORMATION: SCNN1GEX12 982

```
<400> SEQUENCE: 833
gagaactggc ccagrgccct tggagtgtt                                    29

<210> SEQ ID NO 834
<211> LENGTH: 29
<212> TYPE: DNA
<213> ORGANISM: Artificial Sequence
<220> FEATURE:
<223> OTHER INFORMATION: SCNN1GEX2 219

<400> SEQUENCE: 834
tcgtggtgtc ccgckgccgt ctgcgccgc                                    29

<210> SEQ ID NO 835
<211> LENGTH: 29
<212> TYPE: DNA
<213> ORGANISM: Artificial Sequence
<220> FEATURE:
<223> OTHER INFORMATION: SCNN1GEX2 26

<400> SEQUENCE: 835
tcttctttgc ccctscagca cgcccgtcc                                    29

<210> SEQ ID NO 836
<211> LENGTH: 29
<212> TYPE: DNA
<213> ORGANISM: Artificial Sequence
<220> FEATURE:
<223> OTHER INFORMATION: SCNN1GEX2 43

<400> SEQUENCE: 836
gcacgcccgt cctcrgagtc ccgtcctca                                    29

<210> SEQ ID NO 837
<211> LENGTH: 29
<212> TYPE: DNA
<213> ORGANISM: Artificial Sequence
<220> FEATURE:
<223> OTHER INFORMATION: SCNN1GEX3 186

<400> SEQUENCE: 837
ttctcccacc ggatyccgct gctgatctt                                    29

<210> SEQ ID NO 838
<211> LENGTH: 29
<212> TYPE: DNA
<213> ORGANISM: Artificial Sequence
<220> FEATURE:
<223> OTHER INFORMATION: SCNN1GEX3 259

<400> SEQUENCE: 838
ggaagcggaa agtcrgcggt agcatcatt                                    29

<210> SEQ ID NO 839
<211> LENGTH: 29
<212> TYPE: DNA
<213> ORGANISM: Artificial Sequence
<220> FEATURE:
<223> OTHER INFORMATION: SCNN1GEX3 261

<400> SEQUENCE: 839
aagcggaaag tcggyggtag catcattca                                    29

<210> SEQ ID NO 840
<211> LENGTH: 29
```

```
<212> TYPE: DNA
<213> ORGANISM: Artificial Sequence
<220> FEATURE:
<223> OTHER INFORMATION: SCNN1GEX3 301

<400> SEQUENCE: 840
atgtcatgca catcragtcc aagcaagtg                                    29

<210> SEQ ID NO 841
<211> LENGTH: 29
<212> TYPE: DNA
<213> ORGANISM: Artificial Sequence
<220> FEATURE:
<223> OTHER INFORMATION: SCNN1GEX3 99

<400> SEQUENCE: 841
ctgaagtccc tgtayggctt tccagagtc                                    29

<210> SEQ ID NO 842
<211> LENGTH: 29
<212> TYPE: DNA
<213> ORGANISM: Artificial Sequence
<220> FEATURE:
<223> OTHER INFORMATION: SCNN1GEX4 47

<400> SEQUENCE: 842
tcaaatgaca cctcygactg tgccaccta                                    29

<210> SEQ ID NO 843
<211> LENGTH: 29
<212> TYPE: DNA
<213> ORGANISM: Artificial Sequence
<220> FEATURE:
<223> OTHER INFORMATION: SCNN1GEX7 142

<400> SEQUENCE: 843
ggtaacagat tggcrggggc acccagccc                                    29

<210> SEQ ID NO 844
<211> LENGTH: 29
<212> TYPE: DNA
<213> ORGANISM: Artificial Sequence
<220> FEATURE:
<223> OTHER INFORMATION: TBXA2REX1 518

<400> SEQUENCE: 844
gctgggcccg ccccwggtca cagccagac                                    29

<210> SEQ ID NO 845
<211> LENGTH: 29
<212> TYPE: DNA
<213> ORGANISM: Artificial Sequence
<220> FEATURE:
<223> OTHER INFORMATION: TBXA2REX1B 130

<400> SEQUENCE: 845
ctcagcctcc cgagyagctg ggattacag                                    29

<210> SEQ ID NO 846
<211> LENGTH: 29
<212> TYPE: DNA
<213> ORGANISM: Artificial Sequence
<220> FEATURE:
<223> OTHER INFORMATION: TBXA2REX2 292

<400> SEQUENCE: 846
```
tcctcacctt cctcwgcggc ctcgtcctc 29

<210> SEQ ID NO 847
<211> LENGTH: 29
<212> TYPE: DNA
<213> ORGANISM: Artificial Sequence
<220> FEATURE:
<223> OTHER INFORMATION: TBXA2REX2 329

<400> SEQUENCE: 847
cctggggctg ctggwgaccg gtaccatcg 29

<210> SEQ ID NO 848
<211> LENGTH: 29
<212> TYPE: DNA
<213> ORGANISM: Artificial Sequence
<220> FEATURE:
<223> OTHER INFORMATION: TBXA2REX2 333

<400> SEQUENCE: 848
gggctgctgg tgacyggtac catcgtggt 29

<210> SEQ ID NO 849
<211> LENGTH: 29
<212> TYPE: DNA
<213> ORGANISM: Artificial Sequence
<220> FEATURE:
<223> OTHER INFORMATION: TBXA2REX2 371

<400> SEQUENCE: 849
cgccgcgctc ttcgwgtggc acgccgtgg 29

<210> SEQ ID NO 850
<211> LENGTH: 29
<212> TYPE: DNA
<213> ORGANISM: Artificial Sequence
<220> FEATURE:
<223> OTHER INFORMATION: TBXA2REX2 390

<400> SEQUENCE: 850
cacgccgtgg acccwggctg ccgtctctg 29

<210> SEQ ID NO 851
<211> LENGTH: 29
<212> TYPE: DNA
<213> ORGANISM: Artificial Sequence
<220> FEATURE:
<223> OTHER INFORMATION: TBXA2REX2 525

<400> SEQUENCE: 851
ccggcggtcg cctcrcagcg ccgcgcctg 29

<210> SEQ ID NO 852
<211> LENGTH: 29
<212> TYPE: DNA
<213> ORGANISM: Artificial Sequence
<220> FEATURE:
<223> OTHER INFORMATION: TBXA2REX2 568

<400> SEQUENCE: 852
tggtgtgggc ggccrcgctg gcgctgggc 29

<210> SEQ ID NO 853
<211> LENGTH: 29
<212> TYPE: DNA
<213> ORGANISM: Artificial Sequence

<220> FEATURE:
<223> OTHER INFORMATION: TBXA2REX2 617

<400> SEQUENCE: 853
gggtcgctac accgwgcaat acccggggt                                              29

<210> SEQ ID NO 854
<211> LENGTH: 29
<212> TYPE: DNA
<213> ORGANISM: Artificial Sequence
<220> FEATURE:
<223> OTHER INFORMATION: TBXA2REX2 739

<400> SEQUENCE: 854
tcctgctgaa cacgrtcagc gtggccacc                                              29

<210> SEQ ID NO 855
<211> LENGTH: 29
<212> TYPE: DNA
<213> ORGANISM: Artificial Sequence
<220> FEATURE:
<223> OTHER INFORMATION: TBXA2REX2 852

<400> SEQUENCE: 855
atcatggtgg tggcmagcgt gtgttggct                                              29

<210> SEQ ID NO 856
<211> LENGTH: 29
<212> TYPE: DNA
<213> ORGANISM: Artificial Sequence
<220> FEATURE:
<223> OTHER INFORMATION: TBXA2REX3 145

<400> SEQUENCE: 856
gacccctggg tgtayatcct gttccgccg                                              29

<210> SEQ ID NO 857
<211> LENGTH: 29
<212> TYPE: DNA
<213> ORGANISM: Artificial Sequence
<220> FEATURE:
<223> OTHER INFORMATION: TBXA2REX3 358

<400> SEQUENCE: 857
ggggtgctgg atggrcagtg ggcatcagc                                              29

<210> SEQ ID NO 858
<211> LENGTH: 29
<212> TYPE: DNA
<213> ORGANISM: Artificial Sequence
<220> FEATURE:
<223> OTHER INFORMATION: TBXA2REX3 528

<400> SEQUENCE: 858
aagggcatgc agacrttgga agagggtct                                              29

<210> SEQ ID NO 859
<211> LENGTH: 29
<212> TYPE: DNA
<213> ORGANISM: Artificial Sequence
<220> FEATURE:
<223> OTHER INFORMATION: TBXA2REX3 599

<400> SEQUENCE: 859
cccaggctgg agtgyagtgg cgcaatctc                                              29

<210> SEQ ID NO 860
<211> LENGTH: 29
<212> TYPE: DNA
<213> ORGANISM: Artificial Sequence
<220> FEATURE:
<223> OTHER INFORMATION: TBXA2REX3 701

<400> SEQUENCE: 860
ggcgcgcgcc accaygcccg gctaatttt                                29

<210> SEQ ID NO 861
<211> LENGTH: 29
<212> TYPE: DNA
<213> ORGANISM: Artificial Sequence
<220> FEATURE:
<223> OTHER INFORMATION: TBXA2REX3 904

<400> SEQUENCE: 861
tggagtacag tggcrcgatc tcggctcac                                29

<210> SEQ ID NO 862
<211> LENGTH: 29
<212> TYPE: DNA
<213> ORGANISM: Artificial Sequence
<220> FEATURE:
<223> OTHER INFORMATION: TBXA2REX3 906

<400> SEQUENCE: 862
gagtacagtg gcacratctc ggctcactg                                29

<210> SEQ ID NO 863
<211> LENGTH: 29
<212> TYPE: DNA
<213> ORGANISM: Artificial Sequence
<220> FEATURE:
<223> OTHER INFORMATION: TBXA2REX3 953

<400> SEQUENCE: 863
ttcaagcgat tctcstgcct cagcctccc                                29

<210> SEQ ID NO 864
<211> LENGTH: 29
<212> TYPE: DNA
<213> ORGANISM: Artificial Sequence
<220> FEATURE:
<223> OTHER INFORMATION: TBXASEX10 61

<400> SEQUENCE: 864
cagcctcgag gaagkcctgc cctatctgg                                29

<210> SEQ ID NO 865
<211> LENGTH: 29
<212> TYPE: DNA
<213> ORGANISM: Artificial Sequence
<220> FEATURE:
<223> OTHER INFORMATION: TBXASEX10 98

<400> SEQUENCE: 865
attgcagaga cgctraggat gtacccgcc                                29

<210> SEQ ID NO 866
<211> LENGTH: 29
<212> TYPE: DNA
<213> ORGANISM: Artificial Sequence
<220> FEATURE:
<223> OTHER INFORMATION: TBXASEX11 105

<210> SEQ ID NO 866
<211> LENGTH: 29
<212> TYPE: DNA
<213> ORGANISM: Artificial Sequence
<220> FEATURE:
<223> OTHER INFORMATION: TBXASEX11 152

<400> SEQUENCE: 866
gtgctagaga tggcygtggg tgccctgca                29

<210> SEQ ID NO 867
<211> LENGTH: 29
<212> TYPE: DNA
<213> ORGANISM: Artificial Sequence
<220> FEATURE:
<223> OTHER INFORMATION: TBXASEX11 152

<400> SEQUENCE: 867
gccaagcccg gagamcttca accctgaaa                29

<210> SEQ ID NO 868
<211> LENGTH: 29
<212> TYPE: DNA
<213> ORGANISM: Artificial Sequence
<220> FEATURE:
<223> OTHER INFORMATION: TBXASEX11 49

<400> SEQUENCE: 868
cacgggaggc agctsaggac tgcgaggtg                29

<210> SEQ ID NO 869
<211> LENGTH: 29
<212> TYPE: DNA
<213> ORGANISM: Artificial Sequence
<220> FEATURE:
<223> OTHER INFORMATION: TBXASEX11 73

<400> SEQUENCE: 869
aggtgctggg gcagygcatc cccgcaggc                29

<210> SEQ ID NO 870
<211> LENGTH: 29
<212> TYPE: DNA
<213> ORGANISM: Artificial Sequence
<220> FEATURE:
<223> OTHER INFORMATION: TBXASEX11 88

<400> SEQUENCE: 870
gcatccccgc aggcrctgtg ctagagatg                29

<210> SEQ ID NO 871
<211> LENGTH: 29
<212> TYPE: DNA
<213> ORGANISM: Artificial Sequence
<220> FEATURE:
<223> OTHER INFORMATION: TBXASEX12 46

<400> SEQUENCE: 871
tcacggctga ggccmggcag cagcaccgg                29

<210> SEQ ID NO 872
<211> LENGTH: 29
<212> TYPE: DNA
<213> ORGANISM: Artificial Sequence
<220> FEATURE:
<223> OTHER INFORMATION: TBXASEX13 226

<400> SEQUENCE: 872
cctggcatgc aaggrtaaga ggttctttt                29

<210> SEQ ID NO 873

```
<211> LENGTH: 29
<212> TYPE: DNA
<213> ORGANISM: Artificial Sequence
<220> FEATURE:
<223> OTHER INFORMATION: TBXASEX4 130

<400> SEQUENCE: 873
ccaacagaat ggtaygtagt tttctttcc                                   29

<210> SEQ ID NO 874
<211> LENGTH: 29
<212> TYPE: DNA
<213> ORGANISM: Artificial Sequence
<220> FEATURE:
<223> OTHER INFORMATION: TBXASEX5 15

<400> SEQUENCE: 874
ctgaccctct gcttrttact tcccaacag                                   29

<210> SEQ ID NO 875
<211> LENGTH: 29
<212> TYPE: DNA
<213> ORGANISM: Artificial Sequence
<220> FEATURE:
<223> OTHER INFORMATION: TBXASEX6 59

<400> SEQUENCE: 875
agccaagcct gcgamcttct cctggctca                                   29

<210> SEQ ID NO 876
<211> LENGTH: 29
<212> TYPE: DNA
<213> ORGANISM: Artificial Sequence
<220> FEATURE:
<223> OTHER INFORMATION: TBXASEX8 110

<400> SEQUENCE: 876 atggctttttt taacraactc attaggaat                                  29

<210> SEQ ID NO 877
<211> LENGTH: 29
<212> TYPE: DNA
<213> ORGANISM: Artificial Sequence
<220> FEATURE:
<223> OTHER INFORMATION: TBXASEX8 119

<400> SEQUENCE: 877
ttaacaaact cattrggaat gtgattgcc                                   29

<210> SEQ ID NO 878
<211> LENGTH: 29
<212> TYPE: DNA
<213> ORGANISM: Artificial Sequence
<220> FEATURE:
<223> OTHER INFORMATION: TBXASEX9 156

<400> SEQUENCE: 878
cgaacccttc ccggmaacac cagcccagc                                   29

<210> SEQ ID NO 879
<211> LENGTH: 29
<212> TYPE: DNA
<213> ORGANISM: Artificial Sequence
<220> FEATURE:
<223> OTHER INFORMATION: TBXASEX9 276

<400> SEQUENCE: 879
```

```
cttttgccac ctacstactg gccaccaac                                29
```

<210> SEQ ID NO 880
<211> LENGTH: 29
<212> TYPE: DNA
<213> ORGANISM: Artificial Sequence
<220> FEATURE:
<223> OTHER INFORMATION: TRHREX1 56

<400> SEQUENCE: 880

```
ttctgcagaa cttasatgat aagcaacga                                29
```

<210> SEQ ID NO 881
<211> LENGTH: 29
<212> TYPE: DNA
<213> ORGANISM: Artificial Sequence
<220> FEATURE:
<223> OTHER INFORMATION: TRHREX1 84

<400> SEQUENCE: 881

```
acaaagccag ctgcytctag acccctggc                                29
```

<210> SEQ ID NO 882
<211> LENGTH: 29
<212> TYPE: DNA
<213> ORGANISM: Artificial Sequence
<220> FEATURE:
<223> OTHER INFORMATION: TRHREX2 147

<400> SEQUENCE: 882

```
gtcagtgaac tgaamcaaac acagcttca                                29
```

<210> SEQ ID NO 883
<211> LENGTH: 29
<212> TYPE: DNA
<213> ORGANISM: Artificial Sequence
<220> FEATURE:
<223> OTHER INFORMATION: TRHREX2 240

<400> SEQUENCE: 883

```
ggcctgggca ttgtrggcaa catcatggt                                29
```

<210> SEQ ID NO 884
<211> LENGTH: 29
<212> TYPE: DNA
<213> ORGANISM: Artificial Sequence
<220> FEATURE:
<223> OTHER INFORMATION: TRHREX3 1161

<400> SEQUENCE: 884

```
tcccacatga tgggyggaaa aaggcaaaa                                29
```

<210> SEQ ID NO 885
<211> LENGTH: 29
<212> TYPE: DNA
<213> ORGANISM: Artificial Sequence
<220> FEATURE:
<223> OTHER INFORMATION: TRHREX3 1231

<400> SEQUENCE: 885

```
ttaaatttga aaagyatagt caagacaaa                                29
```

<210> SEQ ID NO 886
<211> LENGTH: 29
<212> TYPE: DNA

```
<213> ORGANISM: Artificial Sequence
<220> FEATURE:
<223> OTHER INFORMATION: TRHREX3 1540

<400> SEQUENCE: 886
ttcttttttt gtttwtctca aatgctagt                                    29

<210> SEQ ID NO 887
<211> LENGTH: 29
<212> TYPE: DNA
<213> ORGANISM: Artificial Sequence
<220> FEATURE:
<223> OTHER INFORMATION: TRHREX3 1786

<400> SEQUENCE: 887
gaatctccga gggcwaaaat tgcccttgg                                    29

<210> SEQ ID NO 888
<211> LENGTH: 29
<212> TYPE: DNA
<213> ORGANISM: Artificial Sequence
<220> FEATURE:
<223> OTHER INFORMATION: TRHREX3 1846

<400> SEQUENCE: 888
gtagatcaaa aaagyaccca tacctttac                                    29

<210> SEQ ID NO 889
<211> LENGTH: 29
<212> TYPE: DNA
<213> ORGANISM: Artificial Sequence
<220> FEATURE:
<223> OTHER INFORMATION: TRHREX3 2046

<400> SEQUENCE: 889
cctcattcta gagtrcgctt ttttttttt                                    29

<210> SEQ ID NO 890
<211> LENGTH: 29
<212> TYPE: DNA
<213> ORGANISM: Artificial Sequence
<220> FEATURE:
<223> OTHER INFORMATION: TRHREX3 2175

<400> SEQUENCE: 890
acctgcatga cagtragcaa tctatgtta                                    29

<210> SEQ ID NO 891
<211> LENGTH: 29
<212> TYPE: DNA
<213> ORGANISM: Artificial Sequence
<220> FEATURE:
<223> OTHER INFORMATION: TRHREX3 2283

<400> SEQUENCE: 891
acaagcacat gtgtrtttat aaacacata                                    29

<210> SEQ ID NO 892
<211> LENGTH: 29
<212> TYPE: DNA
<213> ORGANISM: Artificial Sequence
<220> FEATURE:
<223> OTHER INFORMATION: TRHREX3 377

<400> SEQUENCE: 892
gccacaaaag tgtcytttga tgacacctg                                    29
```

<210> SEQ ID NO 893
<211> LENGTH: 29
<212> TYPE: DNA
<213> ORGANISM: Artificial Sequence
<220> FEATURE:
<223> OTHER INFORMATION: TRHREX3 960

<400> SEQUENCE: 893
taagatttta gacayacatg ttaactgta                                  29

<210> SEQ ID NO 894
<211> LENGTH: 29
<212> TYPE: DNA
<213> ORGANISM: Artificial Sequence
<220> FEATURE:
<223> OTHER INFORMATION: ACEEX13 138

<400> SEQUENCE: 894
cctctgctgg tcccyagcca ggaggcatc                                  29

<210> SEQ ID NO 895
<211> LENGTH: 29
<212> TYPE: DNA
<213> ORGANISM: Artificial Sequence
<220> FEATURE:
<223> OTHER INFORMATION: ACEEX17 52

<400> SEQUENCE: 895
aatgtgatgg ccacrtcccg gaaatatga                                  29

<210> SEQ ID NO 896
<211> LENGTH: 29
<212> TYPE: DNA
<213> ORGANISM: Artificial Sequence
<220> FEATURE:
<223> OTHER INFORMATION: ADRB3EX1 416

<400> SEQUENCE: 896
tcgtggccat cgccyggact ccgagactc                                  29

<210> SEQ ID NO 897
<211> LENGTH: 29
<212> TYPE: DNA
<213> ORGANISM: Artificial Sequence
<220> FEATURE:
<223> OTHER INFORMATION: AGTEX2 644

<400> SEQUENCE: 897
gctgctgctg tccayggtgg tgggcgtgt                                  29

<210> SEQ ID NO 898
<211> LENGTH: 29
<212> TYPE: DNA
<213> ORGANISM: Artificial Sequence
<220> FEATURE:
<223> OTHER INFORMATION: AGTEX2 827

<400> SEQUENCE: 898
tggctgctcc ctgaygggag ccagtgtgg                                  29

<210> SEQ ID NO 899
<211> LENGTH: 29
<212> TYPE: DNA
<213> ORGANISM: Artificial Sequence
<220> FEATURE:

-continued

<223> OTHER INFORMATION: AGTEXP1 173

<400> SEQUENCE: 899
tgcttgtgtg ttttyccag tgtctatta                                    29

<210> SEQ ID NO 900
<211> LENGTH: 29
<212> TYPE: DNA
<213> ORGANISM: Artificial Sequence
<220> FEATURE:
<223> OTHER INFORMATION: AGTEXP2 203

<400> SEQUENCE: 900
ctcgaccctg caccrgctca ctctgttca                                   29

<210> SEQ ID NO 901
<211> LENGTH: 29
<212> TYPE: DNA
<213> ORGANISM: Artificial Sequence
<220> FEATURE:
<223> OTHER INFORMATION: AGTEXP3 144

<400> SEQUENCE: 901
gctataaata gggcmtcgtg acccggcca                                   29

<210> SEQ ID NO 902
<211> LENGTH: 29
<212> TYPE: DNA
<213> ORGANISM: Artificial Sequence
<220> FEATURE:
<223> OTHER INFORMATION: ANPEX3 120

<400> SEQUENCE: 902
gtctctgctg cattygtgtc atcttgttg                                   29

<210> SEQ ID NO 903
<211> LENGTH: 29
<212> TYPE: DNA
<213> ORGANISM: Artificial Sequence
<220> FEATURE:
<223> OTHER INFORMATION: ANPEX3 33

<400> SEQUENCE: 903
tctctttgca gtacygaaga taacagcca                                   29

<210> SEQ ID NO 904
<211> LENGTH: 29
<212> TYPE: DNA
<213> ORGANISM: Artificial Sequence
<220> FEATURE:
<223> OTHER INFORMATION: AT1EX5 1138

<400> SEQUENCE: 904
aagaagcctg caccrtgttt tgaggttga                                   29

<210> SEQ ID NO 905
<211> LENGTH: 29
<212> TYPE: DNA
<213> ORGANISM: Artificial Sequence
<220> FEATURE:
<223> OTHER INFORMATION: AT1EX5 1593

<400> SEQUENCE: 905
aaagttttcg tgcckgtttt cagctatta                                   29

```
<210> SEQ ID NO 906
<211> LENGTH: 29
<212> TYPE: DNA
<213> ORGANISM: Artificial Sequence
<220> FEATURE:
<223> OTHER INFORMATION: AT1EX5 649

<400> SEQUENCE: 906
caaaattcaa ccctyccgat agggctggg                                        29

<210> SEQ ID NO 907
<211> LENGTH: 29
<212> TYPE: DNA
<213> ORGANISM: Artificial Sequence
<220> FEATURE:
<223> OTHER INFORMATION: MRLEX2 1504

<400> SEQUENCE: 907
caagaaccag atgayggag ctattaccc                                         29

<210> SEQ ID NO 908
<211> LENGTH: 29
<212> TYPE: DNA
<213> ORGANISM: Artificial Sequence
<220> FEATURE:
<223> OTHER INFORMATION: MRLEX2 545

<400> SEQUENCE: 908
gcgtcatgcg cgccrttgtt aaaagccct                                        29

<210> SEQ ID NO 909
<211> LENGTH: 29
<212> TYPE: DNA
<213> ORGANISM: Artificial Sequence
<220> FEATURE:
<223> OTHER INFORMATION: NCX1EX12 3101

<400> SEQUENCE: 909
actcattttt tagcwgtatt aggaatgtc                                        29
```

POLYMORPHISMS ASSOCIATED WITH HYPERTENSION

CROSS-REFERENCES TO RELATED APPLICATIONS

This application claims the benefit of the U.S. provisional Application No. 60/084,641, filed May 7, 1998, which is incorporated by reference in its entirety for all purposes.

The work described in this application was funded, in part, by a grant from the National Heart, Lung & Blood Institute (U10 HL54466), which may have certain rights in this invention.

BACKGROUND OF THE INVENTION

Hypertension, or high blood pressure, is a common disease affecting 50 million Americans and contributing to over 200,000 deaths annually from stroke, myocardial infarction, and end-stage renal disease. The disease is multifactorial and numerous genetic and nongenetic components, such as salt intake, age, diet, and body mass, are suspected to contribute. A specific cause of hypertension can typically be identified in only a small percentage of patients. Other patients with abnormally high blood pressure of unknown cause are said to have essential hypertension.

The existence of a genetic component to hypertension is known from twin studies, which have revealed a greater concordance of blood pressure in monozygotic twins that in dizygotic twins. Similarly, biological siblings have show greater concordance of blood pressure than adoptive siblings raised in the same household. Such studies have suggested that up to about 40% of the variations in blood pressure in the population are genetically determined.

There is a substantial pool of candidate genes that may contribute to the genetic component of hypertension. Because blood pressure is determined by the product of cardiac output and vascular resistance, candidate genes may act through either pathway. Physiologic pathways which are know to influence these parameters include the renin-angiotensin-aldosterone system, which contributes to determination of both cardiac output and vascular resistance. In this pathway, angiotensinogen, a hormone produced in the liver, is cleaved by an enzyme called renin to angiotensin I, which then undergoes further cleavage by angiotensin I-converting enzyme (ACE) to produce the active hormone angiotensin II (AII). All acts through specific AT1 receptors present on vascular and adrenal cells. Receptors present on vascular cells cause vasoconstriction of blood vessels. Receptors present on adrenal cells cause release of the hormone aldosterone by the adrenal gland. This hormone acts on the mineralocorticoid receptor to cause increase sodium reabsorption largely through a renal epithelial sodium location. Other candidate genes are those of peripheral and central adrenergic pathways, which have dominant effects on cardiac iontropy, heart rate and vascular resistance; a variety of renal ion channels and transporters, which determine net sodium absorption and hence intravascular volume; calcium channels and exchangers and nitric oxide pathways, whose activity influences vascular tone. Another candidate gene encodes atrial natriuretic factor precursor, which is cleaved to atrial natriuretic peptides, found in the heart atrium, an endocrine organ controlling blood pressure and organ volume.

For some of the above candidate genes, variant forms have been identified that occur with increased frequency in individuals with hypertension. For example, a number of the polymorphisms have been reported in the angiotensinogen gene (AGT). In one of these, an M/T substitution at position 235, the T allele occurs more frequently in individuals with hypertension suggesting that this polymorphic form is a cause of hypertension or in equilibrium dislinkage with another polymorphism that is a cause. Jeunmaitre et al., Am. J. Hum. Genet. 60, 1448–1460 (1997). Two other genes within the renin-angiotensin-aldosterone system also have variant forms correlated with specific forms of hypertension, that is, aldosterone synthase gene and the gene encoding the β-subunit of the epithelial sodium channel induced by the mineralocorticoid receptor. Lifton et al., Proc. Natl. Acad. Sci. USA 92, 8548–8551(1995).

Despite these developments, only a minute proportion of the total repository of polymorphisms in candidate genes for hypertension has been identified, and the primary genetic determinants of hypertension remain unknown in most affected subjects, as does the nature of the interaction between different genetic determinants. The paucity of polymorphisms hitherto identified is due to the large amount of work required for their detection by conventional methods. For example, a conventional approach to identifying polymorphisms might be to sequence the same stretch of oligonucleotides in a population of individuals by dideoxy sequencing. In this type of approach, the amount of work increases in proportion to both the length of sequence and the number of individuals in a population and becomes impractical for large stretches of DNA or large numbers of persons.

SUMMARY OF THE INVENTION

The invention provides nucleic acids of between 10 and 100 bases comprising at least 10 contiguous nucleotides including a polymorphic site from a sequence shown in Table 1, column 8 or the complement thereof. The nucleic acids can be DNA or RNA. Some nucleic acids are between 10 and 50 bases and some are between 20 and 50 bases. The base occupying the polymorphic site in such nucleic acids can be either a reference base shown in Table 1, column 3 or an alternative base shown in Table 1, column 5. In the some nucleic acids, the polymorphic site is occupied by a base that correlates with hypertension or susceptibility thereto. Some nucleic acids contain a polymorphic site having two polymorphic forms giving rise two different amino acids specified by the two codons in which the polymorphic site occurs in the two polymorphic forms.

The invention further provides allele-specific oligonucleotides that hybridize to a nucleic acid segment shown in Table 1, column 8 or its complement, including the polymorphic site. Such oligonucleotides are useful as probes or primers.

The invention further provides methods of analyzing a nucleic acid sequence. Such methods entail obtaining the nucleic acid from an individual; and determining a base occupying any one of the polymorphic sites shown in Table 1 or other polymorphic sites in equilibrium dislinkage therewith. Some methods determine a set of bases occupying a set of the polymorphic sites shown in Table 1. In some methods, the nucleic acid is obtained from a plurality of individuals, and a base occupying one of the polymorphic positions is determined in each of the individuals. Each individual is then tested for the presence of a disease phenotype, and correlating the presence of the disease phenotype with the base, particularly hypertension.

In another aspect, the invention provides nucleic acids comprising an isolated nucleic acid sequence of Table 1, column 8 or the complement thereof, wherein the polymorphic site within the sequence or its complement is occupied by a base other than the reference base show in Table 1, column 3. Such nucleic acids are useful, for example, in expression of variant proteins or production of transgenic animals.

The invention further provides methods of diagnosing a phenotype. Such methods entail determining which polymorphic form(s) are present in a sample from a subject at one or more polymorphic sites shown in Table 1, and diagnosing the presence of a phenotype correlated with the form(s) in the subject.

The invention also provides methods of screening polymorphic sites linked to polymorphic sites shown in Table 1 for suitability for diagnosing a phenotype. Such methods entail identifying a polymorphic site linked to a polymorphic site shown in Table 1, wherein a polymorphic form of the polymorphic site shown in Table 1 has been correlated with a phenotype. One then determines haplotypes in a population of individuals to indicate whether the linked polymorphic site has a polymorphic form in equlibrium dislinkage with the polymorphic form correlated with the phenotype.

DEFINITIONS

Figure 1A:
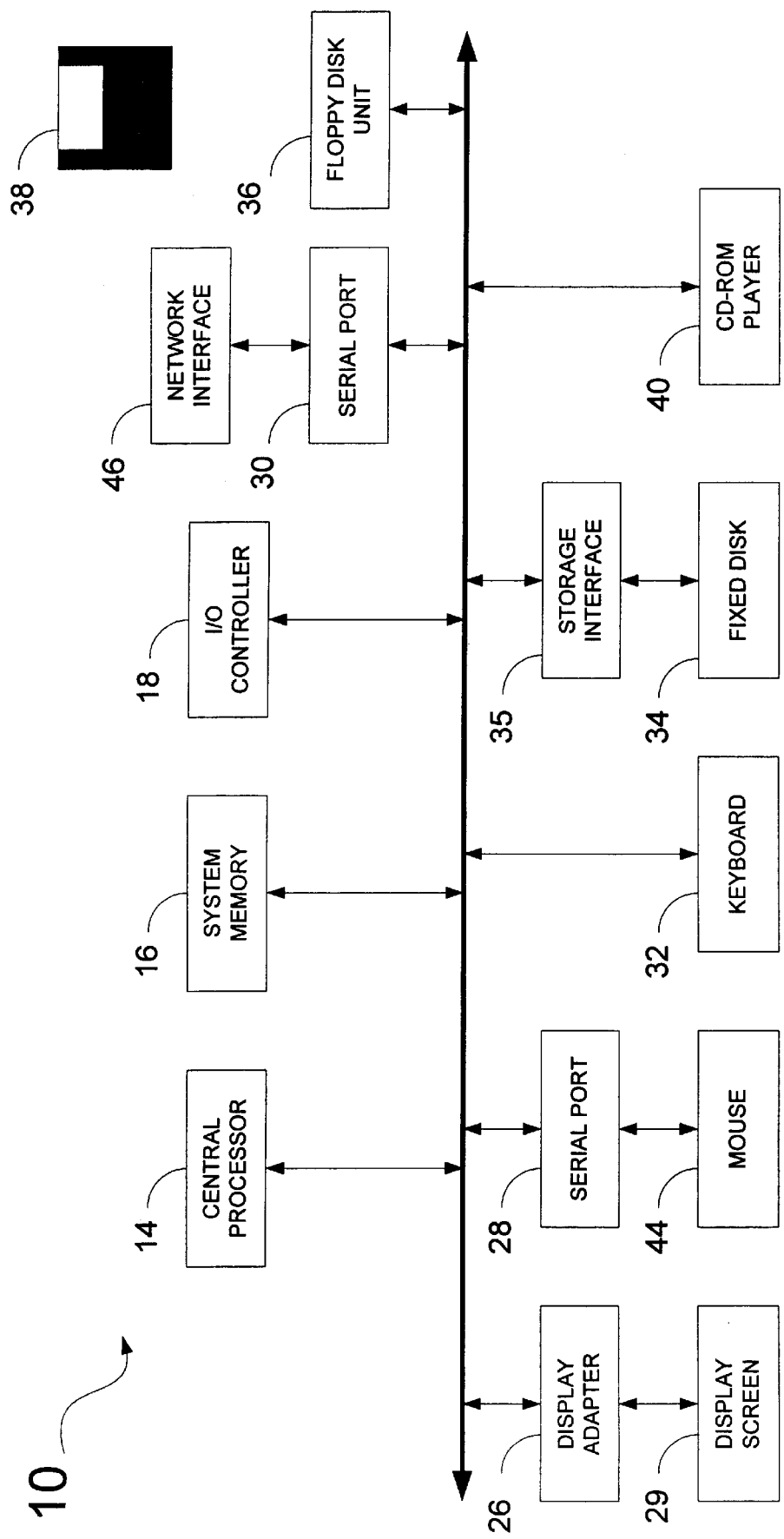
FIGS. 1A and 1B depict computer systems suitable for storing and transmitting information relating to the polymorphisms of the invention.

A nucleic acid can be DNA or RNA, and single- or double-stranded. Oligonucleotides can be naturally occurring or synthetic, but are typically prepared by synthetic means. Preferred nucliec acids of the invention include segments of DNA, or their complements including any one of the polymorphic sites shown in Table 1. The segments are usually between 5 and 100 contiguous bases, and often range from 5, 10, 12, 15, 20, or 25 nucleotides to 10, 15, 30, 25, 20, 50 or 100 nucleotides. Nucleic acids between 5–10, 5–20, 10–20, 12–30, 15–30, 10–50, 20–50 or 20–100 bases are common. The polymorphic site can occur within any position of the segment. The segments can be from any of the allelic forms of DNA shown in Table 1. For brevity in Table 1, the symbol T is used to represent both thymidine in DNA and uracil in RNA. Thus, in RNA oligonucleotides, the symbol T should be construed to indicate a uracil residue.

Hybridization probes are capable of binding in a base-specific manner to a complementary strand of nucleic acid. Such probes include nucleic acids, peptide nucleic acids, as described in Nielsen et al., Science 254, 1497–1500 (1991).

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term primer site refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified.

Linkage describes the tendency of genes, alleles, loci or genetic markers to be inherited together as a result of their location on the same chromosome, and can be measured by percent recombination between the two genes, alleles, loci or genetic markers. Loci occurring within 50 centimorgan of each other are linked. Some linked markers occur within the same gene or gene cluster.

Polymorphism refers to the occurrence of two or more genetically determined alternative sequences or alleles in a population. A polymorphic marker or site is the locus at which divergence occurs. Preferred markers have at least two alleles, each occurring at frequency of greater than 1%, and more preferably greater than 10% or 20% of a selected population. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as a the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A single nucleotide polymorphism occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations).

A single nucleotide polymorphism usually arises due to substitution of one nucleotide for another at the polymorphic site. A transition is the replacement of one purine by another purine or one pyrimidine by another pyrimidine. A transversion is the replacement of a purine by a pyrimidine or vice versa. Single nucleotide polymorphisms can also arise from a deletion of a nucleotide or an insertion of a nucleotide relative to a reference allele.

A set of polymorphisms means at least 2, and sometimes 5, 10, 20, 50 or more of the polymorphisms shown in Table 1.

Hybridizations are usually performed under stringent conditions, for example, at a salt concentration of no more than 1 M and a temperature of at least 25° C. For example, conditions of 5×SSPE (750 mM NaCl, 50 mM Na Phosphate, 5 mM EDTA, pH 7.4) and a temperature of 25–300° C. are suitable for allele-specific probe hybridizations.

An isolated nucleic acid means an object species invention that is the predominant species present (i.e., on a molar basis it is more abundant than any other individual species in the composition). Preferably, an isolated nucleic acid comprises at least about 50, 80 or 90 percent (on a molar basis) of all macromolecular species present. Most preferably, the object species is purified to essential homogeneity (contaminant species cannot be detected in the composition by conventional detection methods).

Linkage disequilibrium or allelic association means the preferential association of a particular allele or genetic marker with a specific allele, or genetic marker at a nearby chromosomal location more frequently than expected by chance for any particular allele frequency in the population. For example, if locus X has alleles a and b, which occur equally frequently, and linked locus Y has alleles c and d, which occur equally frequently, one would expect the haplotype ac to occur with a frequency of 0.25 in a population of individuals. If ac occurs more frequently, then alleles a and c are in linkage disequilibrium. Linkage disequilibrium may result from natural selection of certain combination of alleles or because an allele has been introduced into a population too recently to have reached equilibrium with linked alleles.

A marker in linkage disequilibrium can be particularly useful in detecting susceptibility to disease (or other phenotype) notwithstanding that the marker does not cause the disease. For example, a marker (X) that is not itself a causative element of a disease, but which is in linkage disequilibrium with a gene (including regulatory sequences) (Y) that is a causative element of a phenotype, can be used detected to indicate susceptibility to the disease in circumstances in which the gene Y may not have been identified or may not be readily detectable. Younger alleles (i.e., those arising from mutation relatively late in evolution) are expected to have a larger genomic sequencement in linkage disequilibrium. The age of an allele can be determined from whether the allele is shared between ethnic human groups and/or between humans and related species.

DETAILED DESCRIPTION

The invention provides a substantial collection of novel polymorphisms in several genes encoding products known or suspected to have roles in biochemical pathways relating to blood pressure. Detection of polymorphisms in such genes is useful in designing and performing diagnostic assays for hypertension. Analysis of polymorphisms is also useful in designing prophylactic and therapeutic regimes customized to underlying abnormalities. As with other human polymorphisms, the polymorphisms of the invention also have more general applications, such as forensics, paternity testing, linkage analysis and positional cloning.

I. Novel Polymorphisms of the Invention

The invention provides polymorphic sites in 75 candidate genes, known or suspected to have roles in hypertension. A gene was designated a candidate based on known or suggested involvement in blood pressure homeostasis and/or hypertension in one of the following biochemical pathways: renin-angiotensin, neural, or hormonal pathways regulating blood pressure; regulation of vascular constriction, growth, and repair; ion and other small molecule transportation pathways in the kidney; and, regulation of glucose metabolism. Experimental evidence supporting selection of candidate genes included blood pressure physiology, animal models with altered blood pressure (including transgenic and knockout mouse or rat animal models), and human genetic linkage and association studies.

To maximize the chances of identifying informative single nucleotide polymorphisms (SNPs), DNA samples from 40 Africans and 35 US. individuals of Northern European descent were screened to include both a range of human genetic diversity and hypertension phenotype diversity. Human genetic diversity is greater within African, as compared to European, Asian or American, populations (*The History and Geography of Human Genes* (Cavalli-Sforza et al., Eds.,Princeton University Press, Princeton, N.J., 1994)). There are also significant differences in the prevalence and phenotype of hypertension between Africans (or US Blacks) and Northern Europeans (or US Whites). Hypertension has a greater prevalence, an earlier onset and a higher frequency of salt-sensitive cases in populations of African descent. The individuals sampled were selected from the top and bottom 2.5th percentile of a normalized blood pressure distribution. Regression analysis was performed within each community sample, of systolic, diastolic and mean arterial blood pressure against age and sex, and calculated the ranked frequency distribution of residuals. Equal numbers of individuals were selected from both ends of this latter distribution to maximize potential genetic differences it the genes screened for SNPs.

874 SNPs in 75 individuals were identified at a frequency of one SNP per 217 bases. 387 SNPs were in coding sequences, 150 in introns, and 337 in 5' and 3' UTRs. Of coding sequence chances, 178 and 209 SNPs led to synonymous and nonsynonymouse substitutions in the translated protein. On average, 12 SNPs were identified per gene, with the number ranging from zero (HSD11) to 54 (PGIS), with ten genes harboring 20 or more SNPs.

A large collection of polymorphisms of the invention are listed in Table 1. The first column of the Table 1 lists the gene and exon in which a given polymorphism occurs. For example, ACEEX13 means that a polymorphism occurs in exon 13 of angiotensin I-converting enzyme. AGTEX2 means that a polymorphism occurs in exon 2 of the angiotensinogen gene. The full names of the 75 genes shown in Table 1 are shown in Table 3. Sequences of each of the genes are available at http//World Wide Web.ncbi.nlm.nih.gov/Entrez/nucleotide.html. The second column of Table 1 shows the position of a polymorphism. Numbering of nucleotides follows that of previously published reference sequences with nucleotides in sequence tags shown in column 8 being assigned the same number as the corresponding nucleotide in a reference sequence when the two are maximally aligned. In general, nucleotides in exons are numbered consecutively from the first base of the exon. Column 3 shows the base occupying the polymorphic position in a previously published sequence (arbitrarily designated a reference sequence). Column 4 of Table 1 shows the population frequency of the reference allele. For example at position 138 of exon 13 of ACE, a C nucleotide occurs in 63% of the population. Column 5 of the table shows a nucleotide occupying a polymorphic position that differs from previously published sequences. An allele containing such a nucleotide is designated an alternative allele. Column 6 of the Table shows the population frequency of the alternative allele. Column 7 of the Table shows the population frequency of heterozygosity at a polymorphic position. For example, for the polymorphic position at position 138 of exon 13 of the ACE gene, 37% of the human population are heterozygous. A high frequency of heterozygosity is advantageous in many applications of polymorphisms. The eighth column of the table shows a polymorphic position and about 15 nucleotides of flanking sequence on either side. The bases occupying the polymorphic position are indicated using IUPAC ambiguity nomenclature. For polymorphisms occurring in coding regions, columns 9 and 10 of the Table indicate the codons of the reference and alternate alleles including the polymorphic site. These columns are left blank for polymorphisms occurring in non-coding regions. Column 11 indicates whether the change between reference and alternate alleles is synonymous (i.e., no amino acid substitution due to polymorphic variation), nonsynonymous (i.e, polymorphic variation causes amino acid substitution). If the polymoprhic site does not occur in a coding region, column 11 characterizes the polymorphic site as "other." For polymorphic sites occurring in noncoding regions column 12 indicates the type of region in which the site occurs (e.g., 5' UTR, intron). For polymorphic sites occurring in coding regions, column 12 indicates the amino acid encoded by the codon of the reference allele in which the polymorphic site occurs. Column 13 indicates the amino acid encoded by the codon of the alternative allele in which the polymorphic site occurs.

The polymorphisms shown in Tables 1 were identified by resequencing of target sequences from unrelated individuals of diverse ethnic and geographic backgrounds by hybridization to probes immobilized to microfabricated arrays. About 190 kb of genomic sequence from 75 candidate genes in 75 humans (150 alleles) or about 28 MB total was analyze. The sequence included 87 kb coding DNA, 25 kb intron and 77 kb of 5' and 3' UTR sequences. Multiple target sequences from an individual were amplified from human genomic DNA using primers complementary to published sequences. The amplified target sequences were fluorescently labelled during or after PCR.

Polymorphisms were identified by hybridization of amplified DNA to arrays of oligonucleotide probes. Each genomic region was amplified by the polymerase chain reaction (PCR) in multiple segments, ranging from 80 bp to 14 kb, by both conventional and long PCR protocols. 205 distinct PCR products, averaging 3 kb, representing all 75 genes were pooled for each individual for each chip design The strategy and principles for design and use of arrays of oligonucleotide probes are generally described in WO 95/11995. The strategy provides arrays of probes for analysis of target sequences showing a high degree of sequence identity to the published sequences described above. A typical probe array used in this analysis has two groups of four sets of probes that respectively tile both strands of a reference sequence. A first probe set comprises a plurality of probes exhibiting perfect complementarily with one of the reference sequences. Each probe in the first probe set has an interrogation position that corresponds to a nucleotide in the reference sequence. That is, the interrogation position is aligned with the corresponding nucleotide in the reference sequence, when the probe and reference sequence are aligned to maximize complementarily between the two. For each probe in the first set, there are three corresponding probes from three additional probe sets. Thus, there are four probes corresponding to each nucleotide in the reference sequence. The probes from the three additional probe sets are identical to the corresponding probe from the first probe set except at the interrogation position, which occurs in the same position in each of the four corresponding probes from the four probe sets, and is occupied by a different nucleotide in the four probe sets. Arrays tiled for multiple different references sequences were included on the same substrate.

The labelled target sequences were hybridized with a substrate bearing immobilized arrays of probes. The amount of label bound to probes was measured. Analysis of the pattern of label revealed the nature and position of differences between the target and reference sequence. For example, comparison of the intensities of four corresponding probes reveals the identity of a corresponding nucleotide in the target sequences aligned with the interrogation position of the probes. The corresponding nucleotide is the complement of the nucleotide occupying the interrogation position of the probe showing the highest intensity (see WO 95/11995). The existence of a polymorphism is also manifested by differences in normalized hybridization intensities of probes flanking the polymorphism when the probes hybridized to corresponding targets from different individuals. For example, relative loss of hybridization intensity in a "footprint" of probes flanking a polymorphism signals a difference between the target and reference (i.e., a polymorphism) (see EP 717,113, incorporated by reference in its entirety for all purposes). Additionally, hybridization intensities for corresponding targets from different individuals can be classified into groups or clusters suggested by the data, not defined a priori, such that isolates in a give cluster tend to be similar and isolates in different clusters tend to be dissimilar. See WO 97/29212, filed Feb. 7, 1997 (incorporated by reference in its entirety for all purposes). Hybridizations to samples from different individuals were performed separately.

II. Analysis of Polymorphisms

A. Preparation of Samples

Polymorphisms are detected in a target nucleic acid from an individual being analyzed. For assay of genomic DNA, virtually any biological sample (other than pure red blood cells) is suitable. For example, convenient tissue samples include whole blood, semen, saliva, tears, urine, fecal material, sweat, buccal, skin and hair. For assay of cDNA or mRNA, the tissue sample must be obtained from an organ in which the target nucleic acid is expressed.

Many of the methods described below require amplification of DNA from target samples. This can be accomplished by e.g., PCR. See generally PCR Technology: Principles and Applications for DNA Amplification (ed. H.A. Erlich, Freeman Press, N.Y., N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. No. 4,683,202 (each of which is incorporated by reference for all purposes).

Other suitable amplification methods include the ligase chain reaction (LCR) (see Wu and Wallace, Genomics 4, 560 (1989), Landegren et al., Science 241, 1077 (1988), transcription amplification (Kwoh et al., Proc. Natl. Acad. Sci. USA 86, 1173 (1989)), and self-sustained sequence replication (Guatelli et al., Proc. Nat. Acad. Sci. USA, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

B. Detection of Polymorphisms in Target DNA

The identity of bases occupying the polymorphic sites shown in Table 1 can be determined in an individual (e.g., a patient being analyzed) by several methods, which are described in turn.

1. Allele-Specific Probes

The design and use of allele-specific probes for analyzing polymorphisms is described by e.g., Saiki et al., Nature 324, 163–166 (1986); Dattagupta, EP 235,726, Saiki, WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles. Some probes are designed to hybridize to a segment of target DNA such that the polymorphic site aligns with a central position (e.g., in a 15 mer at the 7 position; in a 16 mer, at either the 8 or 9 position) of the probe. This design of probe achieves good discrimination in hybridization between different allelic forms.

Allele-specific probes are often used in pairs, one member of a pair showing a perfect match to a reference form of a target sequence and the other member showing a perfect match to a variant form. Several pairs of probes can then be immobilized on the same support for simultaneous analysis of multiple polymorphisms within the same target sequence.

2. Tiling Arrays

The polymorphisms can also be identified by hybridization to nucleic acid arrays, some example of which are described by WO 95/11995 (incorporated by reference in its entirety for all purposes). One form of such arrays is described in the Examples section in connection with de novo identification of polymorphisms. The same array or a different array can be used for analysis of characterized polymorphisms. WO 95/11995 also describes subarrays that are optimized for detection of a variant forms of a precharacterized polymorphism. Such a subarray contains probes designed to be complementary to a second reference sequence, which is an allelic variant of the first reference sequence. The second group of probes is designed by the same principles as described in the Examples except that the probes exhibit complementarily to the second reference sequence. The inclusion of a second group (or further groups) can be particular useful for analyzing short subsequences of the primary reference sequence in which multiple mutations are expected to occur within a short distance commensurate with the length of the probes (i.e., two or more mutations within 9 to 21 bases).

3. Allele-Specific Primers

An allele-specific primer hybridizes to a site on target DNA overlapping a polymorphism and only primes amplification of an allelic form to which the primer exhibits perfect complementarily. See Gibbs, Nucleic Acid Res. 17, 2427–2448 (1989). This primer is used in conjunction with a second primer which hybridizes at a distal site. Amplification proceeds from the two primers leading to a detectable product signifying the particular allelic form is present. A control is usually performed with a second pair of primers, one of which shows a single base mismatch at the polymorphic site and the other of which exhibits perfect complementarily to a distal site. The single-base mismatch prevents amplification and no detectable product is formed. The method works best when the mismatch is included in the 3'-most position of the oligonucleotide aligned with the polymorphism because this position is most destabilizing to elongation from the primer. See, e.g., WO 93/22456.

4. Direct-Sequencing

The direct analysis of the sequence of polymorphisms of the present invention can be accomplished using either the dideoxy- chain termination method or the Maxam -Gilbert method (see Sambrook et al., Molecular Cloning, A Laboratory Manual (2nd Ed., CSHP, New York 1989); Zyskind et al., Recombinant DNA Laboratory Manual, (Acad. Press, 1988)).

5. Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. Erlich, ed., PCR Technology, Principles and Applications for DNA Amplification, (W.H. Freeman and Co, New York, 1992), Chapter 7.

6. Single-Strand Conformation Polymorphism Analysis

Alleles of target sequences can be differentiated using single-strand conformation polymorphism analysis, which identifies base differences by alteration in electrophoretic migration of single stranded PCR products, as described in Orita et al., Proc. Nat. Acad. Sci. 86, 2766–2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between alleles of target sequences.

III. Methods of Use

After determining polymorphic form(s) present in an individual at one or more polymorphic sites, this information can be used in a number of methods.

A. Association Studies with Hypertension

The polymorphisms of the invention may contribute to the phenotype of an organism in different ways. Some polymorphisms occur within a protein coding sequence and contribute to phenotype by affecting protein structure. The effect may be neutral, beneficial or detrimental, or both beneficial and detrimental, depending on the circumstances. By analogy, a heterozygous sickle cell mutation confers resistance to malaria, but a homozygous sickle cell mutation is usually lethal. Other polymorphisms occur in noncoding regions but may exert phenotypic effects indirectly via influence on replication, transcription, and translation. A single polymorphism may affect more than one phenotypic trait. Likewise, a single phenotypic trait may be affected by polymorphisms in different genes. Further, some polymorphisms predispose an individual to a distinct mutation that is causally related to a certain phenotype.

The polymorphism shown in Table 1 are analyzed for a correlation with hypertension, the metabolic processes that lead to hypertension, and response to drugs used to treat hypertension. For purposes of these studies, hypertension can be defined as a dichotomous trait (e.g., diastolic blood pressure greater than 90 mm Hg), as a continuous scale of increasing severity based on blood pressure values, or as several intermediate phenotypes. Because it is likely that the causation of hypertension in the population is heterogenous, use of intermediate phenotypes can increase the strength of correlations identified. Some useful subtypes for association studies are mendelian forms of human hypertension, forms characterized by increased erythrocyte sodium-lithium countertransport, forms characterized by altered urinary kallikrein levels, and forms characterized by sensitivity of blood pressure to increases or decreases in sodium intake.

Correlation is performed for a population of individuals who have been tested for the presence or absence of hypertension or an intermediate phenotype and for one or polymorphic markers. To perform such analysis, the presence or absence of a set of polymorphic forms (i.e. a polymorphic set) is determined for a set of the individuals, some of whom exhibit a particular trait, and some of which exhibit lack of the trait. The alleles of each polymorphism of the set are then reviewed to determine whether the presence or absence of a particular allele is associated with the trait of interest. Correlation can be performed by standard statistical methods such as a K-squared test and statistically significant correlations between polymorphic form(s) and phenotypic characteristics are noted. For example, it might be found that the presence of allele A1 at polymorphism A correlates with hypertension as a dichotomous trait. As a further example, it might be found that the combined presence of allele A1 at polymorphism A and allele B1 at polymorphism B correlates with increased erythrocyte sodium lithium counter transport, an intermediate phenotype in development of hypertension.

B. Diagnosis of Hypertension

Polymorphic forms that correlate with hypertension or intermediate phenotypes are useful in diagnosing hypertension or susceptibility thereto. Combined detection of several such polymorphic forms (for example, 2, 5, 10 or 20 of the polymorphisms listed in Table 1) typically increases the probability of an accurate diagnosis. For example, the presence of a single polymorphic form known to correlate with hypertension might indicate a probability of 20% that an individual has or is susceptible to hypertension, whereas detection of five polymorphic forms, each of which correlates with hypertension, might indicate a probability of 80% that an individual has or is susceptible to hypertension. Analysis of the polymorphisms of the invention can be combined with that of other polymorphisms or other risk factors of hypertension, such as family history or obesity, as well as measurements of blood pressure.

Patients diagnosed with hypertension can be treated with conventional therapies and/or can be counselled to undertake remedial life style changes, such as a low fat, low salt diet or more exercise. Conventional therapies include diuretics (e.g., thiazides), which lower blood pressure by depleting the body of sodium and reducing blood volume; sympathoplegic agents (e.g., methyldopa and clonidine), which lower blood pressure by reducing peripheral vascular resistance, inhibiting cardiac function and increasing venous pooling in capacitance vessels; direct vasodilators (e.g., hydralazine, minoxidil, diazoxide and sodium nitroprusside), which reduce pressure by relaxing vascular smooth muscle; agents that block production or action of angiotensin (e.g., captopril, enalapril and lisinopril), and thereby reduce peripheral vascular resistance; and adrenergic neuron blocking agents (e.g., guanethidine, reserpine, propranolol) which prevent release of norepinephrine. See, e.g., Basic and Clinical Pharmacology (Ed. Katzung, Appleton & Lange, CT, 1989).

C. Drug Screening

The polymorphism(s) showing the strongest correlation with hypertension within a given gene are likely to have a causative role in hypertension. Such a role can be confirmed by producing a transgenic animal expressing a human gene bearing such a polymorphism and determining whether the animal develops hypertension. Polymorphisms in coding regions that result in amino acid changes usually cause hypertension by decreasing, increasing or otherwise altering the activity of the protein encoded by the gene in which the polymorphism occurs. Polymorphisms in coding regions that introduce stop codons usually cause hypertension by reducing (heterozygote) or eliminating (homozygote) functional protein produced by the gene. Occasionally, stop codons result in production of a truncated peptide with aberrant activities relative to the full-length protein. Polymorphisms in regulatory regions typically cause hypertension by causing increased or decreased expression of the protein encoded by the gene in which the polymorphism occurs. Polymorphisms in intronic sequences can cause hypertension either through the same mechanism as polymorphisms in regulatory sequences or by causing altered spliced patterns resulting in an altered protein. For example, alternative splice patterns have been reported for the human angiotensin II receptor gene (Curnow et al., Molecular Endocrinology 9, 1250–1262 (1995)).

The precise role of polymorphisms in hypertension can be elucidated by several means. Alterations in expression levels of a protein (e.g., sodium-calcium ion channel) can be determined by measuring protein levels in samples groups of persons characterized as having or not having hypertension (or intermediate phenotypes). Alterations in enzyme activity (e.g., renin), can similarly be detected by assaying for enzyme activity in samples from the above groups of persons. Alterations in receptor transducing activity (e.g., angiotensin II receptor, β-3-adrenergic receptor or bradykinin receptor B2) can be detected by comparing receptor ligand binding, either in vitro or in a cellular expression system.

Having identified certain polymorphisms as having causative roles in hypertension, and having elucidated at least in general terms whether such polymorphisms increase or decrease the activity or expression level of associated proteins, customized therapies can be devised for classes of patients with different genetic subtypes of hypertension. For example, if a polymorphism in a given protein causes hypertension by increasing the expression level or activity of the protein, hypertension associated with the polymorphism can be treated by administering an antagonist of the protein. If a polymorphism in a given protein causes hypertension by decreasing the expression level or activity of a protein, the form of hypertension associated with the polymorphism can be treated by administering the protein itself, a nucleic acid encoding the protein that can be expressed in a patient, or an analog or agonist of the protein.

Agonists, antagonists can be obtained by producing and screening large combinatorial libraries. Combinatorial libraries can be produced for many types of compound that can be synthesized in a step by step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Devlin, WO 91/18980. The libraries of compounds can be initially screened for specific binding to the protein for which agonists or antagonists are to be identified, or to its natural binding partner. Preferred agents bind with a Kd<$\mu$M. For example, for receptor ligand combinations, the assay can be performed using cloned receptor immobilized to a support such as a microtiter well and binding of compounds can be measured in competition with ligand to the receptor. Agonist or antagonist activity can then be assayed using a cellular reporter system or a transgenic animal model.

The polymorphisms of the invention are also useful for conducting clinical trials of drug candidates for hypertension. Such trials are performed on treated or control populations having similar or identical polymorphic profiles at a defined collection of polymorphic sites. Use of genetically matched populations eliminates or reduces variation in treatment outcome due to genetic factors, leading to a more accurate assessment of the efficacy of a potential drug.

D. Other Diseases

The polymorphisms in Table 1 can also be tested for association with other disease that have known but hitherto unmapped genetic components (e.g., agammaglobulinemia, diabetes insipidus, Lesch-Nyhan syndrome, muscular dystrophy, Wiskott-Aldrich syndrome, Fabry's disease, familial hypercholesterolemia, polycystic kidney disease, hereditary spherocytosis, von Willebrand's disease, tuberous sclerosis, hereditary hemorrhagica telangiectasia, familial colonic polyposis, Ehlers-Danlos syndrome, osteogenesis imperfecta, and acute intermittent porphyria). Phenotypic traits also include symptoms of, or susceptibility to, multifactorial diseases of which a component is or may be genetic, such as autoimmune diseases, inflammation, cancer, diseases of the nervous system, and infection by pathogenic microorganisms. Some examples of autoimmune diseases include rheumatoid arthritis, multiple sclerosis, diabetes (insulin-dependent and non-independent), systemic lupus erythematosus and Graves disease. Some examples of cancers include cancers of the bladder, brain, breast, colon, esophagus, kidney, leukemia, liver, lung, oral cavity, ovary, pancreas, prostate, skin, stomach and uterus. Phenotypic traits also include characteristics such as longevity, appearance (e.g., baldness, obesity), strength, speed, endurance, fertility, and susceptibility or receptivity to particular drugs or therapeutic treatments.

Such correlations can be exploited in several ways. In the case of a strong correlation between a set of one or more polymorphic forms and a disease for which treatment is available, detection of the polymorphic form set in a human or animal patient may justify immediate administration of treatment, or at least the institution of regular monitoring of the patient. Detection of a polymorphic form correlated with serious disease in a couple contemplating a family may also be valuable to the couple in their reproductive decisions. For example, the female partner might elect to undergo in vitro fertilization to avoid the possibility of transmitting such a polymorphism from her husband to her offspring. In the case of a weaker, but still statistically significant correlation between a polymorphic set and human disease, immediate therapeutic intervention or monitoring may not be justified. Nevertheless, the patient can be motivated to begin simple life-style changes (e.g., diet, exercise) that can be accomplished at little cost to the patient but confer potential benefits in reducing the risk of conditions to which the patient may have increased susceptibility by virtue of variant alleles. Identification of a polymorphic set in a patient correlated with enhanced receptiveness to one of several treatment regimes for a disease indicates that this treatment regime should be followed.

E. Forensics

Determination of which polymorphic forms occupy a set of polymorphic sites in an individual identifies a set of polymorphic forms that distinguishes the individual. See generally National Research Council, The Evaluation of Forensic DNA Evidence (Eds. Pollard et al., National Academy Press, DC, 1996). The more sites that are analyzed the lower the probability that the set of polymorphic forms in one individual is the same as that in an unrelated individual. Preferably, if multiple sites are analyzed, the sites are unlinked. Thus, polymorphisms of the invention are often used in conjunction with polymorphisms in distal genes. Preferred polymorphisms for use in forensics are diallelic because the population frequencies of two polymorphic forms can usually be determined with greater accuracy than those of multiple polymorphic forms at multi-allelic loci.

The capacity to identify a distinguishing or unique set of forensic markers in an individual is useful for forensic analysis. For example, one can determine whether a blood sample from a suspect matches a blood or other tissue sample from a crime scene by determining whether the set of polymorphic forms occupying selected polymorphic sites is the same in the suspect and the sample. If the set of polymorphic markers does not match between a suspect and a sample, it can be concluded (barring experimental error) that the suspect was not the source of the sample. If the set of markers does match, one can conclude that the DNA from the suspect is consistent with that found at the crime scene. If frequencies of the polymorphic forms at the loci tested have been determined (e.g., by analysis of a suitable population of individuals), one can perform a statistical analysis to determine the probability that a match of suspect and crime scene sample would occur by chance.

p(ID) is the probability that two random individuals have the same polymorphic or allelic form at a given polymorphic site. In diallelic loci, four genotypes are possible: AA, AB, BA, and BB. If alleles A and B occur in a haploid genome of the organism with frequencies x and y, the probability of each genotype in a diploid organism are (see WO 95/12607):

Homozygote: $p(AA)=x^2$

Homozygote: $p(BB)=y^2=(1-x)^2$

Single Heterozygote: $p(AB)=p(BA)=xy=x(1-x)$

Both Heterozygotes: $p(AB+BA)=2xy=2x(1-x)$

The probability of identity at one locus (i.e, the probability that two individuals, picked at random from a population will have identical polymorphic forms at a given locus) is given by the equation:

$$p(ID)=(x^2)^2+(2xy)^2+(y^2)^2.$$

These calculations can be extended for any number of polymorphic forms at a given locus. For example, the probability of identity p(ID) for a 3-allele system where the alleles have the frequencies in the population of x, y and z, respectively, is equal to the sum of the squares of the genotype frequencies:

$$p(ID)=x^4+(2xy)^2+(2yz)^2+(2xz)^2+z^4+y^4$$

In a locus of n alleles, the appropriate binomial expansion is used to calculate p(ID) and p(exc).

The cumulative probability of identity (cum p(ID)) for each of multiple unlinked loci is determined by multiplying the probabilities provided by each locus.

$$\text{cum } p(ID)=p(ID1)p(ID2)p(ID3) \ldots p(IDn)$$

The cumulative probability of non-identity for n loci (i.e. the probability at two random individuals will be different at 1 or more loci) is given by the equation:

$$\text{cum } p(nonID)=1-\text{cum } p(ID).$$

If several polymorphic loci are tested, the cumulative probability of non-entity for random individuals becomes very high (e.g., one billion to one). Such probabilities can be taken into account together with other evidence in determining the guilt or innocence of the suspect.

F. Paternity Testing

The object of paternity testing is usually to determine whether a male is the father of a child. In most cases, the mother of the child is known and thus, the mother's contribution to the child's genotype can be traced. Paternity testing investigates whether the part of the child's genotype not attributable to the mother is consistent with that of the putative father. Paternity testing can be performed by analyzing sets of polymorphisms in the putative father and the child.

If the set of polymorphisms in the child attributable to the father does not match the putative father, it can be concluded, barring experimental error, that the putative father is not the real father. If the set of polymorphisms in the child attributable to the father does match the set of polymorphisms of the putative father, a statistical calculation can be performed to determine the probability of coincidental match.

The probability of parentage exclusion (representing the probability that a random male will have a polymorphic form at a given polymorphic site that makes him incompatible as the father) is given by the equation (see WO 95/12607):

$$p(exc)=xy(1-xy)$$

where x and y are the population frequencies of alleles A and B of a diallelic polymorphic site.

(At a triallelic site $p(exc)=xy(1-xy)+yz(1-yz)+xz(1-xz)+3xyz(1-xyz)$)), where x, y and z and the respective population frequencies of alleles A, B and C).

The probability of non-exclusion is $$p(non-exc)=1-p(exc)$$

The cumulative probability of non-exclusion (representing the value obtained when n loci are used) is thus:

$$\text{cum } p(non-exc)=p(non-exc1)p(non-exc2)p(non-exc3) \ldots p(non-excn)$$

The cumulative probability of exclusion for n loci (representing the probability that a random male will be excluded)

$$\text{cum } p(exc)=1-\text{cum } p(non-exc).$$

If several polymorphic loci are included in the analysis, the cumulative probability of exclusion of a random male is very high. This probability can be taken into account in assessing the liability of a putative father whose polymorphic marker set matches the child's polymorphic marker set attributable to his/her father.

G. Genetic Mapping of Phenotypic Traits

The polymorphisms shown in table I can also be used to establish physical linkage between a genetic locus associated with a trait of interest and polymorphic markers that are not associated with the trait, but are in physical proximity with the genetic locus responsible for the trait and co-segregate with it. Such analysis is useful for mapping a genetic locus associated with a phenotypic trait to a chromosomal position, and thereby cloning gene(s) responsible for the trait. See Lander et al., Proc. Natl. Acad. Sci. (USA) 83, 7353–7357 (1986); Lander et al., Proc. Natl. Acad. Sci. (USA) 84, 2363–2367 (1987); Donis-Keller et al., Cell 51, 319–337 (1987); Lander et al., Genetics 121, 185–199 (1989)). Genes localized by linkage can be cloned by a process known as directional cloning. See Wainwright, Med. J. Australia 159, 170–174 (1993); Collins, Nature Genetics 1, 3–6 (1992) (each of which is incorporated by reference in its entirety for all purposes).

Linkage studies are typically performed on members of a family. Available members of the family are characterized for the presence or absence of a phenotypic trait and for a set of polymorphic markers. The distribution of polymorphic markers in an informative meiosis is then analyzed to determine which polymorphic markers co-segregate with a phenotypic trait. See, e.g., Kerem et al., Science 245, 1073–1080 (1989); Monaco et al., Nature 316, 842 (1985); Yamoka et al., Neurology 40, 222–226 (1990); Rossiter et al., FASEB Journal 5, 21–27 (1991).

Linkage is analyzed by calculation of LOD (log of the odds) values. A lod value is the relative likelihood of obtaining observed segregation data for a marker and a genetic locus when the two are located at a recombination fraction θ, versus the situation in which the two are not linked, and thus segregating independently (Thompson & Thompson, Genetics in Medicine (5th ed, W.B. Saunders Company, Philadelphia, 1991); Strachan, "Mapping the human genome" in The Human Genome (BIOS Scientific Publishers Ltd, Oxford), Chapter 4). A series of likelihood ratios are calculated at various recombination fractions (θ), ranging from θ=0.0 (coincident loci) to θ=0.50 (unlinked). Thus, the likelihood at a given value of 0 is: probability of data if loci linked at θ to probability of data if loci unlinked. The computed likelihoods are-usually expressed as the log10 of this ratio (i.e., a lod score). For example, a lod score of 3 indicates 1000:1 odds against an apparent observed linkage being a coincidence. The use of logarithms allows data collected from different families to be combined by simple addition. Computer programs are available for the calculation of lod scores for differing values of θ (e.g., LIPED, MLINK (Lathrop, Proc. Nat. Acad. Sci. (USA) 81, 3443–3446 (1984)). For any particular lod score, a recombination fraction may be determined from mathematical tables. See Smith et al., Mathematical tables for research workers in human genetics (Churchill, London, 1961); Smith, Ann. Hum. Genet. 32, 127–150 (1968). The value of θ at which the lod score is the highest is considered to be the best estimate of the recombination fraction. Positive lod score values suggest that the two loci are linked, whereas negative values suggest that linkage is less likely (at that value of θ) than the possibility that the two loci are unlinked. By convention, a combined lod score of +3 or greater (equivalent to greater than 1000:1 odds in favor of linkage) is considered definitive evidence that two loci are linked. Similarly, by convention, a negative lod score of −2 or less is taken as definitive evidence against linkage of the two loci being compared. Negative linkage data are useful in excluding a chromosome or a segment thereof from consideration. The search focuses on the remaining non-excluded chromosomal locations.

IV. Modified Polypeptides and Gene Sequences

The invention further provides variant forms of nucleic acids and corresponding proteins. The nucleic acids comprise one of the sequences described in Table 1, column 8, in which the polymorphic position is occupied by an alternative base for that position. Some nucleic acid encode full-length variant forms of proteins. Similarly, variant proteins have the prototypical amino acid sequences of encoded by nucleic acid sequence shown in Table 1, column 8, (read so as to be in-frame with the full-length coding sequence of which it is a component) except at an amino acid encoded by a codon including one of the polymorphic positions shown in the Table. That position is occupied by the amino acid coded by the corresponding codon in the alternative forms shown in the Table.

Variant genes can be expressed in an expression vector in which a variant gene is operably linked to a native or other promoter. Usually, the promoter is a eukaryotic promoter for expression in a mammalian cell. The transcription regulation sequences typically include a heterologous promoter and optionally an enhancer which is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The means of introducing the expression construct into a host cell varies depending upon the particular construction and the target host. Suitable means include fusion, conjugation, transfection, transduction, electroporation or injection, as described in Sambrook, supra. A wide variety of host cells can be employed for expression of the variant gene, both prokaryotic and eukaryotic. Suitable host cells include bacteria such as *E. coli*, yeast, filamentous fungi, insect cells, mammalian cells, typically immortalized, e.g., mouse, CHO, human and monkey cell lines and derivatives thereof. Preferred host cells are able to process the variant gene product to produce an appropriate mature polypeptide. Processing includes glycosylation, ubiquitination, disulfide bond formation, general post-translational modification, and the like.

The protein may be isolated by conventional means of protein biochemistry and purification to obtain a substantially pure product, i.e., 80, 95 or 99% free of cell component contaminants, as described in Jacoby, Methods in Enzymology Volume 104, Academic Press, New York (1984); Scopes, Protein Purification, Principles and Practice, 2nd Edition, Springer-Verlag, New York (1987); and Deutscher (ed), Guide to Protein Purification, Methods in Enzymology, Vol. 182 (1990). If the protein is secreted, it can be isolated from the supernatant in which the host cell is grown. If not secreted, the protein can be isolated from a lysate of the host cells.

The invention further provides transgenic nonhuman animals capable of expressing an exogenous variant gene and/or having one or both alleles of an endogenous variant gene inactivated. Expression of an exogenous variant gene is usually achieved by operably linking the gene to a promoter and optionally an enhancer, and microinjecting the construct into a zygote. See Hogan et al., "Manipulating the Mouse Embryo, A Laboratory Manual," Cold Spring Harbor Laboratory. Inactivation of endogenous variant genes can be achieved by forming a transgene in which a cloned variant gene is inactivated by insertion of a positive selection marker. See Capecchi, Science 244, 1288–1292 (1989). The transgene is then introduced into an embryonic stem cell, where it undergoes homologous recombination with an endogenous variant gene. Mice and other rodents are preferred animals. Such animals provide useful drug screening systems.

In addition to substantially full-length polypeptides expressed by variant genes, the present invention includes biologically active fragments of the polypeptides, or analogs thereof, including organic molecules which simulate the interactions of the peptides. Biologically active fragments include any portion of the full-length polypeptide which confers a biological function on the variant gene product, including ligand binding, and antibody binding. Ligand binding includes binding by nucleic acids, proteins or polypeptides, small biologically active molecules, or large cellular structures.

Polyclonal and/or monoclonal antibodies that specifically bind to variant gene products but not to corresponding prototypical gene products are also provided. Antibodies can be made by injecting mice or other animals with the variant gene product or synthetic peptide fragments thereof. Monoclonal antibodies are screened as are described, for example, in Harlow & Lane, Antibodies, A Laboratory Manual, Cold Spring Harbor Press, New York (1988); Goding, Monoclonal antibodies, Principles and Practice (2d ed.) Academic Press, New York (1986). Monoclonal antibodies are tested for specific immunoreactivity with a variant gene product and lack of immunoreactivity to the corresponding prototypical gene product. These antibodies are useful in diagnostic assays for detection of the variant form, or as an active ingredient in a pharmaceutical composition.

V. Kits

The invention further provides kits comprising at least one allele-specific oligonucleotide as described above. Often, the kits contain one or more pairs of allele-specific oligonucleotides hybridizing to different forms of a polymorphism. In some kits, the allele-specific oligonucleotides are provided immobilized to a substrate. For example, the same substrate can comprise allele-specific oligonucleotide probes for detecting at least 10, 100 or all of the polymorphisms shown in Table 1. Optional additional components of the kit include, for example, restriction enzymes, reverse-transcriptase or polymerase, the substrate nucleoside triphosphates, means used to label (for example, an avidin-enzyme conjugate and enzyme substrate and chromogen if the label is biotin), and the appropriate buffers for reverse transcription, PCR, or hybridization reactions. Usually, the kit also contains instructions for carrying out the methods.

VI. Computer Systems For Storing Polymorphism Data

FIG. 1A depicts a block diagram of a computer system 10 suitable for implementing the present invention. Computer system 10 includes a bus 12 which interconnects major subsystems such as a central processor 14, a system memory 16 (typically RAM), an input/output (I/O) controller 18, an external device such as a display screen 24 via a display adapter 26, serial ports 28 and 30, a keyboard 32, a fixed disk drive 34 via a storage interface 35 and a floppy disk drive 36 operative to receive a floppy disk 38, and a CD-ROM (or DVD-ROM) device 40 operative to receive a CD-ROM 42. Many other devices can be connected such as a user pointing device, e.g., a mouse 44 connected via serial port 28 and a network interface 46 connected via serial port 30.

Many other devices or subsystems (not shown) may be connected in a similar manner. Also, it is not necessary for all of the devices shown in FIG. 1A to be present to practice the present invention, as discussed below. The devices and subsystems may be interconnected in different ways from that shown in FIG. 1A. The operation of a computer system such as that shown in FIG. 1A is well known. Databases storing polymorphism information according to the present invention can be stored, e.g., in system memory 16 or on storage media such as fixed disk 34, floppy disk 38, or CD-ROM 42. An application program to access such databases can be operably disposed in system memory 16 or sorted on storage media such as fixed disk 34, floppy disk 38, or CD-ROM 42.

Figure 1B:
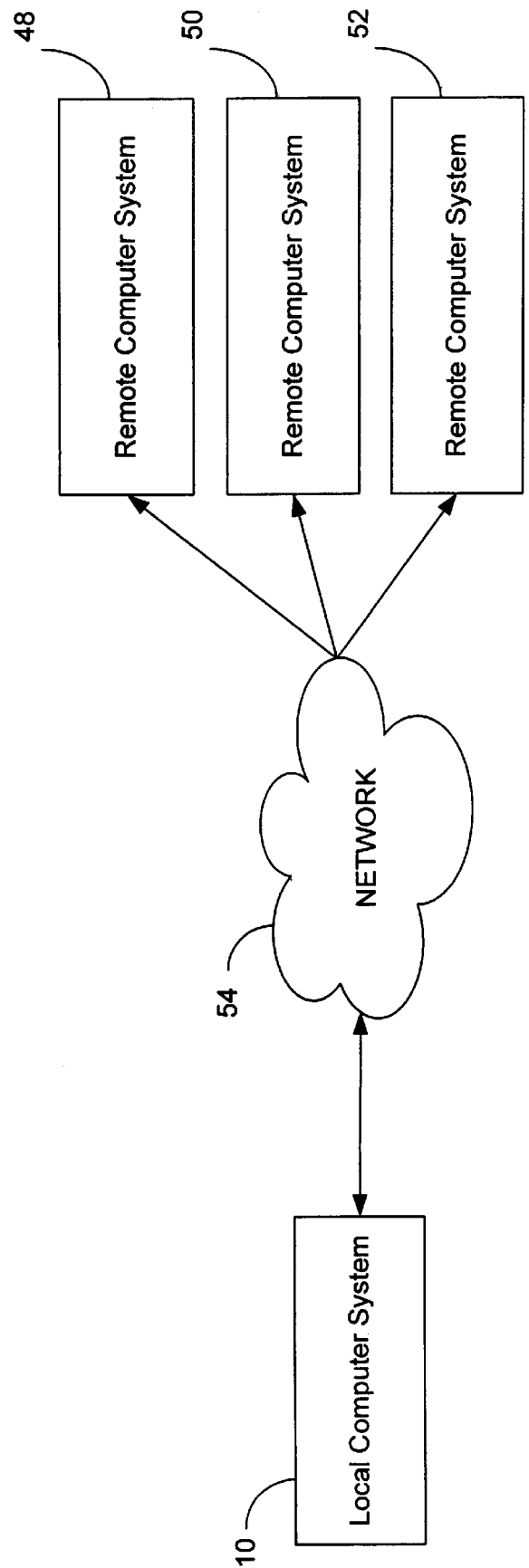

FIG. 1B depicts the interconnection of computer system 10 to remote computers 48, 50, and 52. FIG. 1B depicts a network 54 interconnecting remote servers 48, 50, and 52. Network interface 46 provides the connection from client computer system 10 to network 54. Network 54 can be, e.g., the Internet. Protocols for exchanging data via the Internet and other networks are well known. Information identifying the polymorphisms described herein can be transmitted across network 54 embedded in signals capable of traversing the physical media employed by network 54.

Information identifying polymorphisms shown in Table 1 is represented in records, which optionally, are subdivided into fields. Each record stores information relating to a different polymorphisms in Table 1. Collectively, the records can store information relating to all of the polymorphisms in Table 1, or any subset thereof, such as 5, 10, 50, or 100 polymorphisms from Table 1. In some databases, the information identifies a base occupying a polymorphic position and the location of the polymorphic position. The base can be represented as a single letter code (i.e., A, C, G or T/U) present in a polymorphic form other than that in the reference allele. Alternatively, the base occupying a polymorphic site can be represented in IUPAC ambiguity code as shown in Table 1. The location of a polymorphic site can be identified as its position within one of the sequences shown in Table 1. For example, in the first sequence shown in Table 1, the polymorphic site occupies the 15th base. The position can also be identified by reference to, for example, a chromosome, and distance from known markers within the chromosome. In other databases, information identifying a polymorphism contains sequences of 10–100 bases shown in Table 1 or the complements thereof, including a polymorphic site. Preferably, such information records at least 10, 15, 20, or 30 contiguous bases of sequences including a polymorphic site.

From the foregoing, it is apparent that the invention includes a number of general uses that can be expressed concisely as follows. The invention provides for the use of any of the nucleic acid segments described above in the diagnosis or monitoring of diseases, particularly hypertension. The invention further provides for the use of any of the nucleic acid segments in the manufacture of a medicament for the treatment or prophylaxis of such diseases. The invention further provides for the use of any of the DNA segments as a pharmaceutical.

All publications and patent applications cited above are incorporated by reference in their entirety for all purposes to the same extent as if each individual publication or patent application were specifically and individually indicated to be so incorporated by reference. Although the present invention has been described in some detail by way of illustration and example for purposes of clarity and understanding, it will be apparent that certain changes and modifications may be practiced within the scope of the appended claims.

TABLE 1

| Gene/Exon | Base Position | Ref Allele | Alt Allele | Ref Freq (P) | Alt Freq (Q) | Heterozygosity (H) | Sequence Tag | Ref Codon | Alt Codon | Type of amino acid change | Ref amino acid | Alt amino acid | SEQ ID NO: |
|---|---|---|---|---|---|---|---|---|---|---|---|---|---|
| AADDEX1 | 305 | G | A | 0.98 | 0.03 | 0.05 | ACGGGGGCGGAGCCTGAGCCGGAGCCGAC | . | . | Other | 5' UTR | . | 1 |
| AADDEX10 | 246 | G | T | 0.86 | 0.14 | 0.23 | AAGCTTCCGAGGAAKGGCAGAATGAAGC | GGG | TGG | Nonsynonymous | Gly | Trp | 2 |
| AADDEX12 | 43 | A | T | 0.94 | 0.06 | 0.01 | GATCCGAGACAGAWTTTACAGGACATTA | AAT | AAT | Nonsynonymous | Asn | Ile | 3 |
| AADDEX13 | 173 | C | G | 0.70 | 0.30 | 0.42 | GAAGCAGAAGGGCTSTGAAGGTGAGTGCT | TCT | TGT | Nonsynonymous | Ser | Cys | 4 |
| AADDEX15 | 74 | T | T | 0.73 | 0.27 | 0.40 | CCTAGTAAGTACCGYGCTGCCTCCGCTCT | . | . | Other | Intron | . | 5 |
| AADDEX16 | 1071 | G | A | 0.99 | 0.01 | 0.02 | ATTCCTGTCATAGGRAAGGTATATCAGGA | . | . | Other | 3' UTR | . | 6 |
| AADDEX16 | 1321 | C | T | 0.98 | 0.02 | 0.04 | GCCCCTGGGGCCCCTYGACATRCCGTCAT | . | . | Other | 3' UTR | . | 7 |
| AADDEX16 | 1328 | C | G | 0.91 | 0.09 | 0.17 | GGCCCTGACTAGGTRCAGGCAAGCTTGTG | . | . | Other | 3' UTR | . | 8 |
| AADDEX16 | 1478 | A | T | 0.89 | 0.11 | 0.19 | CAGCTTGCTGCASGTCACCCTCCTGAG | . | . | Other | 3' UTR | . | 9 |
| AADDEX16 | 691 | C | G | 0.99 | 0.01 | 0.02 | CAGCTTTGCTGCASGTCACCCTCCTGAG | . | . | Other | 3' UTR | . | 10 |
| AADDEX16 | 995 | C | T | 0.94 | 0.06 | 0.11 | TATGCATGTCTGACYGACGATCCCTCGAC | . | . | Other | 3' UTR | . | 11 |
| AADDEX2 | 31 | A | G | 0.98 | 0.03 | 0.05 | TTTGATTCTGTAGGRACCTAGAAAGATTG | . | . | Other | 5' UTR | . | 12 |
| AADDEX7 | 96 | T | A | 0.98 | 0.02 | 0.04 | ATTGGAGAAGTGGCTWATCATGACTACCAT | TAT | AAT | Nonsynonymous | Tyr | Asn | 13 |
| AADDEX9 | 173 | A | G | 0.93 | 0.07 | 0.13 | ATTGTGACAGGAGWTTTGAAGCCTCCAT | GAA | GAT | Nonsynonymous | Glu | Asp | 14 |
| ACEEX13 | 151 | T | C | 0.75 | 0.25 | 0.38 | CCAGCCAGGAGGCAYCCCAACAGTGACA | TCT | CCT | Nonsynonymous | Ser | Pro | 15 |
| ACEEX13 | 202 | A | G | 0.75 | 0.25 | 0.38 | AGGCAACACCAGRGCCAGACACCACC | AGC | GGC | Nonsynonymous | Ser | Gly | 16 |
| ACEEX15 | 144 | G | A | 0.80 | 0.20 | 0.32 | CTAGAACGGCAGCRCRGCCGTGCCAGGA | GCG | GCA | Synonymous | Ala | Ala | 17 |
| ACEEX17 | 19 | C | A | 0.59 | 0.31 | 0.43 | CTCAAGCCATTCAAMCCCTACAGATCT | . | . | Other | Intron | . | 18 |
| ACEEX18 | 130 | C | G | 0.95 | 0.05 | 0.09 | CAGCCACTCTACCTSAACCTGCATGCCTA | CTC | CTG | Synonymous | Leu | Leu | 19 |
| ACEEX21 | 150 | T | C | 0.98 | 0.03 | 0.05 | CTTCCATGAGGCCAYTGGGGACGTGCTAG | ATT | ACT | Nonsynonymous | Ile | Thr | 20 |
| ACEEX22 | 19 | T | C | 0.99 | 0.01 | 0.03 | AGCATGACATCAACKTTCTGATGAAGATG | TTT | GTT | Nonsynonymous | Phe | Val | 21 |
| ACEEX24 | 118 | C | T | 0.95 | 0.05 | 0.10 | CAGTCCAAGAGGCGYTGAGGCCTGACG | GCC | GCT | Synonymous | Ala | Ala | 22 |
| ACEEX26 | 16 | T | C | 0.57 | 0.43 | 0.49 | TGCTCCAGGTACTTYGTCAGCTTCATCAT | TTT | TTC | Synonymous | Phe | Phe | 23 |
| ACEEX26 | 154 | G | A | 0.98 | 0.03 | 0.05 | GGGCCTCAGCCAGCRGCTCTTCAGCATCC | CGG | CAG | Nonsynonymous | Arg | Gln | 24 |
| ACEEX26 | 174 | C | G | 0.90 | 0.10 | 0.18 | TCAGCATCCGCCACMGCAGCCTCCACCGG | CGC | AGC | Nonsynonymous | Arg | Ser | 25 |
| ACEEX26 | 205 | A | C | 0.98 | 0.02 | 0.04 | CTCCACGGCCCMGTTCGGCCTCCAGG | CAG | CCG | Nonsynonymous | Gln | Pro | 26 |
| ACEEX26 | 224 | G | A | 0.94 | 0.06 | 0.11 | GGCTCCGAGGTGGARCTGAGACACTCTG | GAG | GAA | Synonymous | Glu | Glu | 27 |
| ADDBEX10 | 81 | G | T | 0.99 | 0.01 | 0.05 | CTCCTGGAGCAAGAKAAGCACCGGCCCCA | GAG | GAT | Nonsynonymous | Glu | Asp | 28 |
| ADDBEX15 | 68 | G | A | 0.99 | 0.01 | 0.03 | GCTCTTGGTCCGGCCRTGTGCGAGTTCTTC | CCG | CCA | Synonymous | Pro | Pro | 29 |
| ADDBEX15 | 85 | C | T | 0.90 | 0.10 | 0.18 | TGCGAGTTCTTCAGYGTTGCCCTCCACAT | GCG | GTG | Nonsynonymous | Ala | Val | 30 |
| ADDBEX17 | 147 | G | A | 0.98 | 0.02 | 0.04 | GAGAAATCCTCAGMAAGGCCTGAGCAG | AGC | AGA | Nonsynonymous | Ser | Arg | 31 |
| ADDBEX3 | 138 | G | A | 0.89 | 0.11 | 0.19 | GCTTTTCTCAGAGGACRACCCCGAGTACATG | GAC | AAC | Nonsynonymous | Asp | Asn | 32 |
| ADDBEX4 | 134 | C | T | 0.99 | 0.01 | 0.02 | CATGCCAGCACCTSCCACGCAGTCTTCC | TCC | TGC | Nonsynonymous | Ser | Cys | 33 |
| ADDBEX8 | 173 | A | G | 0.96 | 0.04 | 0.07 | CACCTTCAAGGTTRGCTTAGCTCTTCTG | . | . | Other | Intron | . | 34 |
| ADDBEX9 | 69 | T | C | 0.99 | 0.01 | 0.02 | GTAGAGGAGGCATTYTACAAGATCTTCCA | TTT | TTC | Synonymous | Phe | Phe | 35 |
| ADDG | 2087 | T | A | 0.98 | 0.02 | 0.03 | TGACATTGCACATCYAAATACCACATTTA | . | . | Other | 3' UTR | . | 36 |
| ADORA2AEX1 | 429 | C | T | 0.97 | 0.03 | 0.07 | GGTGTCACTGGCGGYGGCCGACATCGCAG | GCG | GTG | Nonsynonymous | Ala | Val | 37 |
| ADORA2AEX2 | 1230 | G | T | 0.97 | 0.03 | 0.06 | TGCCAGAGTTCCTCAGMAAGGCCTGAGCAG | . | . | Other | 3' UTR | . | 38 |
| ADORA2AEX2 | 596 | G | A | 0.98 | 0.02 | 0.03 | CCCGGACAGCATCATTCCRCAAGATCATTCGA | CGC | CAC | Nonsynonymous | Arg | His | 39 |
| ADRB3EX1 | 741 | G | A | 0.92 | 0.08 | 0.15 | GGAGTGTGGGCCAAYGGCAGTGCTCCCA | AAC | AAT | Synonymous | Asn | Asn | 40 |
| ADRB3EX1 | 1020 | C | T | 0.96 | 0.04 | 0.07 | GGCCCCGGTGGGAYTGCGCCCGYCCCTCTTCC | ACG | ATG | Nonsynonymous | Thr | Met | 41 |
| ADRB3EX1 | 1354 | G | T | 0.89 | 0.11 | 0.20 | GGTAGGTAACCGGGKCGAGGGACCGCCG | CGC | CGT | Synonymous | Arg | Arg | 42 |
| ADRB3EX1 | 1445 | G | C | 0.90 | 0.10 | 0.18 | GCTACTCTCCCCRAGAGGGTGCACC | . | . | Other | Intron | . | 43 |
| ADRB3EX1 | 44 | A | G | 0.96 | 0.04 | 0.08 | GTGGTAGTGTCCAGSTGCCGTGGAGCAGC | . | . | Other | 5' UTR | . | 44 |
| ADRB3EX2 | 301 | G | T | 0.80 | 0.20 | 0.32 | TGGTTCCATTCCTYTYTGCCACCCAAACCC | . | . | Other | 3' UTR | . | 45 |
| ADRB3EX2 | 408 | C | T | 0.98 | 0.02 | 0.04 | TGGGACGTCTGAGAYTTTCTCCCTTCAAGT | . | . | Other | 3' UTR | . | 46 |
| ADROMEX1 | 1197 | C | T | | | | | . | . | Other | 5' UTR | . | 47 |

TABLE 1-continued

| Gene/Exon | Base Position | Ref Allele | Alt Allele | Ref Freq (P) | Alt Freq (Q) | Heterozygosity (H) | Sequence Tag | Ref Codon | Alt Codon | Type of change | amino acid Ref amino acid | Alt amino acid | SEQ ID NO: |
|---|---|---|---|---|---|---|---|---|---|---|---|---|---|
| ADROMEX1 | 154 | G | T | 0.98 | 0.02 | 0.05 | ATGTTACCTTCCTTKCCTGACTCAAGGGT | . | . | Other | Promoter | . | 48 |
| ADROMEX1 | 723 | C | T | 0.97 | 0.03 | 0.06 | GGGCTTCTTGCTGTYTTCGCCAGGAGCT | . | . | Other | Promoter | . | 49 |
| ADROMEX1 | 981 | G | A | 0.99 | 0.01 | 0.03 | GAGCAGGAGCGCCGRTGGCTGAGGAAAGA | . | . | Other | Promoter | . | 50 |
| ADROMEX2 | 101 | A | C | 0.96 | 0.04 | 0.07 | TCGCTCGCCTTCCMGGCCTGACACCGC | CTA | CTC | Synonymous | Leu | Leu | 51 |
| ADROMEX3 | 81 | C | G | 0.95 | 0.05 | 0.09 | CTGGCGATGTCCAGSAGCTACCCCACCGG | AGC | AGG | Nonsynonymous | Ser | Arg | 52 |
| ADROMEX4 | 1033 | T | C | 0.95 | 0.05 | 0.09 | ACCGAGTCTCGTAYAATCATTATTACATA | . | . | Other | 3' UTR | . | 53 |
| ADROMEX4 | 1292 | G | C | 0.98 | 0.02 | 0.05 | TGTCCTGGGTCGARTCAGGGCTTCGG | . | . | Other | 3' UTR | . | 54 |
| ADROMEX4 | 1389 | A | G | 0.97 | 0.03 | 0.06 | GCGAGCCTGACTCYCGGGTTGCCAACG | . | . | Other | 3' UTR | . | 55 |
| ADROMEX4 | 388 | G | C | 0.98 | 0.02 | 0.05 | CAAGCATCCCGSTGCCTCCCGGGACG | . | . | Other | 3' UTR | . | 56 |
| ADROMEX4 | 536 | T | G | 0.98 | 0.02 | 0.04 | CGCTTCTTAGCCTKGCTCAGGTGCAAGT | . | . | Other | 3' UTR | . | 57 |
| ADROMEX4 | 918 | A | G | 0.91 | 0.09 | 0.16 | ATTTTAAGACTGARTGTCTCAGCGAGT | . | . | Other | 3' UTR | . | 58 |
| AE1EX1 | 298 | G | A | 0.95 | 0.05 | 0.10 | GGGGCATGATCAGRGGTTTGCGAGCTGC | . | . | Other | Promoter | . | 59 |
| AE1EX1 | 80 | A | C | 0.98 | 0.02 | 0.04 | CAAACCTTCATCMCAAGGAAGATCA | . | . | Other | Promoter | . | 60 |
| AE1EX10 | 77 | G | A | 0.99 | 0.01 | 0.02 | CGAGGGAGCTGCTRCACTCCCTAGAGAG | CTG | CTA | Synonymous | Leu | Leu | 61 |
| AE1EX11 | 181 | C | T | 0.95 | 0.05 | 0.10 | GTCATCTTCATCTAYTTGCTCACTGTC | TAC | TAT | Synonymous | Tyr | Tyr | 62 |
| AE1EX11 | 191 | C | T | 0.99 | 0.01 | 0.03 | TCTACTTTGCTCAYTGCATCCCCCATC | CTG | TTG | Synonymous | Leu | Leu | 63 |
| AE1EX11 | 228 | A | T | 0.98 | 0.02 | 0.04 | GGGCCTCCTGGGTWGTGCCAATACCGT | . | . | Other | Intron | . | 64 |
| AE1EX12 | 70 | G | A | 0.93 | 0.07 | 0.13 | GGTCGGAGCTGCTRATCTCCACTGCAGT | CTG | CTA | Synonymous | Leu | Leu | 65 |
| AE1EX12 | 71 | A | T | 0.96 | 0.04 | 0.07 | TGTCGGAGCTGCTYGTWTCCACTGCAGTG | ATC | TTC | Nonsynonymous | Ile | Phe | 66 |
| AE1EX14 | 159 | A | T | 0.93 | 0.07 | 0.13 | CCTTCTTCTTTGCCWTGATGCTGCTGCAAG | ATG | TTG | Nonsynonymous | Met | Leu | 67 |
| AE1EX15 | 107 | T | C | 0.79 | 0.21 | 0.33 | TTCTTCATTCAGGAYACCTACACCCAGGT | GAT | GAC | Synonymous | Asp | Asp | 68 |
| AE1EX16 | 92 | C | T | 0.97 | 0.03 | 0.06 | GGCTGGGTCATCCAYCCACTGGGCTTGCG | CAC | CAT | Synonymous | His | His | 69 |
| AE1EX17 | 34 | A | G | 0.97 | 0.03 | 0.06 | CCTACAGTAGCTGATTGTCRGCAAACCT | ATT | GTT | Nonsynonymous | Ile | Val | 70 |
| AE1EX17 | 40 | T | G | 0.99 | 0.01 | 0.02 | GTAGGCTGATTGTCRGCAAACCTGAGCGC | AGC | GGC | Nonsynonymous | Ser | Gly | 71 |
| AE1EX17 | 72 | C | T | 0.94 | 0.06 | 0.11 | ATGGTCAAGGGCTCYGGCTTCCATCCTCACT | TCC | TCT | Synonymous | Ser | Ser | 72 |
| AE1EX19 | 132 | G | C | 0.96 | 0.04 | 0.07 | TGGCCCTGCCCTTCRTCCATCCTCACT | CGT | CAT | Nonsynonymous | Arg | His | 73 |
| AE1EX19 | 43 | T | G | 0.99 | 0.01 | 0.02 | GGTGAAGACCTGGCCACTTATTCA | CGC | CAC | Nonsynonymous | Arg | His | 74 |
| AE1EX20 | 1007 | G | A | 0.99 | 0.01 | 0.05 | AATCAGTGGACTCCRAGGGACTGAGACA | . | . | Other | 3' UTR | . | 75 |
| AE1EX20 | 1213 | A | T | 0.64 | 0.36 | 0.46 | ATTTGAGACCCATWTCCTCAACTCCATC | . | . | Other | 3' UTR | . | 76 |
| AE1EX20 | 1542 | T | C | 0.94 | 0.06 | 0.12 | AAAAATACAAAAATYAGCTGGGTGTCTCG | . | . | Other | 3' UTR | . | 77 |
| AE1EX20 | 1628 | G | C | 0.95 | 0.05 | 0.10 | CCCAGGAGGTGGAGSTGCAGTGAGCCAA | . | . | Other | 3' UTR | . | 78 |
| AE1EX20 | 1679 | A | G | 0.68 | 0.32 | 0.44 | CTGGGCAACAGAGCCRAGACCCTGTCTCAA | . | . | Other | 3' UTR | . | 79 |
| AE1EX20 | 379 | C | T | 0.97 | 0.03 | 0.06 | TCACTGGGGATCCCCAGMACAGGCAGGGTAG | . | . | Other | 3' UTR | . | 80 |
| AE1EX20 | 418 | G | A | 0.99 | 0.01 | 0.02 | TTACTGAGGCCCCRGAAATCAGTGGACTC | . | . | Other | 3' UTR | . | 81 |
| AE1EX20 | 991 | G | A | 0.99 | 0.01 | 0.03 | CAATACTAACCGACYTCTGGTTTTCAGCT | . | . | Other | 3' UTR | . | 82 |
| AE1EX4 | 17 | T | C | 0.98 | 0.02 | 0.05 | GTTTTCAGCTCACMCAGGAGCAACAG | . | . | Other | Intron | . | 83 |
| AE1EX4 | 36 | A | C | 0.91 | 0.09 | 0.16 | ACCCGGGTACCCACRAGGTGAGGACCCCA | GAC | GCC | Nonsynonymous | Asp | Ala | 84 |
| AE1EX4 | 89 | A | G | 0.78 | 0.23 | 0.35 | CTAGGCTGCCTAGWGTCTTCAGCAGGCCA | AAG | GAG | Nonsynonymous | Lys | Glu | 85 |
| AE1EX4 | 197 | G | C | 0.97 | 0.03 | 0.06 | TTCCCACAGGGAGAYGGGGGCACAGAGG | AGA | AGT | Nonsynonymous | Arg | Ser | 86 |
| AE1EX5 | 35 | T | C | 0.99 | 0.01 | 0.03 | AGAGTACCCTGTGAYAGCTGGCAAAGGCC | GAT | GAC | Synonymous | Asp | Asp | 87 |
| AE1EX8 | 181 | G | T | 0.99 | 0.01 | 0.01 | GTCGGATGCTGGCYAACTTCTTGGGCTTT | CAG | TAG | Nonsynonymous | Gln | STOP | 88 |
| AGTEX2 | 354 | C | G | 0.99 | 0.01 | 0.03 | GTACTTCAAGAACKGGATGTGCTTGCTG | GCC | GCT | Synonymous | Ala | Ala | 89 |
| AGTEX2 | 755 | T | G | 0.96 | 0.04 | 0.08 | TGGCAAGGCCTCTGYCCTGCCCTTTGCTG | CTG | CGG | Nonsynonymous | Leu | Arg | 90 |
| AGTEX5 | 258 | C | G | 0.97 | 0.03 | 0.06 | AGCTGGAAAGCAGCSGTTTCTCCCTTGGTC | . | . | Other | 3' UTR | . | 91 |
| AGTEX5 | 376 | C | T | 0.97 | 0.03 | 0.06 | GCCTTCGGTTTGTAKTTAGTGTCTTGAAT | . | . | Other | 3' UTR | . | 92 |
| AGTEX5 | 385 | T | G | 0.93 | 0.07 | 0.13 | GCCTTCGGTTTGTAKTTAGTGTCTTGAAT | . | . | Other | 3' UTR | . | 93 |
| AGTEX5 | 641 | T | G | 0.93 | 0.07 | 0.13 | GCCTTCGGTTTGTAKTTSTGGTGTTTAACAG | . | . | Other | 3' UTR | . | 94 |
| AGTEXP1 | 101 | G | C | 0.99 | 0.01 | 0.03 | CTGGCTGTCTATTSTTGGTGTTTAACAG | . | . | Other | Promoter | . | 95 |

TABLE 1-continued

| Gene/Exon | Base Position | Ref Allele | Freq (P) | Alt Allele | Freq (Q) | Heterozygosity (H) | Sequence Tag | Ref Codon | Alt Codon | Type of change | amino acid Ref amino acid | Alt amino acid | SEQ ID NO: |
|---|---|---|---|---|---|---|---|---|---|---|---|---|---|
| AGTEXP2 | 160 | G | 0.99 | A | 0.01 | 0.03 | GGAACCTTGGCCCCRACTCCTGCAAACTT | . | . | Other | Promoter | . | 96 |
| AGTEXP2 | 35 | G | 0.97 | A | 0.03 | 0.06 | CCCTCGCACCTCCRGCCTGCATGTCCCT | . | . | Other | Promoter | . | 97 |
| AGTEXP3 | 158 | A | 0.72 | G | 0.29 | 0.41 | CTCGTGACCCGCCRGGGGAAGAAGCTGC | . | . | Other | Promoter | . | 98 |
| AGTEXP3 | 173 | C | 0.96 | T | 0.04 | 0.08 | GGGAAGAAGCTGCYGTTGTTCTGGGTAC | . | . | Other | Promoter | . | 99 |
| ALDREDEX1 | 162 | A | 0.86 | T | 0.14 | 0.23 | CGCCAAGATGCCCWTCCTGGGGTTGGGT | ATC | TTC | Nonsynonymous | Ile | Phe | 100 |
| ALDREDEX1 | 71 | C | 0.41 | G | 0.59 | 0.48 | AAAGGTACGGCCCSSGGCCAAGGCGCAC | . | . | Other | Promoter | . | 101 |
| ALDREDEX10 | 150 | T | 0.91 | G | 0.09 | 0.16 | TTGCAAATGTAGTAKGGCCTGTGTCACTC | . | . | Other | 3' UTR | . | 102 |
| ALDREDEX2 | 180 | C | 0.94 | G | 0.06 | 0.11 | TGAAGCGTGAGGAGSTCTTCATCGTCAGC | CTC | GTC | Nonsynonymous | Leu | Val | 103 |
| ALDREDEX2 | 204 | T | 0.95 | C | 0.05 | 0.11 | TCAGCAAGGTATCGKTCCGCGGTGGGGCT | . | . | Ither | Intron | . | 104 |
| ALDREDEX3 | 88 | A | 0.98 | T | 0.03 | 0.05 | CGTCGGCTGCCGCCWCATCGACTGTGCCC | CAC | CTC | Nonsynonymous | His | Leu | 105 |
| ALDREDEX3 | 28 | A | 0.95 | T | 0.05 | 0.10 | CCCTCTCGCTGGCTTWGCTGTGTGCACGT | . | . | Other | Intron | . | 106 |
| ALDREDEX4 | 101 | G | 0.98 | A | 0.03 | 0.05 | AACATTCTGACACRTGGGCGTAAGACA | ACG | ACA | Synonymous | Thr | Thr | 107 |
| ALDREDEX6 | 87 | G | 0.94 | A | 0.06 | 0.11 | ACTGCCAGTCCAARGCATCGTGGTGACC | GGC | AGC | Nonsynonymous | Gly | Ser | 108 |
| ALDREDEX9 | 67 | C | 0.99 | T | 0.01 | 0.02 | CCAGATATGCCAYCTTACTCAGCTACA | ACC | ATC | Nonsynonymous | Thr | Ile | 109 |
| ANPEX1 | 252 | G | 0.99 | A | 0.01 | 0.03 | CCATGTACAATGCCRTGTCAACGCAGAC | GTG | ATG | Nonsynonymous | Val | Met | 110 |
| ANPEX1 | 297 | C | 0.97 | T | 0.03 | 0.06 | TAGGGCCAGAAAGYGGGTGCAGTCTGGG | . | . | Other | Intron | . | 111 |
| ANPEX3 | 106 | G | 0.97 | T | 0.03 | 0.06 | TCCTGTCCCCTGGGKTCTCTTGCTCATTT | . | . | Other | 3' UTR | . | 112 |
| ANPEX3 | 127 | T | 0.91 | C | 0.09 | 0.16 | TCATTTGTGTCAYCTTGTTGCCATGGA | . | . | Other | 3' UTR | . | 113 |
| APOA1 | 101 | C | 0.76 | T | 0.24 | 0.36 | GCCTTGCCCCAGGCYGGGCCCTCTGGGTAC | . | . | Other | Promoter | . | 114 |
| APOA1 | 1016 | A | 0.76 | T | 0.24 | 0.36 | CGTAACTGGGCACMGTCCACCCTGATAG | . | . | Other | Intron | . | 115 |
| APOA1 | 1162 | G | 0.94 | C | 0.06 | 0.12 | AGGTGTCACCCAGGSCTCACCCTGATAGG | . | . | Other | Intron | . | 116 |
| APOA1 | 1163 | C | 0.93 | C | 0.08 | 0.14 | GCCTGCCCCAGGCYGGCCCTCGGATGGA | . | . | Other | Intron | . | 117 |
| APOA1 | 1401 | G | 0.99 | C | 0.01 | 0.02 | TGCAGCCTACCTOSACGACTTCCAGAAG | GAC | CAC | Nonsynonymous | Asp | His | 118 |
| APOA1 | 1576 | G | 0.98 | A | 0.02 | 0.04 | TGTGGACGCGTGCSCACGCATCTGGCCC | CGC | CCC | Nonsynonymous | Arg | Pro | 119 |
| APOA1 | 1643 | G | 0.98 | C | 0.02 | 0.04 | CTTGAGGCTCTCAARGAGAACGGCGGCGC | AAG | AAA | Synonymous | Lys | Lys | 120 |
| APOA1 | 1757 | C | 0.94 | A | 0.06 | 0.11 | CAAGGCCTGCCCSGTGCCSGTGCTGGAGAGCTT | CCC | CCG | Synonymous | Pro | Pro | 121 |
| APOA1 | 2007 | T | 0.64 | C | 0.36 | 0.46 | CTCCGTGCCCAGACWGACGTCTTTAGGGC | . | . | Other | 3' UTR | . | 122 |
| APOA1 | 334 | T | 0.69 | A | 0.31 | 0.43 | AACCATCGGGGCYTTCTCCCTAAATCC | . | . | Other | Intron | . | 123 |
| APOA1 | 620 | C | 0.92 | T | 0.08 | 0.14 | TTTGAAGGCTCCGCYTTGGGAAAACAGCT | GCC | GCT | Synonymous | Ala | Ala | 124 |
| APOA1 | 771 | C | 0.96 | G | 0.04 | 0.07 | CCTGATGGAGAAAACYGGAATGGATCTCCA | . | . | Other | Intron | . | 125 |
| APOA1 | 840 | G | 0.99 | A | 0.01 | 0.02 | GGGCTGCCCATGCRCRTGATCACAGAGCCA | . | . | Other | Intron | . | 126 |
| APOA2 | 1334 | G | 0.75 | G | 0.25 | 0.38 | AGATTAGGCTTAAWTGCAGAGAAAAAGT | . | . | Other | Intron | . | 127 |
| APOA2 | 1412 | T | 0.82 | C | 0.18 | 0.29 | AAGAACTGGGCCTTSAATTTCAGTCTCTA | . | . | Other | Intron | . | 128 |
| APOA2 | 1414 | A | 0.95 | C | 0.05 | 0.10 | GACAAAGGTCTTGAYTCTTATTCCTACCTA | . | . | Other | Intron | . | 129 |
| APOA2 | 1459 | C | 0.99 | T | 0.01 | 0.03 | AGCAAAGGCTTTGACTCTTAGGG | . | . | Other | Intron | . | 130 |
| APOA2 | 1672 | C | 0.94 | T | 0.06 | 0.11 | AGGCTGGAACGAAVTGGTTAACTTCTTG | CTG | TTG | Synonymous | Leu | Leu | 131 |
| APOA2 | 249 | T | 0.55 | C | 0.45 | 0.50 | TGCTTCCTGTTGCAYTCAGTAAGGAGGCAA | . | . | Other | Promoter | . | 132 |
| APOA2 | 547 | A | 0.99 | G | 0.01 | 0.01 | GCCTGGCTAGGTMAGATAAGGAGGCAA | . | . | Other | Intron | . | 133 |
| APOA2 | 1228 | A | 0.75 | G | 0.25 | 0.38 | GACCAGGTGCCGCTGATGTGGGACTA | ACA | ACG | Synonymous | Thr | Thr | 134 |
| APOA4 | 1338 | T | 0.03 | G | 0.97 | 0.06 | GGGACTACAGTGYGVGGAAGTTTGACGGGA | . | . | Other | Intron | . | 135 |
| APOA4 | 1479 | C | 0.98 | T | 0.03 | 0.05 | CCACATATGTAAACYGGAAGTTTGACCCG | . | . | Other | Intron | . | 136 |
| APOA4 | 1529 | A | 0.86 | C | 0.14 | 0.24 | TTGCTTTGACGTTCYAGAGTTTGACAAAT | . | . | Other | Intron | . | 137 |
| APOA4 | 1597 | T | 0.50 | T | 0.41 | 0.48 | GGAGAAAATTGTCAYGTGAGCCTGATTTCT | . | . | Other | Intron | . | 138 |
| APOA4 | 1617 | G | 0.99 | A | 0.01 | 0.02 | CTGATTCTAATACRTTTCAGAAGACAG | . | . | Other | Intron | . | 139 |
| APOA4 | 1879 | C | 0.94 | G | 0.06 | 0.11 | GATTCTGAGACAAASTATGTGGAGATCC | . | . | Other | Intron | . | 140 |
| APOA4 | 1961 | G | 0.96 | A | 0.04 | 0.07 | CTGCACCACCATAGRGAGGGTGAACTCGG | . | . | Other | Intron | . | 141 |
| APOA4 | 1998 | T | 0.63 | C | 0.37 | 0.47 | AGCACTCACCTGTCYTAGCACGTGTGCAT | . | . | Other | Intron | . | 142 |
| APOA4 | 2134 | C | 0.73 | T | 0.28 | 0.40 | GAAGTGAACACTTAYGCAGGTGACCTGCA | TAC | TAT | Synonymous | Tyr | Tyr | 143 |

TABLE 1-continued

| Gene/Exon | Base Position | Ref Allele | Alt Allele | Freq (P) | Freq (Q) | Heterozygosity (H) | Sequence Tag | Ref Codon | Alt Codon | Type of amino acid change | Ref amino acid | Alt amino acid | SEQ ID NO: |
|---|---|---|---|---|---|---|---|---|---|---|---|---|---|
| APOA4 | 2138 | G | A | 0.99 | 0.01 | 0.02 | TGAACACTTACGCARGTGACCTGCAGAAG | GGT | AGT | Nonsynonymous | Gly | Ser | 144 |
| APOA4 | 2140 | T | C | 0.94 | 0.06 | 0.12 | AACACTTACGCAGGYGACCTGCAGAAGAA | GGT | GGC | Synonymous | Gly | Gly | 145 |
| APOA4 | 2358 | A | G | 0.89 | 0.11 | 0.20 | GCGCACCCAGGTCARCACGCAGGCCGAGC | AAC | AGC | Nonsynonymous | Asn | Ser | 146 |
| APOA4 | 2698 | C | T | 0.95 | 0.05 | 0.10 | ATCTCCGCCAGTGCYGAGGAGCTGCCGCA | GCC | GCT | Synonymous | Ala | Ala | 147 |
| APOA4 | 2764 | C | T | 0.92 | 0.08 | 0.15 | CTGAGGGGCAACACYGAGGGGCTGCAGAA | ACC | ACT | Synonymous | Thr | Thr | 148 |
| APOA4 | 2806 | G | A | 0.99 | 0.01 | 0.02 | CTGGTGGGACCCTRGACCACCAGGTGGA | CTG | CTA | Synonymous | Leu | Leu | 149 |
| APOA4 | 2837 | G | A | 0.98 | 0.02 | 0.04 | AGTTCCGACCGCGGSTGGAGCGCTACGGG | CTG | CTG | Nonsynonymous | Leu | Leu | 150 |
| APOA4 | 2926 | G | T | 0.81 | 0.19 | 0.30 | CATGCGGGGACGTKGAAGGCCACTTGAG | GTG | GTT | Synonymous | Val | Val | 151 |
| APOA4 | 2926 | G | T | 0.16 | 0.84 | 0.26 | CAGCAGGAACAGCAKCAGGAGCAGCAGCA | GTG | GTT | Nonsynonymous | Val | Val | 152 |
| APOA4 | 3058 | T | G | 0.88 | 0.12 | 0.21 | GCCAGCAGGGCCTCRAGGCCATCAGTCCG | CAT | CAG | Nonsynonymous | His | Gln | 153 |
| APOA4 | 350 | G | A | 0.96 | 0.04 | 0.08 | TGGCGATAGGGAGASAGTTTAAATGTCTG | . | . | Other | Promoter | . | 154 |
| APOA4 | 637 | G | C | 0.96 | 0.04 | 0.07 | GTTCCACTGCAGCRCAGGTGAGCTCTCC | . | . | Other | Promoter | . | 155 |
| APOC1EX1 | 687 | G | T | 0.93 | 0.07 | 0.13 | TTGTATTTCAGTAKAGACAGGGTTTCAC | . | . | Other | Promoter | . | 156 |
| APOC1EX1 | 1020 | G | A | 0.95 | 0.05 | 0.10 | TTCACCTGTGTCTCRATCTCCTGACTTTG | . | . | Other | Intron | . | 157 |
| APOC1EX1 | 1044 | T | C | 0.64 | 0.36 | 0.46 | CGATCCTCCTGACTTYGTGATCCGCCTGCC | . | . | Other | Intron | . | 158 |
| APOC1EX1 | 1057 | C | T | 0.89 | 0.11 | 0.49 | CAGGCGTGAGCCACYGCGTCCGGCATTC | . | . | Other | Intron | . | 159 |
| APOC1EX1 | 1111 | G | T | 0.57 | 0.43 | 0.49 | GCAGGCGCCTTGTAGKCCCAGCTACTCGGG | . | . | Other | Intron | . | 160 |
| APOC1EX1 | 1376 | C | T | 0.99 | 0.01 | 0.02 | GACGGAGAATCASTTGAACCCGGAGG | . | . | Other | Intron | . | 161 |
| APOC1EX1 | 1411 | G | A | 0.97 | 0.03 | 0.06 | AGGCTCTTTCCTGTCRCTCCCCGGTCCTGGT | TCG | TCA | Synonymous | Ser | Ser | 162 |
| APOC1EX1 | 432 | C | G | 0.61 | 0.39 | 0.47 | GTGGTTCTGTCGATSGTCTTGGAAGGTAA | ATC | ATG | Nonsynonymous | Ile | Met | 163 |
| APOC1EX1 | 462 | G | C | 0.01 | 0.99 | 0.02 | GGATGGAGAATTGSGGAGTTTGGAGATT | . | . | Other | Intron | . | 164 |
| APOC1EX1 | 496 | T | C | 0.99 | 0.01 | 0.02 | ACCTCTGGATTGGYTGTCCTGCTTCGAC | . | . | Other | Intron | . | 165 |
| APOC1EX1 | 713 | C | A | 0.91 | 0.09 | 0.17 | TCTGAGGACTCAAGKGCCAAGATGGAGGG | . | . | Other | 3' UTR | . | 166 |
| APOC2 | 1084 | T | C | 0.99 | 0.01 | 0.01 | CAGTTCTCTGGACAYTATGGCACACGAC | . | . | Other | 5' UTR | . | 167 |
| APOC2 | 126 | C | T | 0.34 | 0.66 | 0.45 | CTCGGACACCGAGCWCACACAGAAGGA | . | . | Other | Promoter | . | 168 |
| APOC2 | 13 | T | A | 0.99 | 0.01 | 0.02 | CCGAAACCTGTACRAGAAGACATACCTG | GAG | AAG | Nonsynonymous | Glu | Lys | 169 |
| APOC2 | 472 | G | C | 0.99 | 0.01 | 0.02 | TGGCCCATACCACCRACTGCATCCAGGAC | . | . | Other | Intron | . | 170 |
| APOC2 | 553 | G | A | 0.19 | 0.81 | 0.31 | CCCAGAGTCCAGGYCCCCAGACCCTCCT | . | . | Other | Intron | . | 171 |
| APOC2 | 725 | T | C | 0.97 | 0.03 | 0.06 | TGTGCTTTCTCCCWGGACTTGTACAGC | . | . | Other | Intron | . | 172 |
| APOC2 | 804 | A | T | 0.82 | 0.18 | 0.30 | GGGACTTGTACAGCMAAAGCACCAGCAGCC | AAA | CAA | Nonsynonymous | Lys | Gln | 173 |
| APOC3 | 819 | T | A | 0.95 | 0.05 | 0.10 | CAGTTTGTACAAGAAWTTTATGAACACCT | . | . | Other | Intron | . | 174 |
| APOC3 | 1148 | G | A | 0.71 | 0.29 | 0.41 | CACGGGCTTGAATTRGGTCAGGTGGGCC | . | . | Other | Intron | . | 175 |
| APOC3 | 1322 | A | C | 0.97 | 0.03 | 0.06 | ATACGCCTGAGCTCMGCCTCCTGTCAGAT | . | . | Other | Intron | . | 176 |
| APOC3 | 1468 | A | T | 0.95 | 0.05 | 0.10 | GGCTGTGAACCCTRTTGTGAACTGCACA | . | . | Other | Intron | . | 177 |
| APOC3 | 1519 | G | A | 0.96 | 0.04 | 0.07 | GGCCATGAGAAAWTGTCCACCACAAAA | . | . | Other | Intron | . | 178 |
| APOC3 | 1637 | T | A | 0.84 | 0.16 | 0.27 | AGGAAAATGGGCCRCGGCGCAGTGGCTG | . | . | Other | Intron | . | 179 |
| APOC3 | 1722 | C | T | 0.73 | 0.27 | 0.40 | ATGGGGCCAGGCGGCCGRCGTGCTCATGCCTG | . | . | Other | Intron | . | 180 |
| APOC3 | 1728 | G | C | 0.85 | 0.15 | 0.26 | AGGGCCAGTGGCTCRTGCCTGTAATCCA | . | . | Other | Intron | . | 181 |
| APOC3 | 1736 | A | C | 0.76 | 0.24 | 0.36 | GAGGCCAGGCAGMGGATCCCCTGAGGT | . | . | Other | Intron | . | 182 |
| APOC3 | 1774 | A | C | 0.69 | 0.31 | 0.43 | CAACTGGCCAACAYGGTGAAACCCCATC | . | . | Other | Intron | . | 183 |
| APOC3 | 1817 | T | C | 0.98 | 0.02 | 0.04 | TTGAACCCGGGAGAYGAAGTTGCAGTGA | . | . | Other | Intron | . | 184 |
| APOC3 | 1931 | C | T | 0.99 | 0.01 | 0.03 | CTGCACTCCAGCCTRGGTGACAGAGGAG | . | . | Other | Intron | . | 185 |
| APOC3 | 1975 | G | A | 0.96 | 0.04 | 0.08 | AGGGCTAAAACGGRCAGCCCTAGGACTG | . | . | Other | Intron | . | 186 |
| APOC3 | 2221 | G | A | 0.81 | 0.19 | 0.30 | GCGTGCTTCATGTARCCCTCCATGAAGCT | GGC | GGT | Synonymous | Gly | Gly | 187 |
| APOC3 | 2535 | C | T | 0.70 | 0.30 | 0.42 | CCCTGGGGAGGTGGYGTGGCCCCTAAGGT | . | . | Other | Promoter | . | 188 |
| APOC3 | 2854 | A | C | 0.69 | 0.31 | 0.43 | GCAACCTACAGGGMAGCCCTGGAGATTG | . | . | Other | 3' UTR | . | 189 |
| APOC3 | 429 | G | C | 0.99 | 0.01 | 0.03 | GGAACCTCAAGGAGCTSGCAGGATGATAGG | . | . | Other | 3' UTR | . | 190 |
| APOC3 | 460 | G | A | 0.96 | 0.04 | 0.07 | TAAATCAGTCAGGRGGAAGCAACAGAGCAG | . | . | Other | Intron | . | 191 |

TABLE 1-continued

| Gene/Exon | Base Position | Ref Allele | Alt Allele | Ref Freq (P) | Alt Allele Freq (Q) | Heterozygosity (H) | Sequence Tag | Ref Codon | Alt Codon | Type of change | amino acid | Ref amino acid | Alt amino acid | SEQ ID NO: |
|---|---|---|---|---|---|---|---|---|---|---|---|---|---|---|
| APOC3 | 954 | A | G | 0.89 | 0.11 | 0.19 | GTGCAAACAGCACCRCCTGAGTTGCACA | . | . | Other | | Intron | . | 192 |
| APOC4 | 1150 | T | C | 0.39 | 0.61 | 0.47 | AAGTGCTAGGATTAYAGGCGTGAGCCACT | . | . | Other | | Intron | . | 193 |
| APOC4 | 1246 | A | C | 0.33 | 0.67 | 0.44 | AGGCTGGTCTTGAAMTCCTGACCTCAGGT | . | . | Other | | Intron | . | 194 |
| APOC4 | 1281 | C | T | 0.91 | 0.09 | 0.16 | CCCGCCTTGCCTCYCAAAGTGCTGGGAT | . | . | Other | | Intron | . | 195 |
| APOC4 | 1287 | T | C | 0.95 | 0.05 | 0.10 | TGGCCTCCCAAAGYGCTGGGATTACAGG | . | . | Other | | Intron | . | 196 |
| APOC4 | 1313 | A | G | 0.42 | 0.58 | 0.49 | AGGCATGAGCCACCRCCGCCGACCATGTA | . | . | Other | | Intron | . | 197 |
| APOC4 | 1406 | G | A | 0.87 | 0.13 | 0.22 | ACAGGGCCAGGCACRTGGCTCATGCCTG | . | . | Other | | Intron | . | 198 |
| APOC4 | 1446 | G | A | 0.91 | 0.09 | 0.16 | CTTTCGGAGGCTGAGGCMGGAGAATCACTTGA | . | . | Other | | Intron | . | 199 |
| APOC4 | 1587 | C | A | 0.29 | 0.71 | 0.41 | CGGGAGGCTGAGGCTGAGGTGARGCGGCTGATCGCA | . | . | Other | | Intron | . | 200 |
| APOC4 | 1782 | G | C | 0.96 | 0.04 | 0.07 | ATAACCCTGAGGTASATATTATTACCCG | . | . | Other | | Intron | . | 201 |
| APOC4 | 1794 | C | T | 0.94 | 0.06 | 0.11 | TAGATATTATTACCYCGTTCTACAAAAGG | . | . | Other | | Intron | . | 202 |
| APOC4 | 1842 | G | A | 0.98 | 0.03 | 0.05 | CAGGATAAGTCACCRGCCAAGGCACACAG | . | . | Other | | Intron | . | 203 |
| APOC4 | 1858 | T | C | 0.36 | 0.64 | 0.46 | CCAAGCACACAGCYAGCTACATGTGGCC | . | . | Other | | Intron | . | 204 |
| APOC4 | 1875 | C | T | 0.96 | 0.04 | 0.07 | CTACATGTGGCCCCYCCGGTGACGGCTGGT | . | . | Other | | Intron | . | 205 |
| APOC4 | 2206 | A | G | 0.92 | 0.08 | 0.15 | TGAAAGATGCCCRGCCGACGGGGTGG | . | . | Other | | Intron | . | 206 |
| APOC4 | 2237 | C | T | 0.94 | 0.06 | 0.12 | CACATCTGTAATCYAGCATTTTGGAGC | . | . | Other | | Intron | . | 207 |
| APOC4 | 2276 | T | C | 0.65 | 0.35 | 0.46 | TGGATCACTTGAGGYCAGGAGTTCGAGGC | . | . | Other | | Intron | . | 208 |
| APOC4 | 2345 | A | G | 0.74 | 0.26 | 0.38 | ATTAGCCGGCATGRTGGCAAGATGCCTGT | . | . | Other | | Intron | . | 209 |
| APOC4 | 2366 | T | A | 0.51 | 0.49 | 0.50 | ATGCCTGTAATCCCWGCTACTCCTGGAGC | . | . | Other | | Intron | . | 210 |
| APOC4 | 2767 | G | A | 0.99 | 0.01 | 0.02 | AAGATGAGTCGCTGRAGCCTGGTGAGGGG | TGG | TGA | Nonsynonymous | | Trp | Stop | 211 |
| APOC4 | 3027 | G | A | 0.98 | 0.03 | 0.05 | TCACAGAGGAGCRGATAAATGGGCAG | . | . | Other | | Intron | . | 212 |
| APOC4 | 3078 | G | C | 0.96 | 0.04 | 0.08 | GCCTCCACTGTGATSTCCTCTCTCTA | . | . | Other | | Intron | . | 213 |
| APOC4 | 3162 | T | G | 0.51 | 0.49 | 0.50 | GGACTCGGGTCCGCKCCACCAAGGCCTGGT | CTC | CGC | Nonsynonymous | | Leu | Arg | 214 |
| APOC4 | 3252 | A | T | 0.91 | 0.09 | 0.17 | TGGGGACAAGGACCWGGGTTAAAATGTTC | CAG | CTG | Nonsynonymous | | Gln | Leu | 215 |
| APOC4 | 483 | T | G | 0.95 | 0.05 | 0.10 | CTGAGAGTGAAGTGKGAATGTCACATTGG | . | . | Other | | Intron | . | 216 |
| APOC4 | 931 | A | T | 0.97 | 0.03 | 0.06 | CCAAGGCTCCGGAGTGGCCRGTGGATCTTG | . | . | Other | | Intron | . | 217 |
| APOC4 | 968 | C | T | 0.76 | 0.24 | 0.36 | CAAGCTCCGCCTCCYGGGTTCACGCCATT | . | . | Other | | Intron | . | 218 |
| APOC4 | 454 | G | T | 0.98 | 0.02 | 0.04 | CGCGCAAGGACTCSGAGGGCTGAGACGC | . | . | Other | | Intron | . | 219 |
| APOER2EX1 | 68 | A | G | 0.96 | 0.04 | 0.07 | ACCAACTGTCCAGCMTTGACTTCAGTGGA | ATT | CTT | Nonsynonymous | | Ile | Leu | 220 |
| APOER2EX12 | 55 | G | A | 0.99 | 0.01 | 0.02 | CCAGCCATTTTCASTGCAAATCGGCTCA | AGT | ACT | Nonsynonymous | | Ser | Thr | 221 |
| APOER2EX13 | 162 | G | A | 0.98 | 0.03 | 0.05 | GAAGAGGTGCTACCRAGGTAAGCACCT | CGA | CAA | Nonsynonymous | | Arg | Gln | 222 |
| APOER2EX14 | 55 | G | A | 0.98 | 0.03 | 0.05 | TACCTGCATCTGGAGRAACTGGAAGCGGAA | AGA | AGG | Synonymous | | Arg | Arg | 223 |
| APOER2EX17 | 1005 | G | C | 0.52 | 0.48 | 0.50 | AGAGTGCTCAGAAASTCAAGATAGGATAT | . | . | Other | | 3' UTR | . | 224 |
| APOER2EX19 | 1060 | T | G | 0.96 | 0.04 | 0.07 | TAAAGTTCAGCTCTYTGAGTAACTTCTTC | . | . | Other | | 3' UTR | . | 225 |
| APOER2EX19 | 1149 | A | T | 0.98 | 0.03 | 0.05 | TGCCATCCTTACAGWGCTAAGTGGACG | . | . | Other | | 3' UTR | . | 226 |
| APOER2EX19 | 13 | G | A | 0.51 | 0.49 | 0.50 | GTTGTCCCCAGCRAGTGGCATTAAGCC | CGA | CAA | Nonsynonymous | | Arg | Gln | 227 |
| APOER2EX19 | 602 | T | G | 0.93 | 0.07 | 0.13 | TTTAGAAGTGAGRTGTATTTATTTTGG | . | . | Other | | 3' UTR | . | 228 |
| APOER2EX19 | 931 | G | A | 0.99 | 0.01 | 0.02 | CCATGGCTGTGMCTCCACTAGAGGCT | . | . | Other | | 3' UTR | . | 229 |
| APOER2EX9 | 116 | G | A | 0.99 | 0.01 | 0.03 | TGCTCAAGAATGCTRCTGACCCTAGATG | GTG | ATG | Nonsynonymous | | Val | Met | 230 |
| APOER2EX9 | 157 | G | C | 0.99 | 0.01 | 0.01 | AATCGCATCTACTGSTGTGACCTCTCCTA | TGG | TGC | Nonsynonymous | | Trp | Cys | 231 |
| AT1EX5 | 1158 | A | G | 0.95 | 0.05 | 0.10 | TGAGTTGACARTGTTCGAAACCTGT | . | . | Other | | 3' UTR | . | 232 |
| AT1EX5 | 1226 | T | A | 0.92 | 0.08 | 0.15 | TCCTCTGCAGCACTKCACTACCAAATGAG | . | . | Other | | 3' UTR | . | 233 |
| AT1EX5 | 1242 | A | G | 0.53 | 0.47 | 0.50 | ACTACCAAATGAGCMTTAGCTACTTTTCA | . | . | Other | | 3' UTR | . | 234 |
| AT1EX5 | 1249 | A | G | 0.99 | 0.01 | 0.03 | AATGAGCATTAGCTRCTRCTTTCAGAATTGA | . | . | Other | | 3' UTR | . | 235 |
| AT1EX5 | 1473 | G | A | 0.91 | 0.09 | 0.17 | CCTGCTTTTGTCCRTRTTATTTTTATTTC | . | . | Other | | 3' UTR | . | 236 |
| AT2EX3 | 1355 | T | G | 0.39 | 0.61 | 0.47 | GTTTGTACAAGATKTCATTRGTGAGACA | . | . | Other | | 3' UTR | . | 237 |
| AT2EX3 | 1361 | G | A | 0.69 | 0.31 | 0.43 | ACAAGATTTTCATTRGTGAGACATATTTA | . | . | Other | | 3' UTR | . | 238 |
| AT2EX3 | 562 | T | C | 0.99 | 0.01 | 0.03 | TATATAGTTCCCCYTGTTTGTGTATGGC | CTT | CTC | Synonymous | | Leu | Leu | 239 |

TABLE 1-continued

| Gene/Exon | Base Position | Ref Allele | Ref Allele Freq (P) | Alt Allele | Alt Allele Freq (Q) | Heterozygosity (H) | Sequence Tag | Ref Codon | Alt Codon | Type of amino acid change | Ref amino acid | Alt amino acid | SEQ ID NO: |
|---|---|---|---|---|---|---|---|---|---|---|---|---|---|
| AT2EX3 | 807 | G | 0.94 | A | 0.06 | 0.12 | CTATGGAAGAACARGATAACCCGTGACC | AGG | AAG | Nonsynonymous | Arg | Lys | 240 |
| AT2EX3 | 844 | T | 0.93 | C | 0.07 | 0.13 | AAGGATGGCAGCTGCYTGYTTGTTCTGGCCTT | GCT | GCC | Synonymous | Ala | Ala | 241 |
| AVPEX2 | 154 | C | 0.96 | T | 0.04 | 0.08 | GGAGAACTACCTGCYGTCGCCCTGCCAGT | CCG | CTG | Nonsynonymous | Pro | Leu | 242 |
| AVPR2EX1 | 114 | A | 0.97 | T | 0.03 | 0.06 | TCATGGCGTCCACWCTTCCGGTAAGGCT | ACT | TCT | Nonsynonymous | Thr | Ser | 243 |
| AVPR2EX2 | 109 | G | 0.98 | A | 0.02 | 0.04 | ACCCGGACCCGCTRCTAGCCCGGGCGGA | CTG | CTA | Synonymous | Leu | Leu | 244 |
| AVPR2EX2 | 129 | C | 0.85 | T | 0.15 | 0.25 | CCGGGCGAAGCTGGYCTGCTCTTCCATAG | GCG | GTG | Nonsynonymous | Ala | Val | 245 |
| AVPR2EX2 | 184 | G | 0.94 | T | 0.06 | 0.11 | GGCTTCGTGCTGGCKGCCCTAGCTCGGCG | GCC | GCT | Synonymous | Ala | Ala | 246 |
| AVPR2EX2 | 444 | C | 0.87 | T | 0.13 | 0.23 | CCGTCCATGCTGGYGTACCGCCATGGAA | GCG | GTG | Nonsynonymous | Ala | Val | 247 |
| AVPR2EX2 | 112 | C | 0.95 | T | 0.05 | 0.10 | TCTTTCAGCAGCAGYGTGTCCTCAGAGCT | AGC | AGT | Synonymous | Ser | Ser | 248 |
| AVPR2EX3 | 232 | G | 0.95 | A | 0.05 | 0.10 | AAGGACACTTCATCRTGAGGAGCTGTTGG | TCG | TCA | Synonymous | Ser | Ser | 249 |
| AVPR2EX3 | 252 | T | 0.97 | C | 0.03 | 0.06 | AGCTGTTGGGTGTCYTGCCTCTAGAGGCT | . | . | Other | 3' UTR | . | 250 |
| AVPR2EX3 | 46 | A | 0.50 | G | 0.50 | 0.50 | GCGCCTTTGCTRCTCATGTTGCTGGC | CTA | CTG | Synonymous | Leu | Leu | 251 |
| BIR | 1069 | C | 0.98 | T | 0.03 | 0.05 | CAGGaCTGGCTGGAYGCACAGCTCTAGG | . | . | Other | 3' UTR | . | 252 |
| BIR | 1142 | G | 0.67 | T | 0.33 | 0.44 | GGTGAGCCAGTCCTRAATTGGGTTGGAG | . | . | Other | 3' UTR | . | 253 |
| BIR | 1185 | G | 0.98 | T | 0.03 | 0.05 | ATAACCAGTACAGKTTCCTGCTGAGGCC | . | . | Other | 3' UTR | . | 254 |
| BIR | 1265 | G | 0.95 | A | 0.05 | 0.10 | GGAGGCTGACCTGARGCTGCCCAGCCTC | . | . | Other | 3' UTR | . | 255 |
| BIR | 1295 | C | 0.24 | T | 0.76 | 0.37 | CACCAGGCCCTGGCYGGGCTACATACCAC | . | . | Other | 3' UTR | . | 256 |
| BIR | 1441 | T | 0.99 | C | 0.01 | 0.02 | AGGGGCCCGGGCYGAGCGAGGTCAG | TCA | TCG | Synonymous | Ser | Ser | 257 |
| BIR | 1521 | C | 0.26 | T | 0.74 | 0.38 | TGTGGGCACTTTGAYGGTGTTGCCAAACT | GTC | ATC | Nonsynonymous | Val | Ile | 258 |
| BIR | 1729 | G | 0.99 | C | 0.01 | 0.03 | GGTGCCAGTGCTASAGTGGGCTGTTGGC | CTC | CTG | Synonymous | Leu | Leu | 259 |
| BIR | 1946 | G | 0.99 | T | 0.01 | 0.02 | GCATGAAGCAGAGGYGGCCGTGGCGCAGG | CGC | CAC | Nonsynonymous | Arg | His | 260 |
| BIR | 1960 | G | 0.75 | A | 0.25 | 0.38 | CCCGCTAAGAGCCYTTCTCCCCGCCAA | GCC | GCT | Synonymous | Ala | Ala | 261 |
| BIR | 2463 | T | 0.22 | A | 0.78 | 0.34 | ACGGTACCTGGGCTTGCGATRGGGTCTCTG | AAG | GAG | Nonsynonymous | Lys | Glu | 262 |
| BIR | 2664 | T | 0.97 | C | 0.03 | 0.06 | TGTGCTGGCCTCACYTCTGAGATAACTCC | . | . | Other | 5' UTR | . | 263 |
| BIR | 2894 | T | 0.99 | A | 0.01 | 0.03 | TGGTGGTGCCACCKGTAATCCCACTAC | . | . | Other | Promoter | . | 264 |
| BIR | 2954 | G | 0.97 | A | 0.03 | 0.06 | CCGAGAGGCGGAGSTTGCAGTGAGCCAA | . | . | Other | Promoter | . | 265 |
| BIR | 3174 | C | 0.70 | T | 0.30 | 0.42 | TCCCGCTAAGAGCCYTTCTCCCGCCAA | . | . | Other | Promoter | . | 266 |
| BIR | 369 | G | 0.97 | A | 0.03 | 0.06 | CAACACTGCTCCAARGGTCCAGGCACGGG | . | . | Other | 3' UTR | . | 267 |
| BIR | 510 | T | 0.99 | C | 0.01 | 0.02 | CCTTCTGGACAAAGYGAGTGCACAGGCCGATG | . | . | Other | 3' UTR | . | 268 |
| BIR | 657 | G | 0.92 | A | 0.08 | 0.14 | CACAGAGCCTTCACWGCACAGCAGCCGATG | . | . | Other | 3' UTR | . | 269 |
| BIR | 981 | G | 0.98 | A | 0.03 | 0.05 | TTGAGCCACAGACTCAAAGCAGCAGCCC | . | . | Other | 3' UTR | . | 270 |
| BKRB2EX1 | 55 | T | 0.77 | G | 0.23 | 0.35 | GGTGGGACGGTGGKGACGGTGGGACAT | . | . | Other | 5' UTR | . | 271 |
| BKRB2EX3 | 1513 | T | 0.93 | C | 0.07 | 0.13 | ATCTCCAAGAGAAACYGCCATCCAGCTTTG | . | . | Other | 3' UTR | . | 272 |
| BKRB2EX3 | 1833 | G | 0.95 | A | 0.05 | 0.10 | ACTCAAGTGGAACRACYGCACTGCCA | . | . | Other | 3' UTR | . | 273 |
| BKRB2EX3 | 747 | G | 0.93 | A | 0.07 | 0.13 | AAAGAGATCACAGARGAGAGGAGCAGT | ACG | ACA | Synonymous | Thr | Thr | 274 |
| BNPEX1 | 343 | A | 0.99 | T | 0.01 | 0.02 | TTTCCTGGGAGGTCKTTCACACCCGTGG | CGT | CTT | Nonsynonymous | Arg | Leu | 275 |
| BNPEX2 | 15 | G | 0.97 | A | 0.03 | 0.05 | TGAGGCTTGGACGCSCCCAAAWTGGTCCTTCTACACC | . | . | Other | Intron | . | 276 |
| BNPEX2 | 174 | A | 0.94 | T | 0.06 | 0.10 | ATTGCAGGAGCAGCRGCAACCATTTGCAG | ATG | TTG | Nonsynonymous | Met | Leu | 277 |
| BNPEX2 | 37 | G | 0.97 | A | 0.03 | 0.05 | AGAACTGAAGCAAARGAGTATCTGATGT | CGC | CAC | Nonsynonymous | Arg | His | 278 |
| BRS3EX1 | 424 | G | 0.95 | T | 0.05 | 0.10 | GTGCCATCTATATMCTTATGCTGTGATC | . | . | Other | Promoter | . | 279 |
| BRS3EX1 | 730 | A | 0.97 | G | 0.03 | 0.06 | CTAACTTGTGTGCCWGTGGATGCAACTCA | ACT | CCT | Nonsynonymous | Thr | Pro | 280 |
| BRS3EX1 | 879 | A | 0.95 | G | 0.05 | 0.10 | GCTCTACCTTGGCCWATATTTTCAAATGT | CCA | CCT | Synonymous | Pro | Pro | 281 |
| BRS3EX2 | 144 | T | 0.94 | A | 0.06 | 0.11 | CTCCAATGCCATCCWGAAGACTTGTGTAA | GCT | GCA | Nonsynonymous | Ala | Ala | 282 |
| BRS3EX2 | 80 | T | 0.94 | A | 0.02 | 0.04 | GCCATGCATTTCATYTTCACCATTTTCTC | CTG | CAG | Synonymous | Leu | Gln | 283 |
| BRS3EX3 | 173 | T | 0.94 | C | 0.06 | 0.12 | GCCATGCATTTCATYTTCACCATTTTCTC | ATT | ATC | Synonymous | Ile | Ile | 284 |
| CAL/CGRPEX1+2 | 1063 | T | 0.98 | G | 0.02 | 0.05 | CCCAGTCAGGCKCTGGGAGCAAAGAG | . | . | Other | 5' UTR | . | 285 |

TABLE 1-continued

| Gene/Exon | Base Position | Ref Allele | Ref Allele Freq (P) | Alt Allele | Alt Allele Freq (Q) | Heterozygosity (H) | Sequence Tag | Ref Codon | Alt Codon | Type of amino acid change | Ref amino acid | Alt amino acid | SEQ ID NO: |
|---|---|---|---|---|---|---|---|---|---|---|---|---|---|
| CAL/CGRPEX1+2 | 940 | G | 0.86 | A | 0.14 | 0.24 | GTGCGATCAGGACGRGCGTCTGGAGCCCA | . | . | Other | 5' UTR | . | 286 |
| CAL/CGRPEX3 | 112 | G | 0.92 | A | 0.08 | 0.15 | CTGCACTGGTCAGRACTATGTGCAGATG | GAC | AAC | Nonsynonymous | Asp | Asn | 287 |
| CAL/CGRPEX3 | 120 | G | 0.99 | T | 0.01 | 0.02 | GTGCAGGACTATGTKCAGATGAAGGCCAG | GTG | GTT | Synonymous | Val | Val | 288 |
| CAL/CGRPEX4 | 30 | C | 0.91 | A | 0.09 | 0.16 | AGTTTTCCCTGCAGMCTGGACAGCCCAG | AGC | AGA | Nonsynonymous | Ser | Arg | 289 |
| CAL/CGRPEX5 | 309 | A | 0.59 | T | 0.41 | 0.48 | ATGTGTTTTAAAAWATCCATAAGGAAG | . | . | Other | 3' UTR | . | 290 |
| CAL/CGRPEX5 | 433 | C | 0.78 | T | 0.22 | 0.34 | CAGACCAAGAAATAYAGATCCTGTTTATT | . | . | Other | 3' UTR | . | 291 |
| CAL/CGRPEX5 | 719 | G | 0.91 | A | 0.09 | 0.16 | AAAGAGCAAGTGAGRTAATAGATGTTAAG | . | . | Other | 3' UTR | . | 292 |
| CHYEX1 | 158 | T | 0.86 | A | 0.14 | 0.24 | TTGCCTTCTGGGAGWTATAAAACCCAAGA | . | . | Other | 5' UTR | . | 293 |
| CHYEX1 | 65 | T | 0.70 | C | 0.30 | 0.42 | TCTAGGGAACTFCYGATCAGAAACAGCC | . | . | Other | 5' UTR | . | 294 |
| CHYEX2 | 107 | G | 0.95 | C | 0.05 | 0.09 | TTGTAACTTCCAACSGTCCCTCAAAATTT | GGT | CGT | Nonsynonymous | Gly | Arg | 295 |
| CHYEX2 | 168 | A | 0.92 | G | 0.08 | 0.14 | GCTGACGGCTGCTCRTTGTGCAGGAAGGT | CAT | CGT | Nonsynonymous | His | Arg | 296 |
| CHYEX3 | 26 | A | 0.91 | G | 0.09 | 0.17 | CCTTTCCCTCACARCAGGTCTATAACAG | . | . | Other | Intron | . | 297 |
| CHYEX4 | 83 | C | 0.92 | T | 0.08 | 0.15 | CTCCCCTTCCATCMCAATTCAACTTTGT | TCA | TCC | Synonymous | Ser | Ser | 298 |
| CHYEX5 | 274 | C | 0.89 | T | 0.11 | 0.19 | TCCCTCAGCCACAAYCCTAAGCCTCCAGA | . | . | Other | 3' UTR | . | 299 |
| CLCNKBEX10 | 33 | G | 0.56 | C | 0.44 | 0.49 | CTCTGGCCACCTTGSTTCTCCGCCTCCATC | GTT | CTT | Nonsynonymous | Val | Leu | 300 |
| CLCNKBEX13 | 12 | C | 0.94 | T | 0.06 | 0.12 | GGAGAGCTGCTATYGGGCGCCTCTTTTGG | ATC | ATT | Synonymous | Ile | Ile | 301 |
| CLCNKBEX15 | 64 | C | 0.94 | T | 0.06 | 0.11 | ACTGGCCAAGGACAYGCCCACTGAGGAGG | ACG | ATG | Nonsynonymous | Thr | Met | 302 |
| CLCNKBEX15 | 68 | A | 0.34 | G | 0.66 | 0.45 | GCCAAGGACACGCCRCTGGAGGAGTGGT | CCA | CCG | Synonymous | Pro | Pro | 303 |
| CLCNKBEX18 | 51 | C | 0.96 | T | 0.04 | 0.08 | CCTCTTTGTGACGYTGCGGGCAGAGCTG | TCG | TGG | Nonsynonymous | Ser | Trp | 304 |
| CLCNKBEX3 | 34 | A | 0.94 | G | 0.06 | 0.11 | GTCTCTTTCTCTTCRGGCMGCCACTGCTCCG | AGC | CGC | Nonsynonymous | Ser | Arg | 305 |
| CLCNKBEX3 | 96 | G | 0.93 | A | 0.07 | 0.13 | CTGGAATCCCGAGSTGAAGACCATGTTG | TCG | TCA | Synonymous | Ser | Ser | 306 |
| CLCNKBEX4 | 19 | A | 0.35 | C | 0.65 | 0.46 | ACCTGGATATCAAGMACTTTGGGCCAAA | GTG | CTG | Nonsynonymous | Val | Leu | 307 |
| CLCNKBEX4 | 70 | G | 0.92 | A | 0.08 | 0.15 | TTCCGGCTCCTGGCRGTCTTCAACAGCGA | AAC | CAC | Nonsynonymous | Asn | His | 308 |
| CLCNKBEX7 | 108 | G | 0.89 | A | 0.11 | 0.20 | GCAGCGCCAACTTMTGCCTGTATGACTT | GCG | GCA | Synonymous | Ala | Ala | 309 |
| CNPEX1 | 1018 | C | 0.91 | A | 0.09 | 0.16 | GCCTTCACGCTGGKGACAGCCACTGCAC | . | . | Other | 5' UTR | . | 310 |
| CNPEX1 | 144 | G | 0.98 | T | 0.02 | 0.04 | CAGCACTGGGACCSTCTCGCCCTGCAG | . | . | Other | 5' UTR | . | 311 |
| CNPEX1 | 1457 | C | 0.98 | C | 0.02 | 0.05 | ATTGTTCCCACAGARGGAGTTCAACAGCG | . | . | Other | 5' UTR | . | 312 |
| CNPEX1 | 578 | G | 0.91 | A | 0.09 | 0.16 | GGGAGTTCACAGCRGAGTCAGACATGA | . | . | Other | 5' UTR | . | 313 |
| CNPEX1 | 592 | G | 0.94 | A | 0.06 | 0.11 | AACATCCAGCCTCWGACATTGACAGTCA | . | . | Other | 5' UTR | . | 314 |
| CNPEX1 | 1171 | T | 0.92 | A | 0.08 | 0.14 | GGACACCAAGTCGCRGGCAGCGTGGGCTC | . | . | Other | 3' UTR | . | 315 |
| CNPEX2 | 139 | G | 0.96 | A | 0.04 | 0.08 | CCCCCGCCGGCGGYCAGAAGAAGGGCGA | CGG | CAG | Nonsynonymous | Arg | Gln | 316 |
| CNPEX2 | 357 | A | 0.95 | G | 0.05 | 0.10 | GCCTGGGGCGGGGYGCAGCCGCAGCGC | GGT | GGC | Synonymous | Gly | Gly | 317 |
| CNPEX2 | 41 | T | 0.98 | C | 0.02 | 0.03 | TTTCTGCAGCTGARATTTGCACAGGCCGA | AAA | GGA | Nonsynonymous | Lys | Arg | 318 |
| COX1 | 1063 | A | 0.99 | G | 0.01 | 0.02 | ACATGACCACCACCRGATATTGGCATGGCT | ATC | GTC | Nonsynonymous | Ile | Val | 319 |
| COX1 | 1314 | A | 0.98 | G | 0.02 | 0.03 | TCAATGAGTACCGRAGAGTTTGGCATG | AAG | GAG | Nonsynonymous | Lys | Glu | 320 |
| COX1 | 1386 | G | 0.98 | A | 0.02 | 0.03 | CCTTGCAGGAGCCRTTAGGAGAAGGAG | GTA | ATA | Nonsynonymous | Val | Ile | 321 |
| COX1 | 1428 | G | 0.92 | A | 0.08 | 0.14 | GGTGAGTGTTGGGGYTGACATTTAGAACT | . | . | Other | 3' UTR | . | 322 |
| COX1 | 1906 | T | 0.96 | C | 0.04 | 0.08 | ATTATCTGGAATATYGTGATTCTGTTTAT | . | . | Other | 3' UTR | . | 323 |
| COX1 | 1948 | G | 0.99 | T | 0.01 | 0.02 | GTCTGCCAGAATACKGGGTTCTTAGTTGA | . | . | Other | 3' UTR | . | 324 |
| COX1 | 2037 | T | 0.99 | A | 0.01 | 0.02 | TGCCACTTCATCCRAGAGATGCTCATGC | . | . | Other | 3' UTR | . | 325 |
| COX1 | 310 | G | 0.91 | A | 0.09 | 0.16 | TTGCAAACTTCTGMAAGATGGCTCTGG | CGA | CAA | Nonsynonymous | Arg | Gln | 326 |
| COX1 | 626 | C | 0.98 | T | 0.02 | 0.03 | TTTATGGAGACAATMTGGAGCGTCAGTAT | GGC | GGA | Synonymous | Gly | Gly | 327 |
| COX1 | 696 | G | 0.98 | T | 0.02 | 0.04 | GACTTGCTGAAGGCYGAGCACCCCACCTG | CTG | ATG | Nonsynonymous | Leu | Met | 328 |
| COX1 | 938 | T | 0.94 | C | 0.06 | 0.12 | CGATTTTCATTSCGTGGCTAAAAAC | GCT | GCC | Synonymous | Ala | Ala | 329 |
| COX2EX1 | 186 | C | 0.84 | G | 0.16 | 0.27 | GCGACCAATTGTCAKACGACTTGCAGTGA | . | . | Other | Promoter | . | 330 |
| COX2EX1 | 358 | T | 0.84 | G | 0.16 | 0.27 | AAGCTAGAAGYTGAGCACCATTCT | . | . | Other | Promoter | . | 331 |
| COX2EX10 | 156 | T | 0.94 | C | 0.06 | 0.12 | AACCATGTAGAAGYTGAGCACCATTCT | GTT | GCT | Nonsynonymous | Val | Ala | 332 |

TABLE 1-continued

| Gene/Exon | Base Position | Ref Allele | Alt Allele | Ref Freq (P) | Alt Allele Freq (Q) | Heterozygosity (H) | Sequence Tag | Ref Codon | Alt Codon | Type of amino acid change | Ref amino acid | Alt amino acid | SEQ ID NO: |
|---|---|---|---|---|---|---|---|---|---|---|---|---|---|
| COX2EX10 | 379 | C | A | 0.98 | 0.03 | 0.05 | GCAAGTTCTTCCCGMTCCGACTAGATGA | CGC | CGA | Synonymous | Arg | Arg | 333 |
| COX2EX10 | 866 | T | C | 0.51 | 0.49 | 0.50 | AAAGTACTTTTGGTYATTTTCTGTCATC | . | . | Other | 3' UTR | . | 334 |
| COX2EX10 | 87 | A | G | 0.99 | 0.01 | 0.02 | CATCGATGCTGTGRGCGTATCCTGCCC | GAG | GGG | Nonsynonymous | Glu | Gly | 335 |
| COX2EX10 | 937 | G | A | 0.83 | 0.17 | 0.28 | ATTAGACATTACCARTAATTTCATGTCTA | . | . | Other | 3' UTR | . | 336 |
| COX2EX3 | 166 | G | C | 0.93 | 0.07 | 0.13 | ATTATGAGTTATGTSTTGACATGTAAGTA | GTG | GTC | Synonymous | Val | Val | 337 |
| COX2EX7 | 206 | T | C | 0.96 | 0.04 | 0.07 | AACAGAGTATGCGAYGTGCTTAAACAGA | GAT | GAC | Synonymous | Asp | Asp | 338 |
| COX2EX8 | 268 | T | C | 0.95 | 0.05 | 0.10 | ATATTGCTGAACAYGGAATTACCCAGTT | CAT | CAC | Synonymous | His | His | 339 |
| CYP11B1EX1 | 351 | T | C | 0.97 | 0.03 | 0.06 | TGACGTGATCCCTCYCGAAGGCAAGCAC | . | . | Other | Promoter | . | 340 |
| CYP11B1EX1 | 525 | C | G | 0.99 | 0.01 | 0.03 | AGGACAGTGCTGCCSTTTGAAGCCATGC | CCC | CCG | Synonymous | Pro | Pro | 341 |
| CYP11B1EX1 | 542 | G | A | 0.97 | 0.03 | 0.06 | GAAGCCATGCARCCCTGAGGCAGCAACA | CGG | CAG | Nonsynonymous | Arg | Gln | 342 |
| CYP11B1EX1 | 601 | G | C | 0.97 | 0.03 | 0.06 | AGCAGGGTTATGAGSACCTCCACCTGAA | GAC | CAC | Nonsynonymous | Asp | His | 343 |
| CYP11B1EX1 | 184 | C | T | 0.99 | 0.01 | 0.03 | GTGGCGTGTTCTTGYTGTAAGCGGCAGC | CTG | TTG | Synonymous | Leu | Leu | 343 |
| CYP11B1EX2 | 188 | A | G | 0.96 | 0.04 | 0.07 | CGTGTTCTTGCTGTRAGCCGGCAGCTGAG | . | . | Other | Intron | . | 345 |
| CYP11B1EX2 | 36 | T | C | 0.46 | 0.54 | 0.50 | CCCCACAGGTACGAYTTGGAGGAGCAGG | GAT | GAC | Synonymous | Asp | Asp | 346 |
| CYP11B1EX2 | 78 | T | C | 0.96 | 0.04 | 0.08 | ATGCTGCCGGAGAYGTGGAGAAGCTGCA | GAC | GAT | Synonymous | Asp | Asp | 347 |
| CYP11B1EX3 | 114 | G | C | 0.99 | 0.01 | 0.02 | AGGTTCCTCCGCATSGTGATGCCCCAAGGTGT | ATG | ATC | Nonsynonymous | Met | Ile | 348 |
| CYP11B1EX4 | 177 | C | T | 0.98 | 0.02 | 0.04 | CCTGTCTCGCTGGAYCAGCCCAAGGAACT | ACC | ATC | Nonsynonymous | Thr | Ile | 349 |
| CYP11B1EX4 | 205 | T | C | 0.92 | 0.08 | 0.15 | TGGAAGGAGCACTTKGAGGCCTGGACTG | TTT | TTG | Nonsynonymous | Phe | Leu | 350 |
| CYP11B1EX5 | 247 | C | G | 0.91 | 0.09 | 0.16 | GGTGAGGCCAGGASCCGGCAGTGCTAT | . | . | Other | Intron | . | 351 |
| CYP11B1EX5 | 103 | A | G | 0.97 | 0.04 | 0.07 | ACCAGCATCGTGGCRGAGTCCTGTTGAA | GCG | GCA | Synonymous | Ala | Ala | 352 |
| CYP11B1EX5 | 107 | C | T | 0.84 | 0.16 | 0.26 | GCATCGTGGCGGAGTCCTYGTCCTGAA | CTC | GTC | Nonsynonymous | Leu | Val | 353 |
| CYP11B1EX5 | 16 | C | T | 0.58 | 0.42 | 0.49 | TGAGGCTGCCTCCYGTCCCGGATAGG | . | . | Other | Intron | . | 354 |
| CYP11B1EX5 | 55 | T | C | 0.97 | 0.03 | 0.06 | ATCCAGAAAATCTAYCAGGAACTGGCCTT | TAT | TAC | Synonymous | Tyr | Tyr | 355 |
| CYP11B1EX5 | 72 | G | A | 0.99 | 0.01 | 0.03 | GGAACTGGCCTTCARCCCGCCTCAACAGT | AGC | AAC | Nonsynonymous | Ser | Asn | 356 |
| CYP11B1EX7 | 52 | C | T | 0.99 | 0.01 | 0.03 | CTGTGGGTCTGTTYTYTGGAGCGAGTGGCG | CTG | TTG | Synonymous | Leu | Leu | 357 |
| CYP11B1EX8 | 144 | T | C | 0.96 | 0.04 | 0.08 | CCGGCCAGGAACTTCYACACACGTGCCTTT | TAC | CAC | Nonsynonymous | Tyr | His | 358 |
| CYP11B1EX9 | 16 | G | A | 0.96 | 0.04 | 0.08 | CCAGATGGAAACCCSGCTTCTGTCTGAG | . | . | Other | Intron | . | 359 |
| CYP11B1EX9 | 274 | T | G | 0.91 | 0.09 | 0.16 | AGCCCCAGCACAAAYGGAACTCCCGAGGG | . | . | Other | 3' UTR | . | 360 |
| CYP11B1EX9 | 350 | T | C | 0.88 | 0.12 | 0.21 | GCTGGGGAAGATCKGCTGACCTTGTCCC | . | . | Other | 3' UTR | . | 361 |
| CYP11B1EX9 | 459 | G | A | 0.72 | 0.28 | 0.40 | CGTGTGCCAIRCAAGGGTGCTGTGG | . | . | Other | 3' UTR | . | 362 |
| CYP11B1EX9 | 592 | A | C | 0.93 | 0.07 | 0.13 | TCTAGAGTCCAGTCMAGTTCCCTCTGCA | . | . | Other | 3' UTR | . | 363 |
| CYP11B1EX9 | 62 | G | T | 0.99 | 0.01 | 0.03 | GTGGAGACACTAACYCAAGAGGACATAAA | ACC | ACT | Synonymous | Thr | Thr | 364 |
| CYP11B1EX9 | 657 | G | A | 0.66 | 0.34 | 0.45 | CTCTGAAAGTTGTCRCCCRTGCCCTGGCCTCA | . | . | Other | 3' UTR | . | 365 |
| CYP11B2EX1 | 786 | A | C | 0.87 | 0.13 | 0.22 | GTTCCAGGTGGGYTTGGCTCCTCTGC | . | . | Other | 3' UTR | . | 366 |
| CYP11B2EX1 | 835 | C | T | 0.77 | 0.23 | 0.35 | GTTCCAGGTGGGYTTGGCTCCTCTGC | . | . | Other | 3' UTR | . | 367 |
| CYP11B2EX1 | 879 | G | T | 0.68 | 0.32 | 0.44 | CTGGGGAAGGTCCCRAGGATGCTGTCAGG | . | . | Other | 3' UTR | . | 368 |
| CYP11B2EX1 | 163 | A | G | 0.97 | 0.03 | 0.06 | TCCTGGTGAGATARAAGGATTTTGGGCTG | . | . | Other | Promoter | . | 369 |
| CYP11B2EX3 | 138 | C | A | 0.66 | 0.34 | 0.45 | TTCTGCCAGGCCYYTCCCAGGCCCTGAA | TTC | TTT | Synonymous | Phe | Phe | 370 |
| CYP11B2EX3 | 152 | A | G | 0.71 | 0.29 | 0.41 | XTXXXAGGCCCTGARGAAGAGGTGCTGC | AAG | AGG | Nonsynonymous | Lys | Arg | 371 |
| CYP11B2EX3 | 20 | G | A | 0.98 | 0.03 | 0.05 | CAAGCTCTGCCCTGSCCTCTGTAGGAATG | . | . | Other | Intron | . | 372 |
| CYP11B2EX3 | 243 | G | C | 0.97 | 0.03 | 0.06 | GGTGTGGGCCATGCRGGAAGGTCCAGCCC | . | . | Other | Intron | . | 373 |
| CYP11B2EX4 | 177 | T | A | 0.96 | 0.04 | 0.07 | CCTGTCTCGCTGGAYCAGCCCAAGGTGT | ATC | ACC | Nonsynonymous | Ile | Thr | 374 |
| CYP11B2EX4 | 250 | G | A | 0.98 | 0.02 | 0.04 | GTTCCAGGACCCCRGGCAGTCTATGGG | . | . | Other | Intron | . | 375 |
| CYP11B2EX5 | 99 | A | C | 0.94 | 0.06 | 0.12 | TTCTGCCAGCCTGAMCTTCCTCCATGCC | AAC | ACC | Nonsynonymous | Asn | Thr | 376 |
| CYP11B2EX5 | 103 | A | G | 0.05 | 0.95 | 0.10 | ACAGGCATCGTGGCRGAACTGTCACTGAG | GCG | GCA | Synonymous | Ala | Ala | 377 |
| CYP11B2EX5 | 121 | G | A | 0.78 | 0.23 | 0.35 | ATCCTGTTGAAGGRCGAACTATYCAGGAACTGGCCTTT | . | . | Other | Intron | . | 378 |
| CYP11B2EX5 | 55 | C | T | 0.99 | 0.01 | 0.02 | ATCCAGAAAATCTAYCAGCCCTGGCCTTI | TAC | TAT | Synonymous | Tyr | Tyr | 379 |
| CYP11B2EX5 | 72 | A | G | 0.99 | 0.01 | 0.02 | GGAACTGGCCTTCARCCCGCCCTCAACACT | AAC | AGC | Nonsynonymous | Asn | Ser | 380 |

TABLE 1-continued

| Gene/Exon | Base Position | Ref Allele | Freq (P) | Alt Allele | Freq (Q) | Heterozygosity (H) | Sequence Tag | Ref Codon | Alt Codon | Type of amino acid change | Ref amino acid | Alt amino acid | SEQ ID NO: |
|---|---|---|---|---|---|---|---|---|---|---|---|---|---|
| CYP11B2EX6 | 195 | A | 0.84 | C | 0.16 | 0.27 | TCAAGGAGACCTTGMGGTGGGTGCTGGCT | AGG | CGG | Synonymous | Arg | Arg | 381 |
| CYP11B2EX6 | 91 | T | 0.38 | C | 0.63 | 0.47 | CGAGCTGCAGCAGAYCCTGCCGCCAGAGA | ATC | ACC | Nonsynonymous | Ile | Thr | 382 |
| CYP11B2EX7 | 52 | T | 0.99 | C | 0.01 | 0.03 | CTGTGGGTCTGTTTYTGAGCGAGTGGTG | TTG | CTG | Synonymous | Leu | Leu | 383 |
| CYP11B2EX7 | 56 | T | 0.97 | T | 0.03 | 0.06 | GGTCTGTTTTGGWGCGAGTGGTGAGCT | GAG | GTG | Nonsynonymous | Glu | Val | 384 |
| CYP11B2EX7 | 65 | T | 0.91 | C | 0.09 | 0.17 | TTTGGAGCGAGTGGYGAGCTCAGACTTGG | GTG | GCG | Nonsynonymous | Val | Ala | 385 |
| CYP11B2EX7 | 78 | G | 0.82 | A | 0.18 | 0.30 | GTGAGCTCAGACTTRGTGCTTCACGAACTA | TTG | TTA | Synonymous | Leu | Leu | 386 |
| CYP11B2EX8 | 132 | G | 0.97 | A | 0.03 | 0.02 | ACATCAGGGGCTCCRGCAGGAACTTCCAC | GGC | AGC | Nonsynonymous | Gly | Ser | 387 |
| CYP11B2EX8 | 18 | C | 0.99 | T | 0.01 | 0.02 | TGATCCCTGCTCTGYACCGTCCGCAGACA | . | . | Other | Intron | . | 388 |
| CYP11B2EX8 | 182 | C | 0.98 | T | 0.02 | 0.04 | ATGCCCCAGTGCCTYGGGCGGCGCCTGGC | CTC | CTT | Synonymous | Leu | Leu | 389 |
| CYP11B2EX8 | 37 | T | 0.99 | A | 0.01 | 0.02 | TCCCAGACATTGGWACAGGTTTTCCTCT | GTA | GAA | Nonsynonymous | Val | Glu | 390 |
| CYP11B2EX9 | 224 | G | 0.89 | A | 0.11 | 0.20 | GTCTTCTCCCACRTGCACAGCTTCCTG | . | . | Other | 3' UTR | . | 391 |
| CYP11B2EX9 | 90 | T | 0.99 | A | 0.01 | 0.03 | AGATGGTCTACAGCKTCATATTGAGGCCT | TTC | GTC | Nonsynonymous | Phe | Val | 392 |
| DBHEX1 | 152 | G | 0.92 | A | 0.08 | 0.14 | AGTTGCCCTCAGACTCGTGCACCATGGAG | . | . | Other | 5' UTR | . | 393 |
| DBHEX3 | 153 | G | 0.92 | A | 0.08 | 0.14 | AGTTGCCCTCAGACTCGTGCACCATGGAG | GCG | ACG | Nonsynonymous | Ala | Thr | 394 |
| DBHEX3 | 239 | C | 0.97 | C | 0.03 | 0.05 | AAGGACTTCCAAAGGCTTCTCTCGGCA | AAG | AAC | Nonsynonymous | Lys | Asn | 395 |
| DBHEX3 | 257 | C | 0.98 | T | 0.03 | 0.05 | TTCTCTCGGCACCAYATTATCAAGTACG | CAC | CAT | Synonymous | His | His | 396 |
| DBHEX3 | 63 | G | 0.96 | C | 0.04 | 0.08 | CGTTCCGGTCACTGSAGGCCATCAACGGC | GAG | CAG | Nonsynonymous | Glu | Gln | 397 |
| DBHEX4 | 12 | G | 0.96 | A | 0.04 | 0.08 | CCTCCTCACAGTACSAGCCCCAACGTCACC | GAG | CAG | Nonsynonymous | Glu | Gln | 398 |
| DBHEX4 | 132 | G | 0.94 | A | 0.06 | 0.11 | CCAAGATGAAAACCRACCGCCTCAACTAC | GAC | AAC | Nonsynonymous | Asp | Asn | 399 |
| DBHEX5 | 37 | T | 0.94 | C | 0.06 | 0.11 | AGAGGAAGCCGGCCYTGCCTTCCGGGGGTC | CTT | CCT | Nonsynonymous | Leu | Pro | 400 |
| DBHEX5 | 39 | G | 0.84 | T | 0.16 | 0.27 | CCTATTCCCTGCTTRGGAACTTGAGGGGT | GCC | TCC | Nonsynonymous | Ala | Ser | 401 |
| DD1R | 122 | A | 0.96 | G | 0.04 | 0.08 | CTGAACTGCAGATRAATCCTGCCACACA | . | . | Other | Promoter | . | 402 |
| DD1R | 1521 | G | 0.98 | A | 0.02 | 0.04 | TGCTCATCCTGTCCMCGCTTCCTGGGAAC | . | . | Other | 3' UTR | . | 403 |
| DD1R | 278 | C | 0.96 | G | 0.04 | 0.08 | GCTCATCCTGTCCASGCTCCTGGGAACA | ACG | CCG | Nonsynonymous | Thr | Pro | 404 |
| DD1R | 279 | A | 0.98 | G | 0.02 | 0.04 | CTGGTCTGTGCSGTTATCAGGTTCCG | ACG | AGG | Nonsynonymous | Thr | Arg | 405 |
| DD1R | 310 | C | 0.98 | T | 0.02 | 0.04 | GCTGCCGTTATCAGKTTCCGACACCTCCG | GCC | GCG | Synonymous | Ala | Ala | 406 |
| DD1R | 319 | G | 0.99 | T | 0.01 | 0.02 | GCAAAGTGCTGCCTRGTGGGAGGACTCC | AGG | AGT | Nonsynonymous | Arg | Ser | 407 |
| DD1R | 76 | G | 0.98 | A | 0.03 | 0.05 | ATGCCATCCATCKCTGTAATAAGCTTT | . | . | Other | Promoter | . | 408 |
| EDNRAEX6 | 764 | T | 0.28 | G | 0.72 | 0.40 | ACTGTGTATAACAGARATGGACAAGAACCG | TCT | GCT | Nonsynonymous | Ser | Ala | 409 |
| EDNRAEX6 | 124 | A | 0.28 | G | 0.72 | 0.40 | ACTGTGTATAACAGARATGGACAAGAACCG | GAA | GAG | Synonymous | Glu | Glu | 410 |
| EDNRAEX6 | 88 | C | 0.31 | G | 0.69 | 0.43 | TGGTTCCCCTTCAYTTAAGCCGTATATT | CAC | CAT | Synonymous | His | His | 411 |
| EDNRAEX8 | 1157 | G | 0.66 | A | 0.34 | 0.45 | TTTTCAGATGATTCRGAAATTTCATTCA | . | . | Other | 3' UTR | . | 412 |
| EDNRAEX8 | 1380 | C | 0.52 | T | 0.48 | 0.50 | ACGATTCTTCACTTYTTGGGGTTTTCAGT | . | . | Other | 3' UTR | . | 413 |
| EDNRAEX8 | 1687 | A | 0.83 | G | 0.17 | 0.28 | TTGTGCCAAAGTGCRTAGTCTGAGCTAAA | . | . | Other | 3' UTR | . | 414 |
| EDNRAEX8 | 228 | C | 0.47 | G | 0.53 | 0.50 | CAAGGCAACTGASTCCGGGAATCTCTT | . | . | Other | 3' UTR | . | 415 |
| EDNRAEX8 | 295 | A | 0.99 | T | 0.01 | 0.01 | AAGAAATGCTTTCCRAAACCGCAAGTAG | . | . | Other | 3' UTR | . | 416 |
| EDNRAEX8 | 622 | G | 0.38 | A | 0.62 | 0.47 | ACAATATGGCTCARGTCTACTTTTTATTG | . | . | Other | 3' UTR | . | 417 |
| EDNRAEX8 | 655 | G | 0.99 | T | 0.01 | 0.03 | CTATTTATTTTTRAAACACAAATTCTA | . | . | Other | 3' UTR | . | 418 |
| EDNRAHX8 | 788 | A | 0.88 | G | 0.12 | 0.21 | CTATTTATTTTTRAAACACAAATTCTA | . | . | Other | 3' UTR | . | 419 |
| EDNRAEX8 | 950 | T | 0.96 | C | 0.04 | 0.08 | GAACATGTTTGTAYGTTAAATTCAAAG | . | . | Other | 3' UTR | . | 420 |
| EDNRAEX8 | 985 | T | 0.97 | C | 0.03 | 0.06 | TTCAATCAGATAGTYCTTTTTCACAAGTT | . | . | Other | 3' UTR | . | 421 |
| EDNRBEX1 | 33 | T | 0.98 | A | 0.03 | 0.05 | TGCGCCTGCCTTGWGTCGGGACGCGCC | CTG | CAG | Nonsynonymous | Leu | Gln | 422 |
| EDNRBEX1 | 347 | T | 0.99 | C | 0.01 | 0.02 | TCCTGCCTTGTCGTCGTCGGGATC | TTC | GTC | Nonsynonymous | Phe | Val | 423 |
| EDNRBEX2 | 62 | C | 0.99 | T | 0.01 | 0.01 | TGGTTGCCTGGTTYTTGCCTGCGGCC | CTT | TTT | Nonsynonymous | Leu | Phe | 424 |
| EDNRBEX2 | 78 | C | 0.95 | T | 0.05 | 0.10 | ATACAGAAAGCCTCYGTGGGAATCACTGT | TCC | TCT | Synonymous | Ser | Ser | 425 |
| EDNRBEX3 | 87 | C | 0.99 | T | 0.01 | 0.03 | GCCTCCGTGGGAATYACTGTGCTGAGTCT | ATC | ATT | Synonymous | Ile | Ile | 426 |
| EDNRBEX3 | 144 | C | 0.94 | T | 0.06 | 0.11 | TTTGATATAATTAYGATGGACTACAAAG | ACG | ATG | Nonsynonymous | Thr | Met | 427 |
| EDNRBEX4 | 122 | G | 0.99 | A | 0.01 | 0.03 | GTTGAGAAAGAAARTTGGCATGCAGATTG | AGT | AAT | Nonsynonymous | Ser | Asn | 428 |

TABLE 1-continued

| Gene/Exon | Base Position | Ref Allele Freq (P) | Alt Allele | Freq (Q) | Heterozygosity (H) | Sequence Tag | Ref Codon | Alt Codon | Type of amino acid change | Ref amino acid | Alt amino acid | SEQ ID NO: |
|---|---|---|---|---|---|---|---|---|---|---|---|---|
| EDNRBEX4 | 39 | G | A | 0.82 | 0.18 | 0.29 | AAAGATTGGTGGCRTRTTCAGTTTCTATTT | CTG | CTA | Synonymous | Leu | Leu | 429 |
| ELAM1EX1 | 143 | A | G | 0.93 | 0.07 | 0.13 | TCTTTGACCTAAATRATGAAAGTCTTAAA | . | . | Other | Promoter | . | 430 |
| ELAM1EX1 | 209 | T | G | 0.97 | 0.03 | 0.06 | TTATTGCACTAGTGKCCTTTGCCCAAAAT | . | . | Other | Promoter | . | 431 |
| ELAM1EX10 | 107 | C | T | 0.91 | 0.09 | 0.16 | CATTAGCACCATTYTCCTCTGGCTTCGG | CTC | TTC | Nonsynonymous | Leu | Phe | 432 |
| ELAM1EX12 | 54 | T | C | 0.96 | 0.04 | 0.08 | AGCCTTGAATCAGAYGGAAGCTACCAAAA | . | . | Other | 3' UTR | . | 433 |
| ELAM1EX13 | 1004 | G | G | 0.98 | 0.02 | 0.04 | CAGAAATATGTGKTKCACGATGAAAA | GAT | GAC | Nonsynonymous | Asp | Asp | 434 |
| ELAM1EX13 | 1158 | G | A | 0.18 | 0.82 | 0.29 | GATGTTTGTCAGATRTGATATGTAAACAT | . | . | Other | 3' UTR | . | 435 |
| ELAM1EX13 | 1549 | G | A | 0.39 | 0.61 | 0.47 | TGAACACTGCCAACRACAAAGCCAACAGT | . | . | Other | 3' UTR | . | 436 |
| ELAM1EX13 | 967 | T | C | 0.97 | 0.03 | 0.06 | ACTGAATGGAAGGYTYGTATATTGTCAGA | . | . | Other | 3' UTR | . | 437 |
| ELAM1EX2 | 382 | C | A | 0.98 | 0.02 | 0.04 | AATGATGGAGGTGSAGACAAGAAGAGCT | TGC | TGG | Nonsynonymous | Cys | Trp | 438 |
| ELAM1EX3 | 152 | T | C | 0.95 | 0.05 | 0.10 | GTAAGTCTGGTTCTYGCCTCTTTCTTCAC | . | . | Other | Intron | . | 439 |
| ELAM1EX3 | 53 | A | G | 0.97 | 0.03 | 0.06 | CCAATACATCCTGCMGTGGCCACGTGAA | AGT | CGT | Nonsynonymous | Ser | Arg | 440 |
| ELAM1EX5 | 197 | G | A | 0.95 | 0.05 | 0.10 | GAATTGGGACAACRAGAAGCCAACGTGT | GAG | AAG | Nonsynonymous | Glu | Lys | 441 |
| ELAM1EX5 | 55 | T | C | 0.97 | 0.03 | 0.06 | GATGCTGTGACAAAYCACGCCAATGGTT | AAT | AAC | Synonymous | Asn | Asn | 442 |
| ELAM1EX7 | 199 | C | T | 0.94 | 0.06 | 0.12 | GGGGAGTGGGACAAYGAGAAGCCCACATG | AAC | AAT | Synonymous | Asn | Asn | 443 |
| ELAM1EX7 | 200 | G | C | 0.94 | 0.06 | 0.12 | GGAGTGGGACAACSAGAGAGCCCACATGT | GAG | CAG | Nonsynonymous | Glu | Gln | 444 |
| ELAM1EX8 | 152 | C | T | 0.96 | 0.04 | 0.08 | AGGGATTTGAATTAYATGGATCAACTCAA | CAT | TAT | Nonsynonymous | His | Tyr | 445 |
| ELAM1EX8 | 22 | T | C | 0.91 | 0.09 | 0.16 | AGTGCTTCTCCGTGYGTTCCAGATGCTGAG | . | . | Other | Intron | . | 446 |
| ENDOTHELIN2 | 440 | C | T | 0.97 | 0.03 | 0.07 | CCCCTGCAGACGTGYTCCAGACTGGCAAG | TTC | CTC | Nonsynonymous | Phe | Leu | 447 |
| ENDOTHELIN2 | 556 | G | A | 0.99 | 0.01 | 0.02 | ATGCGGGAGCCCTCGRTCCACACATTCCAG | CGG | CGA | Synonymous | Arg | Arg | 448 |
| ENDOTHELIN2 | 976 | A | G | 0.84 | 0.16 | 0.27 | GCCAGCCCTTGGAGRCTGATGGCTCCCC | . | . | Other | 3' UTR | . | 449 |
| ET1EX3 | 114 | G | A | 0.88 | 0.12 | 0.21 | GCAACAGACCCTGARAATAGATGCCAATG | GAG | GAA | Synonymous | Glu | Glu | 450 |
| ET1EX5 | 90 | G | T | 0.69 | 0.31 | 0.43 | AAGCTGAAAGGCAAKCCCTCCAGAGAGCC | AAG | AAT | Nonsynonymous | Lys | Asn | 452 |
| GALNREX1 | 1052 | G | T | 0.94 | 0.06 | 0.11 | CTGCCCACCTGGGTKCTGGGCGCCTTCAT | GTG | GTT | Synonymous | Val | Val | 453 |
| GALNREX1 | 325 | C | G | 0.98 | 0.02 | 0.04 | GGTGCAGCACGCAGSCGCTCCGGGAGCCA | . | . | Other | Promoter | . | 454 |
| GALNREX1 | 327 | G | C | 0.81 | 0.19 | 0.30 | CAGCAGCCAGGTCSCCGGGCCAACAGG | . | . | Other | Promoter | . | 455 |
| GALNREX1 | 553 | G | T | 0.49 | 0.51 | 0.50 | TCTCTCAGAAGGTKCGCGCGAACAGCAG | . | . | Other | Promoter | . | 456 |
| GALNREX1 | 887 | C | T | 0.49 | 0.51 | 0.50 | ATCTTCGCGCTGGGYGTGCTGGGCAACAG | GGC | GGT | Synonymous | Gly | Gly | 457 |
| GALNREX3 | 298 | A | G | 0.68 | 0.32 | 0.43 | TGATACTAAAGACAAARTAAAAGTCGAATAG | AAT | AGT | Nonsynonymous | Asn | Ser | 458 |
| GALNREX3 | 322 | C | T | 0.98 | 0.02 | 0.04 | AATAGACACCCCACYATCAACCAATTGTA | CCA | CTA | Nonsynonymous | Pro | Leu | 459 |
| GALNREX3 | 388 | T | C | 0.98 | 0.02 | 0.04 | AGTTTTCCATATAAGYGGACAGACACAGA | . | . | Other | 3' UTR | . | 460 |
| GALNREX3 | 418 | C | G | 0.97 | 0.03 | 0.04 | ACAAACAGAATGAGSTAGTAAGCGATGCT | . | . | Other | 3' UTR | . | 461 |
| GALNREX3 | 523 | G | T | 0.98 | 0.02 | 0.04 | TAGGAAATTCCTAGKTCTAGTGAGAATTA | . | . | Other | 3' UTR | . | 462 |
| GALNREX3 | 650 | G | A | 0.94 | 0.06 | 0.11 | CCCATATATATGTTYAACTCTTCATAGAT | . | . | Other | 3' UTR | . | 463 |
| GALNREX3 | 799 | A | G | 0.84 | 0.16 | 0.26 | ATGTATTTAAAATRGATCATGACACA | . | . | Other | 3' UTR | . | 464 |
| GH1EX1 | 125 | G | A | 0.98 | 0.02 | 0.04 | CTGCTGTTGCTRCRTCCTGRCTGCCCA | CTG | CTA | Synonymous | Leu | Leu | 465 |
| GH1EX1 | 57 | T | T | 0.91 | 0.09 | 0.16 | CACGAAGTGTCTTYGCCTTCGGCTGATGCC | TTC | TTT | Nonsynonymous | Phe | Phe | 466 |
| GH1EX4 | 68 | G | C | 0.98 | 0.02 | 0.05 | GACCCCCGGGGCAGSCTGCCCTGCCCCTT | CCT | GCT | Nonsynonymous | Pro | Ala | 467 |
| GH1EX5 | 71 | C | G | 0.83 | 0.17 | 0.28 | CTGTCCTGCCTKCTGGTGGATCCTGC | GCC | GCG | Synonymous | Ala | Ala | 468 |
| GH1EX9 | 29 | T | A | 0.93 | 0.07 | 0.12 | TGACAACATGGCTKCTGGGATCCTA | TTC | TGC | Nonsynonymous | Phe | Cys | 469 |
| GH1EX4 | 144 | G | A | 0.94 | 0.06 | 0.12 | CCTCTGACAGCAARTCTATGACCTCCTA | GTC | ATC | Nonsynonymous | Val | Ile | 470 |
| GH2EX3 | 126 | A | T | 0.93 | 0.08 | 0.14 | CAACACCTTCCAACWGGGTGAAACGCAG | AGG | TGG | Nonsynonymous | Arg | Trp | 471 |
| GIPREX2 | 72 | C | G | 0.84 | 0.16 | 0.26 | CTTCGCCGCTCASGATGACTAACCTC | . | . | Other | 5' UTR | . | 472 |
| GIPREX7 | 51 | A | T | 0.79 | 0.21 | 0.33 | CATTGCCACTAGAAAYTATATCACATCAA | AAC | AAT | Synonymous | Asn | Asn | 473 |
| GIPREX8 | 180 | C | T | 0.98 | 0.02 | 0.05 | GCTACTACCTGCTSTCGGCTGGGGTGAG | CTC | GTC | Nonsynonymous | Leu | Val | 474 |
| GLUT2EX1 | 137 | C | A | 0.32 | 0.68 | 0.44 | CCACAGCACTAATMTCTGTGGAGCAGAG | . | . | Other | Promoter | . | 475 |
| GLUT2EX1 | 164 | T | C | 0.31 | 0.69 | 0.43 | AGTGCAGTGTCCTYCCATGCTCCACAGC | . | . | Other | Promoter | . | 476 |
| GLUT2EX1 | 237 | T | C | 0.96 | 0.04 | 0.07 | AAAGATTTCTTTYCACCGGCTCCAAT | . | . | Other | Promoter | . | 476 |

TABLE 1-continued

| Gene/Exon | Base Position | Ref Allele | Alt Allele | Ref Freq (P) | Alt Freq (Q) | Heterozygosity (H) | Sequence Tag | Ref Codon | Alt Codon | Type of amino acid change | Ref amino acid | Alt amino acid | SEQ ID NO: |
|---|---|---|---|---|---|---|---|---|---|---|---|---|---|
| GLUT2EX1 | 242 | G | A | 0.34 | 0.66 | 0.45 | TTTCTCTTTTCACCRGCTCCCAATTACTG | . | . | Other | Promoter | . | 477 |
| GLUT2EX10 | 161 | G | A | 0.99 | 0.01 | 0.02 | GAATTCCAAAAGAARAGTGGCTCAGCCCA | AAG | AAA | Synonymous | Lys | Lys | 478 |
| GLUT2EX10 | 87 | C | G | 0.99 | 0.01 | 0.03 | TCCTGGCCTTTACCSTGTTTACATTTTTT | CTG | GTG | Nonsynonymous | Leu | Val | 479 |
| GLUT2EX10 | 92 | T | C | 0.35 | 0.65 | 0.46 | GCCTTTACCCTGTYACATTTTTAAAGT | TTT | TTC | Synonymous | Phe | Phe | 480 |
| GLUT2EX3 | 250 | C | T | 0.87 | 0.13 | 0.23 | AGTTGGTGGAATGAVTGCATCATTCTTTG | ACT | ATT | Nonsynonymous | Thr | Ile | 481 |
| GLUT2EX4A | 153 | T | C | 0.96 | 0.04 | 0.08 | TCAGGACTATATTGYGGTAAGTCTCACAC | TGT | TGC | Synonymous | Cys | Cys | 482 |
| GLUT2EX4A | 162 | A | T | 0.83 | 0.17 | 0.28 | TATTGTGGTAAGTCWCACACACACACACA | . | . | Other | Intron | . | 483 |
| GLUT2EX4A | 164 | A | T | 0.94 | 0.06 | 0.11 | TTGTGGTAAGTCTCWCACACACACACACA | . | . | Other | Intron | . | 484 |
| GLUT2EX4B | 127 | A | G | 0.28 | 0.72 | 0.40 | CTGGCCATCGTCACRGGCATTCTTATTAG | ACA | ACG | Synonymous | Thr | Thr | 485 |
| GLUT2EX4B | 78 | C | T | 0.93 | 0.08 | 0.14 | ATCTSGCCACATCYTGCTTGGCCTGTCT | CTG | TTG | Synonymous | Leu | Leu | 486 |
| GLUT2EX5 | 15 | T | C | 0.10 | 0.90 | 0.18 | TGTTTCAACCTGATYATTTTCTTGGACAG | . | . | Other | Intron | . | 487 |
| GLUT2EX6 | 21 | T | C | 0.88 | 0.12 | 0.21 | TAATTTCTTTAAAAYTGTCCTAGGTATTC | . | . | Other | Intron | . | 488 |
| GLUT2EX8 | 38 | T | C | 0.95 | 0.05 | 0.10 | CGTTGTGGAACGGMATTTCCTGGCCCCC | CTT | CTC | Synonymous | Leu | Leu | 489 |
| GLUT4EX1 | 1002 | A | C | 0.99 | 0.01 | 0.02 | AGCATGTCGCGGACYCTTTAAGGCGTCAT | . | . | Other | Promoter | . | 490 |
| GLUT4EX1 | 1051 | C | T | 0.74 | 0.26 | 0.38 | TCTCAGGCCCGCTCGWGTTTCCCCGGGCA | . | . | Other | Promoter | . | 491 |
| GLUT4EX1 | 1228 | A | T | 0.86 | 0.14 | 0.24 | CAGCCCCGCTCCACMAGATCCGGGGAGC | . | . | Other | Promoter | . | 492 |
| GLUT4EX1 | 1632 | A | C | 0.71 | 0.29 | 0.42 | CCACTGCTCCCGGRTCCTTGGCTTGTGG | . | . | Other | Promoter | . | 493 |
| GLUT4EX1 | 1662 | A | G | 0.64 | 0.36 | 0.46 | GCTTGTGGCTGTGGSTCCCATGCGGCCCG | . | . | Other | Promoter | . | 494 |
| GLUT4EX1 | 1683 | G | C | 0.98 | 0.02 | 0.05 | CTGTGG6TCCCATGRGGCCCCGCCTTGCA | . | . | Other | Promoter | . | 495 |
| GLUT4EX1 | 1691 | G | A | 0.94 | 0.06 | 0.11 | ACAGGA66AATCGARCCTGACTTCTACCA | . | . | Other | 5' UTR | . | 496 |
| GLUT4EX1 | 368 | A | G | 0.96 | 0.07 | 0.07 | CCGGAAAAGGCGAGARATAGTGGGTTGAGA | . | . | Other | 5' UTR | . | 497 |
| GLUT4EX1 | 560 | G | A | 0.90 | 0.10 | 0.19 | TCGCTGCCCTCCARGTGGCAGCACACC | . | . | Other | 5' UTR | . | 498 |
| GLUT4EX1 | 615 | C | A | 0.93 | 0.07 | 0.14 | CAGGAGGTTTTGTTYACTCTGAAAAGGGA | . | . | Other | Promoter | . | 499 |
| GLUT4EX1 | 91 | A | T | 0.95 | 0.05 | 0.10 | CTGAAAGACAGGACMAAGCAGCCCCGGCCA | . | . | Other | Promoter | . | 500 |
| GLUT4EX1 | 966 | C | G | 0.95 | 0.05 | 0.11 | GTGCTGGAATTACARGCGTGAGCCACCAC | . | . | Other | Promoter | . | 501 |
| GLUT4EX10 | 19 | C | G | 0.94 | 0.06 | 0.11 | GAAAGTATGTGCCCMTGCCGCAAGATG | . | . | Other | Intron | . | 502 |
| GLUT4EX11 | 1005 | G | A | 0.83 | 0.17 | 0.28 | CGAGTGCAGTGGCGYGATCTTGCTTCACT | . | . | Other | 3' UTR | . | 503 |
| GLUT4EX11 | 1099 | A | T | 0.03 | 0.05 | 0.10 | GTCTCCCAGGTTCAYGCCATTCTCCTGCC | . | . | Other | 3' UTR | . | 504 |
| GLUT4EX11 | 791 | G | C | 0.90 | 0.07 | 0.14 | CTGGACTACAGGCRCATGCCACCACC | . | . | Other | 3' UTR | . | 505 |
| GLUT4EX11 | 827 | C | T | 0.79 | 0.21 | 0.33 | GGGACTACAGGCGCMTGCCACCACACCTG | . | . | Other | 3' UTR | . | 506 |
| GLUT4EX11 | 872 | G | A | 0.92 | 0.08 | 0.15 | GCGCATGCCACCACRCCT6GCTAATTTAT | . | . | Other | 3' UTR | . | 507 |
| GLUT4EX11 | 874 | A | G | 0.73 | 0.27 | 0.40 | CACCTGGCTAATTWTTTTGTATTTTTAG | . | . | Other | 3' UTR | . | 508 |
| GLUT4EX11 | 884 | C | T | 0.89 | 0.11 | 0.20 | TACCACCGGTTTCACCRTTGTTAGCCAAATG | . | . | Other | 3' UTR | . | 509 |
| GLUT4EX11 | 897 | A | C | 0.88 | 0.13 | 0.22 | GGTTTCACCATGTTRGCCAGAATGGTCTC | . | . | Other | 3' UTR | . | 510 |
| GLUT4EX11 | 930 | A | T | 0.86 | 0.14 | 0.24 | ACCATGTTAGCCAGRATGGTCTCGATCTC | . | . | Other | 3' UTR | . | 511 |
| GLUT4EX11 | 935 | C | A | 0.49 | 0.51 | 0.50 | TCCAGGACCACCASCCTTYGTGAICTGCCTGCC | . | . | Other | 3' UTR | . | 512 |
| GLUT4EX11 | 941 | A | G | 0.96 | 0.04 | 0.07 | TCCAGGACCACCASCCTCTA | ACC | AGC | Nonsynonymous | Thr | Ser | 513 |
| GLUT4EX11 | 963 | C | G | 0.90 | 0.10 | 0.17 | ATGGGCCTTGGCCAAYGCTGCTGCTCCTA | AAC | AAT | Synonymous | Asn | Asn | 514 |
| GLUT4EX3 | 112 | C | T | 0.71 | 0.29 | 0.42 | TCAGGCCTGACCTTYCCTTCTCCAGGTCT | . | . | Other | Intron | . | 515 |
| GLUT4EX4 | 96 | C | G | 0.95 | 0.05 | 0.09 | ATGCTGTATGTGSAGRCGCACTCCCTTC | . | . | Other | Intron | . | 516 |
| GLUT4EX7 | 19 | T | C | 0.99 | 0.01 | 0.02 | AAAAGGAGGTGAGCRGCACMCTGTGCCCTTC | . | . | Other | 5' UTR | . | 517 |
| GLUT4EX7 | 227 | G | A | 0.95 | 0.05 | 0.10 | GACAGATGGGGAACMCTGTGCCTCCCTGA | . | . | Other | 5' UTR | . | 518 |
| GLUT5EX1 | 184 | 6 | C | 0.89 | 0.11 | 0.20 | GTGCCTCCCTGAACRGAAATGGCAGGGGA | . | . | Other | Promoter | . | 519 |
| GNB3EX1 | 184 | A | A | 0.63 | 0.37 | 0.47 | GCCAGGGCCAGTCARGTCRAGTGTATCACAGAT | . | . | Other | Promoter | . | 520 |
| GNB3EX1 | 201 | A | G | 0.63 | 0.37 | 0.47 | GCCAGGGCCAGTCARGTCRAGTGTATCACAGAT | . | . | Other | Promoter | . | 521 |
| GNB3EX1 | 328 | G | G | 0.93 | 0.07 | 0.13 | AGAGCATCATCTGCRGCATCACGTCCGTG | GGC | AGC | Nonsynonymous | Gly | Ser | 522 |
| GNB3EX10 | 144 | A | T | 0.61 | 0.39 | 0.48 | TGCGGCATCACGTYGTGGCCTTCCTCCCT | TCC | TCT | Synonymous | Ser | Ser | 523 |
| GNB3EX10 | 155 | C | T | 0.61 | 0.39 | 0.48 | TGCGGCATCACGTYGTGGCCTTCCTCCCT | TCC | TCT | Synonymous | Ser | Ser | 524 |

TABLE 1-continued

| Gene/Exon | Base Position | Ref Allele | Alt Allele | Ref Freq (P) | Alt Freq (Q) | Heterozygosity (H) | Sequence Tag | Ref Codon | Alt Codon | Type of amino acid change | Ref amino acid | Alt amino acid | SEQ ID NO: |
|---|---|---|---|---|---|---|---|---|---|---|---|---|---|
| GNB3EX11 | 129 | G | T | 0.97 | 0.03 | 0.06 | CTTCCTCAAAATCTKGAACTGAGGAGGCT | TGG | TTG | Nonsynonymous | Trp | Leu | 525 |
| GNB3EX11 | 254 | C | T | 0.75 | 0.25 | 0.38 | CCACTAAGCTTCYTCYCTTTGAGGCAGTG | . | . | Other | 3' UTR | . | 526 |
| GNB3EX11 | 536 | C | T | 0.60 | 0.40 | 0.48 | TATGGCTCGCACYACTAGGGTCCTGGC | . | . | Other | 3' UTR | . | 527 |
| GSY1EX10 | 46 | A | G | 0.99 | 0.01 | 0.02 | GGAGCCTTCCGACRTGAACAAGATGCTG | ATG | GTG | Nonsynonymous | Met | Val | 528 |
| GSY1EX12 | 152 | A | G | 0.95 | 0.05 | 0.10 | CCTTGGGGCTACACRCCGGTGAGTGTAG | ACA | ACG | Synonymous | Thr | Thr | 529 |
| GSY1EX12 | 163 | G | A | 0.95 | 0.05 | 0.09 | CACACAGCTGAGTTAGTGGCAGGGGA | . | . | Other | Intron | . | 530 |
| GSY1EX15 | 75 | G | C | 0.96 | 0.04 | 0.07 | CCAAGGCCTTTCCASAGCACTTCACCTAC | GAG | CAG | Nonsynonymous | Glu | Gln | 531 |
| GSY1EX16 | 152 | C | T | 0.99 | 0.01 | 0.02 | CCGCTGGAGGAAGAYGGCGAGCGCTACGA | GAC | GAT | Synonymous | Asp | Asp | 532 |
| GSY1EX16 | 210 | C | G | 0.94 | 0.06 | 0.11 | GCAACATCCGTGCASCAGAGTGGCCGGC | CCA | GCA | Nonsynonymous | Pro | Ala | 533 |
| GSY1EX16 | 65 | G | A | 0.94 | 0.06 | 0.11 | CGGCCAGCCTCGGTRCCACCGTCGCCTC | GTG | GTA | Synonymous | Val | Val | 534 |
| GSY1EX2 | 219 | G | A | 0.99 | 0.01 | 0.03 | CTGCAAGGTGGGACRTGGCCCAGCCCAGG | . | . | Other | Intron | . | 535 |
| GSY1EX3 | 117 | G | A | 0.95 | 0.05 | 0.10 | CCCTGGAGCGCTGGGAYACCTGCAACATCGG | AAG | GAG | Nonsynonymous | Lys | Glu | 536 |
| GSY1EX3 | 134 | T | C | 0.96 | 0.04 | 0.08 | AGGAGCTCTGGGAYACCTGCAACATCGG | GAT | GAC | Synonymous | Asp | Asp | 537 |
| GSY1EX3 | 149 | A | G | 0.95 | 0.05 | 0.10 | ACCTGCAACATCGGGRTGTCCGTGCTACGA | GGA | GGG | Synonymous | Gly | Gly | 538 |
| GSY1EX3 | 53 | C | G | 0.99 | 0.01 | 0.03 | GGGGCCTGGCTGATSGAGGGAGGCCCTC | ATC | ATG | Nonsynonymous | Ile | Met | 539 |
| GSY1EX4 | 16 | T | C | 0.93 | 0.07 | 0.12 | ACAGTGGCCCTGTCYCTGTTGCCCACAGT | . | . | Other | Intron | . | 540 |
| GSY1EX5 | 44 | G | A | 0.96 | 0.04 | 0.08 | CTCAACGTGGACAARGAAGCAGGGAGAG | AAG | AAA | Synonymous | Lys | Lys | 541 |
| GSY1EX6 | 54 | A | G | 0.99 | 0.01 | 0.03 | CCCCAATGGGCTGARTGTGAAGAAGTTTT | AAT | AGT | Nonsynonymous | Asn | Ser | 542 |
| GSY1EX6 | 114 | C | T | 0.71 | 0.29 | 0.42 | GGTGCTGACGTCTTYCTGGAGGCATTGGC | TTC | TTT | Synonymous | Phe | Phe | 543 |
| GSY1EX7 | 16 | T | G | 0.98 | 0.02 | 0.04 | GCTTTACCGTGCCTTSGGGTTCTTTTAGG | . | . | Other | Intron | . | 544 |
| GSY1EX7 | 17 | G | T | 0.99 | 0.01 | 0.02 | GGTTACCGTGCCTTSGGGTTCTTTTAGGC | . | . | Other | Intron | . | 545 |
| GSY1EX8 | 43 | A | C | 0.94 | 0.06 | 0.11 | GGTGAACGGCAGCGRGCAGACAGYTGGTTG | GAG | GGG | Nonsynonymous | Glu | Gly | 546 |
| HAPTEX1 | 135 | T | C | 0.90 | 0.10 | 0.18 | GATAAAGAGACAGAYTGATGTTCCTGC | . | . | Other | 5' UTR | . | 547 |
| HAPTEX1 | 188 | C | T | 0.95 | 0.05 | 0.09 | GATTTCAGGAGAAATAYTTTGCAGGTTGT | . | . | Other | 5' UTR | . | 548 |
| HAPTEX1 | 239 | T | A | 0.45 | 0.55 | 0.50 | CTTGGGATTTGTAAKAGACATCACCAGGGC | . | . | Other | 5' UTR | . | 549 |
| HAPTEX1 | 326 | A | G | 0.76 | 0.24 | 0.37 | ACTGGAAAAGATAGTGASCTTACCAGGGCC | . | . | Other | 5' UTR | . | 550 |
| HAPTEX1 | 329 | C | A | 0.88 | 0.12 | 0.21 | GGAAAAGATAGTGASCTTACCAGGGCCAA | . | . | Other | 5' UTR | . | 551 |
| HAPTEX1 | 369 | A | G | 0.89 | 0.11 | 0.19 | ACAGGAATTACGAAMTGGAGAGGGGAG | . | . | Other | 5' UTR | . | 552 |
| HAPTEX1 | 375 | A | T | 0.53 | 0.47 | 0.50 | ATTACGAAATGGAGWGGGGAGAAGTGA | . | . | Other | 5' UTR | . | 553 |
| HAPTEX4 | 34 | G | A | 0.66 | 0.34 | 0.45 | TTTGTTTTCAGGAGWRTACACCTTAAATGA | GTA | GTG | Synonymous | Val | Val | 554 |
| HAPTEX6 | 34 | C | T | 0.98 | 0.02 | 0.03 | TTTTTTCAGGAGTTACACCTTAAACAA | GTA | GTG | Synonymous | Val | Val | 555 |
| HSTSCGENE | 1331 | G | A | 0.98 | 0.02 | 0.03 | CATGCTGTTGCCTCYTCAAAGTGAATTAG | . | . | Other | 3' UTR | . | 556 |
| HSTSCGENE | 367 | T | A | 0.98 | 0.02 | 0.04 | GTGTCTGTTAATGARAGAGTGCTAAGTA | GAG | GAA | Synonymous | Glu | Glu | 557 |
| HSTSCGENE | 610 | C | T | 0.98 | 0.02 | 0.03 | CACACCTTCTGTGCYCAYGACCTGGAGGAGA | GCT | GCC | Synonymous | Ala | Ala | 558 |
| HSTSCGENE | 673 | C | T | 0.95 | 0.05 | 0.10 | GCCTTTGCCCTTCCAYGACCTGGAGGAGGA | CAC | CAT | Synonymous | His | His | 559 |
| HSD11KEX2 | 232 | A | G | 0.83 | 0.18 | 0.29 | ACCAAGGCCCACAACCAGCACCGTCA | ACC | ACA | Synonymous | Thr | Thr | 560 |
| HSD11KEX3 | 139 | G | C | 0.96 | 0.04 | 0.08 | AATTTCTTTGCCGGCRCTCAGATCCACCATTTTAAA | GCG | GCA | Synonymous | Ala | Ala | 561 |
| HSD11KEX5 | 951 | T | C | 0.97 | 0.03 | 0.06 | ATCTTACTTCCCAAWTCCACATTTTAAA | . | . | Other | 3' UTR | . | 562 |
| HSTSCGENE | 1392 | C | T | 0.97 | 0.03 | 0.06 | GCCCTCAGCTACTCRGTGGGCCTCAATGA | ACC | ACT | Synonymous | Thr | Thr | 563 |
| HSTSCGENE | 1881 | G | A | 0.98 | 0.02 | 0.03 | TCGATGTCATTGCYGAGGACCTCCGCAG | TCG | TCA | Synonymous | Ser | Ser | 564 |
| HSTSCGENE | 2139 | C | T | 0.88 | 0.13 | 0.22 | ATGCGCYATGGCCAGATTAACAG | GCC | GCT | Synonymous | Ala | Ala | 565 |
| HSTSCGENE | 2595 | C | T | 0.90 | 0.10 | 0.18 | GGTCTTGTTCGTWAGGCCTAGAGAAATAG | GGC | GGT | Synonymous | Gly | Gly | 566 |
| HSTSCGENE | 3269 | G | A | 0.81 | 0.19 | 0.30 | CTGCAACCTCCTCCYGGTCAAGCATTT | . | . | Other | 3' UTR | . | 567 |
| HSTSCGENE | 3660 | G | A | 0.94 | 0.06 | 0.11 | TAGCTGGGATTACASGCACCTAAGC | . | . | Other | 3' UTR | . | 568 |
| HSTSCGENE | 3710 | T | C | 0.98 | 0.02 | 0.03 | ACCTGCTCAGCTGGRTTACAGGCCTGAGC | . | . | Other | 3' UTR | . | 569 |
| HSTSCGENE | 3727 | C | T | 0.69 | 0.31 | 0.43 | CCCAAAGTCTGGRTTACAGGCCTGAGC | . | . | Other | 3' UTR | . | 570 |
| HSTSCGENE | 3838 | G | A | 0.90 | 0.10 | 0.18 | AGGGCATCTCGAGYTCTCGCCTGGA | . | . | Other | 3' UTR | . | 571 |
| HUMAPNH1A | 3057 | T | C | 0.92 | 0.08 | 0.15 | AGGGCATCTCTGAGYTCTCTGCCTGAG | . | . | Other | 3' UTR | . | 572 |

TABLE 1-continued

| Gene/Exon | Base Position | Ref Allele | Alt Allele | Freq (P) | Freq (Q) | Heterozygosity (H) | Sequence Tag | Ref Codon | Alt Codon | Type of amino acid change | Ref amino acid | Alt amino acid | SEQ ID NO: |
|---|---|---|---|---|---|---|---|---|---|---|---|---|---|
| HUMGFAT | 2930 | T | G | 0.65 | 0.35 | 0.45 | ATCTCCTAAAAGTGKTTTTTATTTCCTTG | . | . | Other | 3' UTR | . | 573 |
| HUMGLUTRN | 2110 | G | C | 0.94 | 0.06 | 0.12 | GGCTATGGCCACCCSTTCTGCTGGCCTGG | . | . | Other | 3' UTR | . | 574 |
| HUMGLUTRN | 933 | A | C | 0.99 | 0.01 | 0.02 | GATGATGCGGGAGAMGAAGGTCACCATCC | AAG | ACG | Nonsynonymous | Lys | Thr | 575 |
| HUMGUANCYC | 2388 | C | T | 0.93 | 0.07 | 0.14 | ATTGTCACTGAATAYTGTCCTCGTGGGAG | TAC | TAT | Synonymous | Tyr | Tyr | 576 |
| HUMGUANCYC | 2571 | A | G | 0.86 | 0.14 | 0.24 | CGTTTTGTGCTCAARATCACAGACTATGG | AAA | AGA | Nonsynonymous | Lys | Arg | 577 |
| HUMGUANCYC | 2643 | G | A | 0.93 | 0.07 | 0.14 | GCCCCTCTATGCCAARAAGCTGTGGACTGC | AAG | AAA | Synonymous | Lys | Lys | 578 |
| HUMGUANCYC | 2787 | C | G | 0.93 | 0.07 | 0.13 | GAGGGCCTGACCTSAGCCCCAAAGAGAT | CTC | CTG | Synonymous | Leu | Leu | 579 |
| HUMGUANCYC | 2905 | C | G | 0.97 | 0.03 | 0.07 | AGCGATGTTGGGCTSAGGACCCAGCTGAG | CAG | GAG | Nonsynonymous | Gln | Glu | 580 |
| HUMGUANCYC | 3300 | G | A | 0.81 | 0.19 | 0.31 | GACAACTTTGATGTSTACAAGGTGGAGAC | GTC | GTG | Synonymous | Val | Val | 581 |
| HUMGUANCYC | 3663 | G | A | 0.96 | 0.04 | 0.08 | CTTCGGGGGATGRTGAAATGAAGGAGAA | GTG | GTA | Synonymous | Val | Val | 582 |
| IAPPEX1-2 | 199 | T | C | 0.97 | 0.03 | 0.06 | TTTATTTAGAGAAAYGCACACTTGGTGTT | . | . | Other | Intron | . | 583 |
| IAPPEX1-2 | 358 | A | C | 0.99 | 0.01 | 0.02 | GACTGTATCAATAAMAATTTTGATCCTTG | . | . | Other | Intron | . | 584 |
| IAPPEX3 | 1050 | T | A | 0.83 | 0.18 | 0.29 | TAAAGTCTATTGTTYGTTGTCTTGCTGG | . | . | Other | 3' UTR | . | 585 |
| IAPPEX3 | 1076 | T | C | 0.75 | 0.25 | 0.38 | TGGTACTAAGAGGCWATTTAAAAGTATAA | . | . | Other | 3' UTR | . | 586 |
| IAPPEX3 | 1184 | A | C | 0.66 | 0.34 | 0.45 | TTTAAGTGGCTTTCMCAAACCTCAGTCA | . | . | Other | 3' UTR | . | 587 |
| IAPPEX3 | 296 | C | T | 0.85 | 0.15 | 0.26 | TGCCCTTTTCATCTYCAGTGTGAATATAT | . | . | Other | 3' UTR | . | 588 |
| IAPPEX3 | 848 | G | A | 0.11 | 0.89 | 0.19 | CCTCAGCCTCGGGTGRCAGAGTGAGACTCG | . | . | Other | 3' UTR | . | 589 |
| IAPPEX3 | 959 | A | G | 0.93 | 0.07 | 0.13 | TTCCTTTTGCAGTRTATTCTGAAATGA | . | . | Other | 3' UTR | . | 590 |
| IAPPEX3 | 683 | A | G | 0.66 | 0.34 | 0.45 | AGAGTTGCAACCTCMGCCTCGCTATGCT | . | . | Other | Promoter | . | 591 |
| ICAM1EX1 | 115 | A | T | 0.70 | 0.30 | 0.42 | CTGTGACCAGCCCAWGTTGTTGGGCATAG | AAG | ATG | Nonsynonymous | Lys | Met | 592 |
| ICAM1EX2 | 151 | G | C | 0.99 | 0.01 | 0.02 | TCCGTGGGAGAASGAGCTGAAACGGGA | AAG | AAC | Nonsynonymous | Lys | Asn | 593 |
| ICAM1EX3 | 115 | G | T | 0.92 | 0.08 | 0.15 | TGTTCCTGCCAGAGYGTTCCCAGTCTC | GGG | GGT | Synonymous | Gly | Gly | 594 |
| ICAM1EX4 | 238 | C | T | 0.95 | 0.05 | 0.10 | GTGACCGCAGAGAYGAGGGCCCAGCG | GAC | GAT | Synonymous | Asp | Asp | 595 |
| ICAM1EX5 | 47 | G | A | 0.99 | 0.01 | 0.02 | TTCCGGCGCCAACRTGATTCTGACGAAG | GTG | ATG | Nonsynonymous | Val | Met | 596 |
| ICAM1EX6 | 18 | G | A | 0.94 | 0.06 | 0.12 | CATGTCATCTCATCRTGTTTTTCCAGATG | . | . | Other | Intron | . | 597 |
| ICAM1EX6 | 254 | G | A | 0.45 | 0.55 | 0.50 | GGGAGGTCACCCGCCRAGGTGACCGTGAAT | GAG | AAG | Nonsynonymous | Glu | Lys | 598 |
| ICAM1EX6 | 39 | C | G | 0.95 | 0.05 | 0.10 | TCCAGATGGCCCCCRACTGACGACAGGG | CGA | CAA | Nonsynonymous | Arg | Gln | 599 |
| ICAM1EX7 | 304 | C | T | 0.99 | 0.01 | 0.03 | GCAGCTACACCTACYGGCCCTGGGACGCC | . | . | Other | 3' UTR | . | 600 |
| ICAM1EX7 | 869 | A | T | 0.96 | 0.03 | 0.03 | TGGCAAAAGATCARATAYGGCCACAAAGCAC | . | . | Other | 3' UTR | . | 601 |
| ICAM1EX7 | 929 | T | C | 0.96 | 0.04 | 0.07 | GAGTGATTTTTCTAYCGGCACAAAGCAC | . | . | Other | 3' UTR | . | 602 |
| ICAM2EX1 | 300 | C | T | 0.99 | 0.01 | 0.02 | GAGATGTCCTCTTYGTTACAGGACCCT | TTC | TTT | Synonymous | Phe | Phe | 603 |
| ICAM2EX2 | 63 | G | A | 0.93 | 0.07 | 0.13 | GCCAAAGAAGCTGRCGGTTGAGCCCAAA | GCG | ACG | Nonsynonymous | Ala | Thr | 604 |
| ICAM2EX3 | 281 | G | A | 0.98 | 0.03 | 0.05 | GACTTGATGTCTCRCGGTGGCAACATCT | CGC | CAC | Nonsynonymous | Arg | His | 605 |
| INSEX1 | 233 | T | A | 0.39 | 0.61 | 0.48 | CAGCCCTGCCTGTCWCCCAGATCACTGTC | . | . | Other | 5' UTR | . | 606 |
| INSEX1 | 247 | C | T | 0.97 | 0.03 | 0.06 | TCCCAGATCACTGTYCTCTCCCATGCC | . | . | Other | 5' UTR | . | 607 |
| INSEX1 | 453 | G | A | 0.78 | 0.22 | 0.34 | CAGGGTGAGCCAACYGCCCATTGCTCCC | . | . | Other | 5' UTR | . | 608 |
| INSEX2 | 14 | C | T | 0.99 | 0.01 | 0.02 | GAACCTGCTCTGCYGCCACGCTCTGGCA | . | . | Other | Intron | . | 609 |
| KALSTEX1 | 133 | G | C | 0.88 | 0.12 | 0.21 | CTGCTCTCTCCTCKGTTGGACTACTGGC | CTG | CTT | Synonymous | Leu | Leu | 610 |
| KALSTEX1 | 511 | A | G | 0.89 | 0.11 | 0.19 | CATGCGTGAAACGTCAGAAAACTGGGCACGTAC | ACA | ACG | Synonymous | Thr | Thr | 611 |
| KALSTEX2 | 318 | A | T | 0.67 | 0.33 | 0.44 | GTAATCAGTGTGCTWTGGGGGCTGAATCT | . | . | Other | Intron | . | 612 |
| KALSTEX3 | 79 | C | T | 0.72 | 0.28 | 0.40 | ACTCCCAAAGACTTYTATGTTGATGAGAA | TTC | TTT | Synonymous | Phe | Phe | 613 |
| KALSTEX3 | 17 | A | T | 0.98 | 0.02 | 0.05 | AATGTTCTACTCARTGCCCCTTTCAGGA | . | . | Other | Intron | . | 614 |
| KLKEX1 | 91 | T | C | 0.97 | 0.02 | 0.03 | CTGTCCTATGTAYTAGATCGATTTTG | TTA | CTA | Synonymous | Leu | Leu | 615 |
| KLKEX1 | 105 | C | T | 0.98 | 0.02 | 0.03 | AGGGCATTCTGAAGKCCAAGCTTATATT | . | . | Other | 5' UTR | . | 616 |
| KLKEX3 | 253 | C | G | 0.68 | 0.32 | 0.44 | TGGAGTTGCCACCSAGGAACCCGAAGTG | CAG | GAG | Nonsynonymous | Gln | Glu | 617 |
| KLKEX3 | 50 | G | A | 0.98 | 0.02 | 0.03 | GCTCTTGGCTGGGTRCCACAACTTGTTTG | CGC | CAC | Nonsynonymous | Arg | His | 618 |
| KLKEX4 | 110 | T | A | 0.97 | 0.03 | 0.07 | CCACGTCCAGAAGWGACAGACTTCATGC | GTG | GAG | Nonsynonymous | Val | Glu | 619 |
| KLKEX4 | 88 | A | G | 0.66 | 0.34 | 0.45 | CTAATGATGAGTGCRAAAAAGCCCACGTC | AAA | GAA | Nonsynonymous | Lys | Glu | 620 |

TABLE 1-continued

| Gene/Exon | Base Position | Ref Allele | Ref Allele Freq (P) | Alt Allele | Alt Allele Freq (Q) | Heterozygosity (H) | Sequence Tag | Ref Codon | Alt Codon | Type of amino acid change | Ref amino acid | Alt amino acid | SEQ ID NO: |
|---|---|---|---|---|---|---|---|---|---|---|---|---|---|
| KLKEX5 | 318 | A | 0.75 | G | 0.25 | 0.38 | CCCCAGCTGTGTCARTCTCATGGCTGGA | . | . | Other | 5' UTR | . | 621 |
| MRLEX1B | 156 | T | 0.46 | C | 0.54 | 0.50 | CCGATCAGCCAATAYTGGACTTGCTGTG | . | . | Other | 5' UTR | . | 622 |
| MRLEX1B | 16 | G | 0.90 | C | 0.10 | 0.18 | GGGCGGGTGCCCGCSTCCCCCTCGCCG | . | . | Other | 5' UTR | . | 623 |
| MRLEX2 | 1338 | A | 0.97 | C | 0.03 | 0.05 | CTCTTTTAAAGGAMTCCAACAGTAAACC | AAT | ACT | Nonsynonymous | Asn | Thr | 624 |
| MRLEX2 | 1405 | T | 0.99 | C | 0.01 | 0.03 | GATGATAAAGACTATTATTCCCTATCAGG | TAT | TAC | Synonymous | Tyr | Tyr | 625 |
| MRLEX2 | 1617 | G | 0.99 | A | 0.01 | 0.03 | AATATCTTTATCACRATGGCCTAGAGACC | CGA | CAA | Nonsynonymous | Arg | Gln | 626 |
| MRLEX2 | 1668 | A | 0.97 | G | 0.03 | 0.05 | CTTTCCTCCTGTCARTACTTTAGTGGAGT | AAT | AGT | Nonsynonymous | Asn | Ser | 627 |
| MRLEX2 | 1696 | C | 0.97 | T | 0.03 | 0.06 | TCATGGAAATCACAYGGCGACCTGTCGTC | CAC | CAT | Synonymous | His | His | 628 |
| MRLEX2 | 1720 | T | 0.50 | C | 0.50 | 0.50 | TCGTCTAGAAGAAGYGATGGGTATCCGGT | AGT | AGC | Synonymous | Ser | Ser | 629 |
| MRLEX9 | 1326 | C | 0.99 | T | 0.01 | 0.03 | GGAATGACACACTGYGGTGTCTGCAGCTC | . | . | Other | 3' UTR | . | 630 |
| MRLEX9 | 1572 | A | 0.43 | G | 0.57 | 0.49 | GTTAAAGATCAGCTRTTCCCTTCTGATCT | . | . | Other | 3' UTR | . | 631 |
| MRLEX9 | 1670 | A | 0.88 | G | 0.13 | 0.22 | GGCCCATCTTGGCARGGTTCAGTCTGAAT | . | . | Other | 3' UTR | . | 632 |
| MRLEX9 | 1964 | G | 0.86 | A | 0.14 | 0.24 | AATCTTTTAAAAATRATGATAATCATCAG | . | . | Other | 3' UTR | . | 633 |
| MRLEX9 | 247 | T | 0.97 | C | 0.03 | 0.06 | ACCTGTTTTTAACAYGTGATGGTTGATTC | . | . | Other | 3' UTR | . | 634 |
| MRLEX9 | 2551 | T | 0.88 | C | 0.13 | 0.22 | CCAAATTGTCTGTCYGCTCTTATTTTTGT | . | . | Other | 3' UTR | . | 635 |
| MRLEX9 | 2635 | G | 0.36 | A | 0.64 | 0.46 | TCATATAATTTAARAAAACTAAATTAG | . | . | Other | 3' UTR | . | 636 |
| MRLEX9 | 869 | C | 0.99 | G | 0.01 | 0.02 | TTTGCTGTGCTTASATTACTGTATGTAT | . | . | Other | 3' UTR | . | 637 |
| MRLEX9 | 916 | A | 0.83 | G | 0.18 | 0.29 | AATAAGGTATAAGMTCTTTTGTAAATGA | . | . | Other | 3' UTR | . | 638 |
| MRLEX9 | 1135 | A | 0.57 | G | 0.43 | 0.49 | AGATTCCCAGAACRTGCAAAATCCTTTC | . | . | Other | 3' UTR | . | 639 |
| NCX1EX12 | 1190 | C | 0.80 | T | 0.20 | 0.32 | TGATTGGCAAGGTCYTTCTTCCAGCATTC | . | . | Other | 3' UTR | . | 640 |
| NCX1EX12 | 1298 | A | 0.99 | G | 0.01 | 0.03 | ATACCCCATTCAARAAGCACATCATCGT | . | . | Other | 3' UTR | . | 641 |
| NCX1EX12 | 1366 | G | 0.99 | C | 0.01 | 0.03 | CGTTGCTTGGGATTSTGTGTCAGTTTAT | . | . | Other | 3' UTR | . | 642 |
| NCX1EX12 | 1407 | G | 0.84 | G | 0.16 | 0.26 | CCATGCTTCCACARTCCTCTGTTCCAGTCA | . | . | Other | 3' UTR | . | 643 |
| NCX1EX12 | 1841 | G | 0.97 | C | 0.03 | 0.06 | ACCCATTAATTCAGSAAGGCCAAGGAGAA | . | . | Other | 3' UTR | . | 644 |
| NCX1EX12 | 2099 | T | 0.94 | C | 0.06 | 0.11 | GAAAGAAGCCAGGGYGACCAACGGCCTT | . | . | Other | 3' UTR | . | 645 |
| NCX1EX12 | 2123 | T | 0.70 | Del | 0.30 | 0.42 | GCCTTTAAAAGTGTTGTCTCCTCTACTTA | . | . | Other | 3' UTR | . | 646 |
| NCX1EX12 | 2614 | T | 0.96 | C | 0.04 | 0.08 | TGTGATTACTATTTYCATGAGTAAAAGTG | . | . | Other | 3' UTR | . | 647 |
| NCX1EX12 | 2810 | G | 0.67 | A | 0.33 | 0.44 | TTTATCTTTGACCGRCTTSCATTTTAAACCAAG | . | . | Other | 3' UTR | . | 648 |
| NCX1EX12 | 2832 | C | 0.99 | G | 0.01 | 0.03 | ATAAATATATCTCTSCATTTTAAAMTTTTTGCACTCATT | . | . | Other | 3' UTR | . | 649 |
| NCX1EX12 | 3079 | A | 0.66 | G | 0.34 | 0.45 | TAAACATTAGAAAAMTTTTGSTTTGTTTGCTTTTT | . | . | Other | 3' UTR | . | 650 |
| NCX1EX12 | 3193 | G | 0.99 | T | 0.01 | 0.03 | TTGAAAGCTTTTTGSTTTGTTTGCTTTTT | . | . | Other | 3' UTR | . | 651 |
| NCX1EX12 | 664 | T | 0.99 | C | 0.01 | 0.03 | TCTCTCCAGGTTGAYAAATCCTTAAGGCT | . | . | Other | 3' UTR | . | 652 |
| NCX1EX12 | 709 | A | 0.94 | G | 0.06 | 0.10 | TTGGTTTTGTTTTCRGTGGAGCTGGGGAG | . | . | Other | 3' UTR | . | 653 |
| NCX1EX12 | 948 | G | 0.89 | A | 0.11 | 0.20 | AGAATGTCTTCATCRTATRTATTACCAAGTTC | . | . | Other | 3' UTR | . | 654 |
| NCX1EX4 | 59 | G | 0.99 | A | 0.01 | 0.03 | TAGAATATTTGACCRTGAGGAATATGAGGAC | CGT | CAT | Nonsynonymous | Arg | His | 655 |
| NETEX11 | 66 | A | 0.97 | T | 0.03 | 0.06 | ACTGACCAGTCCTKCCTCCTGGTGTGTA | . | . | Other | Intron | . | 656 |
| NETEX11 | 123 | T | 0.86 | G | 0.14 | 0.24 | CGTCAGTCCTGCCTKCCTCCTGGTGTGTA | TTC | TGC | Nonsynonymous | Phe | Cys | 657 |
| NETEX12 | 81 | T | 0.93 | C | 0.07 | 0.13 | CACCTACCGACGACYACATCTTCCCGCCC | TAC | CAC | Nonsynonymous | Tyr | His | 658 |
| NETEX13 | 50 | G | 0.93 | A | 0.07 | 0.12 | GCCATGCCTACGACRCCAGAGAACAGGA | ACG | ACA | Synonymous | Thr | Thr | 659 |
| NETEX14 | 29 | G | 0.99 | C | 0.01 | 0.03 | TGTCTTTCTCTGCASTTGCAACACTGGCT | . | . | Other | Intron | . | 660 |
| NETEX5 | 121 | A | 0.93 | G | 0.07 | 0.12 | CTCCAATGGCATCAMTGCCTACCTGCACA | AAT | ACT | Nonsynonymous | Asn | Thr | 661 |
| NETEX5 | 175 | A | 0.96 | G | 0.04 | 0.07 | CACGGTCAGTGCTCRTGCTGACCACCAAGCC | . | . | Other | Intron | . | 662 |
| NETEX5 | 83 | C | 0.95 | T | 0.05 | 0.10 | TTCTTGCCTCCTGGTSCATGCGTCACGCT | GTC | GTG | Synonymous | Val | Val | 663 |
| NETEX7 | 112 | G | 0.92 | C | 0.08 | 0.15 | TCCTTGGTTACATGSCCCATGAACACAAG | GCC | CCC | Nonsynonymous | Ala | Pro | 664 |
| NETEX7 | 131 | A | 0.93 | G | 0.07 | 0.14 | TGAACACAAGGTCARCATTGAGGATGTGG | AAC | AGC | Nonsynonymous | Asn | Ser | 665 |
| NETEX7 | 73 | G | 0.94 | C | 0.06 | 0.11 | GTATCACCAGCTTCSTCTCTGGGTTCGCC | GTC | CTC | Nonsynonymous | Val | Leu | 666 |
| NETEX8 | 17 | C | 0.55 | A | 0.45 | 0.49 | TGAATGAGGTCCTTGMTGTTTCTTACAGGA | . | . | Other | Intron | . | 667 |
| NETEX9 | 157 | A | 0.91 | G | 0.09 | 0.16 | GTTCTGCATAACCARGGTGAGTAGGGCT | AAG | AGG | Nonsynonymous | Lys | Arg | 668 |

TABLE 1-continued

| Gene/Exon | Base Position | Ref Allele | Alt Allele | Freq (P) | Freq (Q) | Heterozygosity (H) | Sequence Tag | Ref Codon | Alt Codon | Type of amino acid change | Ref amino acid | Alt amino acid | SEQ ID NO: |
|---|---|---|---|---|---|---|---|---|---|---|---|---|---|
| NETEX9 | 56 | G | A | 0.96 | 0.04 | 0.07 | GAGGCTGTCATCACRGGCCTGGCAGATGA | ACG | ACA | Synonymous | Thr | Thr | 669 |
| NPYEX1 | 112 | G | A | 0.97 | 0.03 | 0.06 | GCGCTGGCCAGGCRTTACCCCTCCAAGCC | GCG | GCA | Synonymous | Ala | Ala | 670 |
| NPYEX1 | 178 | A | G | 0.90 | 0.10 | 0.18 | GCCAGATACTACTCRGCGCTGGACACTA | TCA | TCG | Synonymous | Ser | Ser | 671 |
| NPYEX1 | 92 | C | A | 0.95 | 0.05 | 0.10 | CCCTGCTCGTGCMTGGGTGCGCTGGCC | CTG | ATG | Nonsynonymous | Leu | Met | 672 |
| NPYEX2 | 45 | T | C | 0.40 | 0.60 | 0.48 | TATGGAAAACGATCYAGCCCAGAGACACT | TCT | TCC | Synonymous | Ser | Ser | 673 |
| NPYEX2 | 100 | A | G | 0.96 | 0.04 | 0.08 | CCTATTTTCAGCCCCRTATTTCATCGTGTA | . | . | Other | 3' UTR | . | 674 |
| NPYFX3 | 78 | G | T | 0.91 | 0.09 | 0.16 | GAGACTTGCTCTCKGCCTTTTCCTATTT | . | . | Other | 3' UTR | . | 675 |
| NPYR1EX2 | 144 | T | G | 0.94 | 0.06 | 0.12 | AACATACTGTCCATKTGTCTAAAATAATC | . | . | Other | 5' UTR | . | 676 |
| NPYR1EX3 | 451 | A | T | 0.94 | 0.06 | 0.12 | AGTCGCATTTAAAMAATCAACACAATG | AAA | ACA | Nonsynonymous | Lys | Thr | 677 |
| PGISEX1 | 196 | C | A | 0.99 | 0.01 | 0.03 | GCATATAATCTTMCTTCCTGTAAATCC | . | . | Other | Promoter | . | 678 |
| PGISFX1 | 396 | G | A | 0.82 | 0.18 | 0.30 | TGCGGGAGCAGGGKTTCTCCAGAGCGC | . | . | Other | Promoter | . | 679 |
| PGISFX1 | 419 | G | A | 0.95 | 0.05 | 0.09 | GAGCGCCCCGTCCRACCCCTGCGACCT | . | . | Other | Promoter | . | 680 |
| PGISEX1 | 568 | C | T | 0.93 | 0.07 | 0.12 | CCCCGCCAGCCCGYCAGCCCGCCAGCC | . | . | Other | 5' UTR | . | 681 |
| PGISEX1 | 636 | C | T | 0.98 | 0.02 | 0.04 | CACTCTTGCTGCTGYCTACTGAGCCGC | CTG | TTG | Synonymous | Leu | Leu | 682 |
| PGISEX1 | 1255 | C | T | 0.95 | 0.05 | 0.09 | TTCTGCATTCACAGYGSCTCCTGGRCCTG | . | . | Other | 3' UTR | . | 683 |
| PGISEX10 | 149 | C | T | 0.99 | 0.01 | 0.03 | GCTACCGCCATCCGCYCATGACACAGGGAG | CCA | TCA | Nonsynonymous | Pro | Ser | 684 |
| PGISEX10 | 1500 | C | T | 0.84 | 0.16 | 0.28 | CCTGGCCAACATGGYGAAACCCCGTCTCT | . | . | Other | 3' UTR | . | 685 |
| PGISEX10 | 1505 | C | T | 0.97 | 0.03 | 0.06 | CCAACATGGCGAAAYCCCGTCTCTACTAA | . | . | Other | 3' UTR | . | 686 |
| PGISEX10 | 1521 | C | A | 0.94 | 0.06 | 0.11 | CCGTCTCTACTAAAMATAAAAAATTAGT | . | . | Other | 3' UTR | . | 687 |
| PGISEX10 | 1525 | A | C | 0.66 | 0.34 | 0.45 | CTCTACTAAACATAMAAAATTAGTCAGG | . | . | Other | 3' UTR | . | 688 |
| PGISEX10 | 1544 | G | C | 0.65 | 0.35 | 0.45 | ATTAGTCAGGTGTGSCGGTGCCGTGCCTG | . | . | Other | 3' UTR | . | 689 |
| PGISEX10 | 1760 | T | C | 0.99 | 0.01 | 0.02 | TTAATGATGCTATTTKTATTAATATAAGT | . | . | Other | 3' UTR | . | 690 |
| PGISEX10 | 1776 | C | T | 0.99 | 0.01 | 0.02 | ATTAATATAAAGTCYTGTTTATTGAGACC | . | . | Other | 3' UTR | . | 691 |
| PGISEX10 | 1852 | A | G | 0.91 | 0.09 | 0.16 | CAGCATCTCTATGARGAGAAGGAGGGTTG | . | . | Other | 3' UTR | . | 692 |
| PGISEX10 | 2474 | C | T | 0.90 | 0.10 | 0.19 | CGCAGGCTGCAAACYTGGTGTGCTGGGCG | . | . | Other | 3' UTR | . | 693 |
| PGISEX10 | 2636 | T | C | 0.48 | 0.52 | 0.50 | ACTCAAGGAAAAGAYGTGCTCCCAGG | . | . | Other | 3' UTR | . | 694 |
| PGISEX10 | 270 | T | C | 0.99 | 0.01 | 0.03 | GCTAGCATTACCACYTCCCTGCTTTTCTC | . | . | Other | 3' UTR | . | 695 |
| PGISEX10 | 2967 | C | T | 0.98 | 0.02 | 0.04 | TTGAGATGGAGTCTYGCTCTGCTGCCAG | . | . | Other | 3' UTR | . | 696 |
| PGISEX10 | 2974 | C | T | 0.52 | 0.48 | 0.50 | GGAGTCTCGCTCTGYTGCCAGGCTAGAG | . | . | Other | 3' UTR | . | 697 |
| PGISEX10 | 3009 | T | C | 0.91 | 0.09 | 0.17 | GGCGTGATCTCGGCYTCACTGCAAGCTCTG | . | . | Other | 3' UTR | . | 698 |
| PGISEX10 | 3022 | T | C | 0.77 | 0.23 | 0.35 | CTCACTGCAAGCTCYCGCCTCCCGTGTTCA | . | . | Other | 3' UTR | . | 699 |
| PGISEX10 | 3061 | T | C | 0.69 | 0.31 | 0.43 | CTGCCTCAGCCTCCYGAGTAGCTGGGACT | . | . | Other | 3' UTR | . | 700 |
| PGISEX10 | 308 | G | T | 0.95 | 0.05 | 0.10 | TGGGTCCAGGGAGKGAAAAGCTAAGAGG | . | . | Other | 3' UTR | . | 701 |
| PGISEX10 | 3082 | A | G | 0.88 | 0.12 | 0.21 | TGGGGACTACAGGCRCCCGCCACCACC | . | . | Other | 3' UTR | . | 702 |
| PGISEX10 | 3139 | A | G | 0.88 | 0.13 | 0.22 | TGGGATTTCACCGTRTTAGCCAGGATGGT | . | . | Other | 3' UTR | . | 703 |
| PGISEX10 | 3140 | T | C | 0.82 | 0.18 | 0.30 | GGGATTTCACCGTAYTAGCCAGGATGGTC | . | . | Other | 3' UTR | . | 704 |
| PGISEX10 | 3186 | C | T | 0.90 | 0.10 | 0.17 | TGATCTGCCCGCCYGGCCTCCAAAGTG | . | . | Other | 3' UTR | . | 705 |
| PGISEX10 | 3214 | T | C | 0.88 | 0.12 | 0.21 | GGGATTACAGGYGTGAGCCACCGCGC | . | . | Other | 3' UTR | . | 706 |
| PGISEX10 | 3217 | G | A | 0.88 | 0.12 | 0.20 | GGGATTACAGGTGRAGCCACCGCCCA | . | . | Other | 3' UTR | . | 707 |
| PGISEX10 | 3244 | A | T | 0.98 | 0.02 | 0.04 | CAGCCAAGAATAAAMACTCTTAAGTTGA | . | . | Other | 3' UTR | . | 708 |
| PGISEX10 | 3339 | C | T | 0.99 | 0.01 | 0.03 | GTTTACCAGGCTGYAGTCAATGGCAGATCT | . | . | Other | 3' UTR | . | 709 |
| PGISEX10 | 3419 | G | A | 0.95 | 0.05 | 0.10 | CAACTGGTTTTTCAYGTTTTTTTAGTAGAC | . | . | Other | 3' UTR | . | 710 |
| PGISEX10 | 3540 | A | T | 0.98 | 0.02 | 0.04 | GACTTACAGGCATGWRCCACCATGCCGC | . | . | Other | 3' UTR | . | 711 |
| PGISEX10 | 3651 | G | A | 0.91 | 0.09 | 0.16 | GATTACAGGCMTGARCCACCATGCCCGC | . | . | Other | 3' UTR | . | 712 |
| PGISEX10 | 3663 | G | A | 0.94 | 0.06 | 0.11 | GAGCCACCATGCCCRGCCTAAACTTTGTT | . | . | Other | 3' UTR | . | 713 |
| PGISEX10 | 3774 | C | T | 0.85 | 0.15 | 0.26 | ATGAAAAATAAATTYGCTGGGAAGG6G | . | . | Other | 3' UTR | . | 714 |
| PGISEX10 | 3840 | C | T | 0.73 | 0.27 | 0.40 | TCTCTGTTACAAAAYGAGATAAGCAAGTR | . | . | Other | 3' UTR | . | 715 |
| PGISEX10 | 400 | C | T | 0.98 | 0.02 | 0.05 | TCAGGCTTTGYGTCTGYTCCCAATTCACCTC | . | . | Other | 3' UTR | . | 716 |

TABLE 1-continued

| Gene/Exon | Base Position | Ref Allele | Alt Allele | Freq (P) | Freq (Q) | Heterozygosity (H) | Sequence Tag | Ref Codon | Alt Codon | Type of amino acid change | Ref amino acid | Alt amino acid | SEQ ID NO: |
|---|---|---|---|---|---|---|---|---|---|---|---|---|---|
| PGISEX10 | 4074 | A | G | 0.96 | 0.04 | 0.07 | GATTTTAATGATTARAAGAATAAACACA | . | . | Other | 3' UTR | . | 717 |
| PGISEX10 | 454 | T | C | 0.98 | 0.02 | 0.04 | AAATGCTATTCAGAYAAGGCAGAACTAGG | . | . | Other | 3' UTR | . | 718 |
| PGISEX10 | 573 | G | T | 0.99 | 0.01 | 0.02 | GGATGCTGGCCACAKAAAGGCCACTCAGG | . | . | Other | 3' UTR | . | 719 |
| PGISEX10 | 578 | G | A | 0.99 | 0.01 | 0.02 | CTGCCACAGAAGRCCACTCAGGATGTC | . | . | Other | 3' UTR | . | 720 |
| PGISEX10 | 948 | C | A | 0.99 | 0.01 | 0.02 | CTCCTTAGACTGATMAAGCCAAAAAGAA | . | . | Other | 3' UTR | . | 721 |
| PGISEX3 | 165 | T | A | 0.98 | 0.02 | 0.05 | CATTACAGCCCCAGWGATGAAAAGGCCAG | AGT | AGA | Nonsynonymous | Ser | Arg | 722 |
| PGISEX3 | 69 | G | T | 0.98 | 0.02 | 0.05 | TCCTACGACGGTKGTGTGGAGCCTCG | GTG | GTT | Synonymous | Val | Val | 723 |
| PGISEX4 | 143 | T | C | 0.96 | 0.04 | 0.07 | ACTTCTCCTACAGCYTCCTGCTCAGGTGA | TTC | CTC | Nonsynonymous | Phe | Leu | 724 |
| PGISEX4 | 93 | C | G | 0.99 | 0.01 | 0.02 | GGGGCGATGCTACAGMAGCAGGCAGTGGCT | GAA | GCA | Nonsynonymous | Glu | Ala | 725 |
| PGISEX5 | 79 | C | T | 0.98 | 0.02 | 0.05 | CCATGCCAGGACCGYGTCCACTCAGCTGA | CGC | CGT | Synonymous | Arg | Arg | 726 |
| PGISEX6 | 35 | C | T | 0.99 | 0.01 | 0.02 | GCAGTGTCAAAAGTYGCCTGTGGAAGCTG | CGC | TGC | Nonsynonymous | Arg | Cys | 727 |
| PGISEX6 | 52 | A | G | 0.98 | 0.02 | 0.05 | CTGTGGAAGCTGCTRTCCCCAGCCAGGCT | CTA | CTG | Synonymous | Leu | Leu | 728 |
| PGISEX6 | 97 | G | A | 0.90 | 0.10 | 0.18 | GGAGCAAATGCTRGAGAGTTACCTGCT | CTG | CTA | Synonymous | Leu | Leu | 729 |
| PGISEX8 | 102 | A | T | 0.26 | 0.74 | 0.38 | CCATGCAGACGGMGAATTCAACCTG | AGA | CGA | Synonymous | Arg | Arg | 730 |
| PGISEX9 | 42 | C | T | 0.99 | 0.01 | 0.02 | TTCCTGAACCCTGAYGGATCAGAGAAGAA | GAC | GAT | Synonymous | Asp | Asp | 731 |
| PLA2AEX1 | 302 | T | A | 0.96 | 0.04 | 0.07 | CCCCGCAGTCTCAAWTCGAGGTTCCCAGT | . | . | Other | Intron | . | 732 |
| PLA2AEX2 | 118 | C | T | 0.95 | 0.05 | 0.10 | GGGAGTGACCCCTTYTTGGAATACAACAA | TTC | TTT | Synonymous | Phe | Phe | 733 |
| PLA2AEX2 | 42 | A | C | 0.95 | 0.05 | 0.10 | AGTGGCCGCCCMGCCGGCATCAGCG | GAC | GCC | Nonsynonymous | Asp | Ala | 734 |
| PLA2AEX3 | 103 | A | C | 0.95 | 0.05 | 0.10 | ATTTCTGCTGGACAMCCGTACACCCACA | AAC | ACC | Nonsynonymous | Asn | Thr | 735 |
| PLA2AEX3 | 104 | C | A | 0.89 | 0.11 | 0.20 | TTTCTGCTGGACAAMCCGTACACCCACAC | AAC | AAA | Nonsynonymous | Asn | Lys | 736 |
| PLA2AEX3 | 131 | G | T | 0.91 | 0.09 | 0.17 | ACCTATTCATACTCRTGCCTCTGGCTCGC | TCG | TCA | Synonymous | Ser | Ser | 737 |
| PLA2AEX3 | 59 | C | T | 0.60 | 0.40 | 0.48 | CATGACAACTGCTAYGACCAGGCCAAGAA | TAC | TAT | Synonymous | Tyr | Tyr | 738 |
| PNMTEX3 | 181 | A | T | 0.89 | 0.11 | 0.19 | GCTTGAAGGCTGTGWCCAGATCTTTGC | AGC | TGC | Nonsynonymous | Ser | Cys | 739 |
| PNMTEX3 | 251 | T | A | 0.89 | 0.11 | 0.19 | GCCTGGGGGCCACCWCCTCCATCGGGG | CTG | CAG | Nonsynonymous | Leu | Gln | 740 |
| PNMTEX3 | 269 | G | A | 0.93 | 0.08 | 0.14 | CCTCATCCGGGACCTCCRCACCTATATCATGC | CGC | CAC | Nonsynonymous | Arg | His | 741 |
| PNMTEX3 | 380 | G | A | 0.96 | 0.04 | 0.08 | GCGTCTTCTTCGCCWAGAAGGTT | CGC | CAC | Nonsynonymous | Arg | His | 742 |
| PNMTEX3 | 445 | C | T | 0.96 | 0.04 | 0.08 | GCGCTTCTGTGCYGCYGCTGCAGTGCT | TGG | AGG | Nonsynonymous | Trp | Arg | 743 |
| PNMTEX3 | 554 | G | T | 0.88 | 0.13 | 0.22 | AAATAATACCCTGCYGCGCTCAGTGC | . | . | Other | 3' UTR | . | 744 |
| PPGLUCEX1 | 75 | A | G | 0.96 | 0.04 | 0.08 | CGAGCCAGGGTGAARCGGTCTCGAACTAA | AAA | AAG | Synonymous | Lys | Lys | 745 |
| PPGLUCEX1 | 133 | C | A | 0.98 | 0.02 | 0.05 | CAGGTATTAAATCCRTAGTCTCGAACTAA | . | . | Other | Intron | . | 746 |
| PPGLUCEX1 | 44 | A | T | 0.99 | 0.01 | 0.03 | ATGAAAAGCATTTAYTTTGTGGCTGGATT | TAC | TAT | Synonymous | Tyr | Tyr | 747 |
| PPGLUCEX1 | 560 | T | C | 0.99 | 0.01 | 0.03 | AAGTACTCAAAATTYCTCTGTCCAAAGAA | . | . | Other | Intron | . | 748 |
| PPGLUCEX1 | 635 | C | A | 0.92 | 0.08 | 0.15 | ACGTAAACTGTACAWAAATATCTTTGGC | . | . | Other | Intron | . | 749 |
| PPGLUCEX2 | 196 | G | T | 0.93 | 0.07 | 0.14 | TTTGAAGAACAGTAAGARAGTCTTAAGCCTGGC | . | . | Other | Intron | . | 750 |
| PPGLUCEX3 | 119 | C | T | 0.99 | 0.01 | 0.02 | CATGGAAACATGGGWAATGTTACATCATT | GAT | GTT | Nonsynonymous | Ala | Val | 751 |
| PPGLUCEX4 | 447 | A | C | 0.99 | 0.01 | 0.02 | TAGTTGAGAACTGGAYACCGAAAAATTCA | . | . | Other | 3' UTR | . | 752 |
| PPGLUCEX4 | 571 | C | T | 0.96 | 0.04 | 0.07 | GATTTTTAAATCTTTAAAYGAAAATATTTTAAG | . | . | Other | 3' UTR | . | 753 |
| PPGLUCEX4 | 615 | T | A | 0.70 | 0.30 | 0.42 | AAAATAATCTTTAAAYGAAAATATTTTAAG | . | . | Other | 3' UTR | . | 754 |
| PPGLUCEX4 | 672 | C | C | 0.98 | 0.02 | 0.04 | CCCCGATCCCGGASCCATCCTGTGAAG | . | . | Other | 3' UTR | . | 755 |
| PPTHREX1 | 106 | G | C | 0.96 | 0.04 | 0.08 | AGAGGGCTCCGGCAGSCGCGCCGATATG | . | . | Other | 5' UTR | . | 756 |
| PPTHREX1 | 36 | G | G | 0.99 | 0.01 | 0.02 | AGAGGGCTCCGGCAGSCGCCGCCCTGGCCCTTG | . | . | Other | 5' UTR | . | 757 |
| PPTHREX1 | 19 | C | A | 0.95 | 0.05 | 0.09 | GCCCTTGTTGCCCTCSTCGCCTCCGGCCCTTG | . | . | Other | 5' UTR | . | 758 |
| PPTHREX2 | 41 | C | T | 0.96 | 0.04 | 0.08 | CTGACGGTGTCCCSGGCGGCCGTGTCA | CTC | GTC | Nonsynonymous | Leu | Val | 759 |
| PPTHREX2 | 79 | C | G | 0.99 | 0.01 | 0.03 | CTGACGGTGTCCCSGGCGGCCGTGTCA | CCC | CCG | Synonymous | Pro | Pro | 760 |
| PPTHREX3 | 1234 | C | T | 0.97 | 0.03 | 0.06 | TAATGATAATAAAASCTGCATCCAGATAA | . | . | Other | 3' UTR | . | 761 |
| PPTHREX3 | 185 | T | G | 0.91 | 0.00 | 0.16 | TCATGGTCAGTCGAYGACCAGCACAA | GAT | GAC | Synonymous | Asp | Asp | 762 |
| PPTHREX3 | 401 | G | A | 0.95 | 0.05 | 0.09 | CCCTTGGGCCCCARGGAGCCTATGGTCA | CAG | CAA | Synonymous | Gln | Gln | 763 |
| PPTHREX3 | 425 | C | T | 0.90 | 0.10 | 0.18 | GGTCAAGCGGGCCYTCTGCTGGGGCTCCT | CTC | CTT | Synonymous | Leu | Leu | 764 |

TABLE 1-continued

| Gene/Exon | Base Position | Ref Allele | Alt Allele | Freq (P) | Freq (Q) | Heterozygosity (H) | Sequence Tag | Ref Codon | Alt Codon | Type of change | amino acid Ref amino acid | Alt amino acid | SEQ ID NO: |
|---|---|---|---|---|---|---|---|---|---|---|---|---|---|
| PPTHREX3 | 512 | G | A | 0.90 | 0.10 | 0.19 | GCAGCCTGGGTCAGRGAGCCCTGAAGGA | AGG | AGA | Synonymous | Arg | Arg | 765 |
| PPTHREX3 | 576 | A | G | 0.91 | 0.09 | 0.16 | CTAAGGATGTTCTTGRGCCCCTGTGTCCC | . | . | Other | 3' UTR | . | 766 |
| PPTHREX3 | 895 | C | A | 0.99 | 0.01 | 0.03 | AGCCCCTGGGAGGMAGCCAGTGAGGGTG | . | . | Other | 3' UTR | . | 767 |
| PPTHREX3 | 963 | G | C | 0.98 | 0.02 | 0.05 | CCCTCCCAACCTSGCAGAATTCCCTCCAT | . | . | Other | 3' UTR | . | 768 |
| PTGFR3EX1 | 232 | C | T | 0.96 | 0.04 | 0.08 | TGCGGCTCTCTGGAYGCCATCCCCTCTC | . | . | Other | 5' UTR | . | 769 |
| PTGFR3EX1 | 371 | C | G | 0.96 | 0.04 | 0.07 | GCGCGGGCAACCTSACGCGCCCTCCAGG | CTC | CTG | Synonymous | Leu | Leu | 770 |
| PTGFR3EX1 | 765 | A | T | 0.98 | 0.02 | 0.04 | GGTATGCGAGCCACWTGAAGACGCGTGCC | ATG | TTG | Nonsynonymous | Met | Leu | 771 |
| PTGFR3EX1 | 878 | G | T | 0.90 | 0.10 | 0.18 | CAGTGGCCCGGACKTGGTGCTTCATCAG | ACG | ACT | Synonymous | Thr | Thr | 772 |
| PTGER3EX10 | 206 | T | C | 0.98 | 0.03 | 0.05 | ACATGTTTTGTACYTTTACTATATCTAC | . | . | Other | 3' UTR | . | 773 |
| PTGER3EX10 | 281 | A | G | 0.85 | 0.15 | 0.26 | GCGTATACATTATCRTATGTAAAATTGC | . | . | Other | 3' UTR | . | 774 |
| PTGER3EX1 | 1293 | T | C | 0.38 | 0.62 | 0.47 | ACTAAAATGTTTTTCYCTACAGTCTACATG | . | . | Other | Intron | . | 775 |
| PTGER3EX2 | 1295 | T | C | 0.86 | 0.14 | 0.23 | GCACTTCTTAAAAAYGTCTCCCCACCAAA | . | . | Other | Intron | . | 776 |
| PTGFR3EX2 | 1393 | C | G | 0.84 | 0.16 | 0.27 | AAAATGTCTCCCAMCAAACATAGTAATC | . | . | Other | Intron | . | 777 |
| PTGER3EX2 | 1403 | C | A | 0.98 | 0.03 | 0.05 | AAAATGTCTCCCAMCAAACATAGTAATC | . | . | Other | Intron | . | 778 |
| PTGER3EX2 | 1614 | T | C | 0.94 | 0.06 | 0.11 | TAAAGAATTAATTTYGATAGGTACAATAT | . | . | Other | Intron | . | 779 |
| PTGER3EX2 | 1719 | G | C | 0.98 | 0.03 | 0.05 | TGGAGACAAAATCSTTGAGAGTGCTTAT | . | . | Other | Intron | . | 780 |
| PTGER3EX2 | 2153 | A | G | 0.99 | 0.01 | 0.03 | AGTCCATCAGCTGRTAAAGTGAATTATT | . | . | Other | Intron | . | 781 |
| PTGER3EX2 | 2517 | T | C | 0.92 | 0.08 | 0.15 | TAGGCATTCGTTAGYATGGGGAAACCTGA | . | . | Other | Intron | . | 782 |
| PTGER3EX2 | 3069 | T | C | 0.93 | 0.08 | 0.14 | TAGTGCTGTATATAYCCCAAGATATTTTA | . | . | Other | Intron | . | 783 |
| PTGER3EX2 | 3101 | A | G | 0.91 | 0.09 | 0.17 | AAATGTAAGTGTTTRATCATGCCAGATTT | . | . | Other | Intron | . | 784 |
| PTGER3EX2 | 326 | T | A | 0.91 | 0.09 | 0.17 | ATATGCTAAACCTWACYTGAATTTAGG | . | . | Other | Intron | . | 785 |
| PTGER3EX2 | 3282 | A | G | 0.98 | 0.02 | 0.05 | ACTAAAAACTGGCARACAGTATTTTAATA | . | . | Other | Intron | . | 786 |
| PTGER3EX2 | 3382 | T | C | 0.63 | 0.37 | 0.47 | TTTTATAATTTGYTCTTTTTGACTCA | . | . | Other | Intron | . | 787 |
| PTGER3EX2 | 557 | G | T | 0.99 | 0.01 | 0.03 | TATAAATGATCTTGKTCTATTGGGAGCG | . | . | Other | Intron | . | 788 |
| PTGER3EX2 | 628 | C | T | 0.83 | 0.17 | 0.28 | AACCACATAGATACCAYTGAAGACAAGGGAT | . | . | Other | Intron | . | 789 |
| PTGER3EX2 | 769 | T | G | 0.91 | 0.09 | 0.17 | GTATAATATTATTTAWAATATTCATCGATA | . | . | Other | Intron | . | 790 |
| PTGER3EX2 | 787 | A | G | 0.94 | 0.06 | 0.12 | ATTCATCGATACCAKTATTCAAATATTGC | . | . | Other | Intron | . | 791 |
| PTGER3EX2 | 805 | G | A | 0.91 | 0.09 | 0.16 | TCAAATATTGCTCAMTACAGCAAATTAGC | . | . | Other | Intron | . | 792 |
| PTGER3EX2 | 850 | G | A | 0.98 | 0.02 | 0.04 | TTTAAGTTTACTTGRATTGATAATTAGGT | . | . | Other | Intron | . | 793 |
| PTGER3EX2 | 852 | T | T | 0.62 | 0.38 | 0.47 | TAAGTTTACTTGGAWTGATAATTAGGTTTACT | . | . | Other | Intron | . | 794 |
| PTGER3EX2 | 855 | A | T | 0.98 | 0.02 | 0.04 | GTTTTACTTGGAWTGATAATTAGGTTTACT | . | . | Other | Intron | . | 795 |
| PTGER3EX3 | 76 | C | T | 0.94 | 0.06 | 0.12 | CTCCACCTCCCTTACYCTGCCAGTGTTCCT | CCC | CTC | Nonsynonymous | Pro | Leu | 796 |
| PTGER3EX3 | 80 | C | G | 0.93 | 0.07 | 0.13 | ACCTCCTTACCCTGYCAGTGTTCCTCAAC | TGC | TGT | Synonymous | Cys | Cys | 797 |
| PTGER3EX4 | 719 | G | T | 0.84 | 0.16 | 0.27 | TCTAGCTTTTGATKACAAAGGAGTGATG | . | . | Other | 3' UTR | . | 798 |
| PTGER3EX4 | 94 | C | T | 0.98 | 0.03 | 0.05 | TTTGCATATTCTTYCCACCTGAGAAGA | . | . | Other | 3' UTR | . | 799 |
| PTGER3EX6 | 197 | G | T | 0.98 | 0.03 | 0.05 | GAGTGCTGTGTTTRAAAAGCAAGCTCC | . | . | Other | 3' UTR | . | 800 |
| PTGER3EX6 | 300 | A | G | 0.91 | 0.09 | 0.16 | GAGATTACCAGCAARCCAGTCATTCATTCCG | . | . | Other | 3' UTR | . | 801 |
| PTGER3EX6 | 387 | T | A | 0.98 | 0.02 | 0.05 | CCAATTTAGACTTWAGTAAGAATAGCAC | . | . | Other | 3' UTR | . | 802 |
| PTGER3EX7 | 85 | A | G | 0.98 | 0.02 | 0.04 | TTGGTTCAGTTCTCRTGATAGTGACTGAG | CAT | CGT | Nonsynonymous | His | Arg | 803 |
| PTGER3EX8 | 116 | C | T | 0.83 | 0.17 | 0.28 | GATTTGTCCTTTCCYGCCATGTTCTTCATC | CCC | CCT | Synonymous | Pro | Pro | 804 |
| PTGER3EX9 | 16 | T | C | 0.94 | 0.06 | 0.12 | TGCCTATCACATAAYAGGAGAACCCTGCA | . | . | Other | Intron | . | 805 |
| RENEX1 | 80 | A | T | 0.76 | 0.24 | 0.37 | ATGAAGAGGCTGACMCTTGGCAACACCAC | GGA | GGT | Synonymous | Gly | Gly | 806 |
| RENEX2 | 135 | A | C | 0.97 | 0.03 | 0.05 | GACATCATCACCGTRAGTTGGGCCCCCT | ACA | ACC | Synonymous | Thr | Thr | 807 |
| RENEX4 | 151 | T | G | 0.66 | 0.34 | 0.45 | AAGTTGGGCCGCCKAGGTCATCTGCCCC | . | . | Other | Intron | . | 808 |
| RENEX9 | 165 | G | A | 0.99 | 0.01 | 0.03 | TTCAGGTGAGGTTCRAGTCGGCCCCCCTCG | . | . | Other | Intron | . | 809 |
| RENEX9 | 138 | T | C | 0.91 | 0.09 | 0.17 | GTTTTGGGCAGTCYTGCTCCTCCGATT | . | . | Other | Intron | . | 810 |
| SAEX1 | 167 | C | T | 0.91 | 0.09 | 0.17 | ATTACCTAAGAGKAACCGCTGGAGTC | . | . | Other | Promoter | . | 811 |
| SAEX1 | 76 | G | T | 0.98 | 0.03 | 0.05 | ATTACCTAAGAGKAACCGCTGGAGTC | . | . | Other | Promoter | . | 812 |

TABLE 1-continued

| Gene/Exon | Base Position | Ref Allele | Alt Allele | Ref Freq (P) | Alt Freq (Q) | Heterozygosity (H) | Sequence Tag | Ref Codon | Alt Codon | Type of amino acid change | Ref amino acid | Alt amino acid | SEQ ID NO: |
|---|---|---|---|---|---|---|---|---|---|---|---|---|---|
| SAEX11 | 143 | C | T | 0.99 | 0.01 | 0.02 | AGAGCAGATGATGTYATATTATCCTCTGG | GTC | GTT | Synonymous | Val | Val | 813 |
| SAEX2 | 54 | T | C | 0.94 | 0.06 | 0.12 | CTCTGTGCAAATCCYAGTCCTAAAGCTT | . | . | Other | 5' UTR | . | 814 |
| SAEX3 | 109 | T | C | 0.99 | 0.01 | 0.03 | GAGTTTTGAGGAACYGGGATCTCTGTCCA | CTG | CCG | Nonsynonymous | Leu | Pro | 815 |
| SAEX4 | 187 | T | C | 0.82 | 0.18 | 0.30 | CACTCCAAGCTGATYGTATCAGAGAACTC | ATT | ATC | Synonymous | Ile | Ile | 816 |
| SAEX5 | 182 | T | C | 0.14 | 0.86 | 0.24 | TGGAAGGTATACTTYCACAAAAGTGCAGC | . | . | Other | Intron | . | 817 |
| SAEX8 | 111 | G | A | 0.97 | 0.03 | 0.06 | AAATGAGAAACAASACGGGCCTGATAT | AAG | AAC | Nonsynonymous | Lys | Asn | 818 |
| SAEX9 | 101 | C | T | 0.98 | 0.03 | 0.05 | CCTTCTCCTGCTTTYGATGTTAAGGTTTG | TTC | TTT | Synonymous | Phe | Phe | 819 |
| SCNN1GEX1 | 167 | G | A | 0.48 | 0.52 | 0.50 | GGTGGCCCAGGAAGRCGCAGCGCCGGCCGG | . | . | Other | Promoter | . | 820 |
| SCNN1GEX1 | 236 | G | T | 0.81 | 0.19 | 0.30 | TGAAGTCGTGGCCCKCTCCGGCGGTCTC | . | . | Other | Promoter | . | 821 |
| SCNN1GEX1 | 498 | G | A | 0.99 | 0.01 | 0.02 | TGGAGCGGATGCCGRGCCAGGGCGTCG | . | . | Other | Intron | . | 822 |
| SCNN1GEX1 | 552 | C | G | 0.70 | 0.30 | 0.42 | GAGCCAGCATCAGCSGGTGCGGCTTCCC | . | . | Other | Intron | . | 823 |
| SCNN1GEX1 | 553 | G | A | 0.99 | 0.01 | 0.02 | AGCCAGCATCAGCCRGTGCGWGGCTTCCCG | . | . | Other | Intron | . | 824 |
| SCNN1GEX12 | 1016 | T | G | 0.80 | 0.20 | 0.32 | AGATACAGAGTGCCWGGTGGAGGTCTGGG | . | . | Other | Intron | . | 825 |
| SCNN1GEX12 | 1085 | A | G | 0.75 | 0.25 | 0.38 | CAGGAGATGATTTRGTTATTCAATTTTG | . | . | Other | 3' UTR | . | 826 |
| SCNN1GEX12 | 407 | C | T | 0.78 | 0.22 | 0.34 | ATGCTGGATGAGCTSTGAGGCAGGGTTGA | CTC | CTG | Synonymous | Leu | Leu | 827 |
| SCNN1GEX12 | 454 | G | A | 0.99 | 0.01 | 0.02 | GACCACCAGCCATGKTCTAAGGACATGGA | . | . | Other | 3' UTR | . | 828 |
| SCNN1GEX12 | 485 | G | A | 0.99 | 0.01 | 0.02 | GGGTGCCCCAGACRTGCACAGGGGAC | . | . | Other | 3' UTR | . | 829 |
| SCNN1GEX12 | 569 | T | G | 0.86 | 0.14 | 0.24 | CCAAGATGGGCCKGGGCATGCCCAGGA | . | . | Other | 3' UTR | . | 830 |
| SCNN1GEX12 | 646 | C | T | 0.80 | 0.20 | 0.32 | ATAAATCCCGGACYTGAACTATTAGCAC | . | . | Other | 3' UTR | . | 831 |
| SCNN1GEX12 | 678 | A | G | 0.80 | 0.20 | 0.32 | ACTAGAGACTGGGARCCGAGGCAGTGGTG | . | . | Other | 3' UTR | . | 832 |
| SCNN1GEX12 | 982 | A | G | 0.76 | 0.24 | 0.37 | GAGAACTGGCCCAGRGCCCTTGGAGTGTT | . | . | Other | 3' UTR | . | 833 |
| SCNN1GEX2 | 219 | G | T | 0.92 | 0.08 | 0.14 | TCGTGGTGTCCCKCGCCGTCTGCCCGC | GGC | TGC | Nonsynonymous | Gly | Cys | 834 |
| SCNN1GEX2 | 26 | G | C | 0.16 | 0.84 | 0.27 | TCTTCTTTGCCCTSCCAGCACGCCCGTC | . | . | Other | Intron | . | 835 |
| SCNN1GEX2 | 43 | G | A | 0.36 | 0.64 | 0.46 | GCACCCCGTCCTCRGAGTCCCGTCCTCA | . | . | Other | 5' UTR | . | 836 |
| SCNN1GEX3 | 186 | T | C | 0.79 | 0.21 | 0.34 | TTCTCCACCGGATYCCGCTGCTGATCTT | ATT | ATC | Synonymous | Ile | Ile | 837 |
| SCNN1GEX3 | 259 | G | A | 0.94 | 0.06 | 0.12 | GAAGCGCAAAGTCRGCCGTAGCATCATT | GGC | AGC | Nonsynonymous | Gly | Ser | 838 |
| SCNN1GEX3 | 261 | C | G | 0.91 | 0.09 | 0.16 | AAGCGGAAAGTCGGYGCGTAGCATCATTCA | GGC | GGT | Synonymous | Gly | Gly | 839 |
| SCNN1GEX3 | 301 | G | A | 0.97 | 0.03 | 0.06 | ATGTCATGCAACATCRAGTCCAAGCAAGTG | GAG | AAG | Nonsynonymous | Glu | Lys | 840 |
| SCNN1GEX3 | 99 | T | C | 0.73 | 0.27 | 0.40 | CTGAAGTCCCTGTAYGCCTTTCCAGAGTC | TAT | TAC | Synonymous | Tyr | Tyr | 841 |
| SCNN1GEX4 | 47 | C | T | 0.96 | 0.04 | 0.07 | GGTAACAGAATTGGCRGGGGCACCCAGCCC | TCC | TCT | Synonymous | Ser | Ser | 842 |
| SCNN1GEX7 | 142 | G | A | 0.70 | 0.30 | 0.42 | GCTGGGCCCCCCWGGTCACAGCCAGAC | . | . | Other | Intron | . | 843 |
| TBXA2REX1 | 518 | T | A | 0.89 | 0.11 | 0.20 | CTCAGCCTCACCTTCCTCWGGCCGCCTCTC | . | . | Other | 5' UTR | . | 844 |
| TBXA2REX1B | 130 | T | C | 0.80 | 0.20 | 0.32 | CTGGGCCCCCGAGYAGCTGGGATTACAG | . | . | Other | 5' UTR | . | 845 |
| TBXA2REX2 | 292 | T | A | 0.98 | 0.02 | 0.04 | TCCTCACCTTCCTCWGGCCGCCTCTC | TGC | AGC | Nonsynonymous | Cys | Ser | 846 |
| TBXA2REX2 | 329 | T | A | 0.98 | 0.03 | 0.05 | CCTGGCTCTGGWGCCGTACCATGG | GTG | GAG | Nonsynonymous | Val | Glu | 847 |
| TBXA2REX2 | 333 | C | A | 0.96 | 0.04 | 0.08 | GGCTGCTGGTGACYGGTAGCATCGTGGT | ACC | ACT | Synonymous | Thr | Thr | 848 |
| TBXA2REX2 | 371 | A | T | 0.96 | 0.04 | 0.03 | CGCCGCGTCTTCGWGACCACGCCGTCTG | GAG | GTG | Nonsynonymous | Glu | Val | 849 |
| TBXA2REX2 | 390 | T | C | 0.94 | 0.06 | 0.12 | CACGGCCGTGACCCWGGCCTGCCGTCTG | CCT | CCA | Synonymous | Pro | Pro | 850 |
| TBXA2REX2 | 525 | G | A | 0.95 | 0.05 | 0.10 | CCGGCCGTGACCCRGCCGCGCCCTG | TCG | TCA | Synonymous | Ser | Ser | 851 |
| TBXA2REX2 | 568 | G | A | 0.99 | 0.01 | 0.02 | TGGTGTGGGCGGCCRCAATACCCGGGT | GCG | ACG | Nonsynonymous | Ala | Thr | 852 |
| TBXA2REX2 | 617 | T | A | 0.98 | 0.03 | 0.05 | GGGTCGCTACACCWGCAATCAGCGTGTTGGC | GTG | GAG | Nonsynonymous | Val | Glu | 853 |
| TBXA2REX2 | 739 | G | A | 0.96 | 0.04 | 0.07 | ATCATGGTGTGCMAGCGTGTGTTGGCT | GTC | ATC | Nonsynonymous | Val | Ile | 854 |
| TBXA2REX3 | 852 | C | A | 0.98 | 0.02 | 0.04 | GACCCTGGGTGTAYATCCTGTTCCGCACC | GCC | GCA | Synonymous | Ala | Ala | 855 |
| TBXA2REX3 | 145 | T | C | 0.36 | 0.64 | 0.46 | ATCATGGTGCWGCMAGCGTGTGTTGGCT | TAT | TAC | Synonymous | Tyr | Tyr | 856 |
| TBXA2REX3 | 358 | A | G | 0.93 | 0.07 | 0.13 | GGGGTGCTGATGGRCAGTGGGCATCAGC | . | . | Other | 3' UTR | . | 857 |
| TBXA2REX3 | 528 | C | G | 0.89 | 0.11 | 0.19 | AAGGCATGCAGACRTTGAAGAGGGTCT | . | . | Other | 3' UTR | . | 858 |
| TBXA2REX3 | 599 | C | T | 0.89 | 0.11 | 0.20 | CCCAGGCTGYAGTGAGTGGCGCAATCTC | . | . | Other | 3' UTR | . | 859 |
| TBXA2REX3 | 701 | C | T | 0.86 | 0.14 | 0.24 | GGGCGCCGCCACCAYGCCCGGCTAATTTT | . | . | Other | 3' UTR | . | 860 |

TABLE 1-continued

| Gene/Exon | Base Position | Ref Allele | Ref Allele Freq (P) | Alt Allele | Alt Allele Freq (Q) | Heterozygosity (H) | Sequence Tag | Ref Codon | Alt Codon | Type of change | amino acid Nonsynonymous | Ref amino acid | Alt amino acid | SEQ ID NO: |
|---|---|---|---|---|---|---|---|---|---|---|---|---|---|---|
| TBXA2REX3 | 904 | A | 0.70 | G | 0.30 | 0.42 | TGGAGTACAGTGGCRCGATCTCGGCTCAC | . | . | Other | | 3' UTR | . | 861 |
| TBXA2REX3 | 906 | G | 0.53 | A | 0.47 | 0.50 | GAGTACAGTGGCACRATCTCGGCTCACTG | . | . | Other | | 3' UTR | . | 862 |
| TBXA2REX3 | 953 | G | 0.39 | C | 0.61 | 0.47 | TTCAAGCGATTCTCSTGCCTCAGCCTCCC | . | . | Other | | 3' UTR | . | 863 |
| TBXASEX10 | 61 | G | 0.97 | T | 0.03 | 0.06 | CAGCCTCGAGGAAGKCCTGCCCTATCTGG | GGC | GTC | Nonsynonymous | | Gly | Val | 864 |
| TBXASEX10 | 98 | G | 0.93 | A | 0.07 | 0.14 | ATTGCAGAGACGCTRAGGATGTACCCGCC | CTG | CTA | Synonymous | | Leu | Leu | 865 |
| TBXASEX11 | 105 | C | 0.91 | T | 0.09 | 0.16 | GTGCTAGAGATGGCYGTGGGTGCCCTGCA | GCC | GCT | Synonymous | | Ala | Ala | 866 |
| TBXASEX11 | 152 | C | 0.99 | T | 0.01 | 0.03 | GCCAAGCCCGAGAMCTTCAACCCTGAAA | ACC | AAC | Nonsynonymous | | Thr | Asn | 867 |
| TBXASEX11 | 49 | C | 0.98 | G | 0.02 | 0.05 | CACGGGAGGCAGCTSAGGACTGCGAGGTG | CAG | GAG | Synonymous | | Gln | Glu | 868 |
| TBXASEX11 | 73 | C | 0.99 | T | 0.01 | 0.02 | AGGTGCTGGGGCAGYGCATCCCCGCAGGC | CGC | TGC | Nonsynonymous | | Arg | Cys | 869 |
| TBXASEX11 | 88 | G | 0.90 | A | 0.10 | 0.18 | GCATCCCCGCAGGCRCTGTGCTAGAGATG | GCT | ACT | Nonsynonymous | | Ala | Thr | 870 |
| TBXASEX12 | 46 | C | 0.98 | A | 0.02 | 0.04 | TCACGCTGAGGCMGGCCMGGCAGCAGCACCGG | CGG | AGG | Synonymous | | Arg | Arg | 871 |
| TBXASEX13 | 226 | A | 0.99 | G | 0.01 | 0.02 | CCTGCATGCAAGGRTAAGATAGTTTCTTTCC | . | . | Other | | 3' UTR | . | 872 |
| TBXASEX4 | 130 | C | 0.99 | T | 0.01 | 0.03 | CCAACAGAATGGTAYGTAGTTTCTTTCC | . | . | Other | | Intron | . | 873 |
| TBXASEX5 | 15 | G | 0.99 | A | 0.01 | 0.02 | CTGACCCTCTGCTTRTTACTTCCCAACAG | . | . | Other | | Intron | . | 874 |
| TBXASEX6 | 59 | C | 0.98 | A | 0.02 | 0.04 | AGCCAAGCCTGCGAMCTTCTCCTGGCTCA | GAA | GAA | Synonymous | | Asp | Asp | 875 |
| TBXASEX8 | 110 | A | 0.89 | G | 0.11 | 0.20 | ATGGCTTTTTAACRAACTCATTAGGAAT | AAA | GAA | Nonsynonymous | | Lys | Asp | 876 |
| TBXASEX8 | 119 | A | 0.99 | G | 0.01 | 0.03 | TTAACAAACTCATTRGGAATGTGATTGCC | AGG | GGG | Nonsynonymous | | Arg | Gly | 877 |
| TBXASEX9 | 156 | C | 0.96 | A | 0.04 | 0.07 | CGAACCCTTCCCGMAACACCAGCCCAAC | CAA | AAA | Nonsynonymous | | Gln | Lys | 878 |
| TBXASEX9 | 276 | C | 0.88 | G | 0.12 | 0.21 | CTTTTGCCACTCASTACTGCCACCAAC | CTA | GTA | Nonsynonymous | | Leu | Val | 879 |
| TRHREX1 | 56 | G | 0.44 | C | 0.56 | 0.49 | TTCTGCAGAACTTASATGATAAGCAACGA | . | . | Other | | Promoter | . | 880 |
| TRHREX1 | 84 | T | 0.98 | C | 0.02 | 0.04 | ACAAAGCCAGCTGCYTCTAGACCCCTGGC | . | . | Other | | Promoter | . | 881 |
| TRHREX2 | 147 | C | 0.99 | G | 0.01 | 0.03 | GTCAGTGACTGAAMCAAACACAGCTTCA | AAC | AAA | Nonsynonymous | | Asn | Lys | 882 |
| TRHREX2 | 240 | A | 0.99 | G | 0.01 | 0.03 | GGCCTGGGCATTGTRGGCAACATCATGGT | GTA | GTG | Synonymous | | Val | Val | 883 |
| TRHREX3 | 1161 | T | 0.58 | C | 0.42 | 0.49 | TCCCACATGATGGGYGGAAAAAGGCAAAA | . | . | Other | | 3' UTR | . | 884 |
| TRHREX3 | 1231 | T | 0.98 | A | 0.03 | 0.05 | TTAAATTTGAAAAGYATAGTCAAGACAAA | . | . | Other | | 3' UTR | . | 885 |
| TRHREX3 | 1540 | T | 0.97 | A | 0.03 | 0.06 | TTCTTTTTTTTGTTWTCTCAAATGCTAGT | . | . | Other | | 3' UTR | . | 886 |
| TRHREX3 | 1786 | A | 0.99 | T | 0.01 | 0.03 | GAATCTCCGAGGGCWAAAATTGCCTTGG | . | . | Other | | 3' UTR | . | 887 |
| TRHREX3 | 1846 | T | 0.94 | C | 0.06 | 0.12 | GTAGATCAAAAAGYACCCATACCTTTAC | . | . | Other | | 3' UTR | . | 888 |
| TRHREX3 | 2046 | G | 0.98 | A | 0.02 | 0.04 | CCTCATTCTAGAGTRCGCTTTTTTTTTT | . | . | Other | | 3' UTR | . | 889 |
| TRHREX3 | 2175 | A | 0.97 | G | 0.03 | 0.06 | ACCTGCATGACAGTRAGCAATCTATGTTA | . | . | Other | | 3' UTR | . | 890 |
| TRHREX3 | 2283 | G | 0.95 | A | 0.05 | 0.10 | ACAAGCACACATGTGTRTTTATAAACACATA | . | . | Other | | 3' UTR | . | 891 |
| TRHREX3 | 377 | T | 0.95 | C | 0.05 | 0.10 | GCCAAAAGTGTCYTTTGATGACACCTG | TCT | TCC | Synonymous | | Ser | Ser | 892 |
| TRHREX3 | 960 | T | 0.96 | C | 0.04 | 0.07 | TAAGATTTTAGACAYACATGTTAACTGTA | . | . | Other | | 3' UTR | . | 893 |

TABLE 2

| Gene/ExOn | Base Position | Ref Allele | Freq (P) | Alt Allele | Freq (Q) | Heterozygosity (H) | Sequence Tag | Ref Codon | Alt Codon | Type of amino acid change | Ref amino acid | Alt amino acid | SEQ ID NO: |
|---|---|---|---|---|---|---|---|---|---|---|---|---|---|
| ACEEX13 | 138 | C | 0.81 | T | 0.19 | 0.30 | CCTCTGCTGGTCCCYAGCCAGGAGGCATC | CCC | CCT | Synonymous | Pro | Pro | 894 |
| ACEEX17 | 52 | A | 0.20 | G | 0.80 | 0.32 | AATGTGATGGCCACRTCCCGGAAAATGA | ACA | ACG | Synonymous | Thr | Thr | 895 |
| ADRB3EX1 | 416 | T | 0.90 | C | 0.10 | 0.18 | TCGTGGCCATCGCCYGGACTCCGAGACTC | TGG | CGC | Nonsynonymous | Trp | Arg | 896 |
| AGTEX2 | 644 | C | 0.86 | T | 0.14 | 0.24 | GCTGCTGCTGTCCAYGGTGGTGGGCGTGT | ACG | ATG | Nonsynonymous | Thr | Met | 897 |
| AGTEX2 | 827 | T | 0.10 | C | 0.90 | 0.18 | TGGCTGCTCCCTGAYGGGAGCCAGTGTGG | ATG | ACT | Nonsynonymous | Mer | Thr | 898 |
| AGTEXP1 | 173 | C | 0.71 | T | 0.29 | 0.41 | TGCTTGTGTGTTTTYCCCAGTGTCTATTA | . | . | Other | Promoter | . | 899 |
| AGTEXP2 | 203 | G | 0.86 | A | 0.14 | 0.24 | CTCGACCCTGCACCRGCTCACTCTGTTCA | . | . | Other | Promoter | . | 900 |
| AGTEXP3 | 144 | C | 0.24 | A | 0.76 | 0.37 | GCTATAAATAGGGCMTCGTGACCCGGCCA | . | . | Other | Promoter | . | 901 |
| ANPEX3 | 120 | T | 0.91 | C | 0.09 | 0.16 | GTCTCTGCTGCATTYGTGTCATCTTGTTG | . | . | Other | 3'UTR | . | 902 |
| ANPEX3 | 33 | T | 0.80 | C | 0.20 | 0.32 | TCTCTTTGCAGTACYGAAGATAACAGCCA | TGA | AGA | Nonsynonymous | Stop | Arg | 903 |
| AT1EX5 | 1138 | A | 0.93 | G | 0.07 | 0.13 | AAGAAGCCTGCACCRTGTTTTGAGGTTGA | CCA | CCG | Synonymous | Pro | Pro | 904 |
| AT1EX5 | 1593 | G | 0.88 | T | 0.12 | 0.21 | AAAGTTTTCGTGCCKGTTTTCAGCTATTA | . | . | Other | 3'UTR | . | 905 |
| AT1EX5 | 649 | T | 0.61 | C | 0.39 | 0.47 | CAAAATTCAACCCTYCCGATAGGGCTGGG | CTT | CTC | Synonymous | Leu | Leu | 906 |
| MRLEX2 | 1504 | C | 0.89 | T | 0.11 | 0.20 | CAAGAACCAGATGAYGGGAGCTATTACCC | GAC | GAT | Synonymous | Asp | Asp | 907 |
| MRLEX2 | 545 | A | 0.81 | G | 0.19 | 0.30 | GCGTCATGCGCGCCRTTGTTAAAAGCCCT | ATT | GTT | Nonsynonymous | Ile | Val | 908 |
| NCX1EX12 | 3101 | A | 0.16 | T | 0.84 | 0.26 | ACTCATTTTTAGCWGTATTAGGAATGTC | . | . | Other | 3'UTR | . | 909 |

TABLE 3

| Gene/Exon | Gene Name |
|---|---|
| Table 1 | |
| AADD | Alpha-Adducin |
| ACE | Angiotensin Converting Enzyme |
| ADDB | Beta Adducin |
| ADDG | Gamma Adducin |
| ADORA2A | A2a Adenosine Receptor |
| ADRB3 | Beta-3-Adrenergic Receptor |
| ADROM | (prepro) Adrenomedullin |
| AE1 | Anion Exchanger |
| AGT | Angiotensinogen |
| ALDRED | Aldose Reductase |
| ANPEX1 | Atrial Natriuretic Factor |
| APOA1 | Apolipoprotein A-I |
| APOA2 | Apolipoprotein A-II |
| APOA4 | Apolipoprotein A-IV |
| APOC1EX1 | Apolipoprotein C-I |
| APOC2 | Apolipoprotein C-II |
| APOC3 | Apolipoprotein C-III |
| APOC4 | Apolipoprotein C-IV |
| APOER2 | Apolipoprotein E Receptor 2 |
| AT1 | Angiotensin II Receptor Type-1 |
| AT2 | Angiotensin II Receptor Type 2 |
| AVP | Arginine Vasopressin |
| AVPR2 | Arginine Vasopressin Receptor Type II |
| BIR | Beta Inward Rectifier Subunit (Pancreatic K Channel) |
| BKRB2 | B2-Bradykinin Receptor |
| BNP | Brain Natriuretic Protein |
| BRS3 | Bombesin Receptor Subtype-3 |
| CAL/CGRP | Calcitonin/Calcitonin Gene Related Peptide |
| CHY | Chymase |
| CLCNKB | Chloride Channel (Human Kidney - B) |
| CNP | C-Type Natriuretic Peptide |
| COX1 | Cyclooxygenase - 1 |
| COX2 | Cyclooxygenase - 2 |
| CYP11B1 | Cytochrome P-450 11 Beta 1 |
| CYP11B2 | Cytochrome P-450 11 Beta 2 |
| DBH | Dopamine Beta-Hydroxylase |
| DD1R | Dopamine D1 Receptor |
| EDNRA | Endothelin Receptor Subtype A |
| EDNRB | Endothelin Receptor Subtype B |
| ELAM1 | Endothelial Leukocyte Adhesion Molecule I |
| ENDOTHEL | Endothelin-2 |
| ET1 | Endothelin-1 |
| GALNR | Galanin Receptor |
| GGR | Glucagon Receptor |
| GH1 | Growth Hormone 1 |
| GH2 | Growth Hormone 2 |
| GIPR | Glucose Insulinotropic Peptide Receptor or Gastric Inhibitory Polypeptide Receptor |
| GLUT2 | Glucose Transporter 2 |
| GLUT4 | Glucose Transporter 4 |
| GLUT5 | Glucose Transport-Like 5 |
| GNB3 | G-Protein Beta-3 Chain |
| GSY1 | Glycogen Synthetase |
| HAPT | Haptoglobin |
| HSD11K | Hydroxysteroid Dehydrogenase 11 Beta Kidney Isozyme |
| HSTSCGENE | Homo sapiens Thiazide-Sensitive Cotransporter |
| HUMAPNH1A | Human Na/II Antiporter |
| HUMGFAT | Human Glutamine: Fructose-6-Phosphate Amidotransferase |
| HUMGLTRN | Human Glucose Transporter |
| HUMGUANCYC | Human Guanylate Cyclase |
| IAPP | Islet Amyloid Polypeptide |

TABLE 3-continued

| Gene/Exon | Gene Name |
|---|---|
| ICAM1 | Intercellular Adhesion Molecule 1 |
| ICAM2 | Intercellular Adhesion Molecule 2 |
| INS | Insulin |
| KALST | Kallistatin |
| KLK | Kallikrein |
| MRL | Mineralocorticoid Receptor |
| NCX1 | Sodium-Calcium Exchanger |
| NET | Norepinephrine Transporter |
| NPY | Neuropeptide Y |
| NPYR1 | Neuropeptide Y Y1 Receptor |
| PGIS | Prostacyclin Synthase |
| PLA2A | Pancreatic Phospholipase A-2 |
| PNMT | Phenylethanolamine N-Methyltransferase |
| PPGLUC | Preproglucagon |
| PPTHR | Preprothyrotropin-Releasing Hormone |
| PTGER3 | Prostaglandin E Receptor EP3 Subtype |
| REN | Renin |

TABLE 3-continued

| Gene/Exon | Gene Name |
|---|---|
| SA | SA Gene Acetyl-CoA Synthetase Homologue ?? (a candidate gene for genetic hypertension) |
| SCNN1G | Amiloride-Sensitive Epithelial Sodium Channel Gamma Subunit |
| TBXA2R | Thromboxane A2 Receptor |
| THXASO | Thromboxane Synthase |
| TRHR | Thyrotropin-Releasing Hormone Receptor |

Table 2

| | |
|---|---|
| ACE | Angiotensin Converting Enzyme |
| ADRB3 | Beta-3-Adrenergic Receptor |
| AGT | Angiotensinogen |
| ANP | Atrial Natriuretic Factor |
| AT1 | Angiotensin II Receptor Type-1 |
| MRL | Mineralocorticoid Receptor |
| NCX1 | Sodium-Calcium Exchanger |

What is claimed is:

1. A nucleic acid of between 10 and 100 bases comprising at least 10 contiguous nucleotides including a polymorphic site from a sequence shown in Table 1, column 8 or the complement thereof, wherein the sequence is selected from the group consisting of SEQ ID NOS: 2, 3, 4, 13, 15, 16, 20, 21, 25, and 26.

2. The nucleic acid of claim 1 that is DNA.

3. The nucleic acid of claim 1 that is RNA.

4. The nucleic acid of claim 1 that is less than 50 bases.

5. The nucleic acid of claim 1 that is less than 20 bases.

6. The nucleic acid of claim 1, wherein the polymorphic form occupying the polymorphic site is a reference base shown in Table 1, column 3.

7. The nucleic acid of claim 1, wherein the polymorphic form occupying the polymorphic site is an alternative base shown in Table 1, column 5.

8. The nucleic acid of claim 7, wherein the alternative base correlates with hypertension or susceptibility thereto.

9. The nucleic acid of claim 1, which is from a gene encoding alpha-adducin.

10. The nucleic acid of claim 1, which is from a gene encoding an angiotensin converting protein.

11. An allele-specific oligonucleotide of no more than 100 bases that hybridizes to a sequence including a polymorphic site shown in Table 1 or the complement thereof, wherein the sequence is selected from the group consisting of SEQ ID NOS: 2, 3, 4, 13, 15, 16, 20, 21, 25, and 26.

12. The allele-specific oligonucleotide of claim 11 that is a probe.

13. An isolated nucleic acid comprising a sequence of Table 1, column 8 or the complement thereof, wherein the polymorphic site within the sequence or its complement is occupied by a base other than the reference base shown in Table 1, column 3, and wherein the sequence is selected from the group consisting of SEQ ID NOS: 2, 3, 4, 13, 15, 16, 20, 21, 25, and 26.

* * * * *